(12) United States Patent
Pinto

(10) Patent No.: US 7,960,411 B2
(45) Date of Patent: Jun. 14, 2011

(54) LACTAM-CONTAINING COMPOUNDS AND DERIVATIVES THEREOF AS FACTOR XA INHIBITORS

(75) Inventor: Donald J. P. Pinto, Churchville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/691,895

(22) Filed: Jan. 22, 2010

(65) Prior Publication Data

US 2010/0119510 A1 May 13, 2010

Related U.S. Application Data

(62) Division of application No. 12/401,401, filed on Mar. 10, 2009, now Pat. No. 7,691,846, which is a division of application No. 11/955,678, filed on Dec. 13, 2007, now Pat. No. 7,531,535, which is a division of application No. 11/198,801, filed on Aug. 5, 2005, now Pat. No. 7,338,963, which is a division of application No. 10/850,587, filed on May 20, 2004, now Pat. No. 6,989,391, which is a division of application No. 10/245,122, filed on Sep. 17, 2002, now Pat. No. 6,967,208.

(60) Provisional application No. 60/324,165, filed on Sep. 21, 2001, provisional application No. 60/402,317, filed on Aug. 9, 2002.

(51) Int. Cl.
*C07D 519/00* (2006.01)
*A61K 31/445* (2006.01)
*A61P 7/02* (2006.01)

(52) U.S. Cl. ...................................... 514/318; 546/194
(58) Field of Classification Search .................. 546/194; 514/318

See application file for complete search history.

(56) References Cited

U.S. PATENT DOCUMENTS

| | | | |
|---|---|---|---|
| 3,340,269 A | 9/1967 | Blatter | |
| 3,365,459 A | 1/1968 | Blatter | |
| 3,423,414 A | 1/1969 | Blatter | |
| 5,998,424 A | 12/1999 | Galemmo, Jr. et al. | |
| 6,020,357 A | 2/2000 | Pinto et al. | |
| 6,060,491 A | 5/2000 | Pruitt et al. | |
| 6,187,797 B1 | 2/2001 | Pruitt et al. | |
| 6,191,159 B1 | 2/2001 | Pinto | |
| 6,271,237 B1 | 8/2001 | Galemmo, Jr. et al. | |
| 6,339,099 B1 | 1/2002 | Lam et al. | |
| 6,369,227 B1 | 4/2002 | Lam et al. | |
| 6,399,644 B1 | 6/2002 | Wexler et al. | |
| 6,403,620 B1 | 6/2002 | Galemmo, Jr. et al. | |
| 6,407,256 B1 | 6/2002 | Pinto | |
| 6,413,980 B1 | 7/2002 | Fevig et al. | |
| 6,426,346 B1 | 7/2002 | Pruitt et al. | |
| 6,429,205 B1 | 8/2002 | Jacobson et al. | |
| 6,436,985 B2 | 8/2002 | Pinto | |
| 6,548,512 B1 | 4/2003 | Pinto et al. | |
| 6,548,525 B2 | 4/2003 | Galemmo, Jr. et al. | |
| 6,569,874 B1 | 5/2003 | Pruitt et al. | |
| 6,602,895 B2 | 8/2003 | Galemmo, Jr. et al. | |
| 6,630,468 B2 | 10/2003 | Pinto | |
| 6,673,810 B2 | 1/2004 | Lam et al. | |
| 6,689,770 B2 | 2/2004 | Wexler et al. | |
| 6,716,841 B2 | 4/2004 | Jacobson et al. | |
| 6,750,225 B2 | 6/2004 | Pinto et al. | |
| 6,919,451 B2 | 7/2005 | Zhou et al. | |
| 6,949,550 B2 | 9/2005 | Quan et al. | |
| 6,967,208 B2 | 11/2005 | Pinto et al. | |
| 6,989,391 B2 | 1/2006 | Pinto et al. | |
| 6,995,172 B2 | 2/2006 | Pinto et al. | |
| 7,005,435 B2 | 2/2006 | Pinto et al. | |
| 7,115,627 B2 | 10/2006 | Pinto et al. | |
| 7,122,557 B2 | 10/2006 | Pinto et al. | |
| 7,135,469 B2 | 11/2006 | Pinto | |
| 7,153,960 B2 | 12/2006 | Zhou et al. | |
| 7,312,214 B2 | 12/2007 | Qiao et al. | |
| 7,338,963 B2 | 3/2008 | Pinto | |
| 7,371,761 B2 | 5/2008 | Pinto et al. | |
| 7,531,535 B2 | 5/2009 | Pinto et al. | |
| 2002/0025963 A1 | 2/2002 | Lam et al. | |
| 2003/0018023 A1 | 1/2003 | Pinto et al. | |
| 2003/0069237 A1 | 4/2003 | Fevig et al. | |
| 2003/0069258 A1 | 4/2003 | Lam et al. | |
| 2003/0078255 A1 | 4/2003 | Pinto | |
| 2004/0038980 A1 | 2/2004 | Lam et al. | |
| 2004/0063772 A1 | 4/2004 | Quan et al. | |
| 2004/0073029 A1 | 4/2004 | Pruitt et al. | |

FOREIGN PATENT DOCUMENTS

WO 94/20460 A1 9/1994

(Continued)

OTHER PUBLICATIONS

Elodi et al., "Optimization of conditions for the catalytic effect of the factor IXa-factor VIII Complex: Probable role of the complex in the amplification of blood coagulation", Thromb. Res., vol. 15, pp. 617-629, 1979. Kumar et al., "Ketone dithioacetals. Part II. Reaction of 3-cyano-4-methylthio-2(1H)-pyridones with hydrazine and guanidine: synthesis of novel substituted and fused pyrazolo[4,3-c]pyridine and pyrido[4,3-d]pyrimidine derivatives", J. Chem. Soc., Perkins Transactions I: Organic and Bio-Organic Chemistry 1978, No. 8, pp. 857-862 (abstract).

F.E. Nielsen et al., Phosphorus Pentoxide in Organic Synthesis-I, Tetrahedron, vol. 38, No. 10, pp. 1435-1441, 1982, RN:83325-18-2.

*Primary Examiner* — Bruck Kifle
(74) *Attorney, Agent, or Firm* — Fitzpatrick, Cella, Harper & Scinto

(57) ABSTRACT

The present application describes lactam-containing compounds and derivatives thereof of Formula I:

$$P_4\text{—}P\text{-}M\text{-}M_4 \qquad I$$

or pharmaceutically acceptable salt forms thereof, wherein ring P, if present is a 5-7 membered carbocycle or heterocycle and ring M is a 5-7 membered carbocycle or heterocycle. Compounds of the present invention are useful as inhibitors of trypsin-like serine proteases, specifically factor Xa.

7 Claims, No Drawings

FOREIGN PATENT DOCUMENTS

| | | | |
|---|---|---|---|
| WO | 96/12720 | A1 | 5/1996 |
| WO | 98/28269 | A1 | 7/1998 |
| WO | 98/28282 | A2 | 7/1998 |
| WO | 98/52948 | A1 | 11/1998 |
| WO | 98/57934 | A1 | 12/1998 |
| WO | 98/57937 | A2 | 12/1998 |
| WO | 98/57951 | A1 | 12/1998 |
| WO | 99/32454 | A1 | 7/1999 |
| WO | 99/32477 | A1 | 7/1999 |
| WO | 99/50255 | A2 | 10/1999 |
| WO | 00/39108 | A1 | 7/2000 |
| WO | 00/39131 | A1 | 7/2000 |
| WO | 00/59902 | A2 | 10/2000 |
| WO | 01/05784 | A1 | 1/2001 |
| WO | 01/19798 | A2 | 3/2001 |
| WO | 01/32628 | A1 | 5/2001 |
| WO | 02/074765 | A1 | 9/2002 |
| WO | 03/048158 | A1 | 6/2003 |
| WO | 03/049681 | A2 | 6/2003 |
| WO | 03/099276 | A1 | 12/2003 |
| WO | 2004/083174 | A2 | 9/2004 |

LACTAM-CONTAINING COMPOUNDS AND DERIVATIVES THEREOF AS FACTOR XA INHIBITORS

CROSS-REFERENCE TO RELATED APPLICATIONS

The present application is a divisional application of U.S. application Ser. No. 12/401,401, filed Mar. 10, 2009, which is a divisional application of U.S. application Ser. No. 11/955, 678, filed Dec. 13, 2007, now issued as U.S. Pat. No. 7,531, 535, which is a divisional application of U.S. application Ser. No. 11/198,801, filed Aug. 5, 2005, now issued as U.S. Pat. No. 7,338,963, which is a divisional application of U.S. application Ser. No. 10/850,587, filed May 20, 2004, now issued as U.S. Pat. No. 6,989,391, which is a divisional application of U.S. application Ser. No. 10/245,122, filed Sep. 17, 2002, now issued as U.S. Pat. No. 6,967,208, which claims the priority benefit of U.S. Provisional Application No. 60/324, 165, filed Sep. 21, 2001 and U.S. Provisional Application No. 60/402,317, filed Aug. 9, 2002; the contents of which are fully incorporated herein by reference.

FIELD OF THE INVENTION

This invention relates generally to lactam-containing compounds and derivatives thereof which are inhibitors of trypsin-like serine protease enzymes, especially factor Xa, pharmaceutical compositions containing the same, and methods of using the same as anticoagulant agents for treatment of thromboembolic disorders.

BACKGROUND OF THE INVENTION

WO94/20460 describes angiotensin II compounds of the following formula:

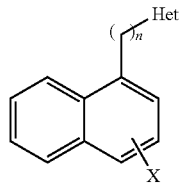

wherein X can be a number of substituents and Het can be a nitrogen-containing heterobicycle. However, WO94/20460 does not suggest Factor Xa inhibition or exemplify compounds like those of the present invention.

WO96/12720 depicts phosphodiesterase type IV and TNF production inhibitors of the following formula:

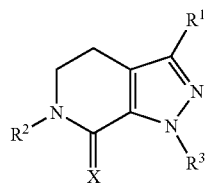

wherein X can be oxygen and $R^2$ and $R^3$ can be a number of substituents including heterocycle, heterocycloalkyl, and phenyl. However, the presently claimed compounds do not correspond to the compounds of WO96/12720. Furthermore, WO96/12720 does not suggest Factor Xa inhibition.

WO98/52948 details inhibitors of ceramide-mediated signal transduction. One of the types of inhibitors described is of the following formula:

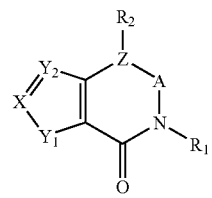

wherein $Y_1$ can be N—$R_6$, $R_6$ can be unsubstituted aryl-alkyl or unsubstituted heterocyclic-alkyl and $R_1$ can be a substituted aryl group. WO98/52948 does not mention factor Xa inhibition or show compounds like those of the present invention.

U.S. Pat. Nos. 3,365,459, 3,340,269, and 3,423,414 illustrate anti-inflammatory inhibitors of the following formula:

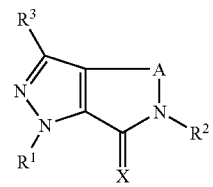

wherein A is 2-3 carbon atoms, X can be O, and $R^1$ and/or $R^3$ can bSpece substituted or unsubstituted aromatic groups. Neither of these patents, however, exemplifies compounds of the present invention.

WO99/32477 reports Factor Xa inhibitors of the following formula:

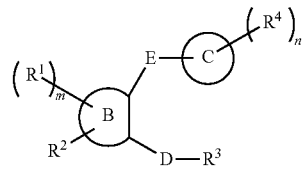

wherein the inhibitors contain at least three aryl or heterocyclic groups (i.e., C, B, and $R^3$) separated by two linking groups (i.e., E and D). Compounds of this sort are not considered to be part of the present invention.

WO00/39131 describes heterobicyclic Factor Xa inhibitors of which the following is an example formula:

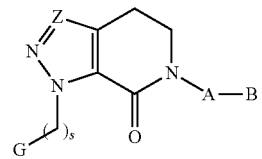

wherein Z is C or N, C is a mono- or bicyclic group, A is a cyclic moiety and B is a basic group or a cyclic moiety.

Compounds specifically described in WO00/39131 are not considered to be part of the present invention.

WO98/28269, WO98/28282, WO99/32454, U.S. Pat. No. 6,020,357, and U.S. Pat. No. 6,271,237 describe Factor Xa inhibitors of the following formula:

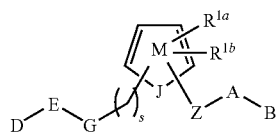

wherein ring M is a heterocycle, Z is a linker, A is a ring, B is a basic or cyclic group, D is a basic moiety, and E is a ring. Compounds specifically described in WO98/28269, WO98/28282, WO99/32454, U.S. Pat. No. 6,020,357, and U.S. Pat. No. 6,271,237 are not considered to be part of the present invention.

WO98/57951 describes Factor Xa inhibitors of the following formula:

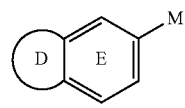

wherein ring M can be a variety of heterocycles and rings D-E represent a heterobicyclic group. Compounds specifically described in WO98/57951 are not considered to be part of the present invention.

WO98/57934 and U.S. Pat. No. 6,060,491 describe Factor Xa inhibitors of the following formula:

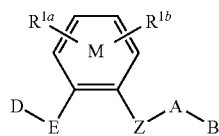

wherein ring M is a 6-membered heteroaryl, Z is a linker, A is a ring, B is a basic or cyclic group, D is a basic moiety, and E is a ring. Compounds specifically described in WO98/57934 and U.S. Pat. No. 6,060,491 are not considered to be part of the present invention.

WO98/57937 and U.S. Pat. No. 5,998,424 describe Factor Xa inhibitors of the following formula:

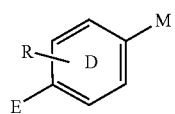

wherein ring M is a variety of rings, ring D is an aromatic ring, and R and E are non-basic groups. Compounds specifically described in WO98/57937 and U.S. Pat. No. 5,998,424 are not considered to be part of the present invention.

WO99/50255 and U.S. Pat. No. 6,191,159 describe pyrazoline and triazoline Factor Xa inhibitors of the following formulas:

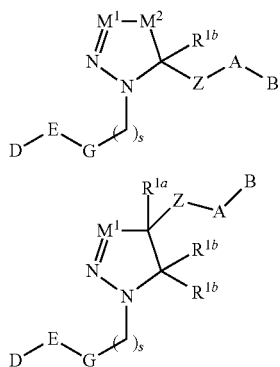

Compounds specifically described in WO99/50255 and U.S. Pat. No. 6,191,159 are not considered to be part of the present invention.

WO00/59902 describes Factor Xa inhibitors of the following formula:

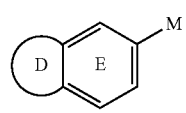

wherein ring M can be a variety of rings all of which are substituted with Z-A-B, Z is a linker, A is a ring, B is a sulfonyl-containing heterobicycle, and rings D-E represent a heterobicyclic group or a 6-membered ring. Compounds specifically described in WO00/59902 are not considered to be part of the present invention.

WO01/32628 describes cyano-pyrroles, cyano-imidazoles, cyano-pyrazoles, and cyano-triazoles that are Factor Xa inhibitors. Compounds specifically described in WO01/32628 are not considered to be part of the present invention.

WO01/05784 describes Factor Xa inhibitors of the following formulas:

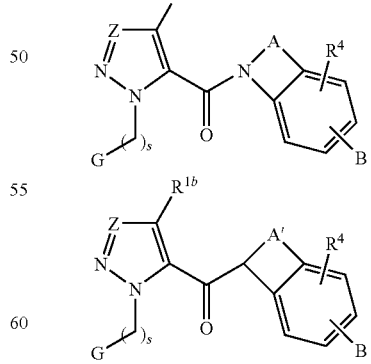

wherein Z is C or N, G is a mono- or bicyclic ring M, A is a linker, B is a basic or cyclic group. Compounds specifically described in WO01/05784 are not considered to be part of the present invention.

WO00/39108 describes Factor Xa inhibitors of the following formula:

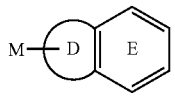

wherein ring M can be a variety of heterocycles and rings D-E represent a heterobicyclic group. Compounds specifically described in WO00/39108 are not considered to be part of the present invention.

WO01/19798 describes factor Xa inhibitors of the following formula:

A-Q-D-E-G-J-X wherein A, D, G, and X can be phenyl or heterocycle. However, none of the presently claimed compounds are exemplified or suggested in WO01/19798.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617-629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties (e.g., solubility, permeability, and amenability to sustained release formulations); (b) dosage requirements (e.g., lower dosages and/or once-daily dosing); (c) factors which decrease blood concentration peak-to-trough characteristics (e.g., clearance and/or volume of distribution); (d) factors that increase the concentration of active drug at the receptor (e.g., protein binding, volume of distribution); (e) factors that decrease the liability for clinical drug-drug interactions (e.g., cytochrome P450 enzyme inhibition or induction); (f) factors that decrease the potential for adverse side-effects (e.g., pharmacological selectivity beyond serine proteases, potential chemical or metabolic reactivity, and limited CNS penetration); and, (g) factors that improve manufacturing costs or feasibility (e.g., difficulty of synthesis, number of chiral centers, chemical stability, and ease of handling).

SUMMARY OF THE INVENTION

Accordingly, the present invention provides novel lactam-containing compounds and derivatives thereof that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a host in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt form thereof in an amount effective to treat a thromboembolic disorder.

The present invention provides a novel method, comprising: administering a compound of the present invention or a pharmaceutically acceptable salt form thereof in an amount effective to treat a thromboembolic disorder.

The present invention provides novel lactam-containing compounds and derivatives thereof for use in therapy.

The present invention provides the use of novel lactam-containing compounds for the manufacture of a medicament for the treatment of a thromboembolic disorder.

These and other objects, which will become apparent during the following detailed description, have been achieved by the inventors' discovery that lactam-containing compounds of Formula I:

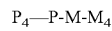

wherein $P_4$, P, M, and $M_4$ are defined below, or pharmaceutically acceptable salt or prodrug forms thereof, are effective factor Xa inhibitors.

DETAILED DESCRIPTION OF PREFERRED EMBODIMENTS

[1] In an embodiment, the present invention provides a novel compound of Formula I:

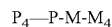

or a stereoisomer or pharmaceutically acceptable salt thereof, wherein;

M is a 3-10 membered carbocycle or a 4-10 membered heterocycle, consisting of: carbon atoms and 1-3 heteroatoms selected from O, $S(O)_p$, N, and $NZ^2$;

ring M is substituted with 0-3 $R^{1a}$ and 0-2 carbonyl groups, and there are 0-3 ring double bonds;

P is fused onto ring M and is a 5, 6, or 7 membered carbocycle or a 5, 6, or 7 membered heterocycle, consisting of: carbon atoms and 1-3 heteroatoms selected from O, $S(O)_p$, and N;

ring P is substituted with 0-3 $R^{1a}$ and 0-2 carbonyl groups, and there are 0-3 ring double bonds;

alternatively, ring P is absent and $P_4$ is directly attached to ring M, provided that when ring P is absent, $P_4$ and $M_4$ are attached to the 1,2, 1,3, or 1,4 positions of ring M;

one of $P_4$ and $M_4$ is —Z-A-B and the other -$G_1$-G;

G is a group of Formula IIa or IIb:

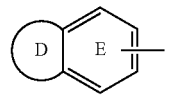

IIa

-continued

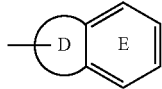

IIb ring D, including the two atoms of Ring E to which it is attached, is a 5-6 membered ring consisting of: carbon atoms and 0-2 heteroatoms selected from the group consisting of N, O, and $S(O)_p$; ring D is substituted with 0-2 R and there are 0-3 ring double bonds;

E is selected from phenyl, pyridyl, pyrimidyl, pyrazinyl, and pyridazinyl, and is substituted with 1-2 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1-2 R;

alternatively, ring D is absent and ring E is selected from phenyl, pyridyl, pyrimidyl, pyrazinyl, pyridazinyl, pyrrolyl, pyrazolyl, imidazolyl, isoxazolyl, oxazolyl, triazolyl, thienyl, and thiazolyl, and ring E is substituted with 1 R and with a 5-6 membered heterocycle consisting of: carbon atoms and 1-4 heteroatoms selected from the group consisting of N, O, and $S(O)_p$, wherein the 5-6 membered heterocycle is substituted with 0-1 carbonyl and 1-2 R and there are 0-3 ring double bonds;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)$ $NR^7R^9$, $NHC(=NR^8)NR^7R^9$, $ONHC(=NR^8)NR^7R^9$, $NR^8CH(=NR^7)$, $NH_2$, $NH(C_{1-3}$ alkyl), $N(C_{1-3}$ alkyl$)_2$, $C(=NH)NH_2$, $CH_2NH_2$, $CH_2NH(C_{1-3}$ alkyl), $CH_2N(C_{1-3}$ alkyl$)_2$, $CH_2CH_2NH_2$, $CH_2CH_2NH(C_{1-3}$ alkyl), $CH_2CH_2N(C_{1-3}$ alkyl$)_2$, $(CR^8R^9)_tC(O)H$, $(CR^8R^9)_tC(O)R^{2c}$, $(CR^8R^9)_t$ $NR^7R^8$, $(CR^8R^9)_tC(O)NR^7R^8$, $(CR^8R^9)_tNR^7C(O)R^7$, $(CR^8R^9)_tOR^3$, $(CR^8R^9)_tS(O)_pNR^7R^8$, $(CR^8R^9)_tNR^7S(O)_pR^7$, $(CR^8R^9)_tSR^3$, $(CR^8R^9)_tS(O)R^3$, $(CR^8R^9)_tS(O)_2R^3$, and $OCF_3$;

alternatively, when 2 R groups are attached to adjacent atoms, they combine to form methylenedioxy or ethylenedioxy;

A is selected from: $C_{3-10}$ carbocycle substituted with 0-2 $R^4$, and 5-12 membered heterocycle consisting of: carbon atoms and 1-4 heteroatoms selected from the group consisting of N, O, and $S(O)_p$ and substituted with 0-2 $R^4$; provided that A is other than a dihydro-benzopyran;

B is

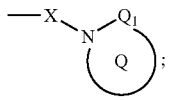

provided that Z and B are attached to different atoms on A and that the A-X—N moiety forms other than a N—N—N group; provided that B is other than triazolone, quinolone, or isoquinolone, wherein the triazolone, quinolone, and isoquinolone groups are substituted or unsubstituted;

$Q_1$ is selected from C=O and $SO_2$;

ring Q is a 4-8 membered monocyclic or bicyclic ring consisting of, in addition to the N-$Q_1$ group shown, carbon atoms and 0-2 heteroatoms selected from $NR^{4c}$, O, S, S(O), and $S(O)_2$, wherein: 0-2 double bonds are present within the ring and the ring is substituted with 0-2 $R^{4a}$;

alternatively, ring Q is a 4-8 membered monocyclic or bicyclic ring to which another ring is fused, wherein: the 4-8 membered ring consists of, in addition to the shown amide group, carbon atoms and 0-2 heteroatoms selected from $NR^{4c}$, O, S, S(O), and $S(O)_2$ and 0-2 double bonds are present within the ring;

the fusion ring is phenyl or a 5-6 membered heteroaromatic consisting of carbon atoms and 1-2 heteroatoms selected from $NR^{4c}$, O, S, S(O), and $S(O)_2$;

ring Q, which includes the 4-7 membered ring and the fusion ring, is substituted with 0-3 $R^{4a}$;

alternatively, two non-adjacent atoms of one of the rings of ring Q are bridged with 1-2 atoms selected from: carbon atoms, $NR^{4c}$, O, S, S(O), and $S(O)_2$, provided bonds other than O—O, $S(O)_p$—O, $S(O)_p$—$S(O)_p$, N—O, and N—$S(O)_p$ are present;

X is absent or is selected from —$(CR^2R^{2a})_{1-4}$—, —$CR^2$ $(CR^2R^{2b})(CH_2)_t$—, —C(O)—, —C(=$NR^{1c}$)—, —$CR^2$ $(NR^{1c}R^2)$—, —$CR^2(OR^2)$—, —$CR^2(SR^2)$—, —C(O) $CR^2R^{2a}$—, —$CR^2R^{2a}C(O)$—, —S(O)—, —$S(O)_2$—, —$SCR^2R^{2a}$—, —$S(O)CR^2R^{2a}$—, —$S(O)_2CR^2R^{2a}$—, —$CR^2R^{2a}S(O)$—, —$CR^2R^{2a}S(O)_2$—, —$S(O)_2$ $NR^2CR^2R^{2a}$—, —$NR^2S(O)_2$—, —$CR^2R^{2a}NR^2S(O)_2$—, —$NR^2S(O)_2CR^2R^{2a}$—, —$NR^2C(O)$—, —C(O) $NR^2CR^2R^{2a}$—, —$NR^2C(O)CR^2R^{2a}$—, $CR^2R^{2a}NR^2C(O)$—, $NR^2CR^2R^{2a}$, and —$OCR^2R^{2a}$—;

$G_1$ is absent or is selected from $(CR^3R^{3a})_{1-5}$, $(CR^3R^{3a})_{0-2}$ $CR^3$=$CR^3(CR^3R^{3a})_{0-2}$, $(CR^3R^{3a})_{0-2}$C≡C$(CR^3R^{3a})_{0-2}$, $(CR^3R^{3a})_uC(O)$ $(CR^3R^{3a})_w$, $(CR^3R^{3a})_uC(O)O(CR^3R^{3a})_w$, $(CR^3R^{3a})_uOC(O)(CR^3R^{3a})_w$, $(CR^3R^{3a})_uO(CR^3R^{3a})_w$, $(CR^3R^{3a})_uN^{3b}(CR^3R^{3a})_w$, $(CR^3R^{3a})_uC(O)N^{3b}(CR^3R^{3a})_w$, $(CR^3R^{3a})_uN^{3b}C(O)(CR^3R^{3a})_w$, $(CR^3R^{3a})_uOC(O)N^{3b}$ $(CR^3R^{3a})_w$, $(CR^3R^{3a})_uN^{3b}C(O)O(CR^3R^{3a})_w$, $(CR^3R^{3a})_u$ $N^{3b}C(O)N^{3b}(CR^3R^{3a})_w$, $(CR^3R^{3a})_uN^{3b}C(S)N^{3b}(CR^3R^{3a})_w$, $(CR^3R^{3a})_uS(CR^3R^{3a})_w$, $(CR^3R^{3a})_uS(O)$ $(CR^3R^{3a})_w$, $(CR^3R^{3a})_uS(O)_2(CR^3R^{3a})_w$, $(CR^3R^{3a})_uS(O)N^{3b}(CR^3R^{3a})_w$, $(CR^3R^{3a})_uN^{3b}S(O)_2(CR^3R^{3a})_w$, $(CR^3R^{3a})_uS(O)_2N^{3b}$ $(CR^3R^{3a})_w$, $(CR^3R^{3a})_uN^{3b}S(O)_2N^{3b}(CR^3R^{3a})_w$, $(CR^3R^{3a})_u$ $NR^{3b}(CR^3R^{3a})_w$, $(CR^3R^{3a})_uC(O)(CR^3R^{3a})_uC(O)(CR^3$ $R^{3a})_w$, $(CR^3R^{3a})_uNR^{3b}(CR^3R^{3a})_uC(O)NR^{3b}(CR^3R^{3a})_w$, $(CR^3R^{3a})_uNR^{3b}C(O)(CR^3R^{3a})_uC(O)(CR^3R^{3a})_w$, $(CR^3R^{3a})_u$ $C(O)(CR^3R^{3a})_uC(O)NR^{3b}(CR^3R^{3a})_w$, $(CR^3R^{3a})_uNR^{3b}C(O)$ $(CR^3R^{3a})_uC(O)NR^{3b}(CR^3R^{3a})_w$, $(CR^3R^{3a})_uS(O)NR^{3b}C(O)$ $(CR^3R^{3a})_w$, $(CR^3R^{3a})_uC(O)NR^{3b}S(O)_2(CR^3R^{3a})_w$, and $(CR^3R^{3a})_uS(O)_2NR^{3b}C(O)NR^{3b}(CR^3R^{3a})_w$, wherein u+w total 0, 1, 2, 3, or 4, provided that $G_1$ does not form an N—S, $NCH_2N$, $NCH_2O$, or $NCH_2S$ bond with either group to which it is attached;

Z is selected from a bond, —$(CR^3R^{3e})_{1-4}$—, $(CR^3R^{3e})_qO$ $(CR^3R^{3e})_{q1}$, $(CR^3R^{3e})_qNR^{3b}(CR^3R^{3e})_{q1}$, $(CR^3R^{3e})_qC(O)$ $(CR^3R^{3e})_{q1}$, $(CR^3R^{3e})_qC(O)O(CR^3R^{3e})_{q1}$, $(CR^3R^{3e})_qOC(O)$ $(CR^3R^{3e})_{q1}$, $(CR^3R^{3e})_qC(O)NR^{3b}(CR^3R^{3e})_{q1}$, $(CR^3R^{3e})_q$ $NR^{3b}C(O)(CR^3R^{3e})_{q1}$, $(CR^3R^{3e})_qOC(O)O(CR^3R^{3e})_{q1}$, $(CR^3R^{3e})_qOC(O)NR^{3b}(CR^3R^{3e})_{q1}$, $(CR^3R^{3e})_qNR^{3b}C(O)O$ $(CR^3R^{3e})_{q1}$, $(CR^3R^{3e})_qNR^{3b}C(O)NR^{3b}(CR^3R^{3e})_{q1}$, $(CR^3R^{3e})_qC(O)(CR^3R^{3e})_qC(O)(CR^3R^{3e})_{q1}$, $(CR^3R^{3e})_qNR^{3b}$ $(CR^3R^{3e})_qC(O)NR^{3b}(CR^3R^{3e})_{q1}$, $(CR^3R^{3e})_qNR^{3b}C(O)$ $(CR^3R^{3e})_qC(O)(CR^3R^{3e})_{q1}$, $(CR^3R^{3e})_qC(O)(CR^3R^{3e})_qC(O)$ $NR^{3b}(CR^3R^{3e})_{q1}$, $(CR^3R^{3e})_qNR^{3b}C(O)(CR^3R^{3e})_qC(O)NR^{3b}$ $(CR^3R^{3e})_{q1}$, $(CR^3R^{3e})_qS(CR^3R^{3e})_{q1}$, $(CR^3R^{3e})_qS(O)$ $(CR^3R^{3e})_{q1}$, $(CR^3R^{3e})_qS(O)_2(CR^3R^{3e})_{q1}$, $(CR^3R^{3e})_q$ $SO_2NR^{3b}(CR^3R^{3e})_{q1}$, $(CR^3R^{3e})_qNR^{3b}SO_2(CR^3R^{3e})_{q1}$, $(CR^3R^{3e})_qS(O)NR^{3b}C(O)$ $(CR^3R^{3e})_{q1}$, $(CR^3R^{3e})_qC(O)$ $NR^{3b}S(O)_2(CR^3R^{3e})_{q1}$, and $(CR^3R^{3e})_qNR^{3b}SO_2NR^{3b}$ $(CR^3R^{3e})_q$, wherein q+q1 total 0, 1, 2, 3, or 4, provided that Z does not form a N—S, $NCH_2N$, $NCH_2O$, or $NCH_2S$ bond with either group to which it is attached;

provided that B-A-Z form other than a pyridone-phenyl-$CH_2$, pyridone-pyridyl-$CH_2$, or pyridone-pyrimidyl-$CH_2$, wherein the pyridone, phenyl, pyridyl, and pyrimidyl groups are substituted or unsubstituted;

$Z^2$ is selected from H, $S(O)_2NHR^{3b}$, $C(O)R^{3b}$, $C(O)NHR^{3b}$, $C(O)OR^{3f}$, $S(O)R^{3f}$, $S(O)_2R^{3f}$, $C_{1-6}$ alkyl substituted with 0-2 $R^{1a}$, $C_{2-6}$ alkenyl substituted with 0-2 $R^{1a}$, $C_{2-6}$ alkynyl substituted with 0-2 $R^{1a}$, —$(C_{0-4}$ alkyl)-$C_{3-10}$ carbocycle substituted with 0-3 $R^{1a}$, and —$(C_{0-4}$ alkyl)-5-10 membered heterocycle substituted with 0-3 $R^{1a}$ and consisting of: carbon atoms and 1-4 heteroatoms selected from the group consisting of N, O, and $S(O)_p$;

$R^{1a}$, at each occurrence, is selected from H, —$(CR^3R^{3a})_r$—$R^{1b}$, —$(CR^3R^{3a})_r$—$CR^3R^{1b}R^{1b}$, —$(CR^3R^{3a})_r$—O—$(CR^3R^{3a})_r$—$R^{1b}$, —$C_{2-6}$ alkenylene-$R^{1b}$, —$C_{2-6}$ alkynylene-$R^{1b}$, —$(CR^3R^{3a})_r$—$C(=NR^{1b})NR^3R^{1b}$, $NR^3CR^3R^{3a}R^{1c}$, $OCR^3R^{3a}R^{1c}$, $SCR^3R^{3a}R^{1c}$, $NR^3(CR^3R^{3a})_2(CR^3R^{3a})_rR^{1b}$, $C(O)NR^2(CR^3R^{3a})_2(CR^3R^{3a})_rR^{1b}$, $CO_2(CR^3R^{3a})_2(CR^3R^{3a})_rR^{1b}$, $O(CR^3R^{3a})_2(CR^3R^{3a})_rR^{1b}$, $S(CR^3R^{3a})_2(CR^3R^{3a})_rR^{1b}$, $S(O)_p(CR^3R^{3a})_rR^{1d}$, $O(CR^3R^{3a})_rR^{1d}$, $NR^3$ $(CR^3R^{3a})_rR^{1d}$, $OC(O)NR^3$ $(CR^3R^{3a})_rR^{1d}$, $NR^3C(O)NR^3$ $(CR^3R^{3a})_rR^{1d}$, $NR^3C(O)O(CR^3R^{3a})_rR^{1d}$, and $NR^3C(O)$ $(CR^3R^{3a})_rR^{1d}$, provided that $R^{1a}$ forms other than an N-halo, N—S, O—O, or N—CN bond;

alternatively, when two $R^{1a}$ groups are attached to adjacent atoms, together with the atoms to which they are attached they form a 5-7 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, $C_{3-6}$ carbocycle substituted with 0-2 $R^{4b}$, and 5-10 membered heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^{1d}$ is selected from $C_{3-6}$ carbocycle substituted with 0-2 $R^{4b}$ and 5-10 membered heterocycle consisting of carbon atoms and from 1-4 heteroatoms selected from the group consisting of N, O, and $S(O)_p$, and substituted with 0-2 $R^{4b}$, provided that $R^{1d}$ forms other than an N—S bond;

$R^2$, at each occurrence, is selected from H, $CF_3$, $C_{1-6}$ alkyl, benzyl, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from the group consisting of N, O, and $S(O)_p$, and substituted with 0-2 $R^{4b}$;

$R^{2a}$, at each occurrence, is selected from H, $CF_3$, $C_{1-6}$ alkyl, benzyl, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from the group consisting of N, O, and $S(O)_p$, and substituted with 0-2 $R^{4b}$;

alternatively, $R^2$ and $R^{2a}$, together with the atom to which they are attached, combine to form a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from $CF_3$, $C_{1-4}$ alkoxy substituted with 0-2 $R^{4b}$, $C_{1-6}$ alkyl substituted with 0-2 $R^{4b}$, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0-2 $R^{4b}$, and —$(CH_2)_r$-5-10 membered heterocycle containing from 1-4 heteroatoms selected from the group consisting of N, O, and $S(O)_p$, and substituted with 0-2 $R^{4b}$;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0-1 additional heteroatoms selected from the group consisting of N, O, and $S(O)_p$;

$R^{3b}$, at each occurrence, is selected from H, $C_{1-6}$ alkyl substituted with 0-2 $R^{1a}$, $C_{2-6}$ alkenyl substituted with 0-2 $R^{1a}$, $C_{2-6}$ alkynyl substituted with 0-2 $R^{1a}$, —$(C_{0-4}$ alkyl)-5-10 membered carbocycle substituted with 0-3 $R^{1a}$, and —$(C_{0-4}$ alkyl)-5-10 membered heterocycle substituted with 0-3 $R^{1a}$ and consisting of: carbon atoms and 1-4 heteroatoms selected from the group consisting of N, O, and $S(O)_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

$R^{3e}$, at each occurrence, is selected from H, $SO_2NHR^3$, $SO_2NR^3R^3$, $C(O)R^3$, $C(O)NHR^3$, $C(O)OR^{3f}$, $S(O)R^{3f}$, $S(O)_2R^{3f}$, $C_{1-6}$ alkyl substituted with 0-2 $R^{1a}$, $C_{2-6}$ alkenyl substituted with 0-2 $R^{1a}$, $C_{2-6}$ alkynyl substituted with 0-2 $R^{1a}$, —$(C_{0-4}$ alkyl)-5-10 membered carbocycle substituted with 0-3 $R^{1a}$, and —$(C_{0-4}$ alkyl)-5-10 membered heterocycle substituted with 0-3 $R^{1a}$ and consisting of: carbon atoms and 1-4 heteroatoms selected from the group consisting of N, O, and $S(O)_p$;

$R^{3f}$, at each occurrence, is selected from: $C_{1-6}$ alkyl substituted with 0-2 $R^{1a}$, $C_{2-6}$ alkenyl substituted with 0-2 $R^{1a}$, $C_{2-6}$ alkynyl substituted with 0-2 $R^{1a}$, —$(C_{0-4}$ alkyl)-5-10 membered carbocycle substituted with 0-3 $R^{1a}$, and —$(C_{0-4}$ alkyl)-5-10 membered heterocycle substituted with 0-3 $R^{1a}$ and consisting of: carbon atoms and 1-4 heteroatoms selected from the group consisting of N, O, and $S(O)_p$;

$R^4$, at each occurrence, is selected from H, =O, $(CR^3R^{3a})_rOR^2$, F, Cl, Br, I, $C_{1-4}$ alkyl, $(CR^3R^{3a})_rCN$, $(CR^3R^{3a})_rNO_2$, $(CR^3R^{3a})_rNR^2R^{2a}$, $(CR^3R^{3a})_rC(O)R^{2c}$, $(CR^3R^{3a})_rNR^2C(O)R^{2b}$, $(CR^3R^{3a})_rC(O)NR^2R^{2a}$, $(CR^3R^{3a})_rNR^2C(O)NR^2R^{2a}$, $(CR^3R^{3a})_rC(=NR^2)NR^2R^{2a}$, $(CR^3R^{3a})_rC(=NS(O)_2R^5)NR^2R^{2a}$, $(CR^3R^{3a})_rNHC(=NR^2)NR^2R^{2a}$, $(CR^3R^{3a})_rC(O)NHC(=NR^2)NR^2R^{2a}$, $(CR^3R^{3a})_rSO_2NR^2R^{2a}$, $(CR^3R^{3a})_rNR^2SO_2NR^2R^{2a}$, $(CR^3R^{3a})_rNR^2SO_2$—$C_{1-4}$ alkyl, $(CR^3R^{3a})_rNR^2SO_2R^5$, $(CR^3R^{3a})_rS(O)_pR^{5a}$, $(CR^3R^{3a})_r(CF_2)_rCF_3$, $NHCH_2R^{1c}$, $OCH_2R^{1c}$, $SCH_2R^{1c}$, $NH(CH_2)_2(CH_2)_rR^{1b}$, $O(CH_2)_2(CH_2)_rR^{1b}$, $S(CH_2)_2(CH_2)_rR^{1b}$, $(CR^3R^{3a})_r$-5-6 membered carbocycle substituted with 0-1 $R^5$, and a $(CR^3R^{3a})_r$-5-6 membered heterocycle consisting of: carbon atoms and 1-4 heteroatoms selected from the group consisting of N, O, and $S(O)_p$ and substituted with 0-1 $R^5$;

$R^{4a}$, at each occurrence, is selected from H, =O, $(CR^3R^{3a})_r$ $OR^2$, $(CR^3R^{3a})_rF$, $(CR^3R^{3a})_rBr$, $(CR^3R^{3a})_rCl$, $C_{1-4}$ alkyl, $(CR^3R^{3a})_rCN$, $(CR^3R^{3a})_rNO_2$, $(CR^3R^{3a})_r$ $NR^2R^{2a}$, $(CR^3R^{3a})_r$ $C(O)R^{2c}$, $(CR^3R^{3a})_rNR^2C(O)R^{2b}$, $(CR^3R^{3a})_rC(O)NR^2R^{2a}$, $(CR^3R^{3a})_rN=CHOR^3$, $(CR^3R^{3a})_r$ C(O)NH(CH$_2$)$_2$NR$^2$R$^{2a}$, (CR$^3$R$^{3a}$)$_r$NR$^2$C(O)NR$^2$R$^{2a}$, (CR$^3$R$^{3a}$)$_r$C(=NR$^2$)NR$^2$R$^{2a}$, (CR$^3$R$^{3a}$)$_r$NHC(=NR$^2$)NR$^2$R$^{2a}$, (CR$^3$R$^{3a}$)$_r$SO$_2$NR$^2$R$^{2a}$, (CR$^3$R$^{3a}$)$_r$NR$^2$SO$_2$NR$^2$R$^{2a}$, (CR$^3$R$^{3a}$)$_r$NR$^2$SO$_2$—C$_{1-4}$ alkyl, (CR$^3$R$^{3a}$)$_r$C(O)NHSO$_2$—C$_{1-4}$ alkyl, (CR$^3$R$^{3a}$)$_r$NR$^2$SO$_2$R$^5$, (CR$^3$R$^{3a}$)$_r$S(O)$_p$R$^{5a}$, (CR$^3$R$^{3a}$)$_r$(CF$_2$)$_r$CF$_3$, (CR$^3$R$^{3a}$)$_r$-5-6 membered carbocycle substituted with 0-1 R$^5$, and a (CR$^3$R$^{3a}$)$_r$-5-6 membered heterocycle consisting of: carbon atoms and 1-4 heteroatoms selected from the group consisting of N, O, and S(O)$_p$, and substituted with 0-1 R$^5$;

R$^{4b}$, at each occurrence, is selected from H, =O, (CH$_2$)$_r$OR$^3$, (CH$_2$)$_r$F, (CH$_2$)$_r$Cl, (CH$_2$)$_r$Br, (CH$_2$)$_r$I, C$_{1-4}$ alkyl, (CH$_2$)$_r$CN, (CH$_2$)$_r$NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$—C(O)NR$^3$R$^{3a}$, (CH$_2$)$_r$NR$^3$C(O)NR$^3$R$^{3a}$, (CH$_2$)$_r$—C(=NR$^3$)NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, and (CH$_2$)$_r$(CF$_2$)$_r$CF$_3$;

R$^{4c}$, at each occurrence, is selected from H, C$_{1-4}$ alkyl, (CR$^3$R$^{3a}$)$_r$OR$^2$, (CR$^3$R$^{3a}$)$_{r1}$F, (CR$^3$R$^{3a}$)$_{r1}$Br, (CR$^3$R$^{3a}$)$_{r1}$Cl, (CR$^3$R$^{3a}$)$_{r1}$CN, (CR$^3$R$^{3a}$)$_{r1}$NO$_2$, (CR$^3$R$^{3a}$)$_{r1}$NR$^2$R$^{2a}$, (CR$^3$R$^{3a}$)$_r$C(O)R$^{2c}$, (CR$^3$R$^{3a}$)$_{r1}$NR$^2$C(O)R$^{2b}$, (CR$^3$R$^{3a}$)$_r$C(O)NR$^2$R$^{2a}$, (CR$^3$R$^{3a}$)$_{r1}$N=CHOR$^3$, (CR$^3$R$^{3a}$)$_r$C(O)NH(CH$_2$)$_2$NR$^2$R$^{2a}$, (CR$^3$R$^{3a}$)$_{r1}$NR$^2$C(O)NR$^2$R$^{2a}$, (CR$^3$R$^{3a}$)$_{r1}$C(=NR$^2$)NR$^2$R$^{2a}$, (CR$^3$R$^{3a}$)$_{r1}$NHC(=NR$^2$)NR$^2$R$^{2a}$, (CR$^3$R$^{3a}$)$_r$SO$_2$NR$^2$R$^{2a}$, (CR$^3$R$^{3a}$)$_{r1}$NR$^2$SO$_2$NR$^2$R$^{2a}$, (CR$^3$R$^{3a}$)$_{r1}$NR$^2$SO$_2$—C$_{1-4}$ alkyl, (CR$^3$R$^{3a}$)$_r$C(O)NHSO$_2$—C$_{1-4}$ alkyl, (CR$^3$R$^{3a}$)$_{r1}$NR$^2$SO$_2$R$^5$, (CR$^3$R$^{3a}$)$_r$S(O)$_p$R$^{5a}$, (CR$^3$R$^{3a}$)$_r$(CF$_2$)$_r$CF$_3$, (CR$^3$R$^{3a}$)$_r$-5-6 membered carbocycle substituted with 0-1 R$^5$, and a (CR$^3$R$^{3a}$)$_r$-5-6 membered heterocycle consisting of: carbon atoms and 1-4 heteroatoms selected from the group consisting of N, O, and S(O)$_p$, and substituted with 0-1 R$^5$;

R$^5$, at each occurrence, is selected from H, C$_{1-6}$ alkyl, =O, (CH$_2$)$_r$OR$^3$, F, Cl, Br, I, —CN, NO$_2$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CH$_2$)$_r$NR$^3$C(O)NR$^3$R$^{3a}$, (CH$_2$)$_r$CH(=NOR$^{3d}$), (CH$_2$)$_r$C(=NR$^3$)NR$^3$R$^{3a}$, (CH$_2$)$_r$NR$^3$C(=NR$^3$)NR$^3$R$^{3a}$, (CH$_2$)$_r$SO$_2$NR$^3$R$^{3a}$, (CH$_2$)$_r$NR$^3$SO$_2$NR$^3$R$^{3a}$, (CH$_2$)$_r$NR$^3$SO$_2$—C$_{1-4}$ alkyl, (CH$_2$)$_r$NR$^3$SO$_2$CF$_3$, (CH$_2$)$_r$NR$^3$SO$_2$-phenyl, (CH$_2$)$_r$S(O)$_p$CF$_3$, (CH$_2$)$_r$S(O)$_p$—C$_{1-4}$ alkyl, (CH$_2$)$_r$S(O)$_p$-phenyl, (CF$_2$)$_r$CF$_3$, phenyl substituted with 0-2 R$^6$, naphthyl substituted with 0-2 R$^6$, and benzyl substituted with 0-2 R$^6$;

R$^{5a}$, at each occurrence, is selected from C$_{1-6}$ alkyl, (CH$_2$)$_r$OR$^3$, (CH$_2$)$_r$NR$^3$R$^{3a}$, (CH$_2$)$_r$C(O)R$^3$, (CH$_2$)$_r$C(O)OR$^{3c}$, (CH$_2$)$_r$NR$^3$C(O)R$^{3a}$, (CH$_2$)$_r$C(O)NR$^3$R$^{3a}$, (CF$_2$)$_r$CF$_3$, phenyl substituted with 0-2 R$^6$, naphthyl substituted with 0-2 R$^6$, and benzyl substituted with 0-2 R$^6$, provided that R$^{5a}$ does not form a S—N or S(O)$_p$—C(O) bond;

R$^6$, at each occurrence, is selected from H, OH, (CH$_2$)$_r$OR$^2$, halo, C$_{1-4}$ alkyl, CN, NO$_2$, (CH$_2$)$_r$NR$^2$R$^{2a}$, (CH$_2$)$_r$C(O)R$^{2b}$, NR$^2$C(O)R$^{2b}$, NR$^2$C(O)NR$^2$R$^{2a}$, C(=NH)NH$_2$, NHC(=NH)NH$_2$, SO$_2$NR$^2$R$^{2a}$, NR$^2$SO$_2$NR$^2$R$^{2a}$, and NR$^2$SO$_2$C$_{1-4}$ alkyl;

R$^7$, at each occurrence, is selected from H, OH, C$_{1-6}$ alkyl, C$_{1-6}$ alkyl-C(O)—, C$_{1-6}$ alkyl-O—, (CH$_2$)$_n$-phenyl, C$_{1-4}$ alkyl-OC(O)—, C$_{6-10}$ aryl-O—, C$_{6-10}$ aryl-OC(O)—, C$_{6-10}$ aryl-CH$_2$—C(O)—, C$_{1-4}$ alkyl-C(O)O—C$_{1-4}$ alkyl-OC(O)—, C$_{6-10}$ aryl-C(O)O—C$_{1-4}$ alkyl-OC(O)—, C$_{1-6}$ alkyl-NH$_2$—C(O)—, phenyl-NH$_2$—C(O)—, and phenyl-C$_{1-4}$ alkyl-C(O)—;

R$^8$, at each occurrence, is selected from H, C$_{1-6}$ alkyl, and (CH$_2$)$_n$-phenyl;

alternatively, R$^7$ and R$^8$, when attached to the same nitrogen, combine to form a 5-10 membered heterocyclic ring consisting of carbon atoms and 0-2 additional heteroatoms selected from the group consisting of N, O, and S(O)$_p$;

R$^9$, at each occurrence, is selected from H, C$_{1-6}$ alkyl, and (CH$_2$)$_n$-phenyl;

n, at each occurrence, is selected from 0, 1, 2, and 3;
p, at each occurrence, is selected from 0, 1, and 2;
r, at each occurrence, is selected from 0, 1, 2, 3, 4, 5, and 6;
r1, at each occurrence, is selected from 1, 2, 3, 4, 5, and 6;
t, at each occurrence, is selected from 0, 1, 2, and 3; and
provided that when:

(a) ring M is phenyl and is substituted 1,2 by M$_4$ and P$_4$ and G$_1$ is present, then Z-A is other than NHC(O)-thienyl, NHCH$_2$-thienyl, NHC(O)-benzothienyl, and NHCH$_2$-benzothienyl; and (b) B is 2-oxo-1-pyrrolidinyl and rings P-M are 1,7-dihydro-2-methyl-6H-purin-6-one, then G-G$_1$ is other than unsubstituted phenyl.

[2] In a preferred embodiment, the present invention provides a novel compound of Formula II:

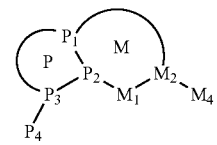

or a stereoisomer or pharmaceutically acceptable salt thereof, wherein;

ring M, including P$_1$, P$_2$, M$_1$, and M$_2$, is a 5, 6, or 7 membered carbocycle or a 5, 6, or 7 membered heterocycle, consisting of: carbon atoms and 1-3 heteroatoms selected from O, S(O)$_p$, N, and NZ$^2$;

ring M is substituted with 0-2 R$^{1a}$ and 0-2 carbonyl groups, and there are 0-3 ring double bonds;

ring P, including P$_1$, P$_2$, and P$_3$, is a 5 or 6 membered aromatic heterocycle, consisting of: carbon atoms and 1-3 heteroatoms selected from O, S(O)$_p$, and N;

alternatively, ring P, including P$_1$, P$_2$, and P$_3$, is a 5 or 6 membered dihydro-aromatic heterocycle, consisting of: carbon atoms and 1-3 heteroatoms selected from O, S(O)$_p$, and N;

ring P is substituted with 0-2 R$^{1a}$;
one of P$_4$ and M$_4$ is —Z-A-B and the other -G$_1$-G;
G is a group of Formula IIa or IIb:

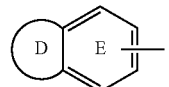

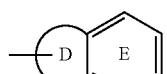

ring D, including the two atoms of Ring E to which it is attached, is a 5-6 membered ring consisting of: carbon atoms and 0-2 heteroatoms selected from the group consisting of N, O, and S(O)$_p$; ring D is substituted with 0-2 R and there are 0-3 ring double bonds;

E is selected from phenyl, pyridyl, pyrimidyl, pyrazinyl, and pyridazinyl, and is substituted with 1-2 R;

alternatively, ring D is absent, and ring E is selected from phenyl, pyridyl, pyrimidyl, and thienyl, and ring E is substituted with 1-2 R;

alternatively, ring D is absent, ring E is selected from phenyl, pyridyl, and thienyl, and ring E is substituted with 1 R and substituted with a 5 membered heterocycle consisting of: carbon atoms and 1-4 heteroatoms selected from the group consisting of N, O, and $S(O)_p$, wherein the 5 membered heterocycle is substituted with 0-1 carbonyl and 1-2 R and there are 0-3 ring double bonds;

R is selected from H, $C_{1-4}$ alkyl, F, Cl, OH, $OCH_3$, $OCH_2CH_3$, $OCH(CH_3)_2$, CN, $C(=NH)NH_2$, $C(=NH)NHOH$, $C(=NH)NHOCH_3$, $NH_2$, $NH(C_{1-3}$ alkyl), $N(C_{1-3}$ alkyl$)_2$, $CH_2NH_2$, $CH_2NH(C_{1-3}$ alkyl), $CH_2N(C_{1-3}$ alkyl$)_2$, $(CR^8R^9)_rNR^7R^8$, $C(O)NR^7R^8$, $CH_2C(O)NR^7R^8$, $S(O)_pNR^7R^8$, $CH_2S(O)_pNR^7R^8$, $SO_2R^3$, and $OCF_3$;

alternatively, when 2 R groups are attached to adjacent atoms, they combine to form methylenedioxy or ethylenedioxy;

A is selected from: $C_{5-10}$ carbocycle substituted with 0-2 $R^4$, and 5-10 membered heterocycle consisting of: carbon atoms and 1-4 heteroatoms selected from the group consisting of N, O, and $S(O)_p$ and substituted with 0-2 $R^4$; provided that A is other than a dihydro-benzopyran;

B is

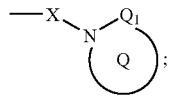

provided that Z and B are attached to different atoms on A and that the A-X—N moiety forms other than a N—N—N group; provided that B is other than triazolone, quinolone, or isoquinolone, wherein the triazolone, quinolone, and isoquinolone groups are substituted or unsubstituted;

$Q_1$ is selected from C=O and $SO_2$;

ring Q is a 4-7 membered monocyclic or bicyclic ring consisting of, in addition to the $N-Q_1$ group shown, carbon atoms and 0-2 heteroatoms selected from $NR^{4c}$, O, S, S(O), and $S(O)_2$, wherein: 0-2 double bonds are present within the ring and the ring is substituted with 0-2 $R^{4a}$;

alternatively, ring Q is a 4-7 membered ring to which another ring is fused, wherein: the 4-7 membered ring consists of, in addition to the shown amide group, carbon atoms and 0-2 heteroatoms selected from $NR^{4c}$, O, S, S(O), and $S(O)_2$ and 0-1 double bonds are present within the ring;

the fusion ring is phenyl or a 5-6 membered heteroaromatic consisting of carbon atoms and 1-2 heteroatoms selected from $NR^{4c}$, O, and S;

ring Q, which includes the 4-7 membered ring and the fusion ring, is substituted with 0-3 $R^{4a}$;

X is absent or is selected from $-(CR^2R^{2a})_{1-4}-$, $-C(O)-$, $-C(O)CR^2R^{2a}-$, $-CR^2R^{2a}C(O)-$, $-S(O)_2-$, $-S(O)_2CR^2R^{2a}-$, $-CR^2R^{2a}S(O)_2-$, $-NR^2S(O)_2-$, $-NR^2CR^2R^{2a}-$, and $-OCR^2R^{2a}-$;

Z is selected from a bond, $CH_2$, $CH_2CH_2$, $CH_2O$, $OCH_2$, $C(O)$, NH, $CH_2NH$, $NHCH_2$, $CH_2C(O)$, $C(O)CH_2$, $C(O)NH$, $NHC(O)$, $NHC(O)CH_2C(O)NH$, $S(O)_2$, $CH_2S(O)_2$, $S(O)_2(CH_2)$, $SO_2NH$, and $NHSO_2$, provided that Z does not form a N—S, $NCH_2N$, $NCH_2O$, or $NCH_2S$ bond with either group to which it is attached;

$Z^2$ is selected from H, $C_{1-4}$ alkyl, phenyl, benzyl, $C(O)R^{3b}$, $S(O)R^{3f}$, and $S(O)_2R^{3f}$;

$R^{1a}$ is selected from H, $-(CH_2)_r-R^{1b}$, $-(CH(CH_3))_r-R^{1b}$, $-(C(CH_3)_2)_r-R^{1b}$, $NHCH_2R^{1c}$, $OCH_2R^{1c}$, $SCH_2R^{1c}$, $NH(CH_2)_2(CH_2)_rR^{1b}$, and $O(CH_2)_2(CH_2)_rR^{1b}$, provided that $R^{1a}$ forms other than an N-halo, N—S, or N—CN bond;

alternatively, when two $R^{1a}$ groups are attached to adjacent atoms, together with the atoms to which they are attached they form a 5-7 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, $CH_3$, $CH_2CH_3$, $CH_2CH_2CH_3$, $CH(CH_3)_2$, F, Cl, Br, I, $-CN$, $-CHO$, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C_{5-6}$ carbocycle substituted with 0-2 $R^{4b}$, and 5-6 membered heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, a $C_{5-6}$ carbocyclic-$CH_2$-group substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

alternatively, $R^2$ and $R^{2a}$, together with the atom to which they are attached, combine to form a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, and 5-6 membered heterocycle containing from 1-4 heteroatoms selected from the group consisting of N, O, and $S(O)_p$, and substituted with 0-2 $R^{4b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5-6 membered carbocycle substituted with 0-1 $R^5$, and a 5-6 membered heterocycle consisting of: carbon atoms and 1-4 heteroatoms selected from the group consisting of N, O, and $S(O)_p$, and substituted with 0-1 $R^5$;

$R^{4a}$, at each occurrence, is selected from H, =O, $CH_2OR^2$, $OR^2$, $CH_2F$, F, $CH_2Br$, Br, $CH_2Cl$, Cl, $C_{1-4}$ alkyl, $CH_2$—CN, —CN, $CH_2NO_2$, $NO_2$, $CH_2NR^2R^{2a}$, $NR^2R^{2a}$, $CH_2$—$C(O)R^{2c}$, $C(O)R^{2c}$, $NR^2C(O)R^{2b}$, $(CH_2)_rC(O)NR^2R^{2a}$, $NR^2C(O)NR^2R^{2a}$, $(CH_2)_rSO_2NR^2R^{2a}$, $NR^2SO_2NR^2R^{2a}$, $NR^2SO_2$—$C_{1-4}$ alkyl, $NR^2SO_2R^5$, $(CH_2)_rS(O)_pR^{5a}$, $CH_2CF_3$, $CF_3$, $CH_2$-5-6 membered carbocycle substituted with 0-1 $R^5$, 5-6 membered carbocycle substituted with 0-1 $R^5$, a $CH_2$-5-6 membered heterocycle consisting of: carbon atoms and 1-4 heteroatoms selected from the group consisting of N, O, and $S(O)_p$, and substituted with 0-1 $R^5$, and 5-6 membered heterocycle consisting of: carbon atoms and 1-4 heteroatoms selected from the group consisting of N, O, and $S(O)_p$, and substituted with 0-1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2CF_3$;

$R^{4c}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2OR^2$, $CH_2F$, $CH_2Br$, $CH_2Cl$, $CH_2CN$, $CH_2NO_2$, $CH_2NR^2R^{2a}$, $C(O)R^{2c}$, $CH_2C(O)R^{2c}$, $CH_2NR^2C(O)R^{2b}$, $C(O)NR^2R^{2a}$, $CH_2C(O)NR^2R^{2a}$, $CH_2NR^2C(O)NR^2R^{2a}$, $SO_2NR^2R^{2a}$, $CH_2SO_2NR^2R^{2a}$, $CH_2NR^2SO_2NR^2R^{2a}$, $CH_2NR^2SO_2$—$C_{1-4}$ alkyl, $C(O)NHSO_2$—$C_{1-4}$ alkyl, $CH_2C(O)NHSO_2$—$C_{1-4}$ alkyl, $CH_2NR^2SO_2R^5$, $S(O)_pR^{5a}$, $CH_2S(O)_pR^{5a}$, $CF_3$, $CH_2CF_3$, 5-6 membered carbocycle substituted with 0-1 $R^5$, $CH_2$-5-6 membered carbocycle substituted with 0-1 $R^5$, 5-6 membered heterocycle consisting of: carbon atoms and 1-4 heteroatoms selected from the group consisting of N, O, and $S(O)_p$, and substituted with 0-1 $R^5$, and a $CH_2$-5-6 membered heterocycle consisting of: carbon atoms and 1-4 heteroatoms selected from the group consisting of N, O, and $S(O)_p$, and substituted with 0-1 $R^5$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

[3] In another preferred embodiment, the present invention provides a novel compound, wherein:

ring M is substituted with 0-2 $R^{1a}$ and is selected from the group:

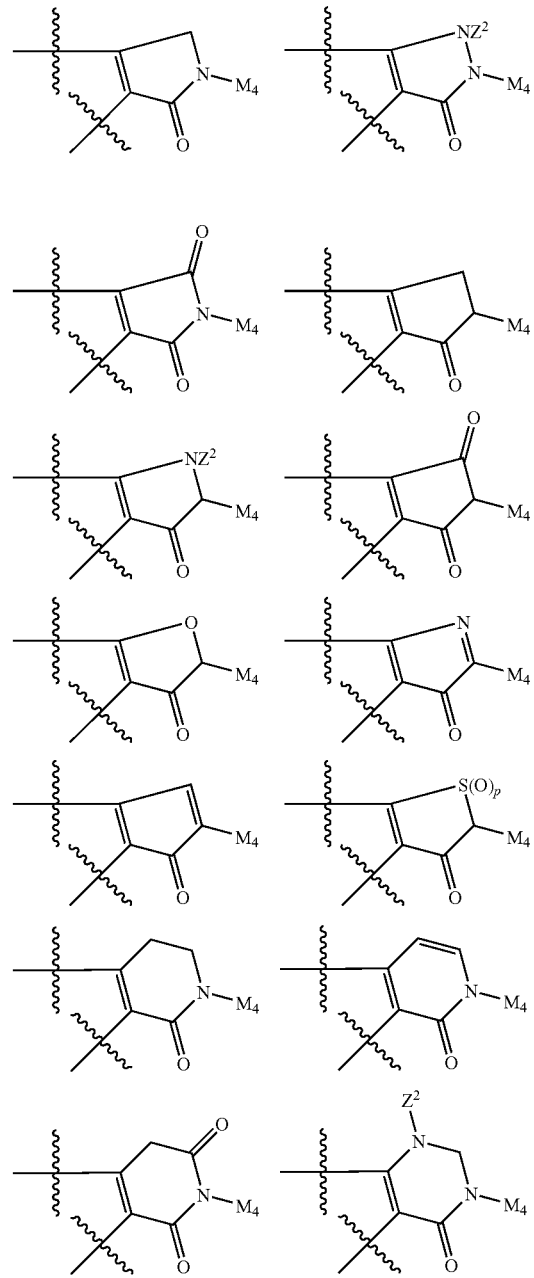

-continued
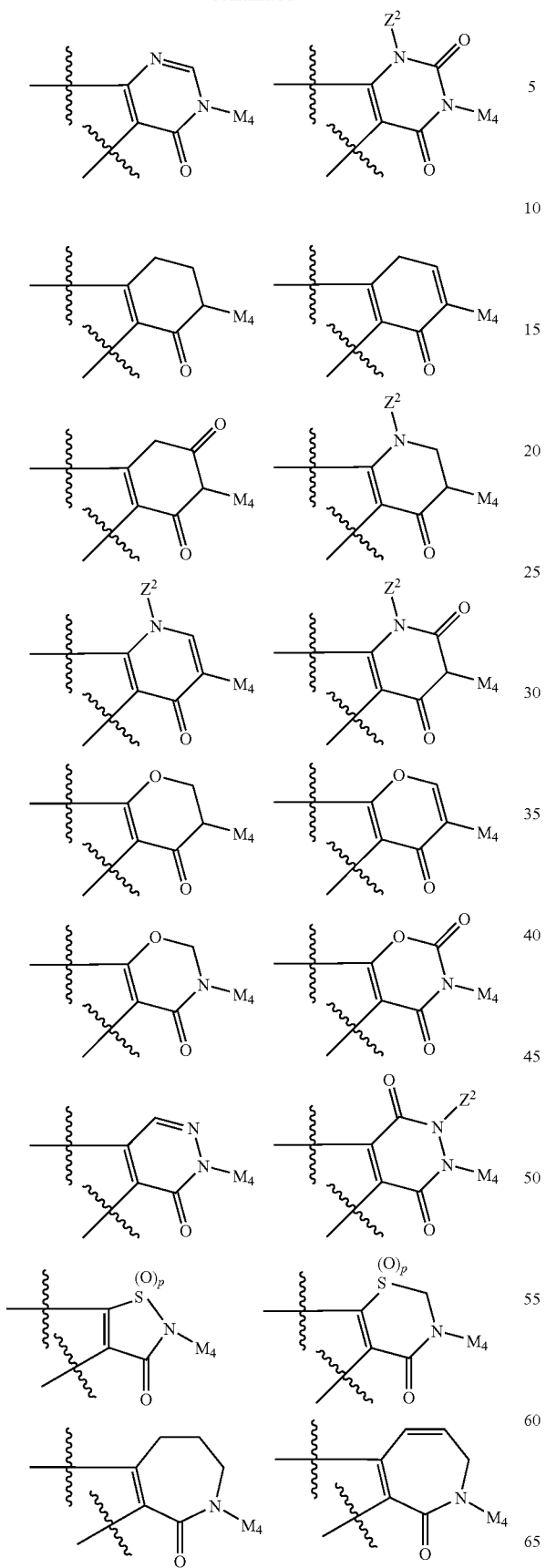
-continued
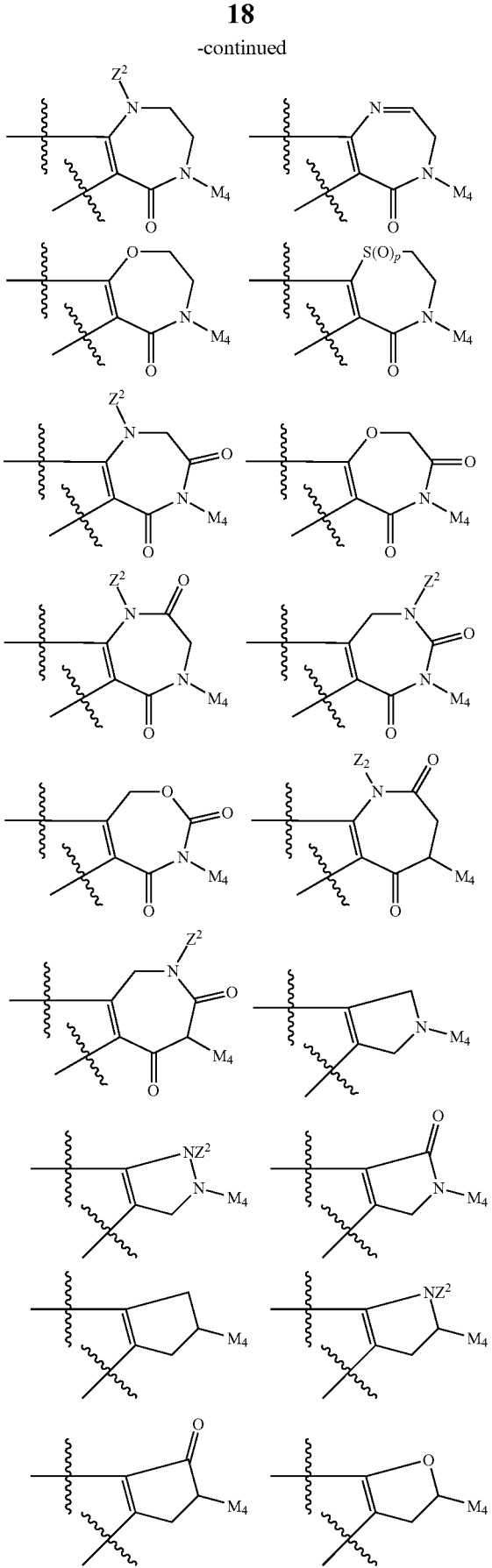

-continued
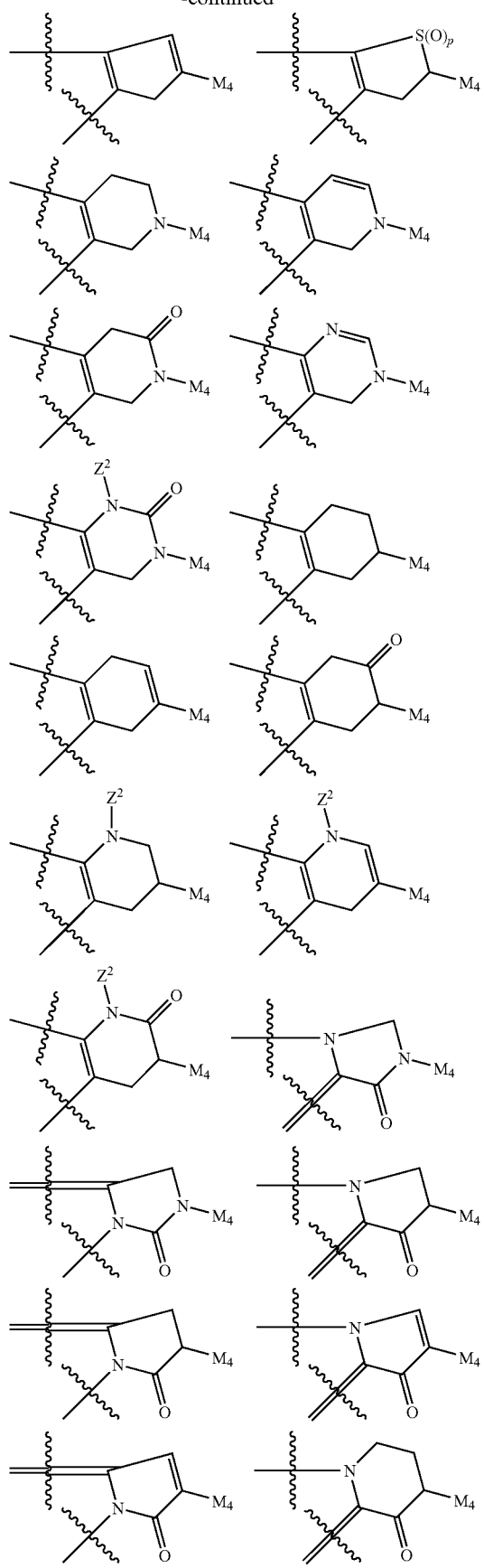
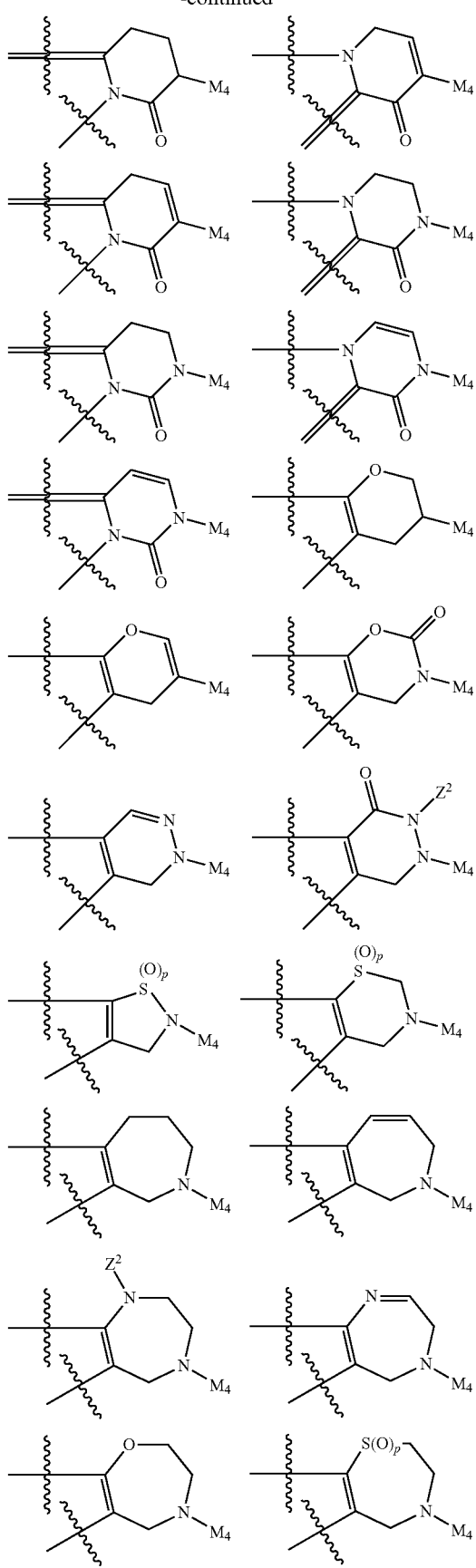

-continued
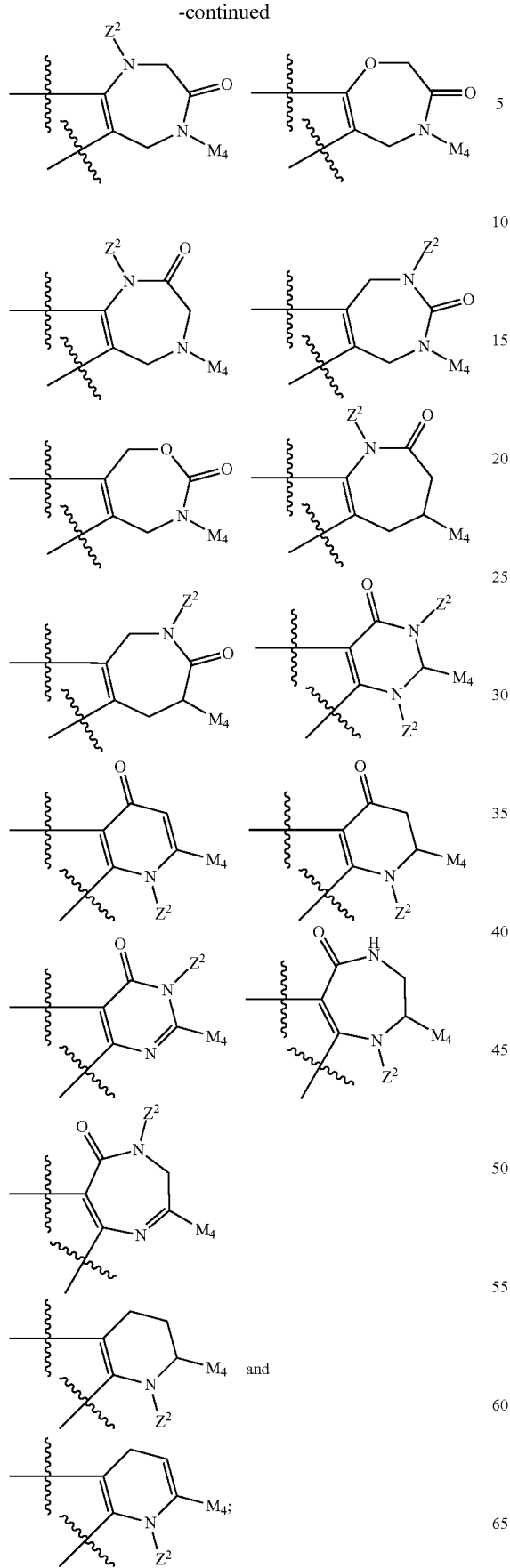
ring P, including $P_1$, $P_2$, $P_3$, and $P_4$ is selected from group:
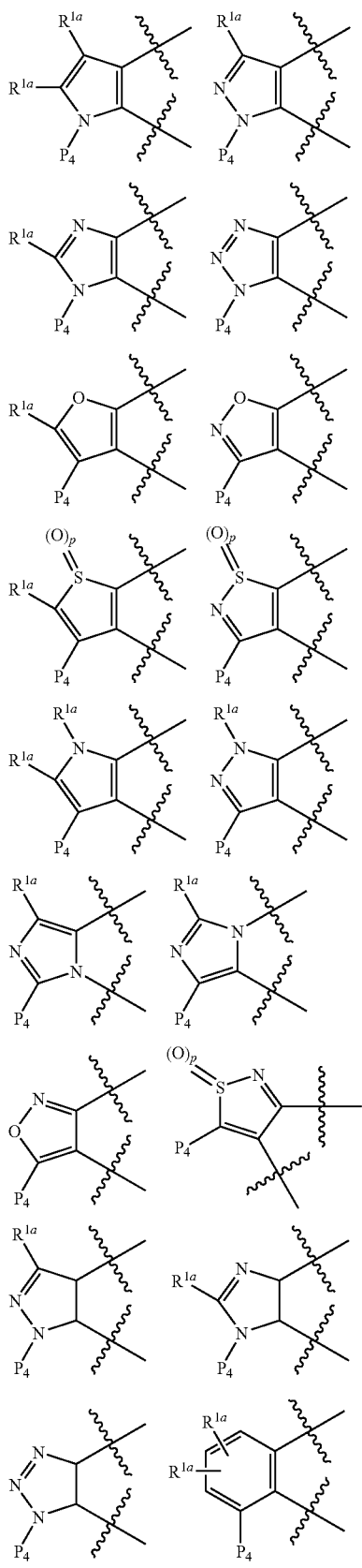

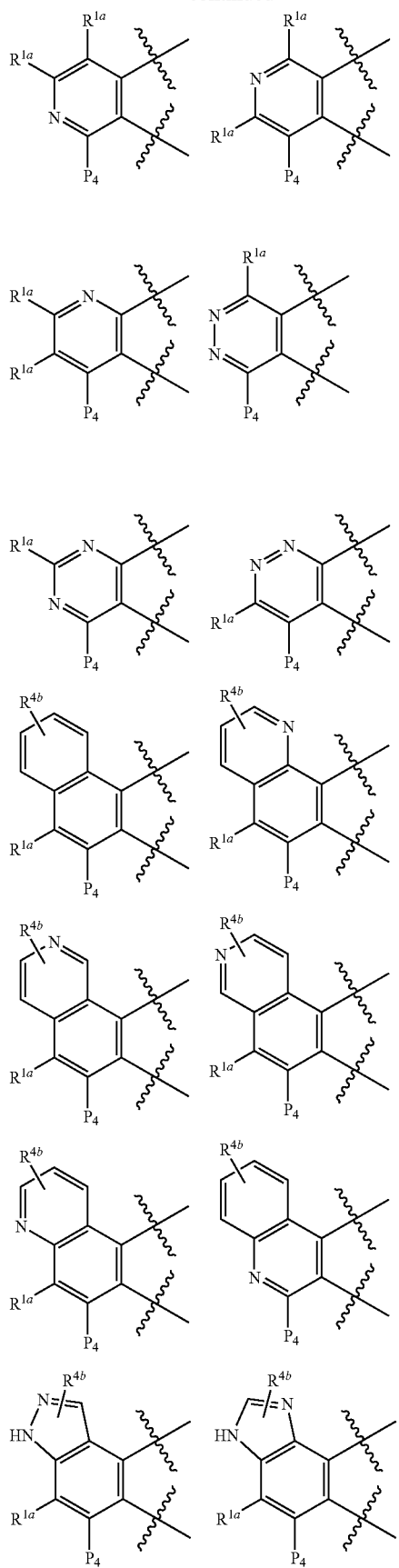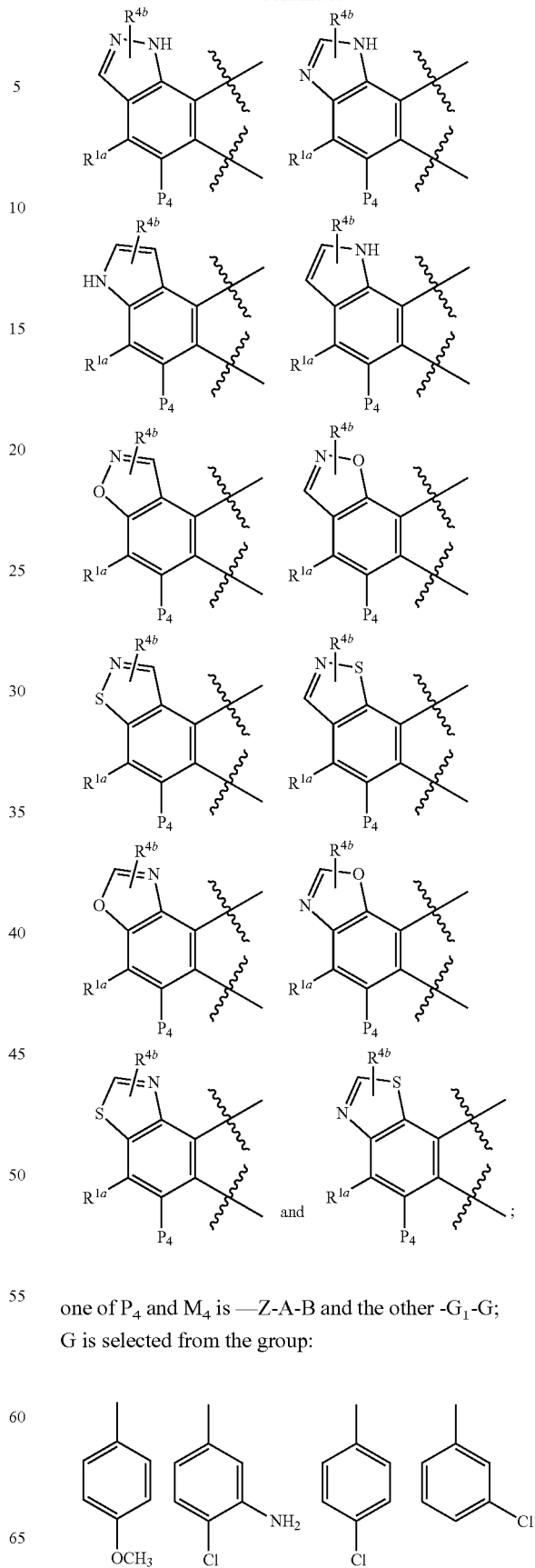
one of $P_4$ and $M_4$ is —Z-A-B and the other -$G_1$-G;
G is selected from the group:

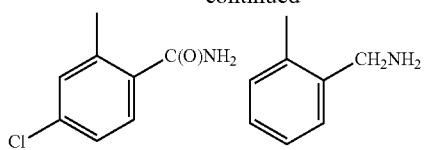
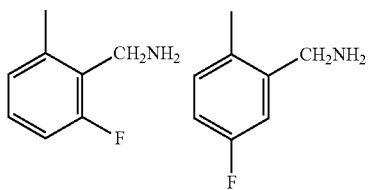
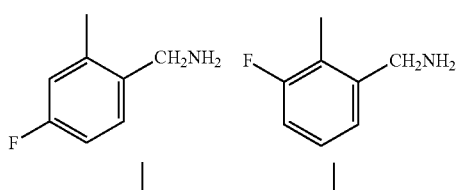
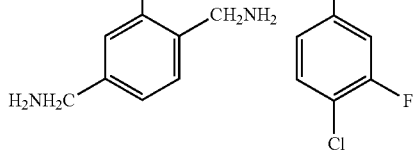
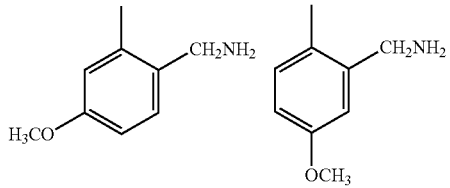
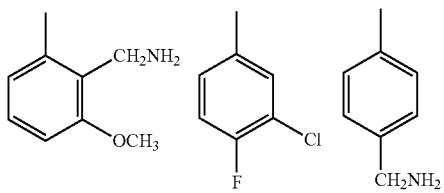
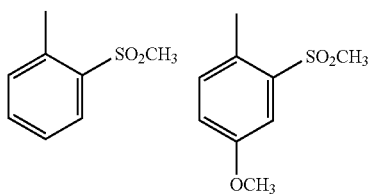
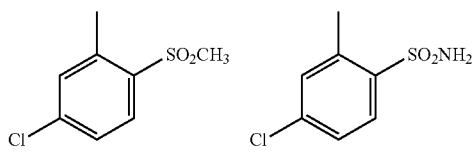
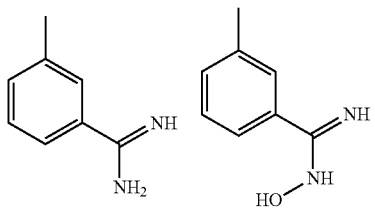
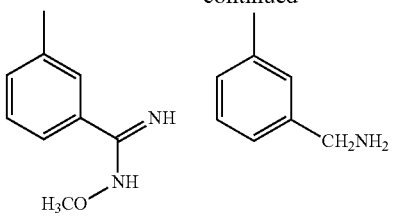
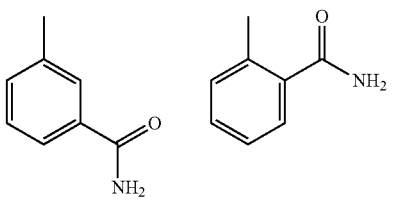
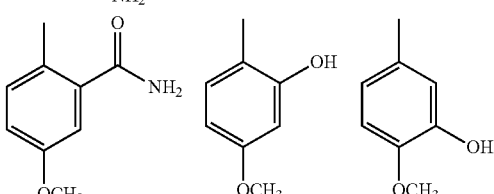
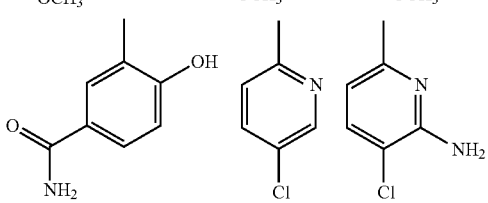
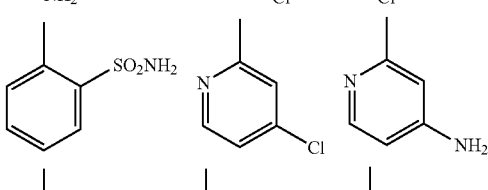
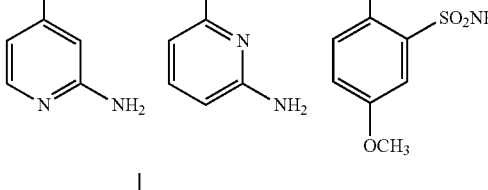
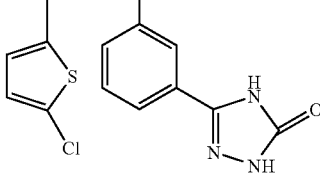
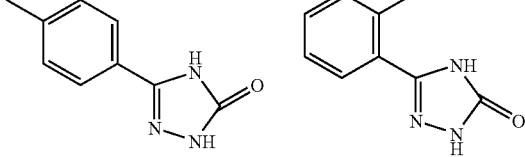
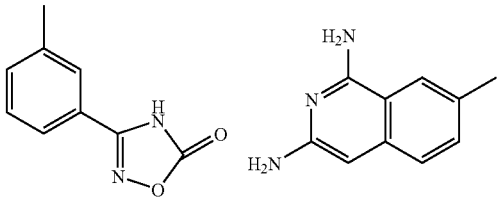

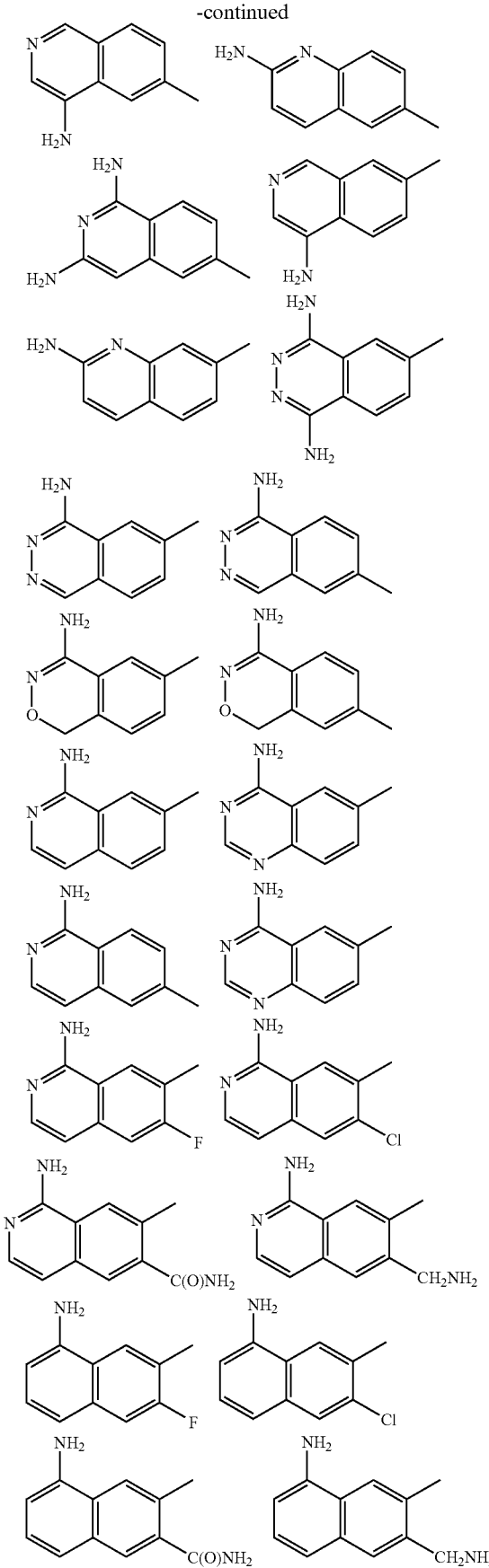
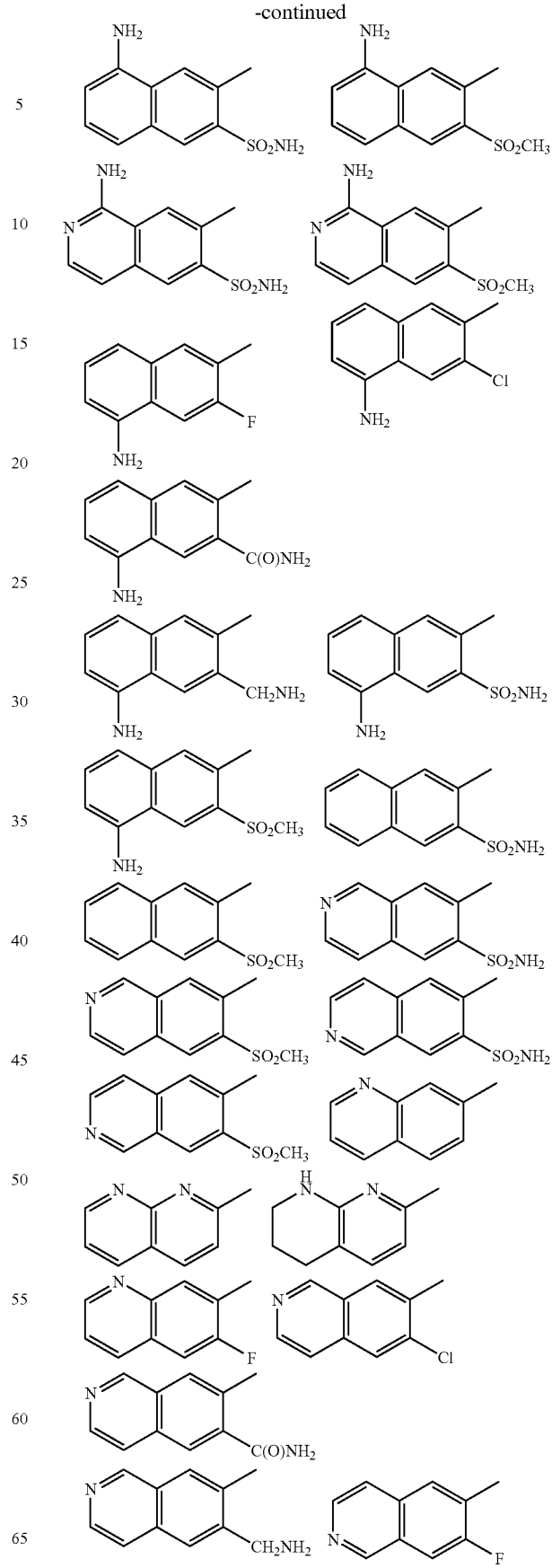

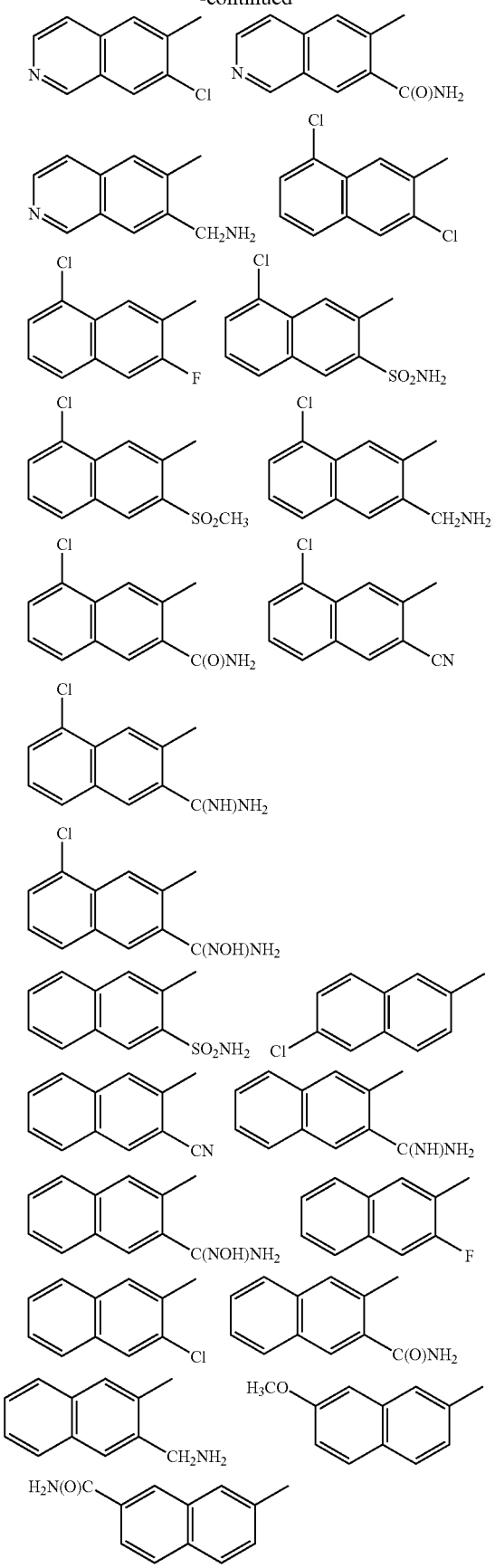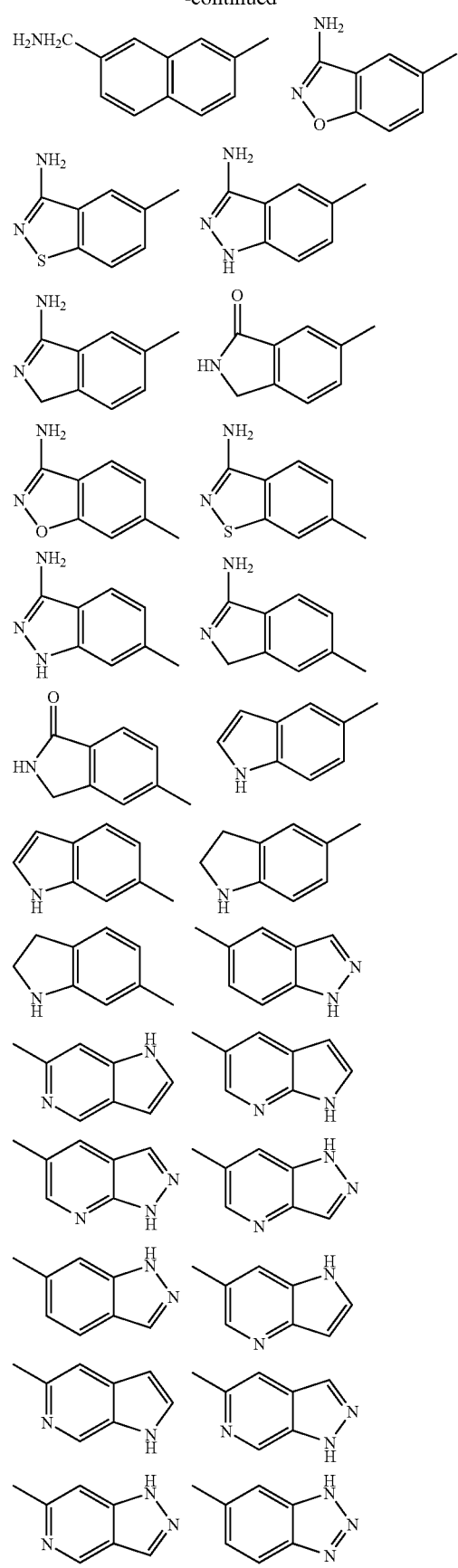

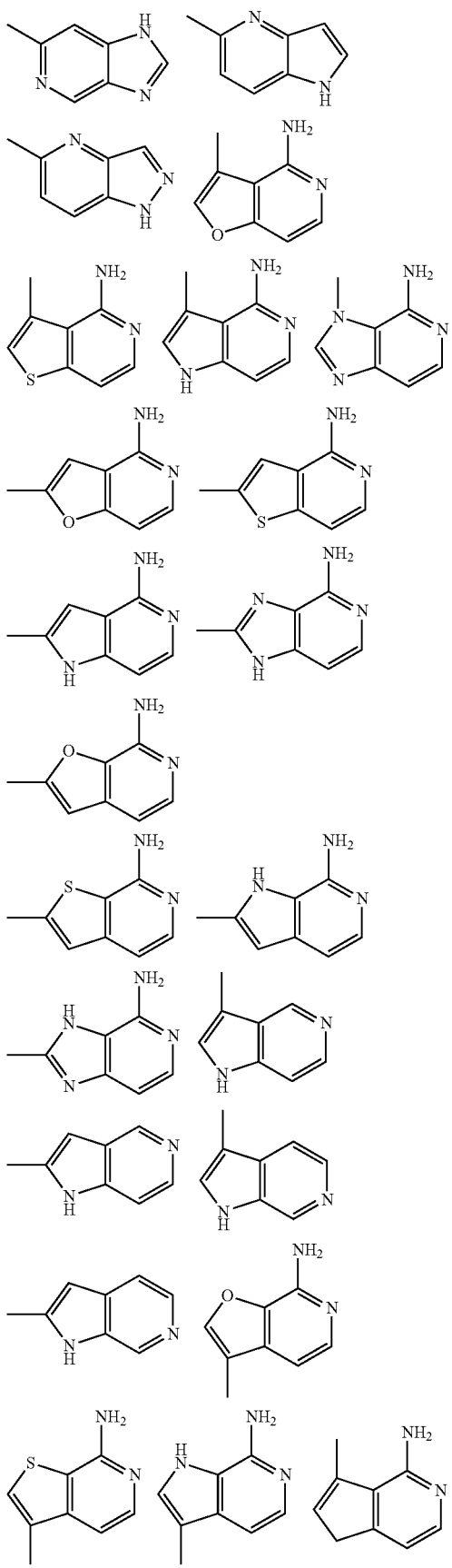

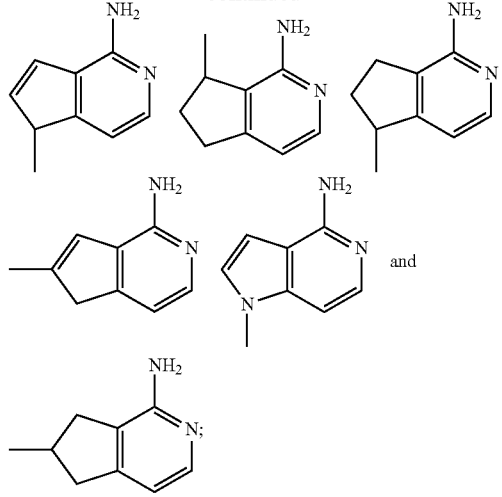

G₁ is absent or is selected from $(CR^3R^{3a})_{1-3}$, $(CR^3R^{3a})_nC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_u$ $NR^{3b}S(O)_2(CR^3R^{3a})_w$, and $(CR^3R^{3a})_uS(O)_2NR^{3b}(CR^3R^{3a})_w$, wherein u+w total 0, 1, or 2, provided that G₁ does not form a N—S, NCH₂N, NCH₂O, or NCH₂S bond with either group to which it is attached;

A is selected from one of the following carbocyclic and heterocyclic groups which are substituted with 0-2 R⁴: phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

B is

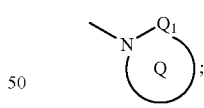

provided that Z and B are attached to different atoms on A; provided that B is other than triazolone, quinolone, or isoquinolone, wherein the triazolone, quinolone, and isoquinolone groups are substituted or unsubstituted;

Q₁ is selected from C=O and SO₂;

ring Q is a 5-7 membered ring consisting of, in addition to the N-Q₁ group shown, carbon atoms and 0-2 heteroatoms selected from NR⁴ᶜ, O, S, S(O), and S(O)₂, wherein: 0-2 double bonds are present within the ring and the ring is substituted with 0-2 R⁴ᵃ;

alternatively, ring Q is a 5-7 membered ring to which another ring is fused, wherein: the 5-7 membered ring consists of, in addition to the shown amide group, carbon atoms and 0-2 heteroatoms selected from NR⁴ᶜ, O, S, S(O), and S(O)₂, and 0-1 double bonds are present within the ring;

the fusion ring is phenyl or a 5-6 membered heteroaromatic consisting of carbon atoms and 1-2 heteroatoms selected from $NR^{4c}$, O, and S;

ring Q, which includes the 5-7 membered ring and the fusion ring, is substituted with 0-3 $R^{4a}$;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5-6 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0-2 $R^{4b}$, and 5-6 membered aromatic heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0-2 $R^{4b}$, a benzyl substituted with 0-2 $R^{4b}$, and a 5-6 membered aromatic heterocycle consisting of: carbon atoms and 1-4 heteroatoms selected from the group consisting of N, O, and $S(O)_p$, and substituted with 0-2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl, phenyl substituted with 0-2 $R^{4b}$, and 5-6 membered aromatic heterocycle consisting of: carbon atoms and 1-4 heteroatoms selected from the group consisting of N, O, and $S(O)_p$, and substituted with 0-2 $R^{4b}$;

alternatively, $R^2$ and $R^{2a}$, together with the atom to which they are attached, combine to form a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0-2 $R^{4b}$, and 5-6 membered aromatic heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0-2 $R^{4b}$, and 5-6 membered aromatic heterocycle containing from 1-4 heteroatoms selected from the group consisting of N, O, and $S(O)_p$, and substituted with 0-2 $R^{4b}$;

$R^4$, at each occurrence, is selected from H, $CH_2OR^2$, $(CH_2)_2OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$, at each occurrence, is selected from H, =O, $CH_2OR^2$, $OR^2$, F, Br, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $CH_2NR^2R^{2a}$, $NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, and —$CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2OR^2$, $CH_2F$, $CH_2Br$, $CH_2Cl$, $CH_2CN$, $CH_2NO_2$, $CH_2NR^2R^{2a}$, $C(O)R^{2c}$, $CH_2C(O)R^{2c}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $S(O)_pR^{5a}$, $CH_2S(O)_pR^{5a}$, $CF_3$, phenyl substituted with 0-1 $R^5$, and benzyl substituted with 0-1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

[4] In another preferred embodiment, the present invention provides a novel compound, wherein:

ring M is substituted with 0-2 $R^{1a}$ and is selected from the group:

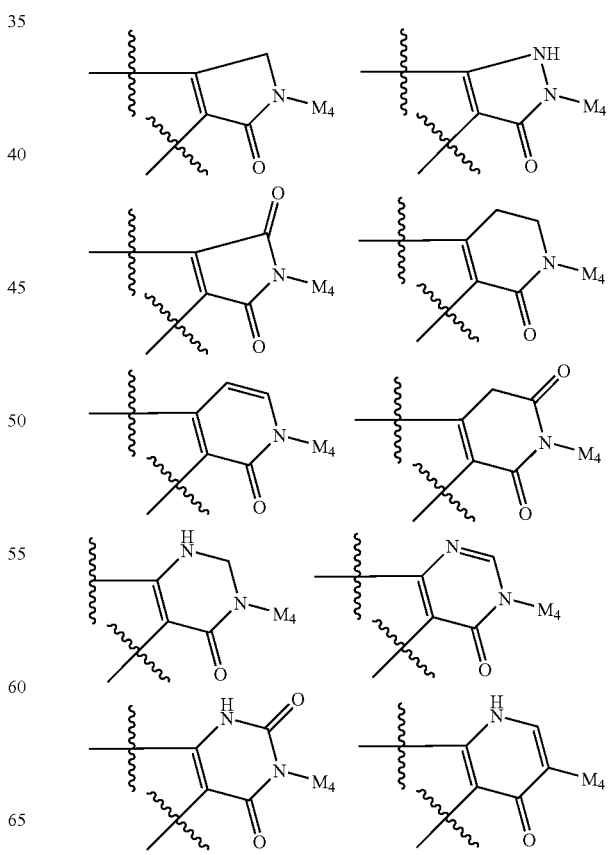

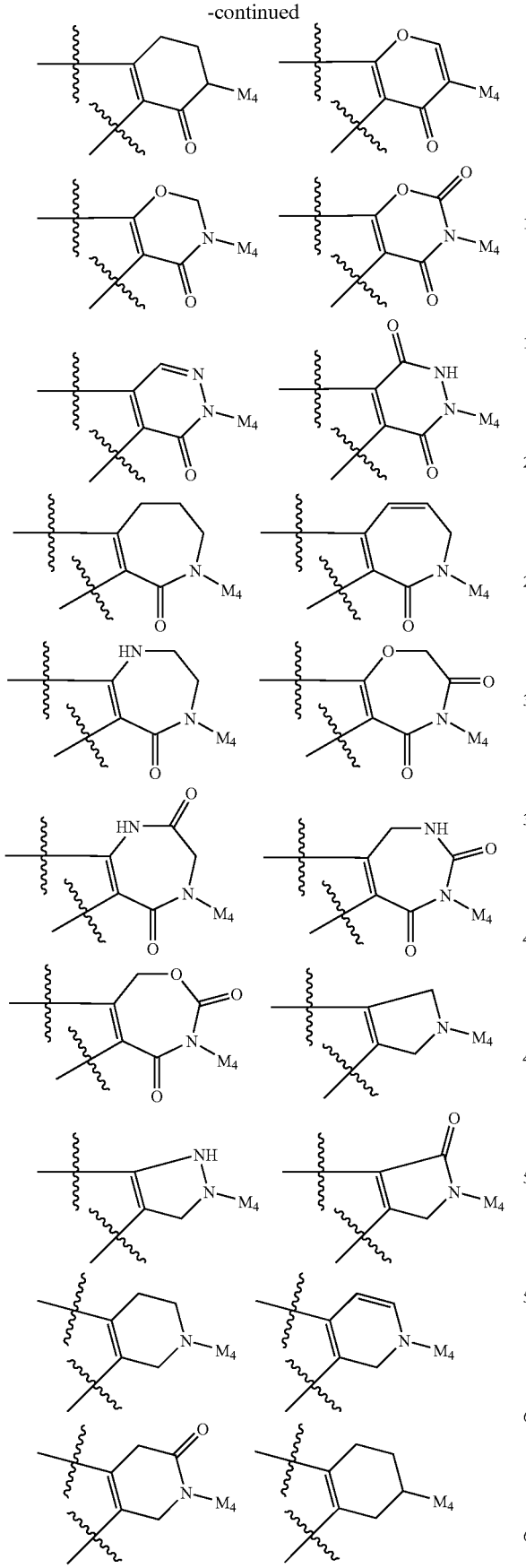
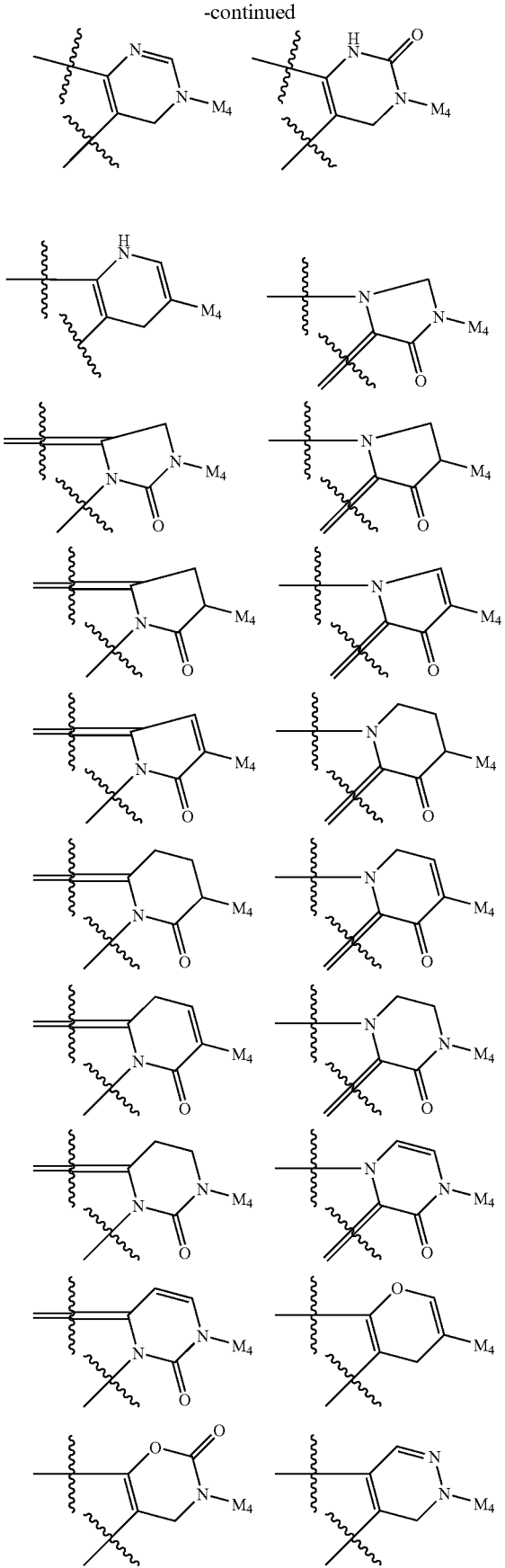

-continued
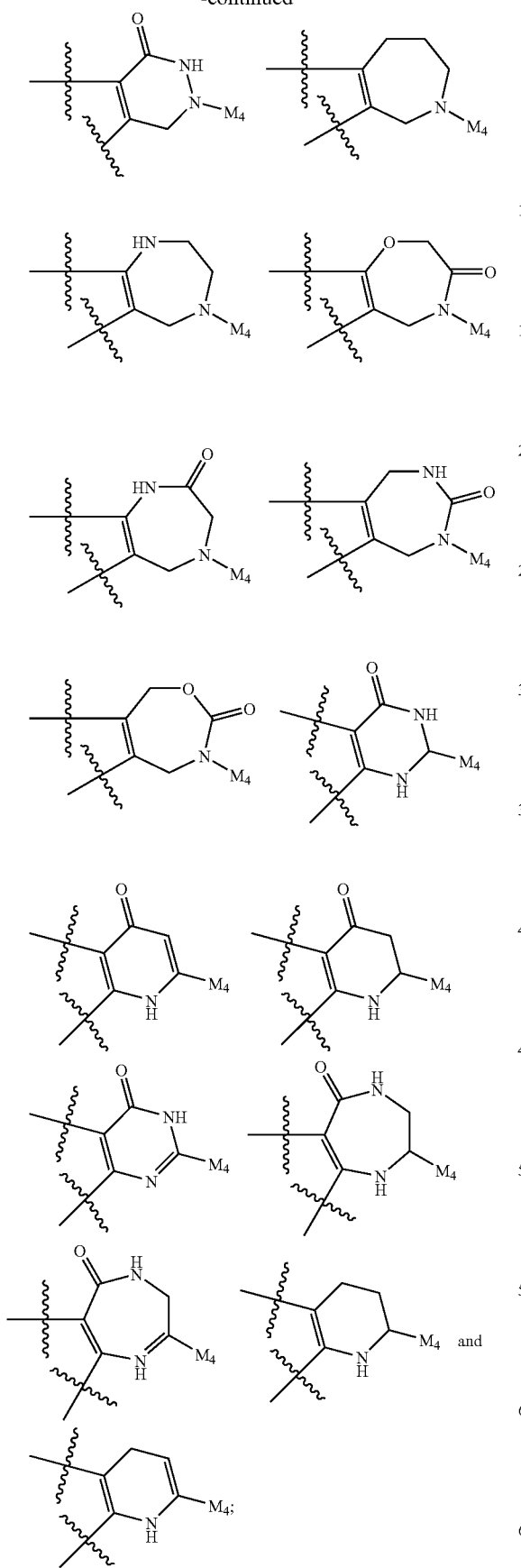
ring P, including $P_1$, $P_2$, $P_3$, and $P_4$ is selected from group:
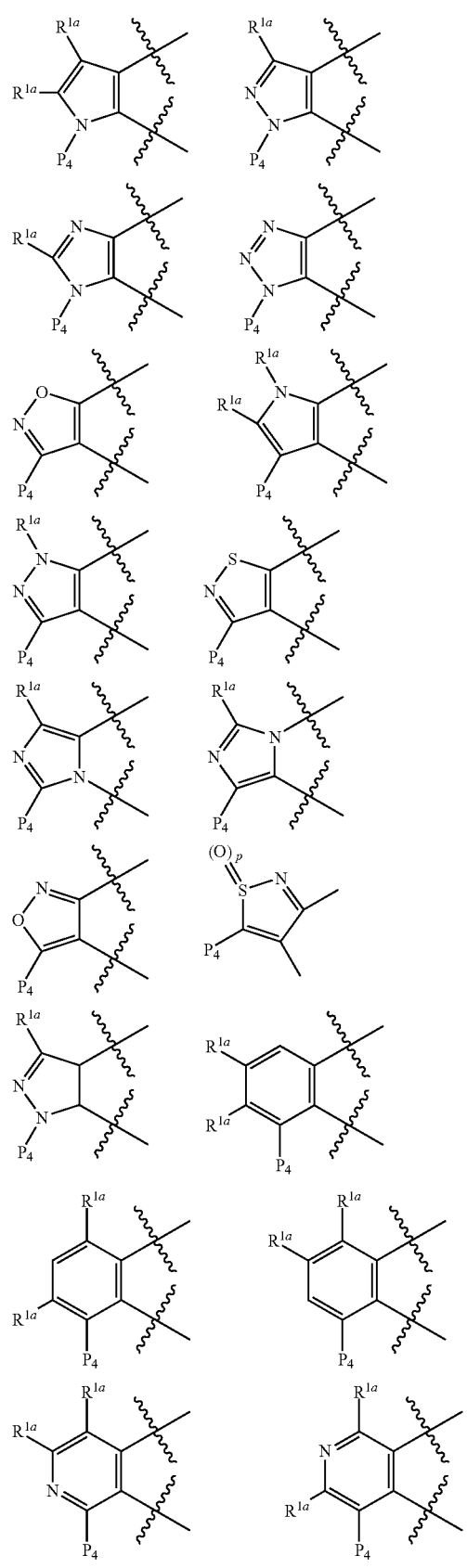

-continued
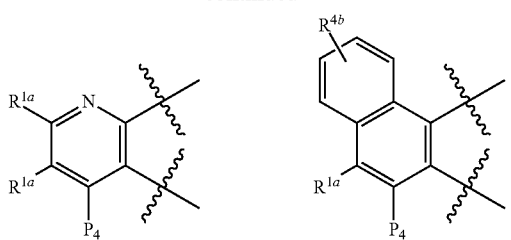
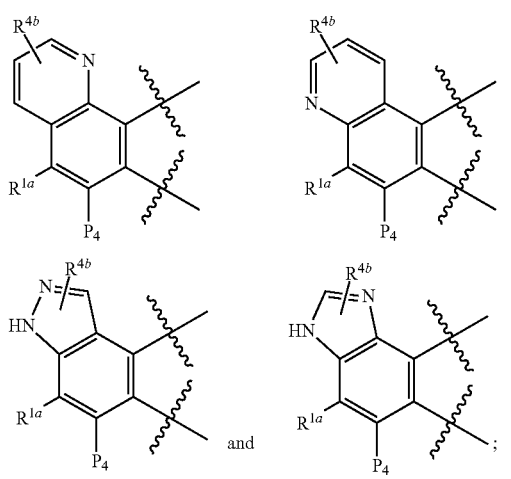
one of P₄ and M₄ is -A-B and the other -G;
G is selected from the group:
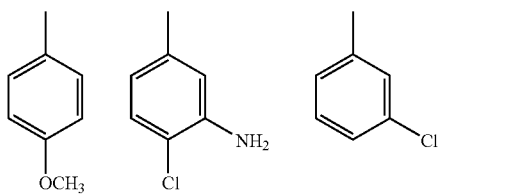
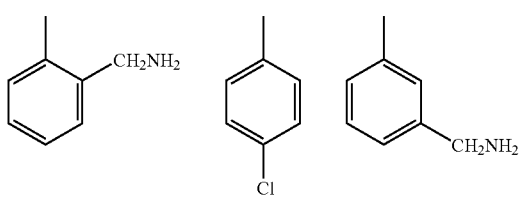
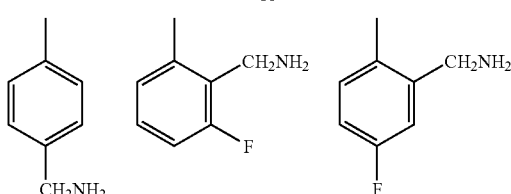
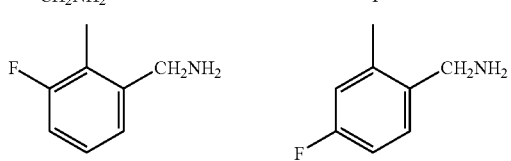
-continued
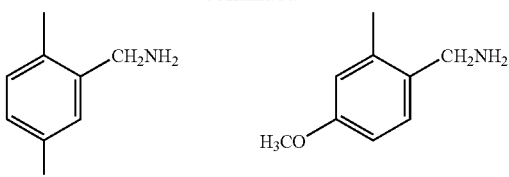
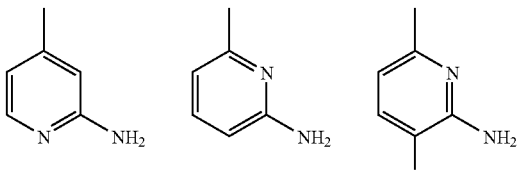
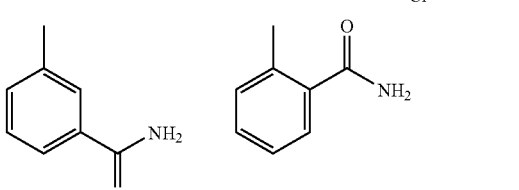
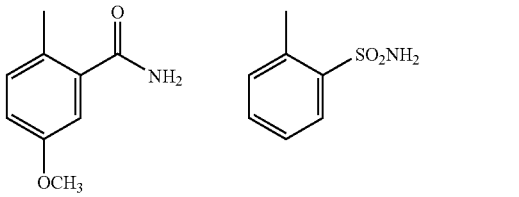
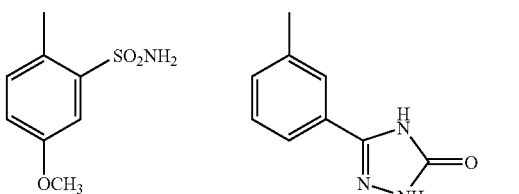
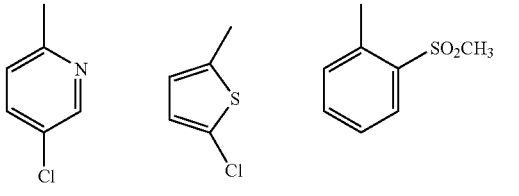
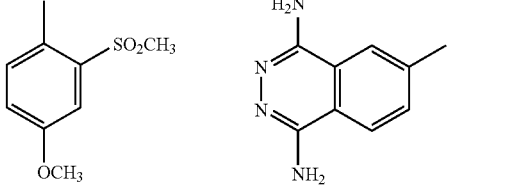
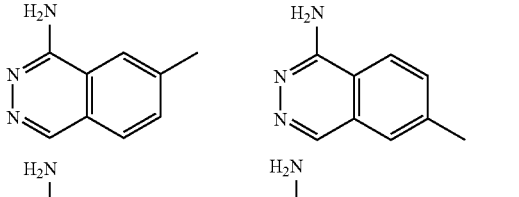
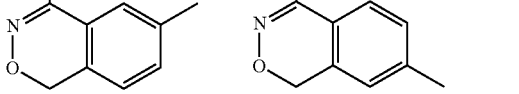

-continued
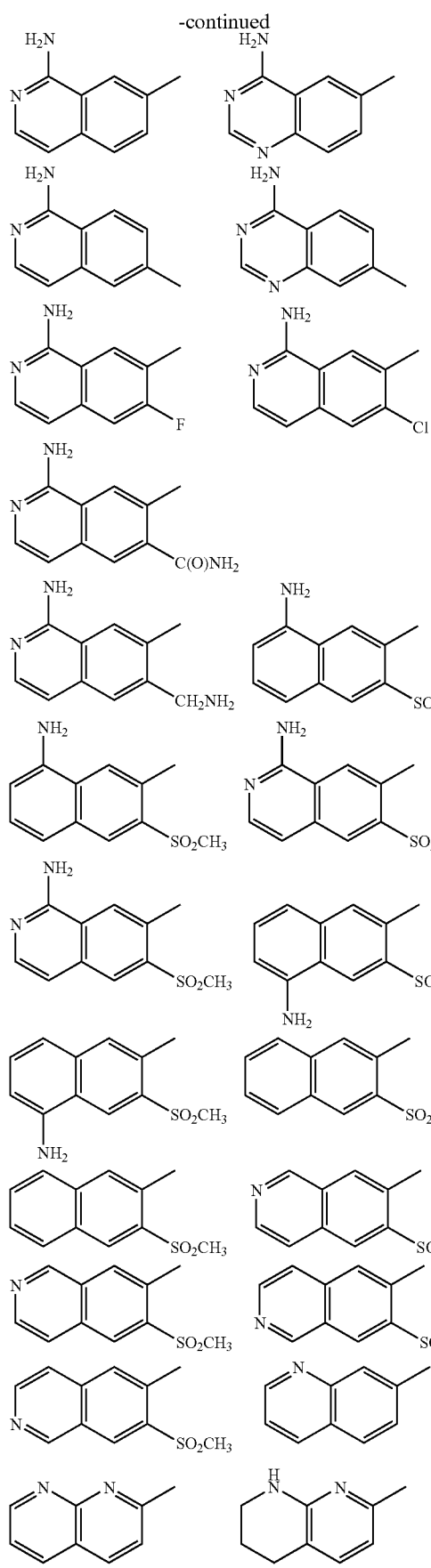
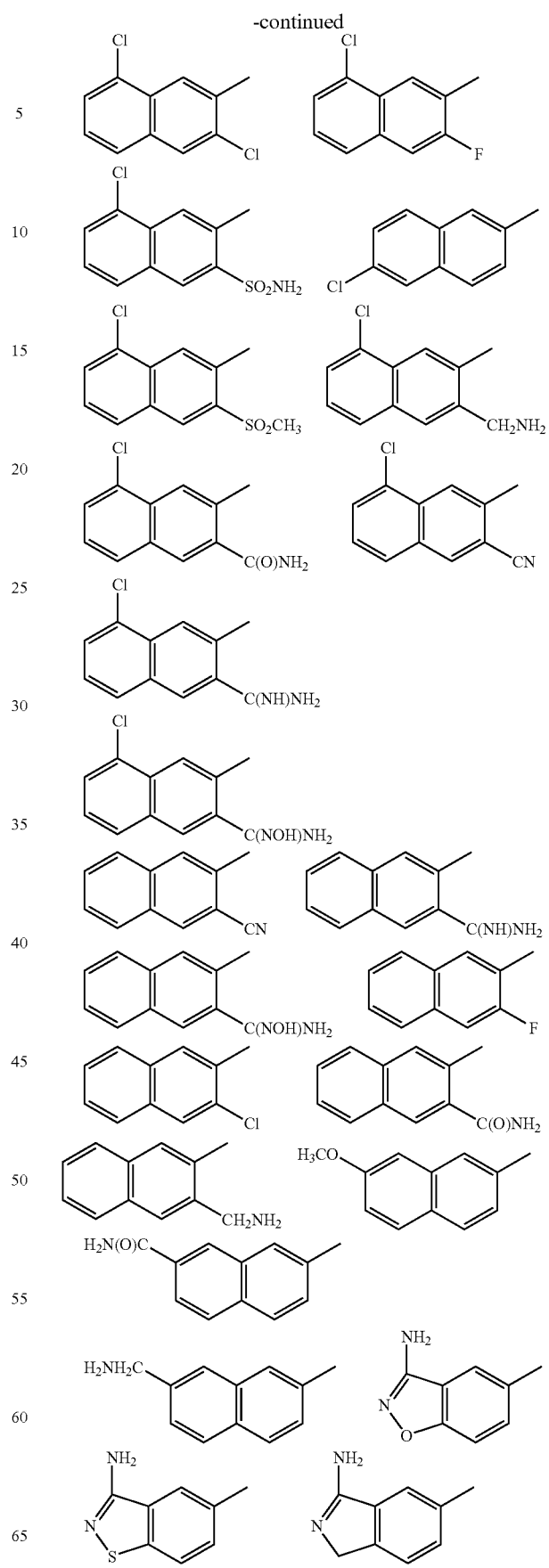

-continued

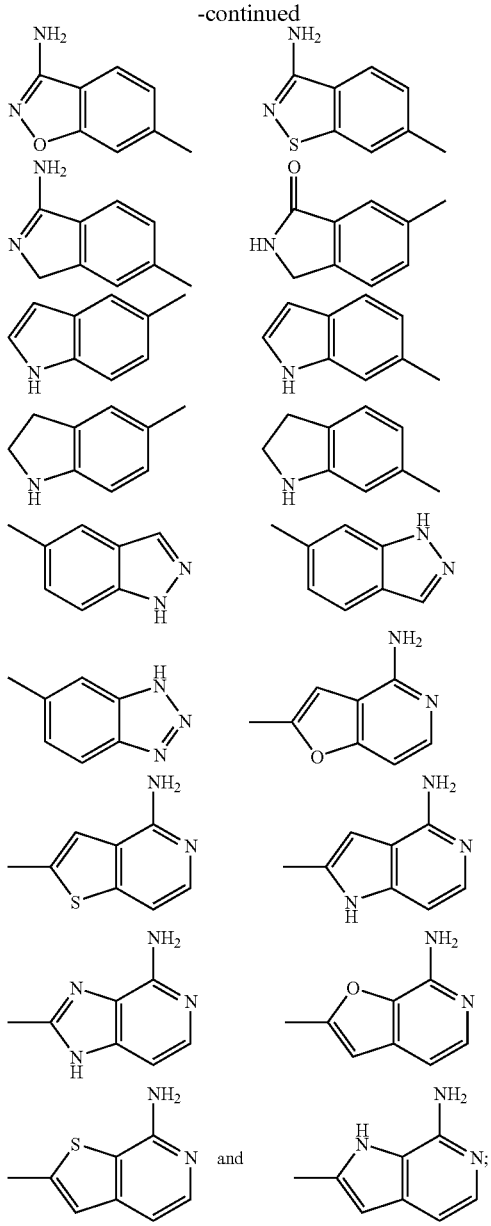

$G_1$ is absent or is selected from $CH_2$, $CH_2CH_2$, $CH_2O$, $OCH_2$, NH, $CH_2NH$, $NHCH_2$, $CH_2C(O)$, $C(O)CH_2$, $C(O)NH$, $NHC(O)$, $CH_2S(O)_2$, $S(O)_2(CH_2)$, $SO_2NH$, and $NHSO_2$, provided that $G_1$ does not form a N—S, $NCH_2N$, $NCH_2O$, or $NCH_2S$ bond with either group to which it is attached;

A is selected from phenyl, pyridyl, and pyrimidyl, and is substituted with 0-2 $R^4$;

B is

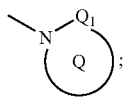

provided that Z and B are attached to different atoms on A;
provided that B is other than triazolone, quinolone, or isoquinolone, wherein the triazolone, quinolone, and isoquinolone groups are substituted or unsubstituted;

$Q_1$ is selected from C=O and $SO_2$;

ring Q is a 6-7 membered ring consisting of, in addition to the N-Q$_1$ group shown, carbon atoms and 0-1 heteroatoms selected from $NR^{4c}$, O, S, S(O), and $S(O)_2$, wherein: 0-2 double bonds are present within the ring and the ring is substituted with 0-2 $R^{4a}$;

alternatively, ring Q is a 5-7 membered ring to which another ring is fused, wherein: the 5-7 membered ring consists of, in addition to the shown amide group, carbon atoms and 0-1 heteroatoms selected from $NR^{4c}$, O, S, S(O), and $S(O)_2$, and 0-1 double bonds are present within the ring;

the fusion ring is phenyl;

ring Q, which includes the 5-7 membered ring and the fusion ring, is substituted with 0-2$R^{4a}$;

$R^{1a}$ is selected from H, $R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, and 5-6 membered aromatic heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0-1 $R^{4b}$, benzyl substituted with 0-1 $R^{4b}$, and 5-6 membered aromatic heterocycle consisting of: carbon atoms and 1-4 heteroatoms selected from the group consisting of N, O, and $S(O)_p$, and substituted with 0-1 $R^{4b}$;

$R^{2a}$, at each occurrence, is selected from H, $CH_3$, $CH_2CH_3$, $CH_2CH_2CH_3$, $CH(CH_3)_2$, benzyl, phenyl substituted with 0-1 $R^{4b}$, and 5-6 membered aromatic heterocycle consisting of: carbon atoms and 1-4 heteroatoms selected from the group consisting of N, O, and $S(O)_p$, and substituted with 0-1 $R^{4b}$;

alternatively, $R^2$ and $R^{2a}$, together with the atom to which they are attached, combine to form a 5 or 6 membered saturated, partially saturated or unsaturated ring substituted with 0-1 $R^{4b}$ and consisting of: 0-1 additional heteroatoms selected from the group consisting of N, O, and $S(O)_p$;

$R^{2b}$, at each occurrence, is selected from $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0-1 $R^{4b}$, and 5-6 membered aromatic heterocycle consisting of: carbon atoms and 1-4 heteroatoms selected from the group consisting of N, O, and $S(O)_p$, and substituted with 0-1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0-1 $R^{4b}$, and 5-6 membered aromatic heterocycle containing from 1-4 heteroatoms selected from the group consisting of N, O, and $S(O)_p$, and substituted with 0-1 $R^{4b}$;

$R^4$, at each occurrence, is selected from OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $CF_3$, and $CF_2CF_3$;

$R^{4a}$, at each occurrence, is selected from H, =O, $CH_2OR^2$, $OR^2$, F, Br, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2NR^2R^{2a}$, $NR^2R^{2a}$, $C(O)R^{2c}$, $NR^2C(O)R^{2b}$, $C(O)NR^2R^{2a}$, $SO_2NR^2R^{2a}$, and $CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from H, $CH_3$, $CH_2CH_3$, phenyl substituted with 0-1 $R^5$, and benzyl substituted with 0-1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and, $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[5] In another preferred embodiment, the present invention provides a novel compound, wherein:

ring M is substituted with 0-1 $R^{1a}$ and is selected from the group:

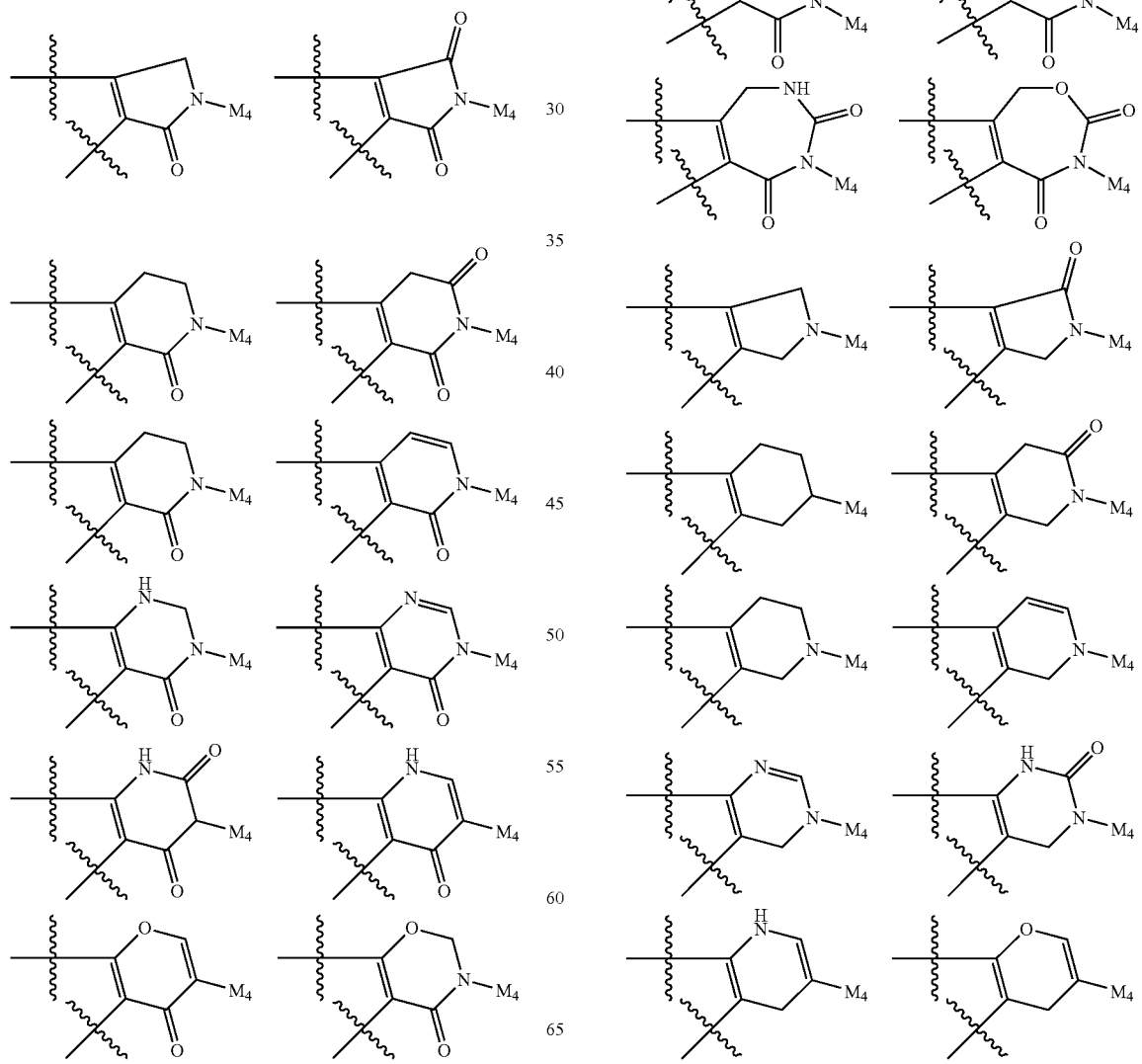

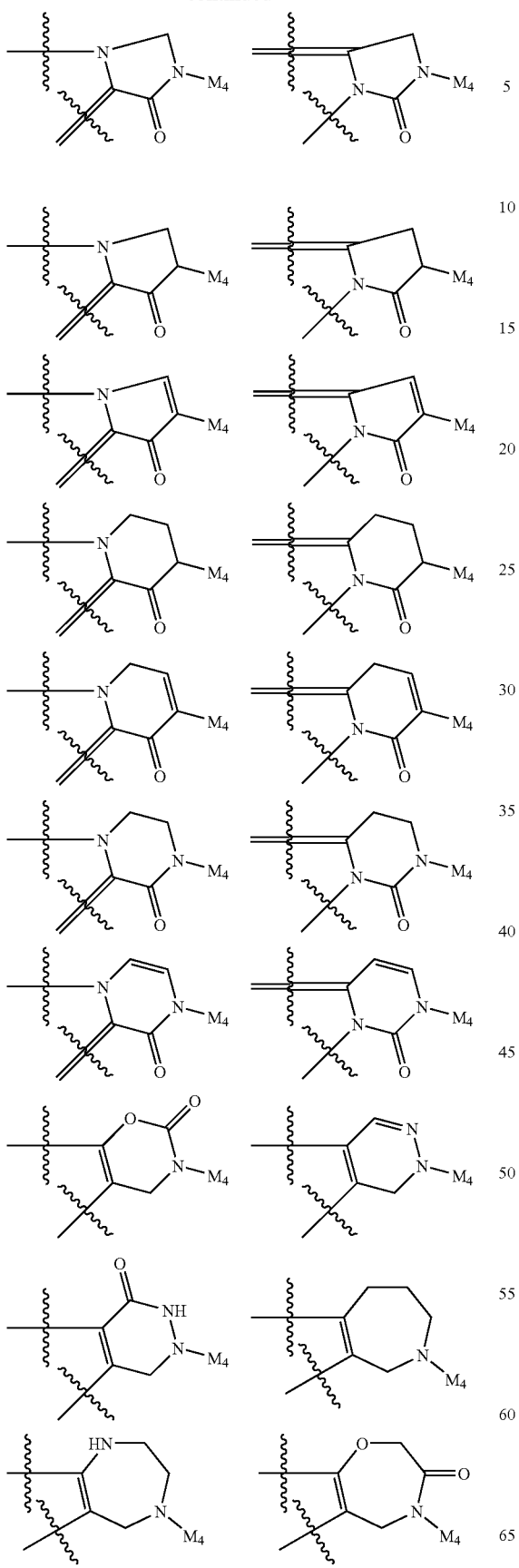
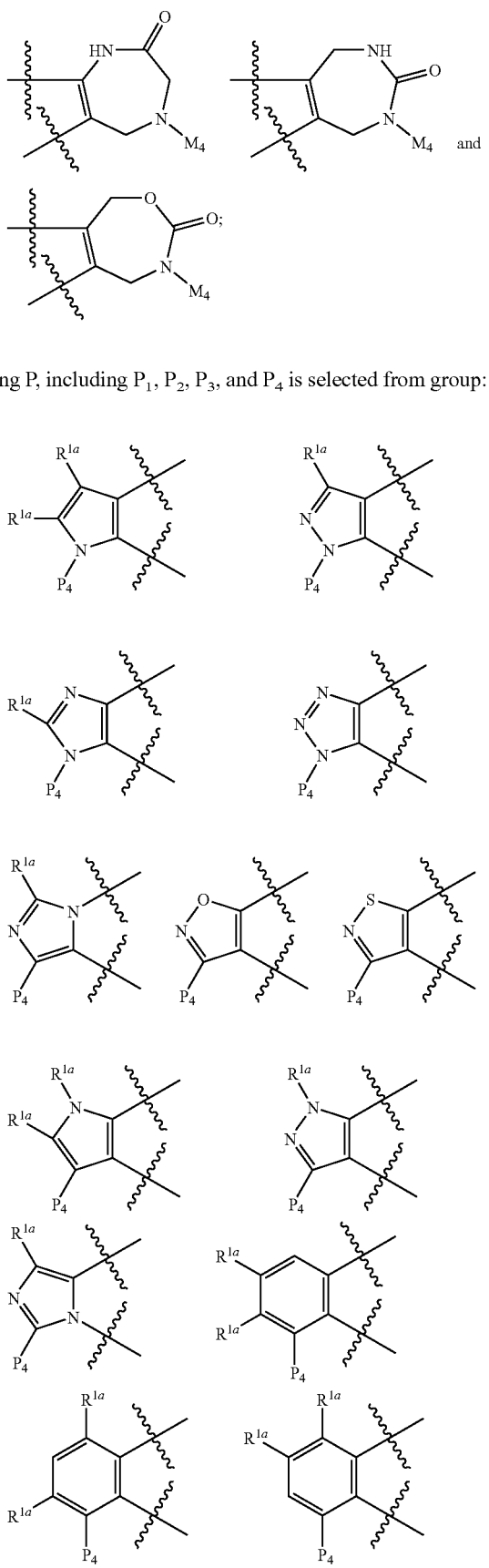
ring P, including $P_1$, $P_2$, $P_3$, and $P_4$ is selected from group:

-continued
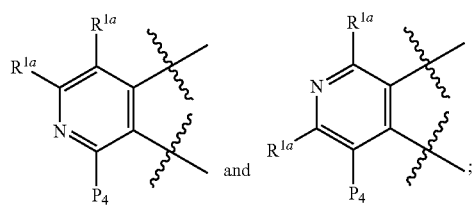
one of $P_4$ and $M_4$ is -A-B and the other -G;
G is selected from:
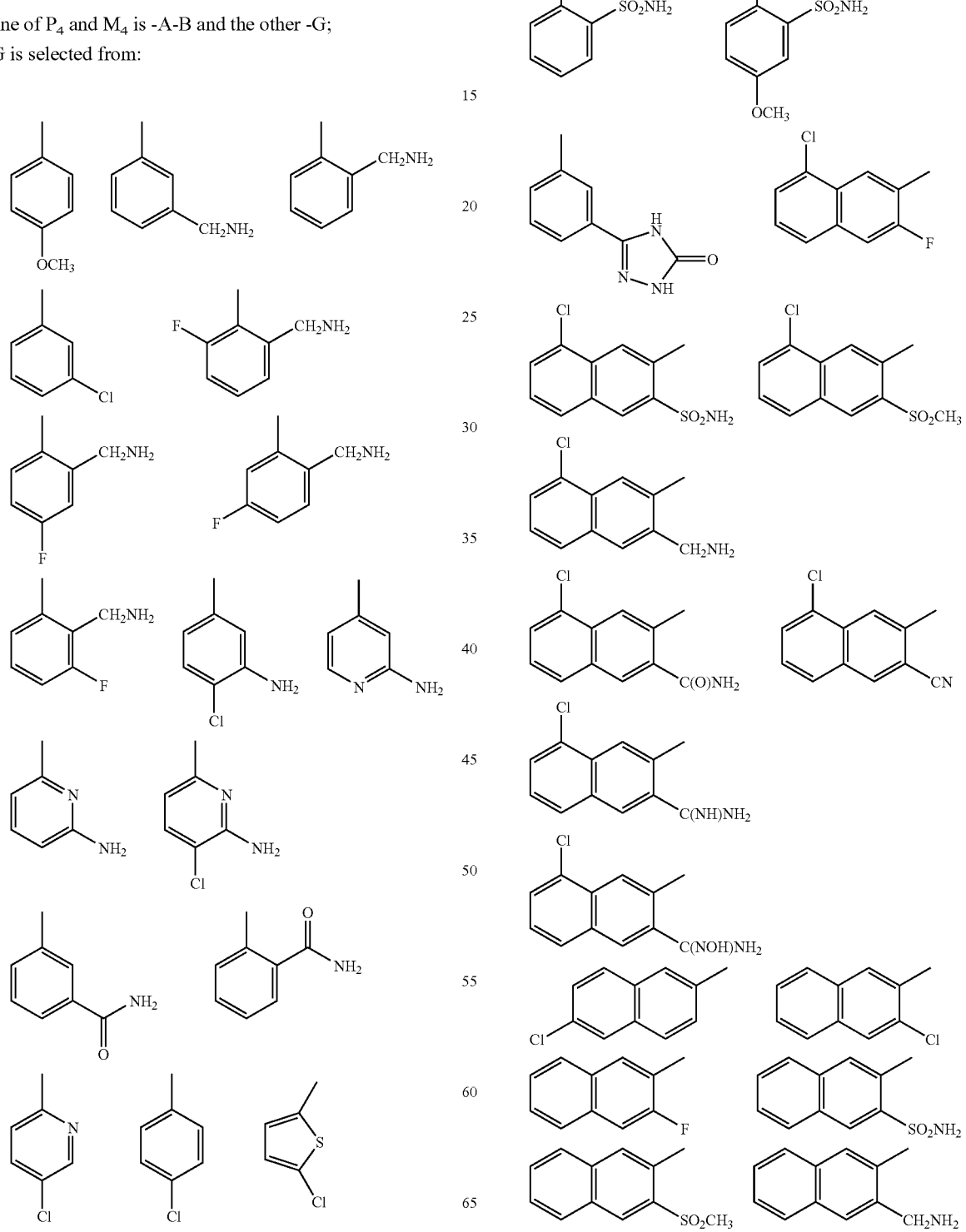

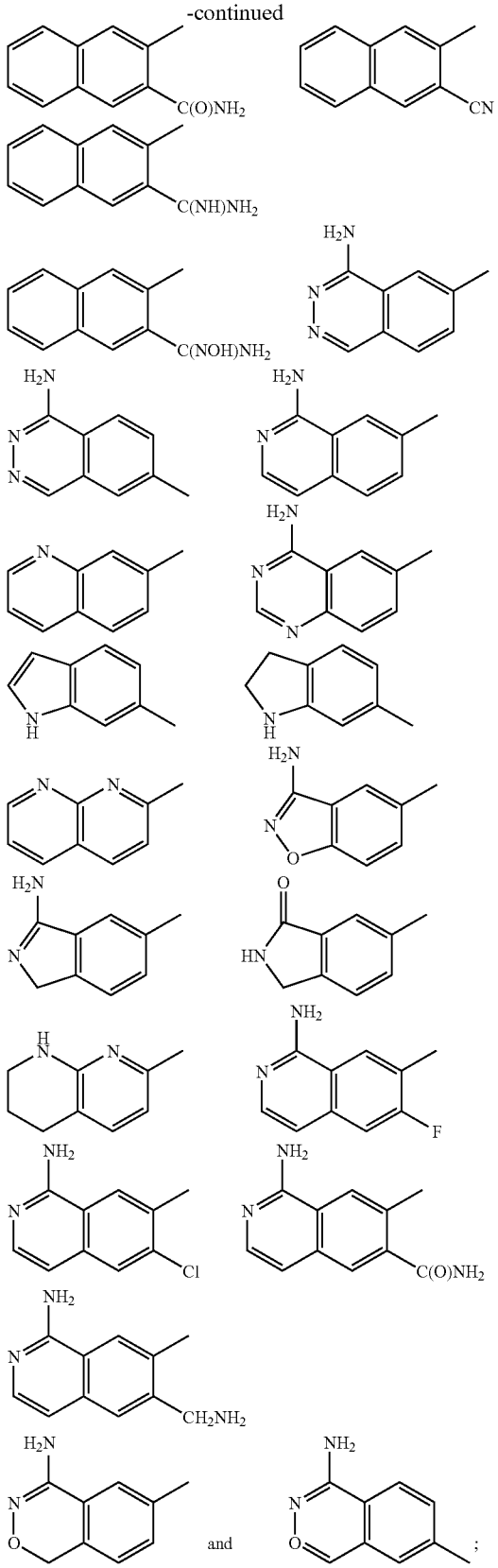
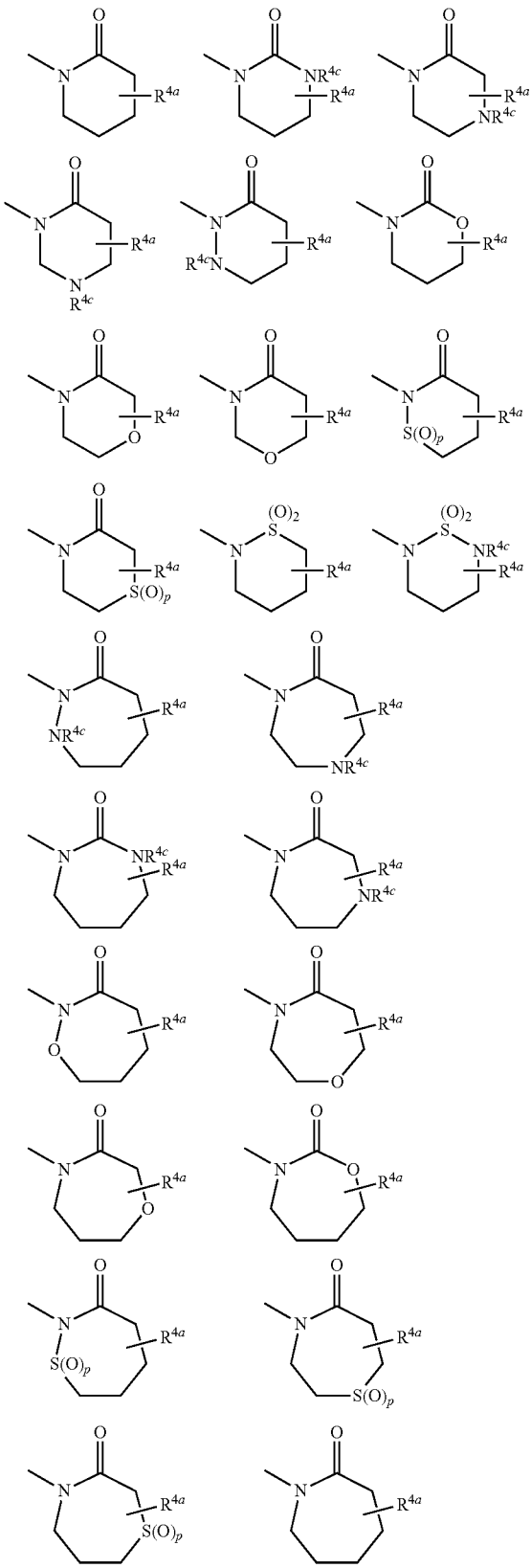
A is selected from the group: phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;
B is attached to a different atom on A than M and is selected from the group:

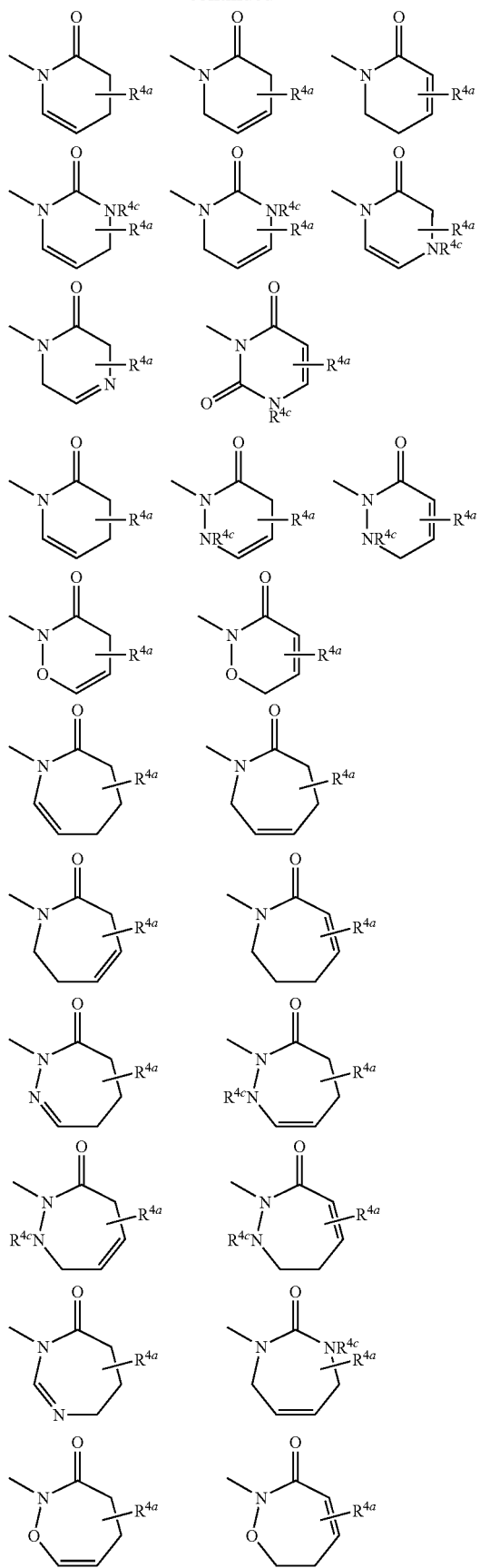

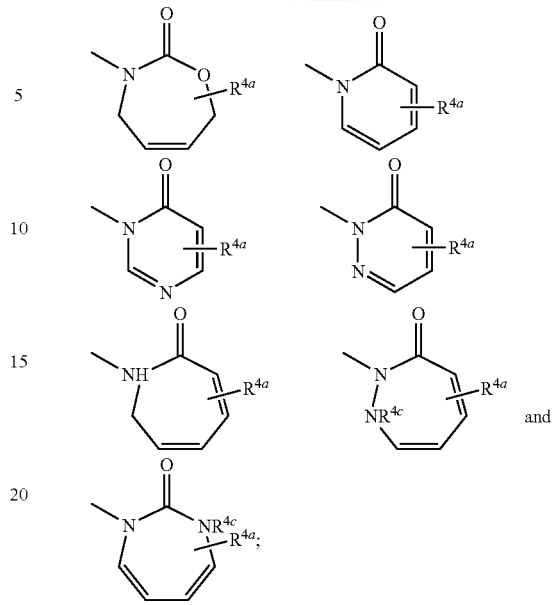

$R^{1a}$ is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl;

$R^2$, at each occurrence, is selected from H, $CH_3$, $CH_2CH_3$, $CH_2CH_2CH_3$, $CH(CH_3)_2$, phenyl substituted with 0-1 $R^{4b}$, benzyl substituted with 0-1 $R^{4b}$, and 5 membered aromatic heterocycle consisting of: carbon atoms and 1-4 heteroatoms selected from the group consisting of N, O, and $S(O)_p$, and substituted with 0-1 $R^{4b}$;

$R^{2a}$, at each occurrence, is selected from H, $CH_3$, and $CH_2CH_3$;

alternatively, $R^2$ and $R^{2a}$, together with the atom to which they are attached, combine to form a 5 or 6 membered saturated, partially saturated or unsaturated ring substituted with 0-1 $R^{4b}$ and consisting of: 0-1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{4a}$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, and $C(CH_3)_3$;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_2$—$CH_3$, $S(O)_2$- phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[6] In another preferred embodiment, the present invention provides a novel compound, wherein the compound is selected from:

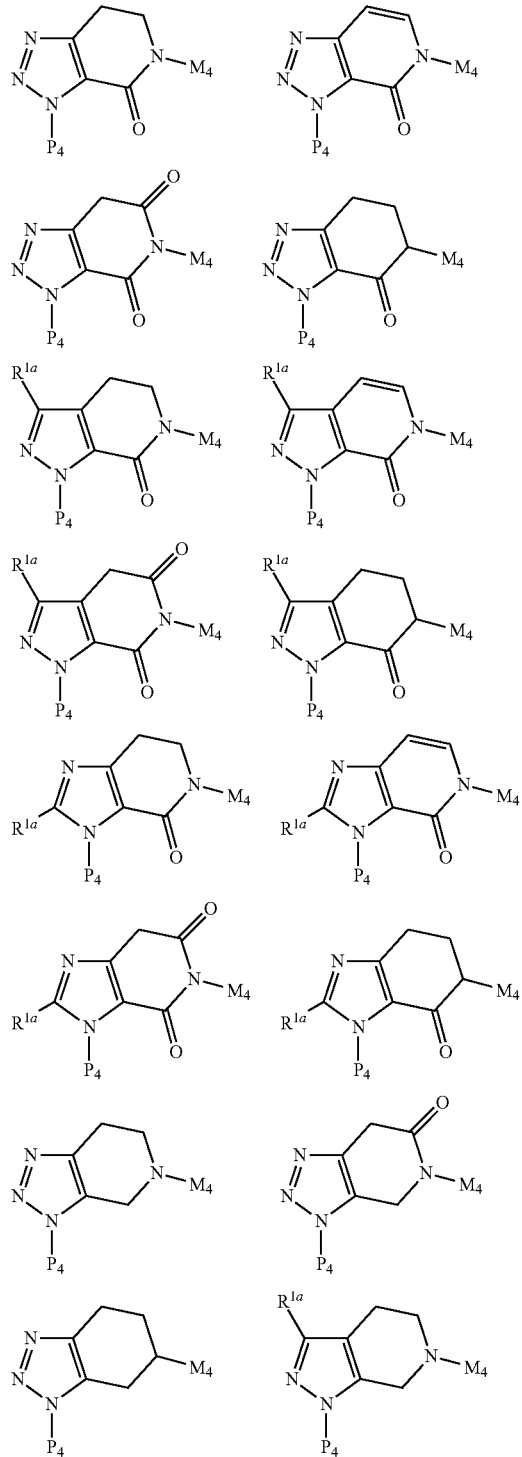

-continued

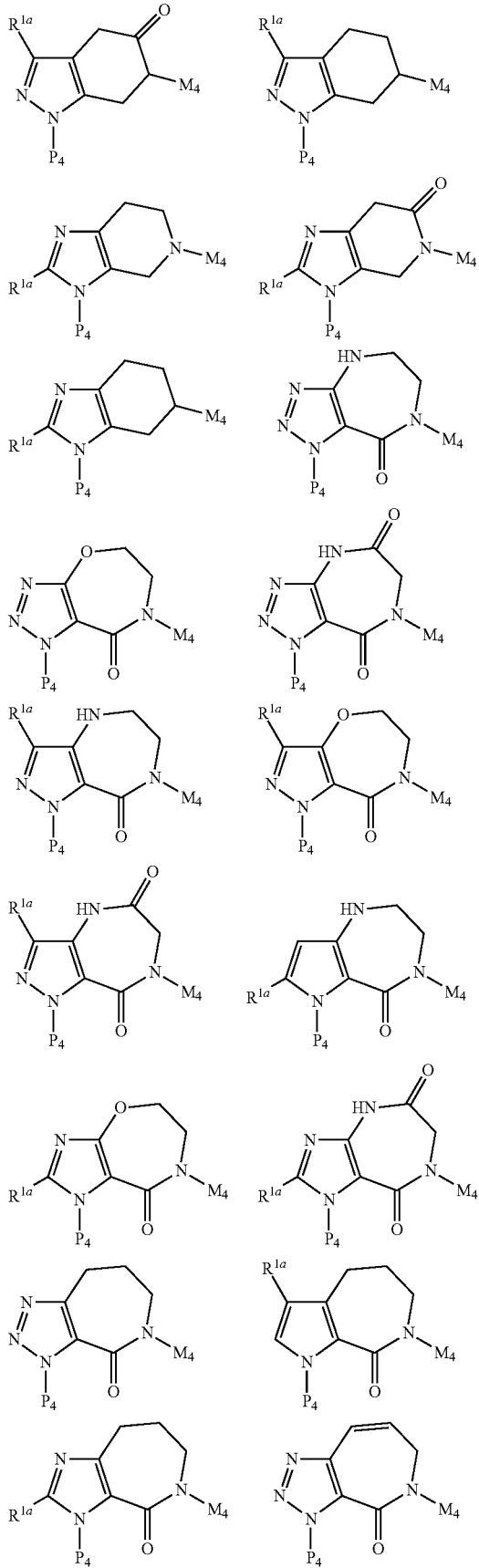

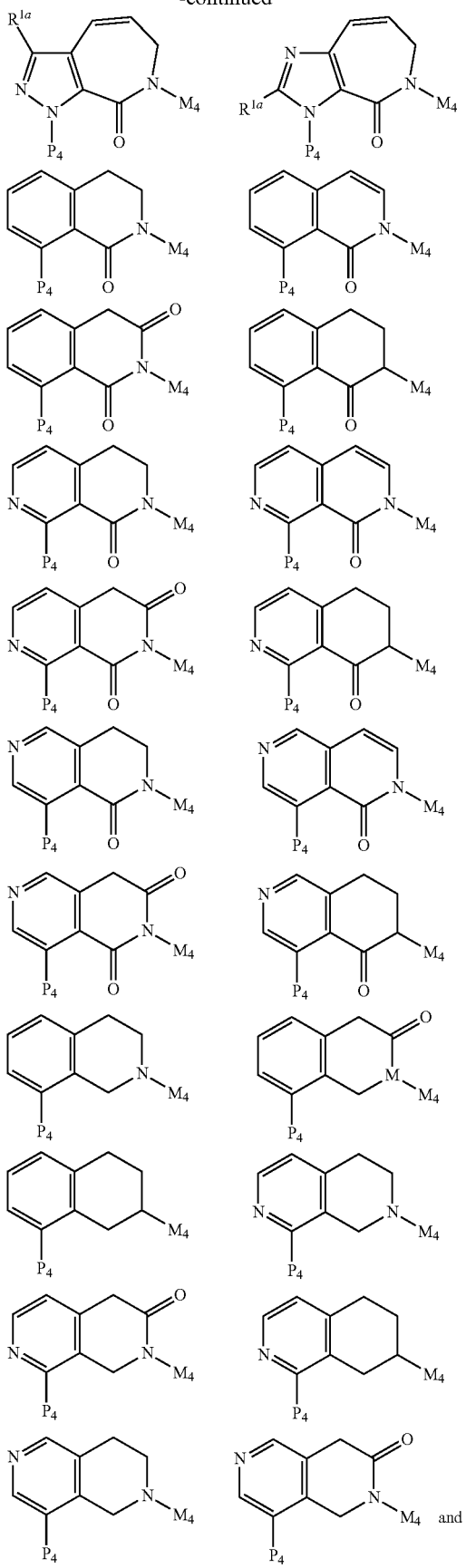
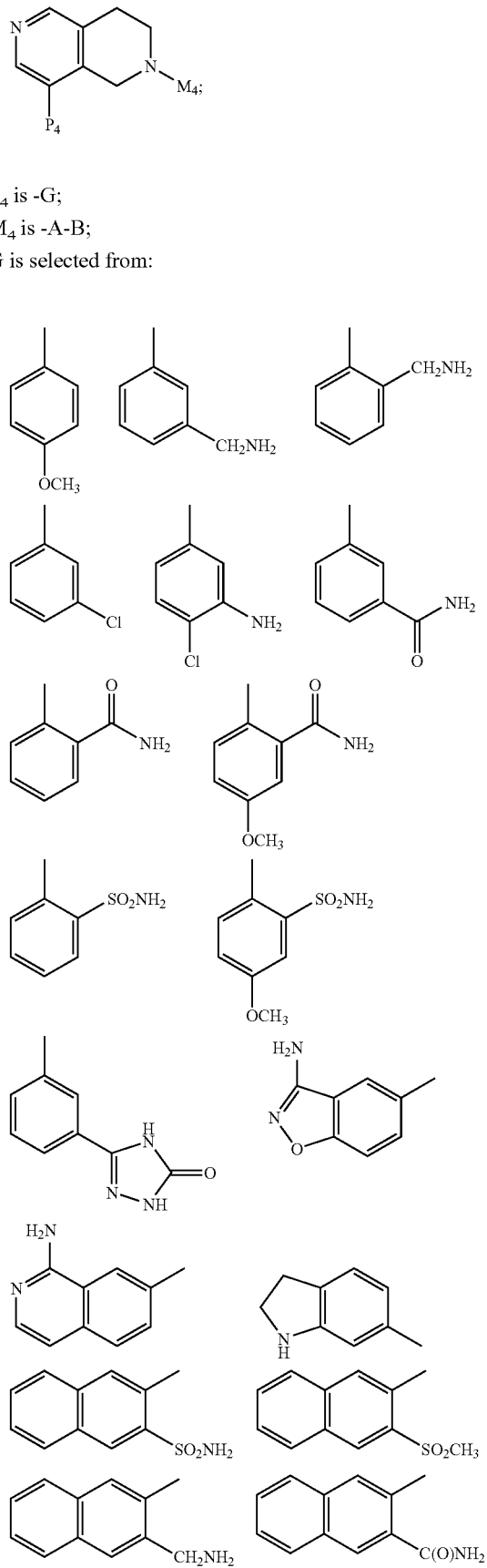
P$_4$ is -G;
M$_4$ is -A-B;
G is selected from:

-continued
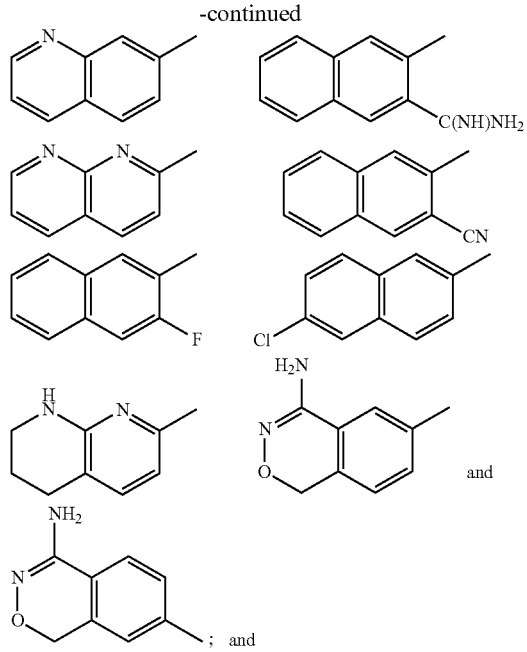
; and
and
A-B is selected from:
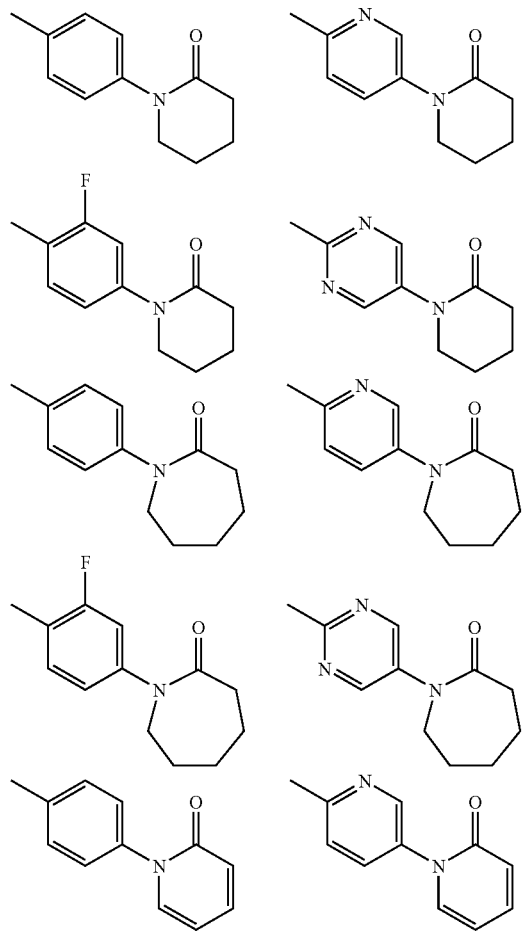
-continued
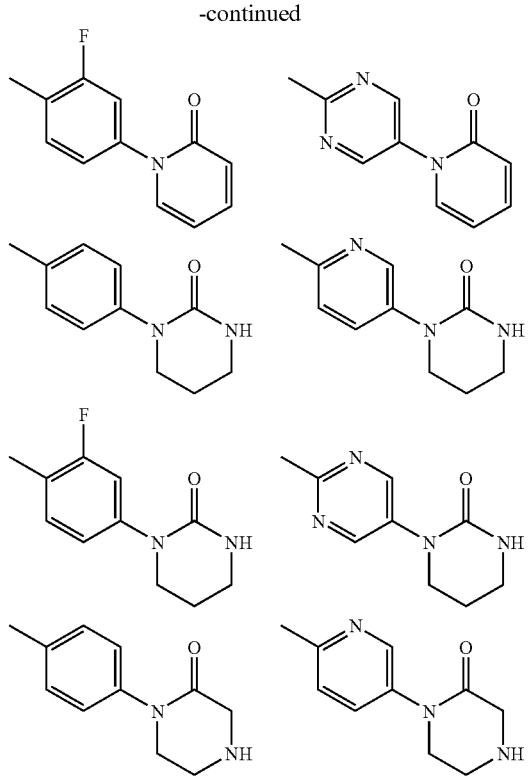
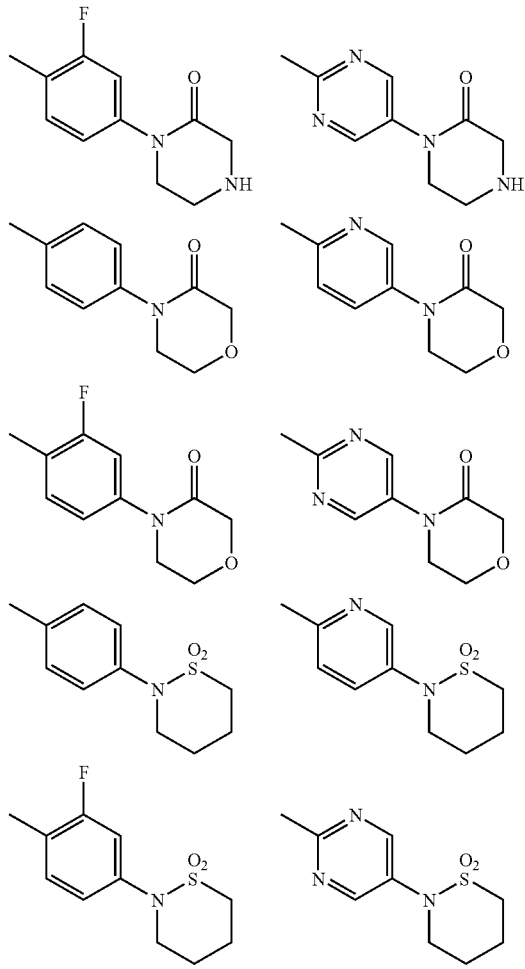

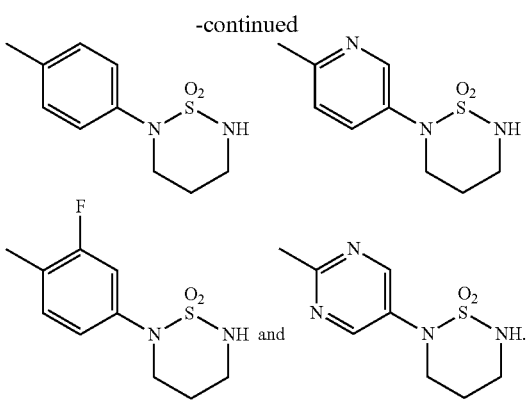

[7] In another preferred embodiment, the present invention provides a novel compound, wherein the compound is selected from:

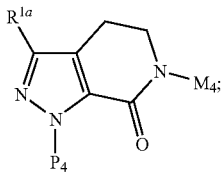

P$_4$ is -G;
M$_4$ is -A-B;
A-B is selected from:

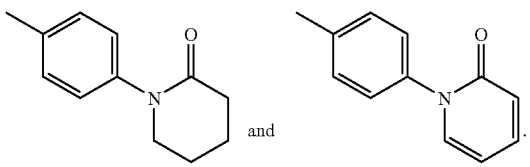

[8] In another preferred embodiment, the present invention provides a novel compound, wherein the compound is selected from the group:

3-methoxy-1-(4-methoxyphenyl)-6-[4-(2-oxo-1-piperidinyl)phenyl]-1,4,5,6-tetrahydro-7-H-pyrazolo[3,4-c]pyridin-7-one;
1-(4-methoxyphenyl)-3-[(methylamino)methyl]-6-[4-(2-oxo-1-piperidinyl)phenyl]-1,4,5,6-tetrahydro-7H-pyrazolo[3,4-c]pyridin-7-one;
1-(3-chloro-4-fluorophenyl)-6-[4-(2-oxo-1-piperidinyl)phenyl]-3-(trifluoromethyl)-1,4,5,6-tetrahydro-7H-pyrazolo[3,4-c]pyridin-7-one;
1-[3-(aminomethyl)-4-fluorophenyl]-6-[4-(2-oxo-1-piperidinyl)phenyl]-3-(trifluoromethyl)-1,4,5,6-tetrahydro-7H-pyrazolo[3,4-c]pyridin-7-one;
1-(3-amino-1,2-benzisoxazol-5-yl)-6-[4-(2-oxo-1-piperidinyl)phenyl]-3-(trifluoromethyl)-1,4,5,6-tetrahydro-7H-pyrazolo[3,4-c]pyridin-7-one;
1-(4-methoxyphenyl)-6-[4-(2-oxo-1-piperidinyl)phenyl]-3-(trifluoromethyl)-1,4,5,6-tetrahydro-7H-pyrazolo[3,4-c]pyridin-7-one;
1-(4-methoxyphenyl)-6-[4-(2-oxo-hexahydro-1H-azepin-1-yl)phenyl]-3-(trifluoromethyl)-1,4,5,6-tetrahydro-7H-pyrazolo[3,4-c]pyridin-7-one;
1-(4-methoxyphenyl)-6-[4-(2-oxo-1-piperazinyl)phenyl]-3-(trifluoromethyl)-1,4,5,6-tetrahydro-7H-pyrazolo[3,4-c]pyridin-7-one;
1-(4-methoxyphenyl)-6-[4-(2-oxo-1-imidazolidinyl)phenyl]-3-(trifluoromethyl)-1,4,5,6-tetrahydro-7H-pyrazolo[3,4-c]pyridin-7-one;
1-(4-methoxyphenyl)-6-[4-(2-oxotetrahydro-1(2H)-pyrimidinyl)phenyl]-3-(trifluoromethyl)-1,4,5,6-tetrahydro-7H-pyrazolo[3,4-c]pyridin-7-one;
6-[4-(3-ethyl-2-oxo-2,3-dihydro-1H-benzimidazol-1-yl)phenyl]-1-(4-methoxyphenyl)-3-(trifluoromethyl)-1,4,5,6-tetrahydro-7H-pyrazolo[3,4-c]pyridin-7-one;
1-(4-methoxyphenyl)-7-oxo-6-[4-(2-oxo-1-piperidinyl)phenyl]-4,5,6,7-tetrahydro-1H-pyrazolo[3,4-c]pyridine-3-carbonitrile;
1-(4-methoxyphenyl)-6-[4-(2-oxo-1-piperidinyl)phenyl]-3-(1H-tetrazol-5-yl)-1,4,5,6-tetrahydro-7H-pyrazolo[3,4-c]pyridin-7-one;
1-(4-methoxyphenyl)-7-oxo-6-[4-(2-oxo-1-piperidinyl)phenyl]-4,5,6,7-tetrahydro-1H-pyrazolo[3,4-c]pyridine-3-carboxamide;
3-bromo-1-(4-methoxyphenyl)-6-[4-(2-oxo-1-piperidinyl)phenyl]-1,4,5,6-tetrahydro-7H-pyrazolo[3,4-c]pyridin-7-one;
1-(4-methoxyphenyl)-6-[4-(2-oxo-1-piperidinyl)phenyl]-3-(4-pyridinyl)-1,4,5,6-tetrahydro-7H-pyrazolo[3,4-c]pyridin-7-one;
1-(4-methoxyphenyl)-6-[4-(2-oxo-1-piperidinyl)phenyl]-3-(4-pyridinyl-N-oxide)-1,4,5,6-tetrahydro-7H-pyrazolo[3,4-c]pyridin-7-one;
1-(4-methoxyphenyl)-6-[4-(2-oxo-1-piperidinyl)phenyl]-3-(3-pyridinyl)-1,4,5,6-tetrahydro-7H-pyrazolo[3,4-c]pyridin-7-one;
1-(4-methoxyphenyl)-6-[4-(2-oxo-1-piperidinyl)phenyl]-3-(3-pyridinyl-N-oxide)-1,4,5,6-tetrahydro-7H-pyrazolo[3,4-c]pyridin-7-one;
1-(4-methoxyphenyl)-6-[4-(2-oxo-1-piperidinyl)phenyl]-3-(2-pyridinyl)-1,4,5,6-tetrahydro-7H-pyrazolo[3,4-c]-7-one;
1-(4-methoxyphenyl)-6-[4-(2-oxo-1-piperidinyl)phenyl]-1,4,5,6-tetrahydro-7H-pyrazolo[3,4-c]pyridin-7-one;
1-(4-methoxyphenyl)-7-oxo-6-[5-(2-oxo-1-piperidinyl)2-pyridinyl]-4,5,6,7-tetrahydro-1H-pyrazolo[3,4-c]pyridine-3-carboxamide;
1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carboxamide;
1-(4-methoxyphenyl)-3-(methylsulfonyl)-6-[4-(2-oxo-1-piperidinyl)phenyl]-1,4,5,6-tetrahydro-7H-pyrazolo[3,4-c]pyridin-7-one;
1-(4-methoxyphenyl)-6-(4-(2-oxo-1(2H)-pyridinyl)phenyl]-3-(2-pyridinyl)-1,4,5,6-tetrahydro-7H-pyrazolo[3,4-c]pyridin-7-one;
1-[3-(aminomethyl)phenyl]-6-[4-(2-oxo-1-piperidinyl)phenyl]-3-(trifluoromethyl)-1,4,5,6-tetrahydro-7H-pyrazolo[3,4-c]pyridin-7-one;
3-[7-oxo-6-[4-(2-oxo-1-piperidinyl)phenyl]-3-(trifluoromethyl)-4,5,6,7-tetrahydro-1H-pyrazolo[3,4-c]pyridin-1-yl]benzamide;
1-(3-chlorophenyl)-7-oxo-6-[4-(2-oxo-1-piperidinyl)phenyl]-4,5,6,7-tetrahydro-1H-pyrazolo[3,4-c]pyridine-3-carboxamide;
1-(3-chlorophenyl)-7-oxo-6-[4-(2-oxo-1(2H)pyridinyl)phenyl]-4,5,6,7-tetrahydro-1H-pyrazolo[3,4-c]pyridine-3-carboxamide;

1-(3-chlorophenyl)-N,N-dimethyl-7-oxo-6-[4-(2-oxo-1-piperidinyl)phenyl]-4,5,6,7-tetrahydro-1H-pyrazolo[3,4-c]pyridine-3-carboxamide;

1-(3-chloro-4-fluorophenyl)-7-oxo-6-[4-(2-oxo-1-piperidinyl)phenyl]-4,5,6,7-tetrahydro-1H-pyrazolo[3,4-c]pyridine-3-carboxamide;

1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carbonitrile;

1-(3-amino-1H-indazol-5-yl)-7-oxo-6-[4-(2-oxo-1-piperidinyl)phenyl]-4,5,6,7-tetrahydro-1H-pyrazolo[3,4-c]pyridine-3-carboxamide;

1-(3-amino-1,2-benzisoxazol-5-yl)-7-oxo-6-[4-(2-oxo-1-piperidinyl)phenyl]-4,5,6,7-tetrahydro-1H-pyrazolo[3,4-c]pyridine-3-carboxamide;

1-(2,3-dihydro-1H-indol-6-yl)-6-[4-(2-oxo-1(2H)-pyridinyl)phenyl]-3-(trifluoromethyl)-1,4,5,6-tetrahydro-7H-pyrazolo[3,4-c]pyridin-7-one;

1-(2,3-dihydro-1H-indol-6-yl)-6-[4-(2-oxo-1-piperidinyl)phenyl]-3-(trifluoromethyl)-1,4,5,6-tetrahydro-7H-pyrazolo[3,4-c]pyridin-7-one;

1-(2,3-dihydro-1H-isoindol-5-yl)-6-[4-(2-oxo-2H-pyridin-1-yl)phenyl]-3-trifluoromethyl-1,4,5,6-tetrahydropyrazolo[3,4-c]pyridin-7-one;

1-(4-methoxyphenyl)-6-[4-(2-oxo-piperidin-1-yl)-phenyl]-3-(2-pyrrolidin-1-ylmethyl-phenyl)-1,4,5,6-tetrahydro-pyrazolo[3,4-c]pyridin-7-one;

ethyl 1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carboxylate;

1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carboxylic acid;

1-(4-methoxyphenyl)-N,N-dimethyl-7-oxo-6-[4-(2-oxo-1(2H)-pyridinyl)phenyl]-4,5,6,7-tetrahydro-1H-pyrazolo[3,4-c]pyridine-3-carboxamide;

N-({1-(4-methoxyphenyl)-7-oxo-6-[4-(2-oxo-1(2H)-pyridinyl)phenyl]-4,5,6,7-tetrahydro-1H-pyrazolo[3,4-c]pyridin-3-yl}carbonyl)methanesulfonamide;

1-(4-hydroxy-phenyl)-7-oxo-6-[4-(2-oxo-piperidin-1-yl)-phenyl]-4,5,6,7-tetrahydro-1H-pyrazolo[3,4-c]pyridine-3-carboxylic acid amide;

1-(4-methoxyphenyl)-6-[4-(2-oxo-1(2H)-pyridinyl)phenyl]-3-(1H-tetrazol-5-yl)-1,4,5,6-tetrahydro-7H-pyrazolo[3,4-c]pyridin-7-one;

3-{4-[(dimethylamino)methyl]-1,3-oxazol-2-yl}-1-(4-methoxyphenyl)-6-[4-(2-oxo-1(2H)-pyridinyl)phenyl]-1,4,5,6-tetrahydro-7H-pyrazolo[3,4-c]pyridin-7-one;

3-{4-[(dimethylamino)methyl]-1,3-oxazol-2-yl}-1-(4-methoxyphenyl)-6-[4-(2-oxo-1-piperidinyl)phenyl]-1,4,5,6-tetrahydro-7H-pyrazolo[3,4-c]pyridin-7-one;

1-(4-methoxyphenyl)-7-oxo-6-[4-(2-oxo-1-piperazinyl)phenyl]-4,5,6,7-tetrahydro-1H-pyrazolo[3,4-c]pyridine-3-carboxamide;

1-(4-methoxyphenyl)-3-(methylsulfonyl)-6-[4-(2-oxo-1-piperazinyl)phenyl]-1,4,5,6-tetrahydro-7H-pyrazolo[3,4-c]pyridin-7-one;

1-(4-methoxy-phenyl)-3-(4-methyl-oxazol-2-yl)-6-[4-(2-oxo-piperidin-1-yl)-phenyl]-1,4,5,6-tetrahydro-pyrazolo[3,4-c]pyridin-7-one;

1-(4-methoxy-phenyl)-3-(4-methyl-oxazol-2-yl)-6-[4-(2-oxo-2H-pyridin-1-yl)-phenyl]-1,4,5,6-tetrahydro-pyrazolo[3,4-c]pyridin-7-one;

3-acetyl-1-(4-methoxy-phenyl)-6-[4-(2-oxo-2H-pyridin-1-yl)-phenyl]-1,4,5,6-tetrahydro-pyrazolo[3,4-c]pyridin-7-one;

3-(4,5-dihydro-1H-imidazol-2-yl)-1-(4-methoxy-phenyl)-6-[4-(2-oxo-2H-pyridin-1-yl)-phenyl]-1,4,5,6-tetrahydro-pyrazolo[3,4-c]pyridin-7-one;

1-(4-methoxy-phenyl)-3-(1-methyl-4,5-dihydro-1H-imidazol-2-yl)-6-[4-(2-oxo-piperidin-1-yl)-phenyl]-1,4,5,6-tetrahydro-pyrazolo[3,4-c]pyridin-7-one;

1-(4-methoxy-phenyl)-3-(1-methyl-1H-imidazol-2-yl)-6-[4-(2-oxo-piperidin-1-yl)-phenyl]-1,4,5,6-tetrahydro-pyrazolo[3,4-c]pyridin-7-one;

1-(4-methoxy-phenyl)-3-methyl-6-[4-(2-oxo-piperidin-1-yl)-phenyl]-1,4,5,6-tetrahydro-pyrazolo[3,4-c]pyridin-7-one;

3-hydroxymethyl-1-(4-methoxy-phenyl)-6-[4-(2-oxo-2H-pyridin-1-yl)-phenyl]-1,4,5,6-tetrahydro-pyrazolo[3,4-c]pyridin-7-one;

3-(1-hydroxy-1-methyl-ethyl)-1-(4-methoxy-phenyl)-6-[4-(2-oxo-piperidin-1-yl)-phenyl]-1,4,5,6-tetrahydropyrazolo[3,4-c]pyridin-7-one;

3-(1-hydroxy-1-methyl-ethyl)-1-(4-methoxy-phenyl)-6-[4-(2-oxo-2H-pyridin-1-yl)-phenyl]-1,4,5,6-tetrahydro-pyrazolo[3,4-c]pyridin-7-one;

2-dimethylamino-N-{1-(4-methoxyphenyl)-7-oxo-6-[4-(2-oxopiperidin-1-yl)phenyl]-4,5,6,7-tetrahydro-1H-pyrazolo[3,4-c]pyridin-3-ylmethyl}-N-methylacetamide;

2-dimethylamino-N-{1-(4-methoxyphenyl)-7-oxo-6-[4-(2-oxo-2H-pyridin-1-yl)-phenyl]-4,5,6,7-tetrahydro-1H-pyrazolo[3,4-c]pyridin-3-ylmethyl}acetamide;

N-{1-(4-methoxyphenyl)-7-oxo-6-[4-(2-oxopiperidin-1-yl)phenyl]-4,5,6,7-tetrahydro-1H-pyrazolo[3,4-c]pyridin-3-ylmethyl}-2-pyridin-2-yl-acetamide;

N-{1-(4-methoxyphenyl)-7-oxo-6-[4-(2-oxopiperidin-1-yl)phenyl]-4,5,6,7-tetrahydro-1H-pyrazolo[3,4-c]pyridin-3-ylmethyl}-2-(1-oxo-pyridin-2-yl)acetamide;

6-[4-(1,1-dioxo-1,6-isothiazolidin-2-yl)-phenyl]-1-(4-methoxy-phenyl)-7-oxo-4,5,6,7-tetrahydro-1H-pyrazolo[3,4-c]pyridine-3-carboxylic acid amide;

N-hydroxy-3-{7-oxo-6-[4-(2-oxo-2H-pyridin-1-yl)-phenyl]-3-trifluoromethyl-4,5,6,7-tetrahydro-pyrazolo[3,4-c]pyridin-1-yl}-benzamidine;

N-methoxy-3-{7-oxo-6-[4-(2-oxo-2H-pyridin-1-yl)-phenyl]-3-trifluoromethyl-4,5,6,7-tetrahydro-pyrazolo[3,4-c]pyridin-1-yl}-benzamidine;

1-(3-cyano-4-fluorophenyl)-7-oxo-6-[4-(2-oxo-1-piperidinyl)phenyl]-4,5,6,7-tetrahydro-1H-pyrazolo[3,4-c]pyridine-3-carboxamide;

1-(3-aminomethyl-4-fluoro-phenyl)-7-oxo-6-[4-(2-oxo-piperidin-1-yl)-phenyl]-4,5,6,7-tetrahydro-1H-pyrazolo[3,4-c]pyridine-3-carboxylic acid amide;

2-{7-oxo-6-[4-(2-oxo-piperidin-1-yl)-phenyl]-3-trifluoromethyl-4,5,6,7-tetrahydro-pyrazolo[3,4-c]pyridin-1-yl}-benzenesulfonamide;

2-{7-oxo-6-[4-(2-oxo-2H-pyridin-1-yl)-phenyl]-3-trifluoromethyl-4,5,6,7-tetrahydro-pyrazolo[3,4-c]pyridin-1-yl}-benzenesulfonamide;

N-acetyl-2-{7-oxo-6-[4-(2-oxo-2H-pyridin-1-yl)-phenyl]-3-trifluoromethyl-4,5,6,7-tetrahydro-pyrazolo[3,4-c]pyridin-1-yl}-benzenesulfonamide;

1-(3-chloro-phenyl)-3-methanesulfonyl-6-[4-(2-oxo-piperidin-1-yl)-phenyl]-1,4,5,6-tetrahydro-pyrazolo[3,4-c]pyridin-7-one;

1-(3-chloro-phenyl)-3-methanesulfonyl-6-[4-(2-oxo-2H-pyridin-1-yl)-phenyl]-1,4,5,6-tetrahydro-pyrazolo[3,4-c]pyridin-7-one;

1-(3-chloro-phenyl)-3-(1-hydroxy-1-methyl-ethyl)-6-[4-(2-oxo-piperidin-1-yl)-phenyl]-1,4,5,6-tetrahydro-pyrazolo[3,4-c]pyridin-7-one; and 3-{7-oxo-6-[4-(2-oxo-2H-pyridin-1-yl)-phenyl]-3-trifluoromethyl-4,5,6,7-tetrahydro-pyrazolo[3,4-c]pyridin-1-yl}-benzamide;

or a pharmaceutically acceptable salt form thereof.

[9] In another preferred embodiment, the present invention provides a novel compound, wherein the compound is of Formula IIIa, IIIb, or IIIc:

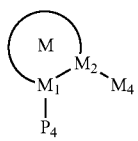

IIIa

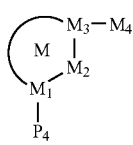

IIIb

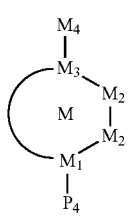

IIIc or a stereoisomer or pharmaceutically acceptable salt thereof, wherein;

ring M, including $M_1$, $M_2$, and, if present, $M_3$, is phenyl or a 3-10 membered carbocyclic or 4-10 membered heterocyclic ring consisting of: carbon atoms and 1-4 heteroatoms selected from O, $S(O)_p$, N, and $NZ^2$;

ring M is substituted with 0-3 $R^{1a}$ and 0-2 carbonyl groups, and there are 0-3 ring double bonds;

one of $P_4$ and $M_4$ is —Z-A-B and the other -$G_1$-G;

G is a group of Formula IIa or IIb:

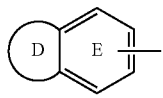

IIa

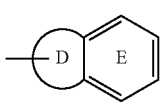

IIb ring D, including the two atoms of Ring E to which it is attached, is a 5-6 membered ring consisting of: carbon atoms and 0-2 heteroatoms selected from the group consisting of N, O, and $S(O)_p$; ring D is substituted with 0-2 R and there are 0-3 ring double bonds;

E is selected from phenyl, pyridyl, pyrimidyl, pyrazinyl, and pyridazinyl, and is substituted with 1-2 R;

alternatively, ring D is absent, and ring E is selected from phenyl, pyridyl, pyrimidyl, and thienyl, and ring E is substituted with 1-2 R;

alternatively, ring D is absent, ring E is selected from phenyl, pyridyl, and thienyl, and ring E is substituted with 1 R and substituted with a 5 membered heterocycle consisting of: carbon atoms and 1-4 heteroatoms selected from the group consisting of N, O, and $S(O)_p$, wherein the 5 membered heterocycle is substituted with 0-1 carbonyl and 1-2 R and there are 0-3 ring double bonds;

R is selected from H, $C_{1-4}$ alkyl, F, Cl, OH, $OCH_3$, $OCH_2CH_3$, $OCH(CH_3)_2$, CN, $C(=NH)NH_2$, $C(=NH)NHOH$, $C(=NH)NHOCH_3$, $NH_2$, $NH(C_{1-3}$ alkyl), $N(C_{1-3}$ alkyl)$_2$, $CH_2NH_2$, $CH_2NH(C_{1-3}$ alkyl), $CH_2N(C_{1-3}$ alkyl)$_2$, $(CR^8R^9)_rNR^7R^8$, $C(O)NR^7R^8$, $CH_2C(O)NR^7R^8$, $S(O)_pNR^7R^8$, $CH_2S(O)_pNR^7R^8$, $SO_2R^3$, and $OCF_3$;

alternatively, when 2 R groups are attached to adjacent atoms, they combine to form methylenedioxy or ethylenedioxy;

A is selected from: $C_{5-10}$ carbocycle substituted with 0-2 $R^4$, and 5-10 membered heterocycle consisting of: carbon atoms and 1-4 heteroatoms selected from the group consisting of N, O, and $S(O)_p$ and substituted with 0-2 $R^4$; provided that A is other than a dihydro-benzopyran;

B is

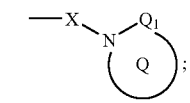

provided that Z and B are attached to different atoms on A and that the A-X—N moiety forms other than a N—N—N group;

provided that B is other than triazolone, quinolone, or isoquinolone, wherein the triazolone, quinolone, and isoquinolone groups are substituted or unsubstituted;

$Q_1$ is selected from C=O and $SO_2$;

ring Q is a 4-7 membered monocyclic or bicyclic ring consisting of, in addition to the $N-Q_1$ group shown, carbon atoms and 0-2 heteroatoms selected from $NR^{4c}$, O, S, S(O), and $S(O)_2$, wherein: 0-2 double bonds are present within the ring and the ring is substituted with 0-2 $R^{4a}$;

alternatively, ring Q is a 4-7 membered ring to which another ring is fused, wherein: the 4-7 membered ring consists of, in addition to the shown amide group, carbon atoms and 0-2 heteroatoms selected from $NR^{4c}$, O, S, S(O), and $S(O)_2$ and 0-1 double bonds are present within the ring;

the fusion ring is phenyl or a 5-6 membered heteroaromatic consisting of carbon atoms and 1-2 heteroatoms selected from $NR^{4c}$, O, and S;

ring Q, which includes the 4-7 membered ring and the fusion ring, is substituted with 0-3 $R^{4a}$;

X is absent or is selected from —$(CR^2R^{2a})_{1-4}$—, —C(O)—, —$C(O)CR^2R^{2a}$—, —$CR^2R^{2a}C(O)$—, —$S(O)_2$—, —$S(O)_2CR^2R^{2a}$—, —$CR^2R^{2a}S(O)_2$—, —$NR^2S(O)_2$—, —$NR^2CR^2R^{2a}$—, and —$OCR^2R^{2a}$—;

Z is selected from a bond, $CH_2$, $CH_2CH_2$, $CH_2O$, $OCH_2$, C(O), NH, $CH_2NH$, $NHCH_2$, $CH_2C(O)$, $C(O)CH_2$, $C(O)NH$, NHC(O), NHC(O)NH, $NHC(O)CH_2C(O)NH$, C(O)NHS (O)$_2$, $S(O)_2$, $CH_2S(O)_2$, $S(O)_2(CH_2)$, $SO_2NH$, and $NHSO_2$, provided that Z does not form a N—S, $NCH_2N$, $NCH_2O$, or $NCH_2S$ bond with either group to which it is attached;

$Z^2$ is selected from H, $C_{1-4}$ alkyl, phenyl, benzyl, $C(O)R^{3b}$, $S(O)R^{3f}$, and $S(O)_2R^{3f}$;

$R^{1a}$ is selected from H, —$(CH_2)_r$—$R^{1b}$, —$(CH(CH_3))_r$—$R^{1b}$, —$(C(CH_3)_2)_r$—$R^{1b}$, $NHCH_2R^{1c}$, $OCH_2R^{1c}$, $SCH_2R^{1c}$, $NH(CH_2)_2(CH_2)_rR^{1b}$, and $O(CH_2)_2(CH_2)_rR^{1b}$, provided that $R^{1a}$ forms other than an N-halo, N—S, or N—CN bond;

alternatively, when two $R^{1a}$ groups are attached to adjacent atoms, together with the atoms to which they are attached they form a 5-7 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, $CH_3$, $CH_2CH_3$, $CH_2CH_2CH_3$, $CH(CH_3)_2$, F, Cl, Br, I, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_r$ $OR^2$, $NR^2C(O)R^{2b}$, $NR^2C(O)NHR^2$, $NR^2C(O)_2R^{2a}$, $OC(O)$ $NR^2R^{2a}$, $C(O)NR^2R^{2a}$, $C(O)NR^2(CH_2)_rOR^2$, $SO_2NR^2R^{2a}$, $NR^2SO_2R^2$, $C_{5-6}$ carbocycle substituted with 0-2 $R^{4b}$, and 5-6 membered heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)$ $NR^2R^{2a}$, $S(O)R^2$, $S(O)_2R^2$, and $SO_2NR^2R^{2a}$;

$R^2$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, a $C_{5-6}$ carbocyclic-$CH_2$- group substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

$R^{2a}$, at each occurrence, is selected from H, $CF_3$, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

alternatively, $R^2$ and $R^{2a}$, together with the atom to which they are attached, combine to form a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, and 5-6 membered heterocycle containing from 1-4 heteroatoms selected from the group consisting of N, O, and $S(O)_p$, and substituted with 0-2 $R^{4b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)$ $R^{2b}$, $C(O)NR^2R^{2a}$, $SO_2NR^2R^{2a}$, $S(O)_pR^{5a}$, $CF_3$, $CF_2CF_3$, 5-6 membered carbocycle substituted with 0-1 $R^5$, and a 5-6 membered heterocycle consisting of: carbon atoms and 1-4 heteroatoms selected from the group consisting of N, O, and $S(O)_p$, and substituted with 0-1 $R^5$;

$R^{4a}$, at each occurrence, is selected from H, =O, $CH_2OR^2$, $OR^2$, $CH_2F$, F, $CH_2Br$, Br, $CH_2Cl$, Cl, $C_{1-4}$ alkyl, $CH_2$—CN, —CN, $CH_2NO_2$, $NO_2$, $CH_2NR^2R^{2a}$, $NR^2R^{2a}$, $CH_2$—$C(O)$ $R^{2c}$, $C(O)R^{2c}$, $NR^2C(O)R^{2b}$, $(CH_2)_rC(O)NR^2R^{2a}$, $NR^2C(O)$ $NR^2R^{2a}$, $(CH_2)_rSO_2NR^2R^{2a}$, $NR^2SO_2NR^2R^{2a}$, $NR^2SO_2$— $C_{1-4}$ alkyl, $NR^2SO_2R^5$, $(CH_2)_rS(O)_pR^{5a}$, $CH_2CF_3$, $CF_3$, $CH_2$-5-6 membered carbocycle substituted with 0-1 $R^5$, 5-6 membered carbocycle substituted with 0-1 $R^5$, a $CH_2$-5-6 membered heterocycle consisting of: carbon atoms and 1-4 heteroatoms selected from the group consisting of N, O, and $S(O)_p$, and substituted with 0-1 $R^5$, and 5-6 membered heterocycle consisting of: carbon atoms and 1-4 heteroatoms selected from the group consisting of N, O, and $S(O)_p$, and substituted with 0-1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C$ $(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C$ $(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$— $C_{1-4}$ alkyl, $S(O)_p$-phenyl, $CH_2S(O)_p$-phenyl, $CF_3$, and $CH_2CF_3$;

$R^{4c}$, at each occurrence, is selected from H, $CH_3$, $CH_2CH_3$, $CH_2CH_2CH_3$, $CH(CH_3)_2$, $CH_2CH_2CH_3$, $CH_2CH(CH_3)_2$, $CH(CH_3)CH_2CH_3$, $C(CH_3)_3$, $CH_2OR^2$, $CH_2F$, $CH_2Br$, $CH_2Cl$, $CH_2CN$, $CH_2NO_2$, $CH_2NR^2R^{2a}$, $C(O)R^{2c}$, $CH_2C(O)R^{2c}$, $CH_2NR^2C(O)R^{2b}$, $C(O)NR^2R^{2a}$, $CH_2C(O)$ $NR^2R^{2a}$, $CH_2NR^2C(O)NR^2R^{2a}$, $SO_2NR^2R^{2a}$, $CH_2SO_2NR^2R^{2a}$, $CH_2NR^2SO_2NR^2R^{2a}$, $CH_2NR^2SO_2$—$C_{1-4}$ alkyl, $C(O)NHSO_2$—$C_{1-4}$ alkyl, $CH_2C(O)NHSO_2$—$C_{1-4}$ alkyl, $CH_2NR^2SO_2R^5$, $S(O)_pR^{5a}$, $CH_2S(O)_pR^{5a}$, $CF_3$, $CH_2CF_3$, 5-6 membered carbocycle substituted with 0-1 $R^5$, $CH_2$-5-6 membered carbocycle substituted with 0-1 $R^5$, 5-6 membered heterocycle consisting of: carbon atoms and 1-4 heteroatoms selected from the group consisting of N, O, and $S(O)_p$, and substituted with 0-1 $R^5$, and a $CH_2$-5-6 membered heterocycle consisting of: carbon atoms and 1-4 heteroatoms selected from the group consisting of N, O, and $S(O)_p$, and substituted with 0-1 $R^5$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)$ $NR^3R^{3a}$, $NR^3C(O)NR^3R^{3a}$, $CH(=NOR^{3d})$, $C(=NR^3)$ $NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)$ $R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

[10] In another preferred embodiment, the present invention provides a novel compound, wherein:

ring M, including $M_1$, $M_2$, and, if present, $M_3$, is selected from phenyl, pyrrole, furan, thiophene, pyrazole, imidazole, isoxazole, oxazole, isothiazole, thiazole, 1,2,3-triazole, 1,2,4-triazole, 1,3,4-triazole, 1,2,3-oxadiazole, 1,2,4-oxadiazole, 1,3,4-oxadiazole, 1,2,3-thiadiazole, 1,2,4-thiadiazole, 1,3,4-thiadiazole, 1,2,3,4-tetrazole, 1,2,3,5-tetrazole, pyran, thiopyran, thiopyran-1,1-dioxide, pyridine, pyrimidine, pyridazine, pyrazine, 1,2,3-triazine, 1,2,4-triazine, 1,2,3,4-tetrazine, dihydro-pyrrole, dihydro-furan, dihydro-thiophene, dihydro-pyrazole, dihydro-imidazole, dihydro-isoxazole, dihydro-oxazole, dihydro-isothiazole, dihydro-thiazole, dihydro-1,2,3-triazole, dihydro-1,2,4-triazole, dihydro-1,3,4-triazole, dihydro-1,2,3-oxadiazole, dihydro-1,2,4-oxadiazole, dihydro-1,3,4-oxadiazole, dihydro-1,2,3-thiadiazole, dihydro-1,2,4-thiadiazole, dihydro-1,3,4-thiadiazole, dihydro-1,2,3,4-tetrazole, dihydro-1,2,3,5-tetrazole, dihydro-pyran, dihydro-thiopyran, dihydro-thiopyran-1,1-dioxide, dihydro-pyridine, dihydro-pyrimidine, dihydro-pyridazine, dihydro-pyrazine, dihydro-1,2,3-triazine, dihydro-1,2,4-triazine, dihydro-1,2,3,4-tetrazine, cyclopentene, cyclopentane, cyclohexene, cyclohexane, tetrahydro-pyrrole, tetrahydro-furan, tetrahydro-thiophene, tetrahydro-thiophene-1,1-dioxide, tetrahydro-pyrazole, tetrahydro-imidazole, tetrahydro-isoxazole, tetrahydro-oxazole, tetrahydro-isothiazole, tetrahydro-thiazole, tetrahydro-1,2,3-triazole, tetrahydro-1,2,4-triazole, tetrahydro-1,3,4-triazole, tetrahydro-1,2,3-oxadiazole, tetrahydro-1,2,4-oxadiazole, tetrahydro-1,3,4-oxadiazole, tetrahydro-1,2,3-thiadiazole, tetrahydro-1,2,4-thiadiazole, tetrahydro-1,3,4-thiadiazole, tetrahydro-1,2,3,4-tetrazole, tetrahydro-1,2,3,5-tetrazole, tetrahydro-pyran, tetrahydro-thiopyran, tetrahydro-thiopyran-1,1-dioxide, tetrahydro-pyridine, tetrahydro-pyrimidine, tetrahydro-pyridazine, tetrahydro-pyrazine, tetrahydro-1,2,3-triazine, tetrahydro-1,2,4-triazine, and tetrahydro-1,2,3,4-tetrazine;

ring M is substituted with 0-3 $R^{1a}$ and 0-1 carbonyl group;

G is selected from the group:

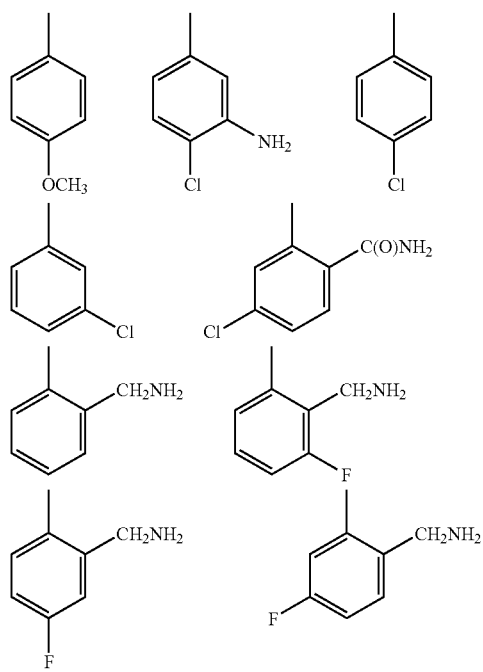

-continued

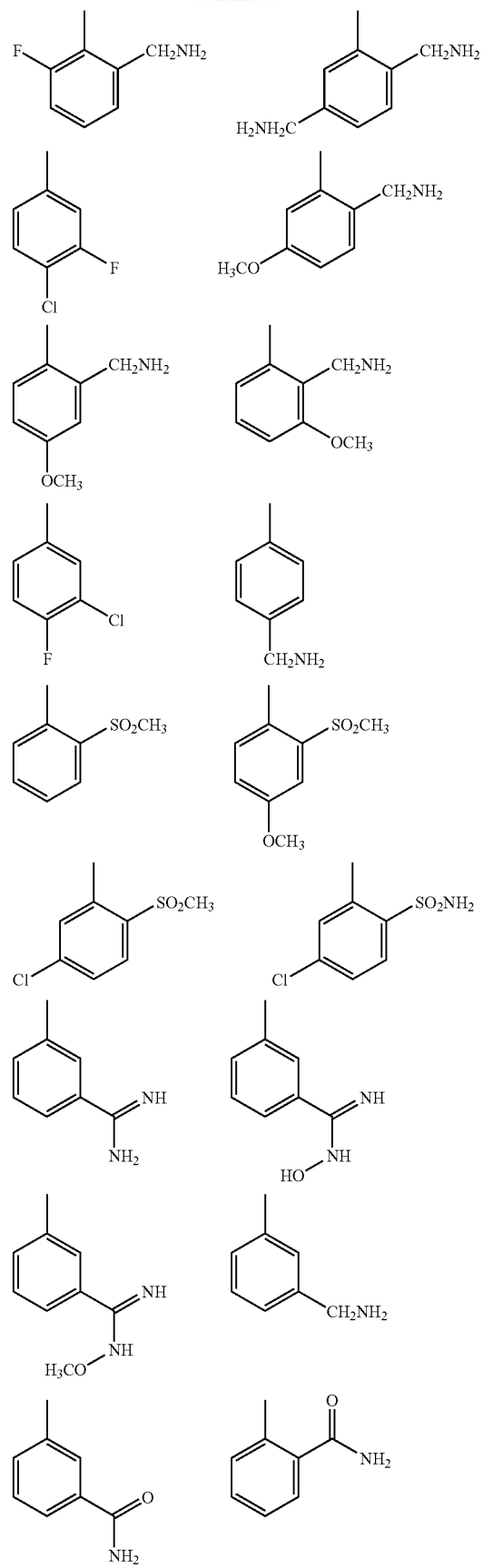

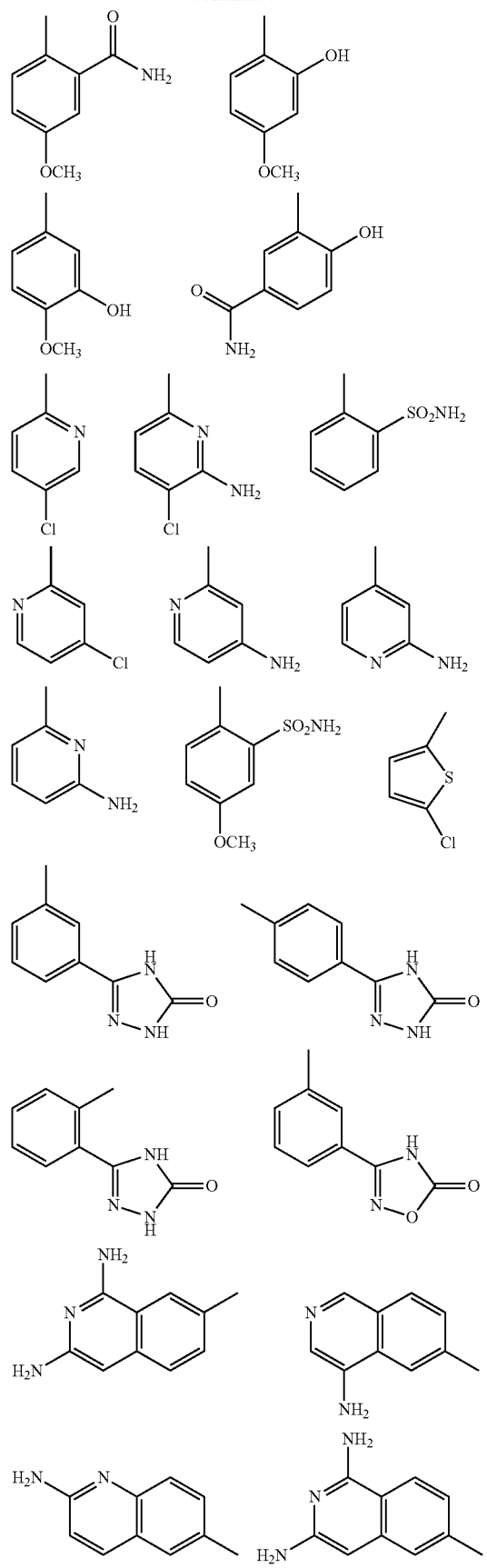
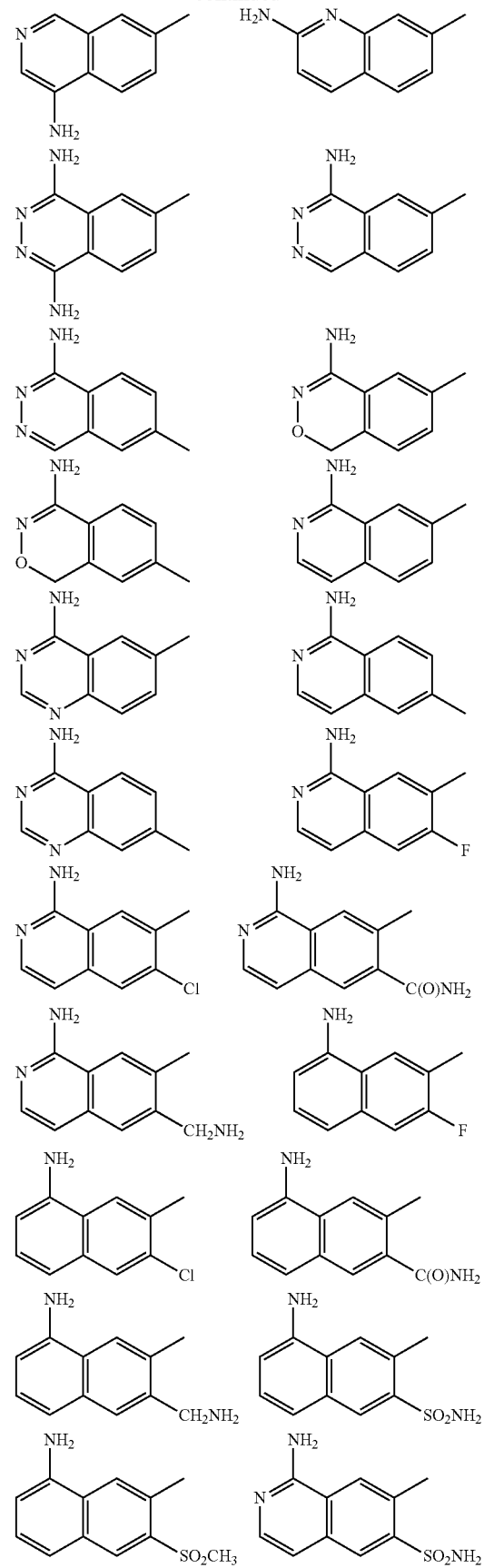

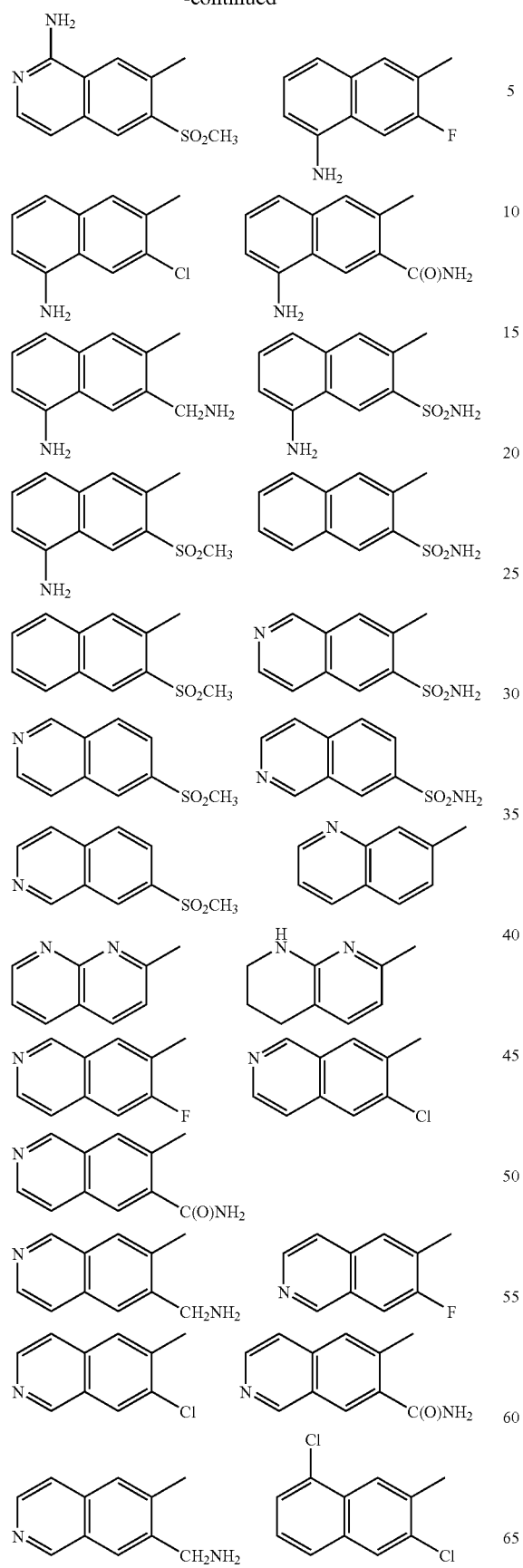
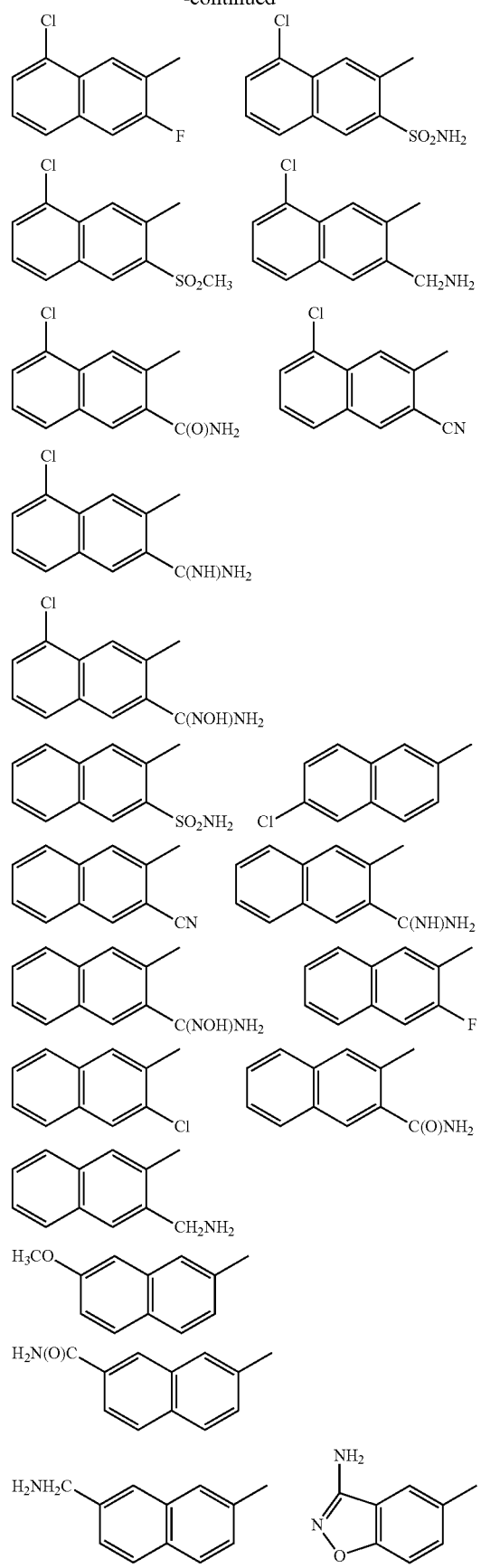

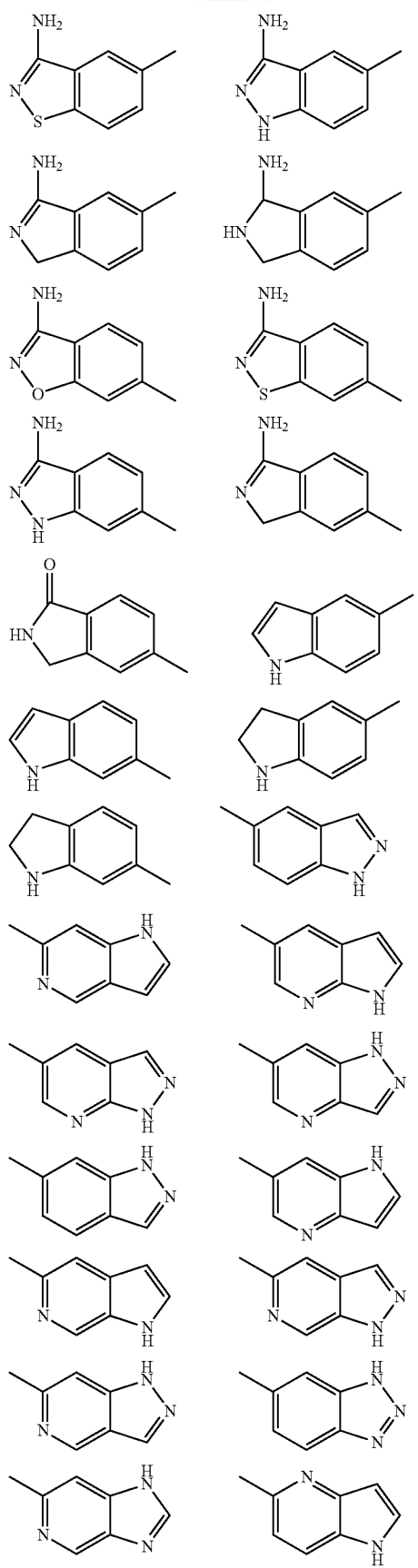
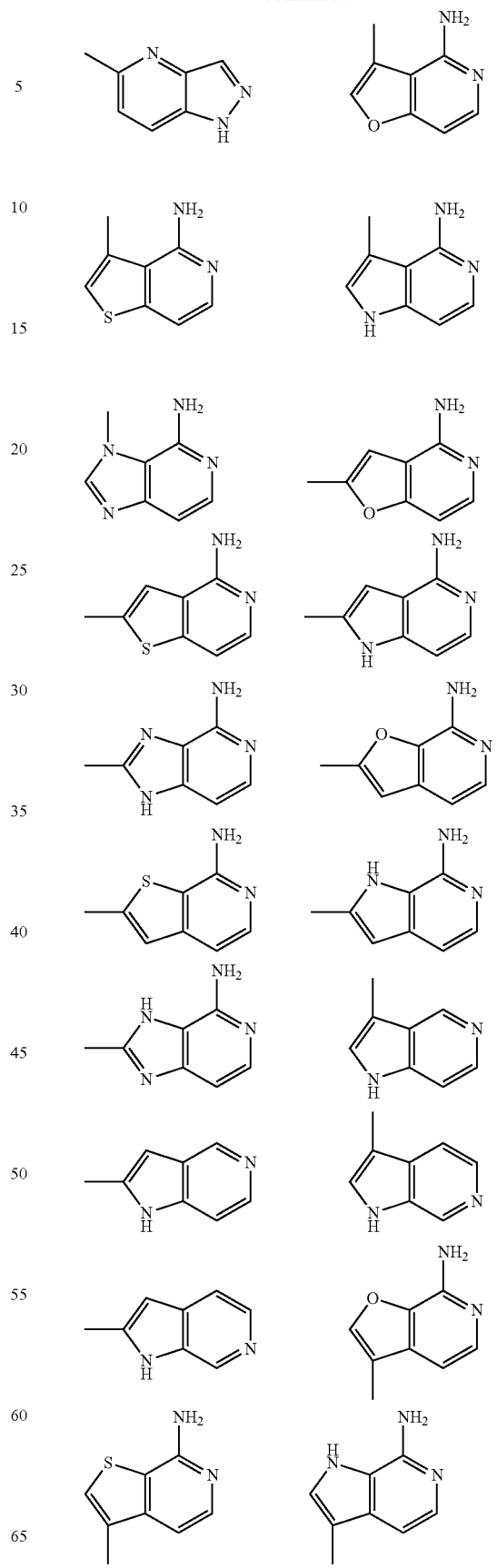

-continued

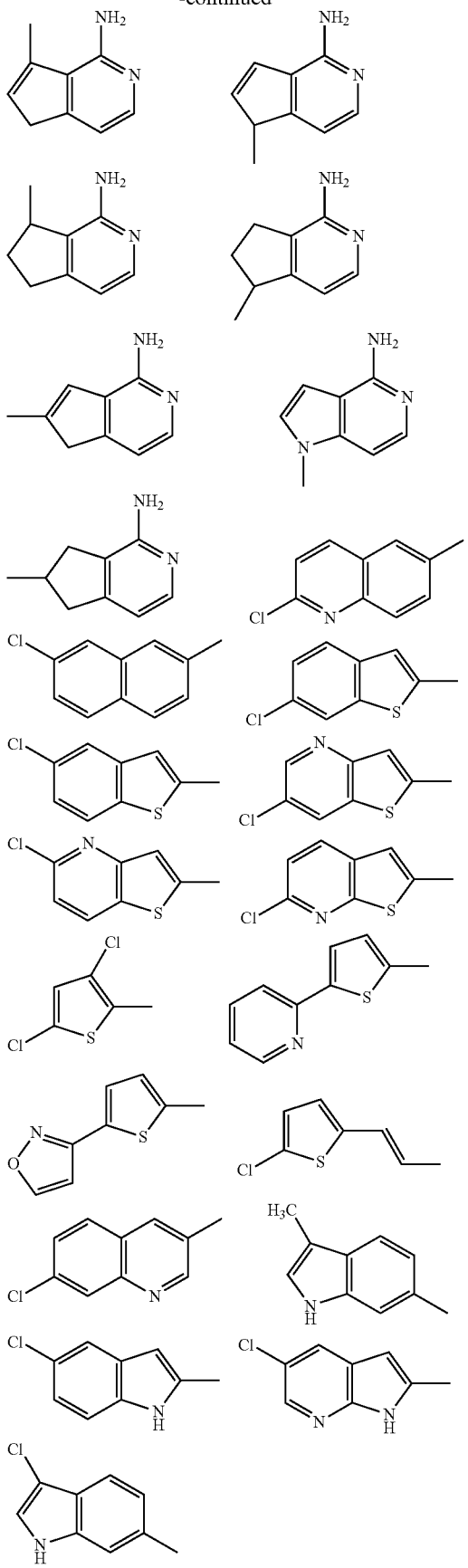

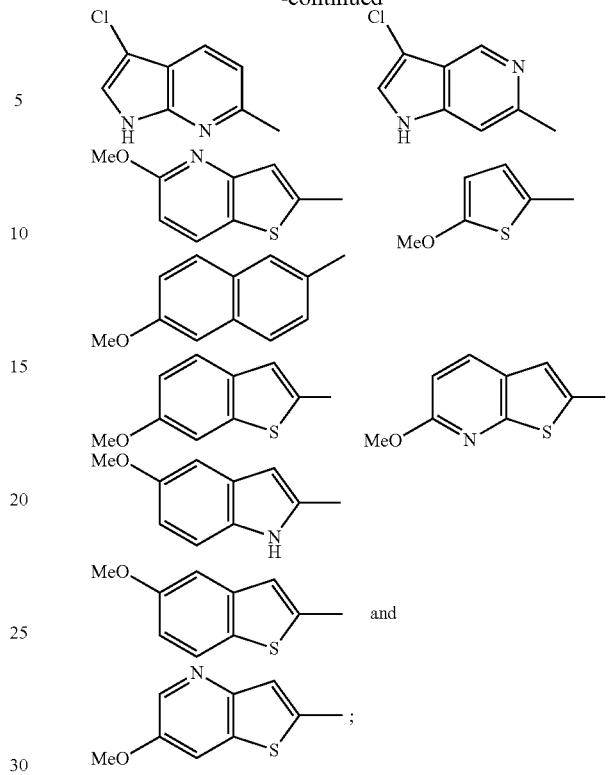

and

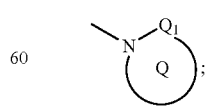

;

$G_1$ is absent or is selected from $(CR^3R^{3a})_{1-3}$, $(CR^3R^{3a})_nC(O)(CR^3R^{3a})_w$, $(CR^3R^{3a})_uO(CR^3R^{3a})_w$, $(CR^3R^{3a})_uNR^{3b}(CR^3R^{3a})_w$, $(CR^3R^{3a})_uC(O)NR^{3b}(CR^3R^{3a})_w$, $(CR^3R^{3a})_uNR^{3b}C(O)(CR^3R^{3a})_w$, $(CR^3R^{3a})_uNR^{3b}C(O)(CR^3R^{3a})_uC(O)NR^{3b}(CR^3R^{3a})_w$, $(CR^3R^{3a})_uS(CR^3R^{3a})_w$, $(CR^3R^{3a})_uS(O)(CR^3R^{3a})_w$, $(CR^3R^{3a})_uS(O)_2(CR^3R^{3a})_w$, $(CR^3R^{3a})_uS(O)NR^{3b}(CR^3R^{3a})_w$, $(CR^3R^{3a})_uNR^{3b}S(O)_2(CR^3R^{3a})_w$, $(CR^3R^{3a})_uS(O)_2NR^{3b}(CR^3R^{3a})_w$, and $(CR^3R^{3a})_uC(O)NR^{3b}S(O)_2(CR^3R^{3a})_w$, wherein u+w total 0, 1, or 2, provided that $G_1$ does not form a N—S, NCH$_2$N, NCH$_2$O, or NCH$_2$S bond with either group to which it is attached;

A is selected from one of the following carbocyclic and heterocyclic groups which are substituted with 0-2 $R^4$; phenyl, piperidinyl, piperazinyl, pyridyl, pyrimidyl, furanyl, morpholinyl, thienyl, pyrrolyl, pyrrolidinyl, oxazolyl, isoxazolyl, thiazolyl, isothiazolyl, pyrazolyl, imidazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, 1,2,5-triazolyl, 1,3,4-triazolyl, benzofuranyl, benzothiofuranyl, indolinyl, indolyl, benzimidazolyl, benzoxazolyl, benzthiazolyl, indazolyl, benzisoxazolyl, benzisothiazolyl, and isoindazolyl;

B is provided that Z and B are attached to different atoms on A; provided that B is other than triazolone, quinolone, or isoquinolone, wherein the triazolone, quinolone, and isoquinolone groups are substituted or unsubstituted;

$Q_1$ is selected from C=O and $SO_2$;

ring Q is a 5-7 membered ring consisting of, in addition to the N-Q, group shown, carbon atoms and 0-2 heteroatoms selected from $NR^{4c}$, O, S, S(O), and $S(O)_2$, wherein: 0-2 double bonds are present within the ring and the ring is substituted with 0-2 $R^{4a}$;

alternatively, ring Q is a 5-7 membered ring to which another ring is fused, wherein: the 5-7 membered ring consists of, in addition to the shown amide group, carbon atoms and 0-2 heteroatoms selected from $NR^{4c}$, O, S, S(O), and $S(O)_2$ and 0-1 double bonds are present within the ring;

the fusion ring is phenyl or a 5-6 membered heteroaromatic consisting of carbon atoms and 1-2 heteroatoms selected from $NR^{4c}$, O, and S;

ring Q, which includes the 5-7 membered ring and the fusion ring, is substituted with 0-3 $R^{4a}$;

$R^{1a}$ is selected from H, $R^{1b}$, $CH(CH_3)R^{1b}$, $C(CH_3)_2R^{1b}$, $CH_2R^{1b}$, and $CH_2CH_2R^{1b}$, provided that $R^{1a}$ forms other than an N-halo, N—S, or N—CN bond;

alternatively, when two $R^{1a}$ groups are attached to adjacent atoms, together with the atoms to which they are attached they form a 5-6 membered ring consisting of: carbon atoms and 0-2 heteroatoms selected from the group consisting of N, O, and $S(O)_p$, this ring being substituted with 0-2 $R^{4b}$ and 0-3 ring double bonds;

$R^{1b}$ is selected from H, $CH_3$, $CH_2CH_3$, F, Cl, Br, —CN, —CHO, $CF_3$, $OR^2$, $NR^2R^{2a}$, $C(O)R^{2b}$, $CO_2R^{2b}$, $OC(O)R^2$, $CO_2R^{2a}$, $S(O)_pR^2$, $NR^2(CH_2)_rOR^2$, $NR^2C(O)R^{2b}$, $C(O)NR^2R^{2a}$, $SO_2NR^2R^{2a}$, $NR^2SO_2R^2$, phenyl substituted with 0-2 $R^{4b}$, and 5-6 membered aromatic heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^2$, at each occurrence, is selected from H, $CF_3$, $CH_3$, $CH_2CH_3$, $CH_2CH_2CH_3$, $CH(CH_3)_2$, phenyl substituted with 0-2 $R^{4b}$, a benzyl substituted with 0-2 $R^{4b}$, and 5-6 membered aromatic heterocycle consisting of: carbon atoms and 1-4 heteroatoms selected from the group consisting of N, O, and $S(O)_p$, and substituted with 0-2 $R^{4b}$;

$R^{2a}$, at each occurrence, is selected from H, $CF_3$, $CH_3$, $CH_2CH_3$, $CH_2CH_2CH_3$, $CH(CH_3)_2$, benzyl, phenyl substituted with 0-2 $R^{4b}$, and 5-6 membered aromatic heterocycle consisting of: carbon atoms and 1-4 heteroatoms selected from the group consisting of N, O, and $S(O)_p$, and substituted with 0-2 $R^{4b}$;

alternatively, $R^2$ and $R^{2a}$, together with the atom to which they are attached, combine to form a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, benzyl, phenyl substituted with 0-2 $R^{4b}$, and 5-6 membered aromatic heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from $CF_3$, OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0-2 $R^{4b}$, and 5-6 membered aromatic heterocycle containing from 1-4 heteroatoms selected from the group consisting of N, O, and $S(O)_p$, and substituted with 0-2 $R^{4b}$;

$R^4$, at each occurrence, is selected from H, $CH_2OR^2$, $(CH_2)_2 OR^2$, $OR^2$, F, Cl, Br, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $CF_3$, and $CF_2CF_3$;

$R^{4a}$, at each occurrence, is selected from H, =O, $CH_2OR^2$, $OR^2$, F, Br, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $CH_2NR^2R^{2a}$, $NR^2R^{2a}$, $C(O)R^{2c}$, $NR^2C(O)R^{2b}$, $C(O)NR^2R^{2a}$, $NR^2C(O)NR^2R^{2a}$, $SO_2NR^2R^{2a}$, and —$CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $CH_2$—$C(O)R^3$, $C(O)OR^{3c}$, $CH_2$—$C(O)OR^{3c}$, $NR^3C(O)R^{3a}$, $CH_2NR^3C(O)R^{3a}$, $C(O)NR^3R^{3a}$, $CH_2$—$C(O)NR^3R^{3a}$, $SO_2NR^3R^{3a}$, $CH_2SO_2NR^3R^{3a}$, $NR^3SO_2$—$C_{1-4}$ alkyl, $CH_2NR^3SO_2$—$C_{1-4}$ alkyl, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, and $CF_3$;

$R^{4c}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2OR^2$, $CH_2F$, $CH_2Br$, $CH_2Cl$, $CH_2CN$, $CH_2NO_2$, $CH_2NR^2R^{2a}$, $C(O)R^{2c}$, $CH_2C(O)R^{2c}$, $CH_2NR^2C(O)R^{2b}$, $C(O)NR^2R^{2a}$, $CH_2C(O)NR^2R^{2a}$, $SO_2NR^2R^{2a}$, $CH_2SO_2NR^2R^{2a}$, $S(O)_pR^{5a}$, $CH_2S(O)_p R^{5a}$, $CF_3$, phenyl substituted with 0-1 $R^5$, and benzyl substituted with 0-1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $SO_2NR^2R^{2a}$, and $NR^2SO_2C_{1-4}$ alkyl.

[11] In another preferred embodiment, the present invention provides a novel compound, wherein the compound is selected from:

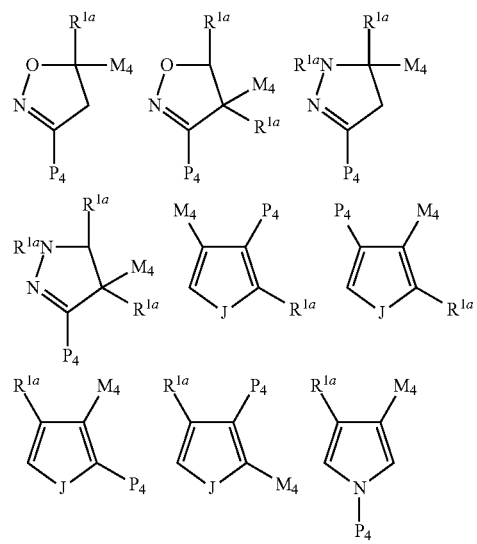

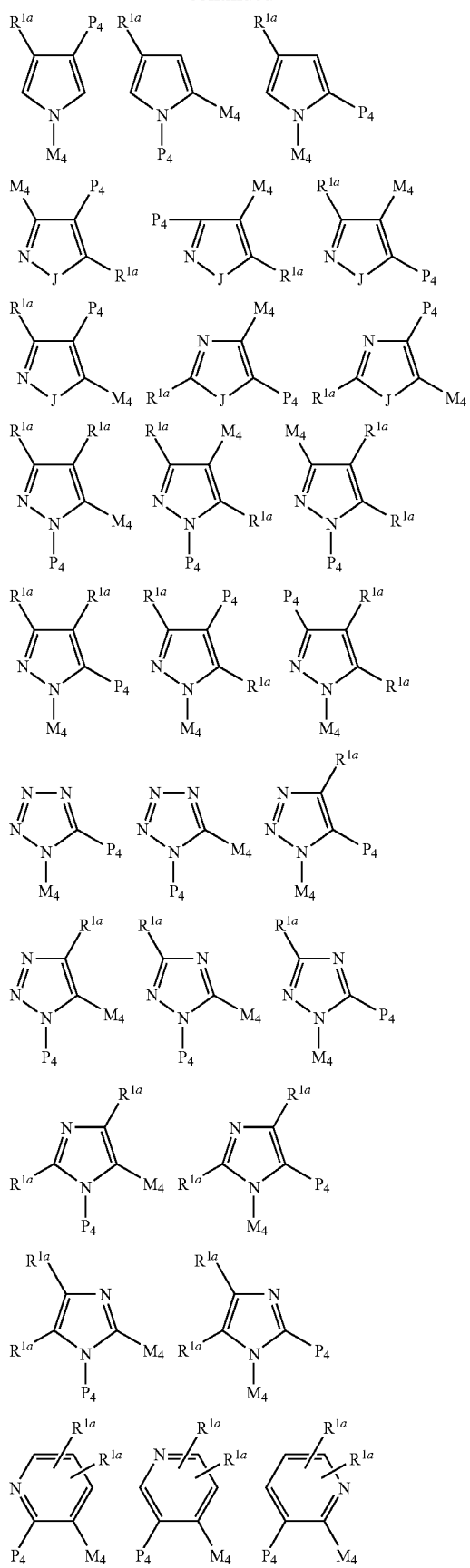
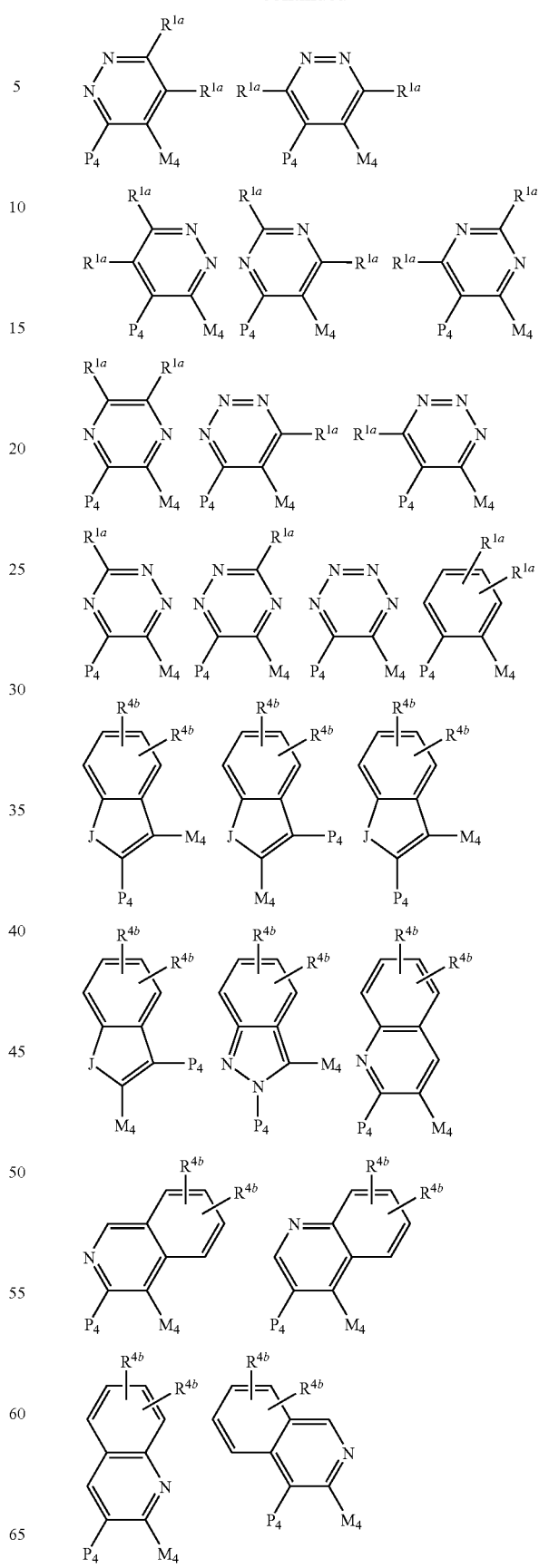

-continued
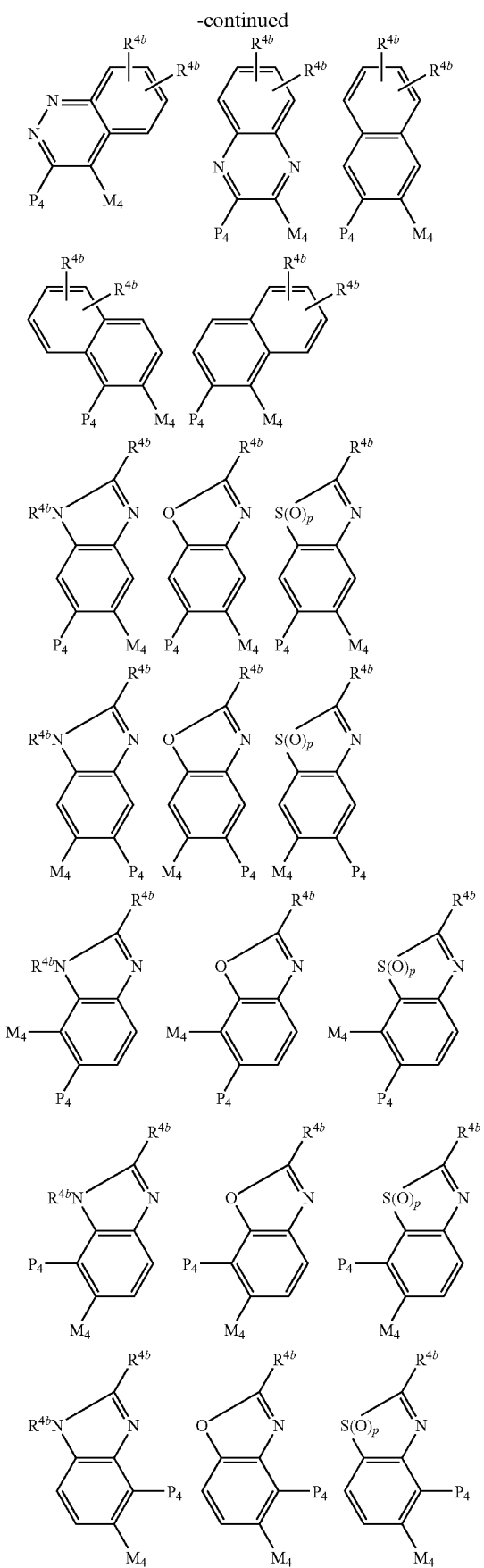
-continued
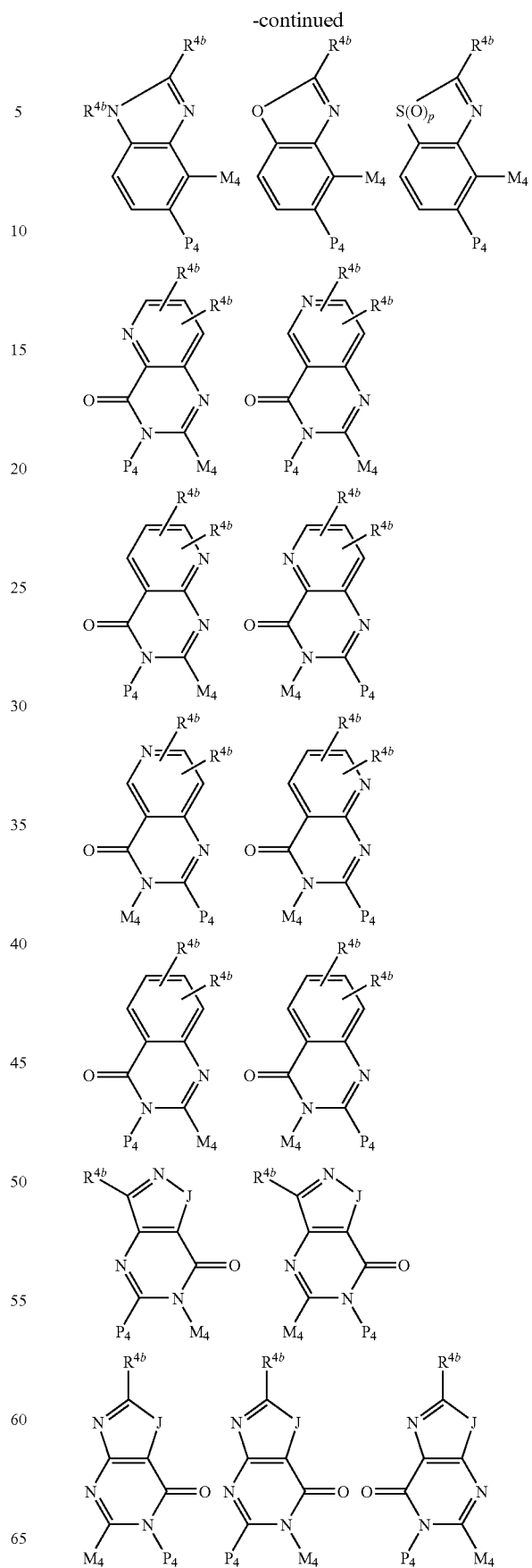

-continued
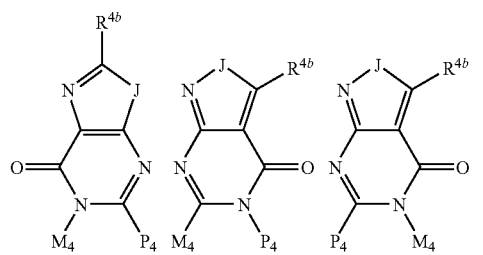
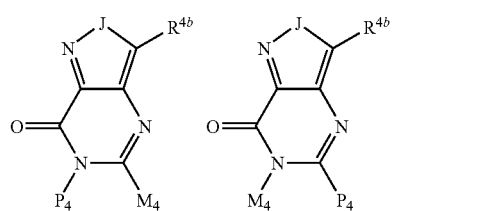
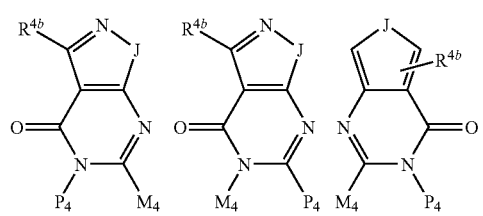
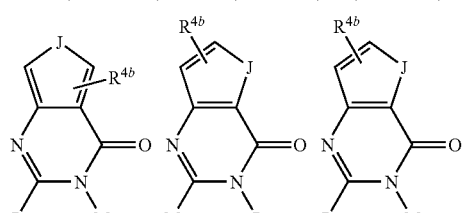
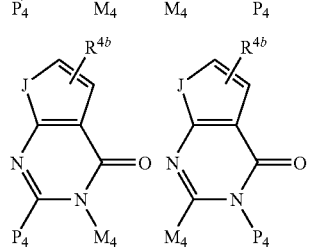
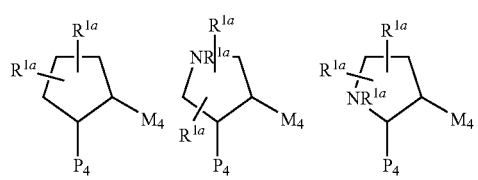
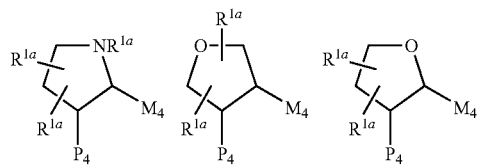
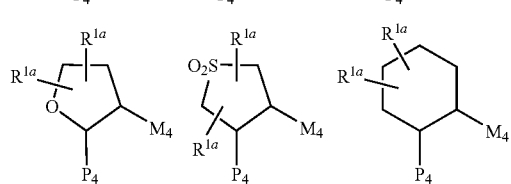
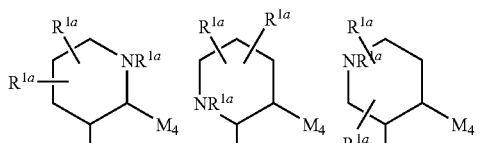
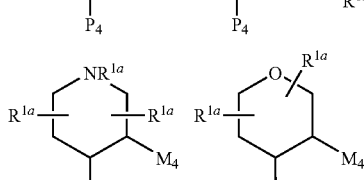
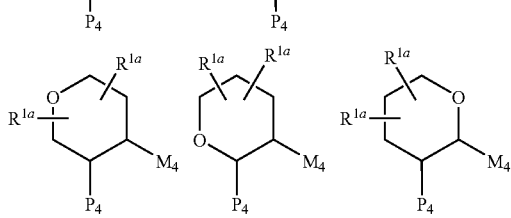
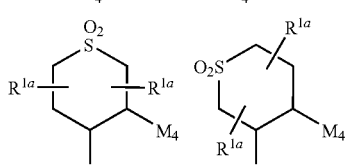
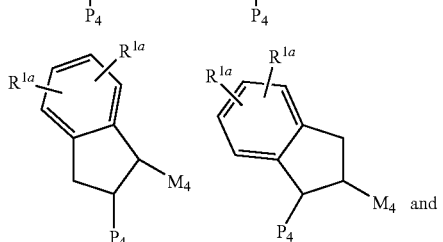
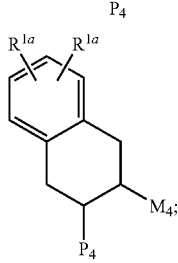
J is selected from O, S, NH, and $NR^{1a}$;
G is selected from the group:
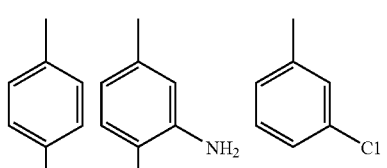
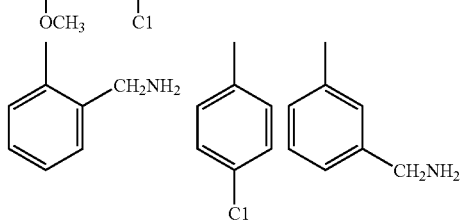

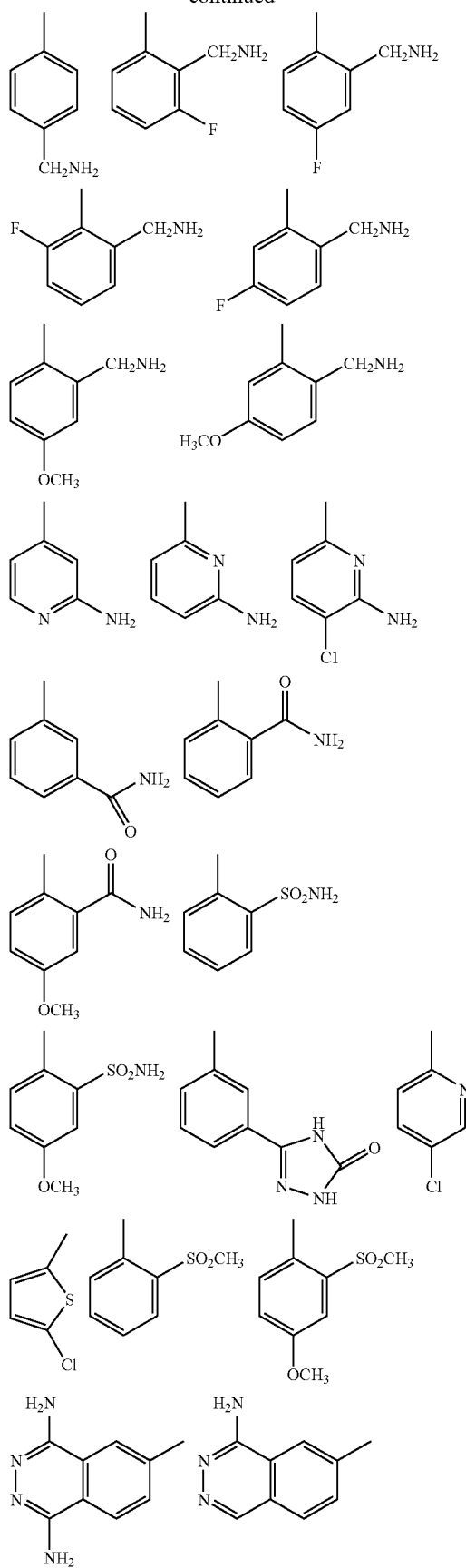
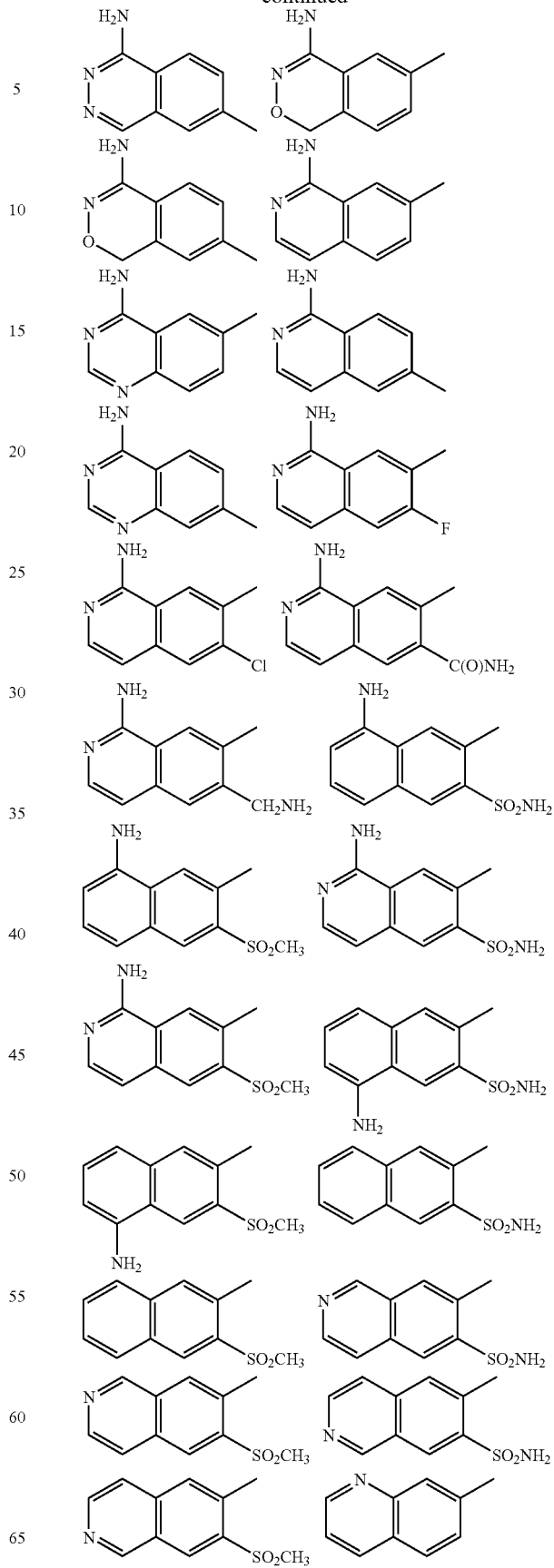

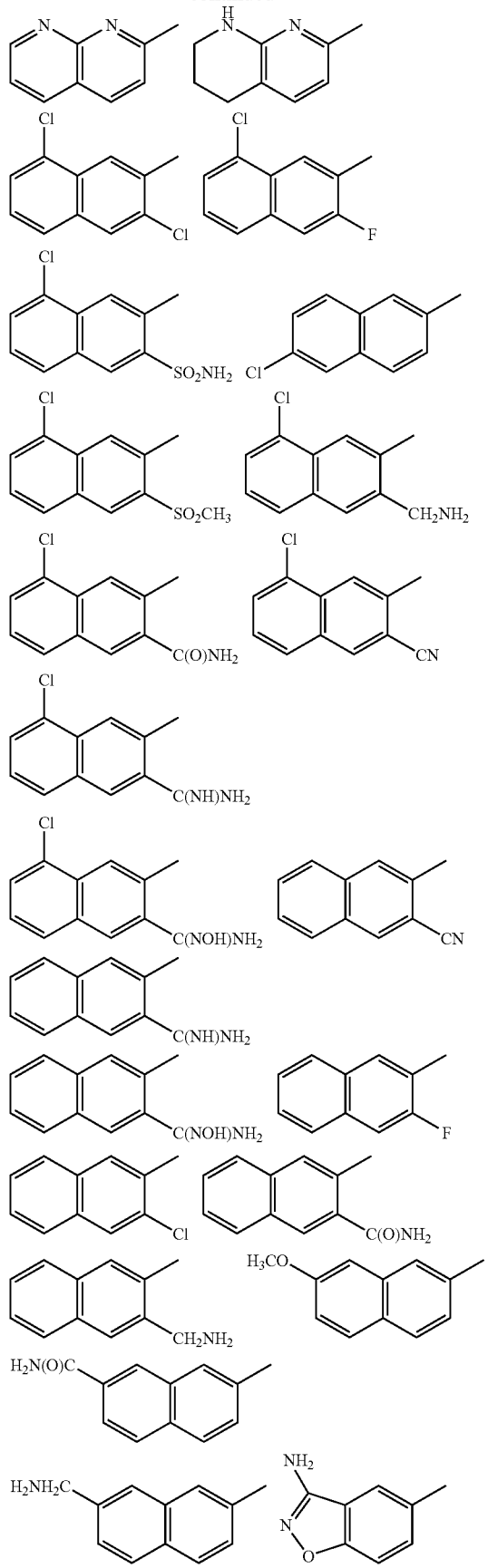
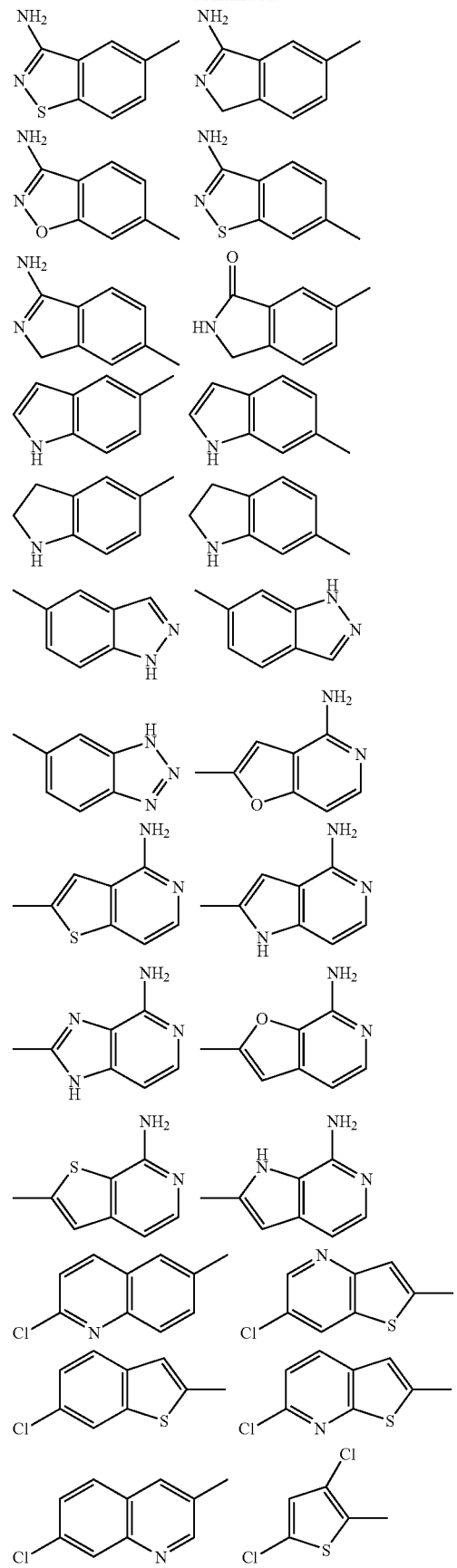

-continued

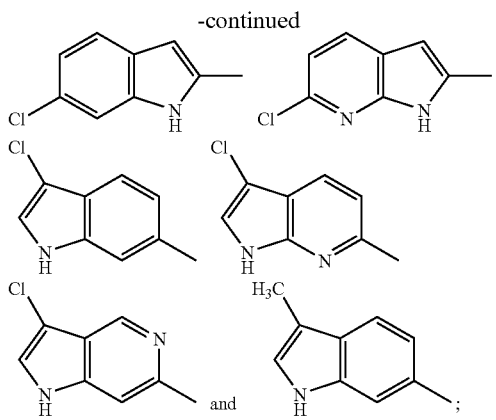

and $G_1$ is absent or is selected from $CH_2$, $CH_2CH_2$, $CH_2O$, $OCH_2$, $NH$, $CH_2NH$, $NHCH_2$, $CH_2C(O)$, $C(O)CH_2$, $C(O)NH$, $NHC(O)$, $NHC(O)NH$, $C(O)NHS(O)_2$, $CH_2S(O)_2$, $S(O)_2(CH_2)$, $SO_2NH$, and $NHSO_2$, provided that $G_1$ does not form a N—S, $NCH_2N$, $NCH_2O$, or $NCH_2S$ bond with either group to which it is attached;

A is selected from indolinyl, phenyl, pyridyl, and pyrimidyl, and is substituted with 0-2 $R^4$;

B is

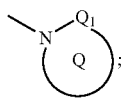

provided that Z and B are attached to different atoms on A;

provided that B is other than triazolone, quinolone, or isoquinolone, wherein the triazolone, quinolone, and isoquinolone groups are substituted or unsubstituted;

$Q_1$ is selected from C=O and $SO_2$;

ring Q is a 6-7 membered ring consisting of, in addition to the N-$Q_1$ group shown, carbon atoms and 0-1 heteroatoms selected from $NR^{4c}$, O, S, S(O), and $S(O)_2$, wherein: 0-2 double bonds are present within the ring and the ring is substituted with 0-2 $R^{4a}$;

alternatively, ring Q is a 5-7 membered ring to which another ring is fused, wherein: the 5-7 membered ring consists of, in addition to the shown amide group, carbon atoms and 0-1 heteroatoms selected from $NR^{4c}$, O, S, S(O), and $S(O)_2$ and 0-1 double bonds are present within the ring;

the fusion ring is phenyl;

ring Q, which includes the 5-7 membered ring and the fusion ring, is substituted with 0-2$R^{4a}$;

$R^{1a}$ is selected from H, $R^{1b}$, $C(CH_3)_2R^{1b}$, and $CH_2R^{1b}$, provided that $R^{1a}$ forms other than an N-halo, N—S, or N—CN bond;

$R^{1b}$ is selected from $CH_3$, $CH_2CH_3$, F, Cl, Br, —CN, $CF_3$, $OR^2$, $NR^2R^{2a}$, $C(O)R^{2b}$, $CO_2R^{2b}$, $CO_2R^{2a}$, $S(O)_pR^2$, $C(O)NR^2R^{2a}$, $SO_2NR^2R^{2a}$, $NR^2SO_2R^2$, and 5-6 membered aromatic heterocycle consisting of carbon atoms and from 1-4 heteroatoms selected from the group consisting of N, O, and $S(O)_p$, and substituted with 0-2 $R^{4b}$, provided that $R^{1b}$ forms other than an O—O, N-halo, N—S, or N—CN bond;

$R^2$, at each occurrence, is selected from H, $CH_3$, $CH_2CH_3$, $CH_2CH_2CH_3$, $CH(CH_3)_2$, phenyl substituted with 0-1 $R^{4b}$, benzyl substituted with 0-1 $R^{4b}$, and 5-6 membered aromatic heterocycle consisting of: carbon atoms and 1-4 heteroatoms selected from the group consisting of N, O, and $S(O)_p$, and substituted with 0-1 $R^{4b}$;

$R^{2a}$, at each occurrence, is selected from H, $CH_3$, $CH_2CH_3$, $CH_2CH_2CH_3$, $CH(CH_3)_2$, benzyl, phenyl substituted with 0-1 $R^{4b}$, and 5-6 membered aromatic heterocycle consisting of: carbon atoms and 1-4 heteroatoms selected from the group consisting of N, O, and $S(O)_p$, and substituted with 0-1 $R^{4b}$;

alternatively, $R^2$ and $R^{2a}$, together with the atom to which they are attached, combine to form a 5 or 6 membered saturated, partially saturated or unsaturated ring substituted with 0-1 $R^{4b}$ and consisting of: 0-1 additional heteroatoms selected from the group consisting of N, O, and $S(O)_p$;

$R^{2b}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0-1 $R^{4b}$, and 5-6 membered aromatic heterocycle consisting of: carbon atoms and 1-4 heteroatoms selected from the group consisting of N, O, and $S(O)_p$, and substituted with 0-1 $R^{4b}$;

$R^{2c}$, at each occurrence, is selected from OH, $OCH_3$, $OCH_2CH_3$, $OCH_2CH_2CH_3$, $OCH(CH_3)_2$, $CH_3$, $CH_2CH_3$, $CH_2CH_2CH_3$, $CH(CH_3)_2$, benzyl, phenyl substituted with 0-1 $R^{4b}$, and 5-6 membered aromatic heterocycle containing from 1-4 heteroatoms selected from the group consisting of N, O, and $S(O)_p$, and substituted with 0-1 $R^{4b}$;

$R^4$, at each occurrence, is selected from OH, $OR^2$, $CH_2OR^2$, $(CH_2)_2OR^2$, F, Br, Cl, I, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $NR^2R^{2a}$, $CH_2NR^2R^{2a}$, $(CH_2)_2NR^2R^{2a}$, $CF_3$, and $CF_2CF_3$;

$R^{4a}$, at each occurrence, is selected from H, =O, $CH_2OR^2$, $OR^2$, F, Br, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $CH_2NR^2R^{2a}$, $NR^2R^{2a}$, $C(O)R^{2c}$, $NR^2C(O)R^{2b}$, $C(O)NR^2R^{2a}$, $SO_2NR^2R^{2a}$, and $CF_3$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, and $CF_3$;

$R^{4c}$, at each occurrence, is selected from H, $CH_3$, $CH_2CH_3$, phenyl substituted with 0-1 $R^5$, and benzyl substituted with 0-1 $R^5$;

$R^5$, at each occurrence, is selected from H, =O, $CH_3$, $CH_2CH_3$, $CH_2CH_2CH_3$, $CH(CH_3)_2$, $OR^3$, $CH_2OR^3$, F, Cl, —CN, $NO_2$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_p$—$C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[12] In another preferred embodiment, the present invention provides a novel compound, wherein the compound is selected from:

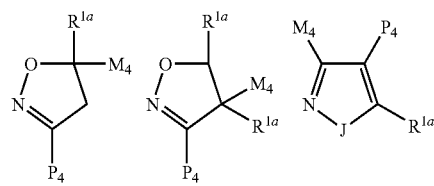

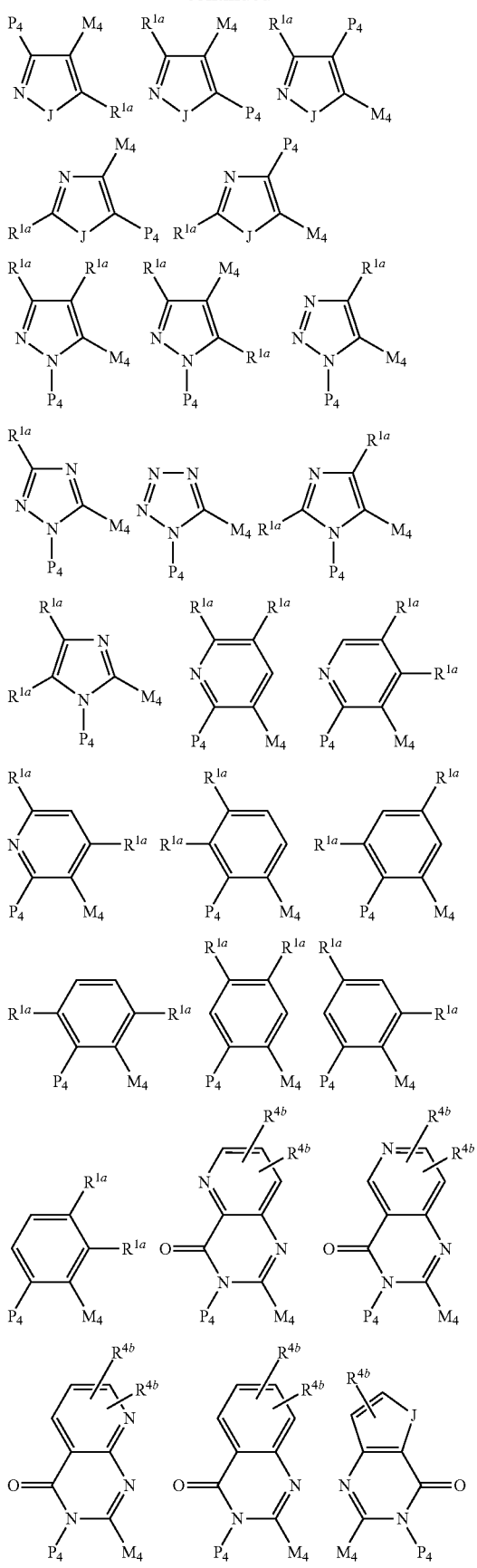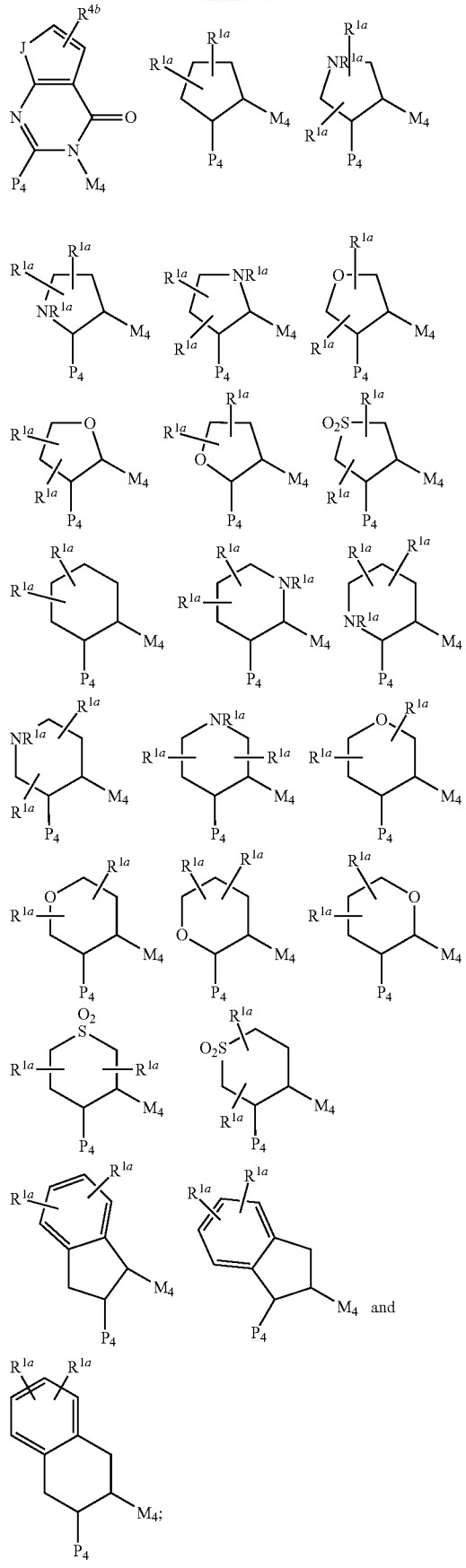

J is selected from O, S, NH, and $NR^{1a}$;
$P_4$ is $-G_1-G$;
$M_4$ is $-Z-A-B$;
G is selected from:
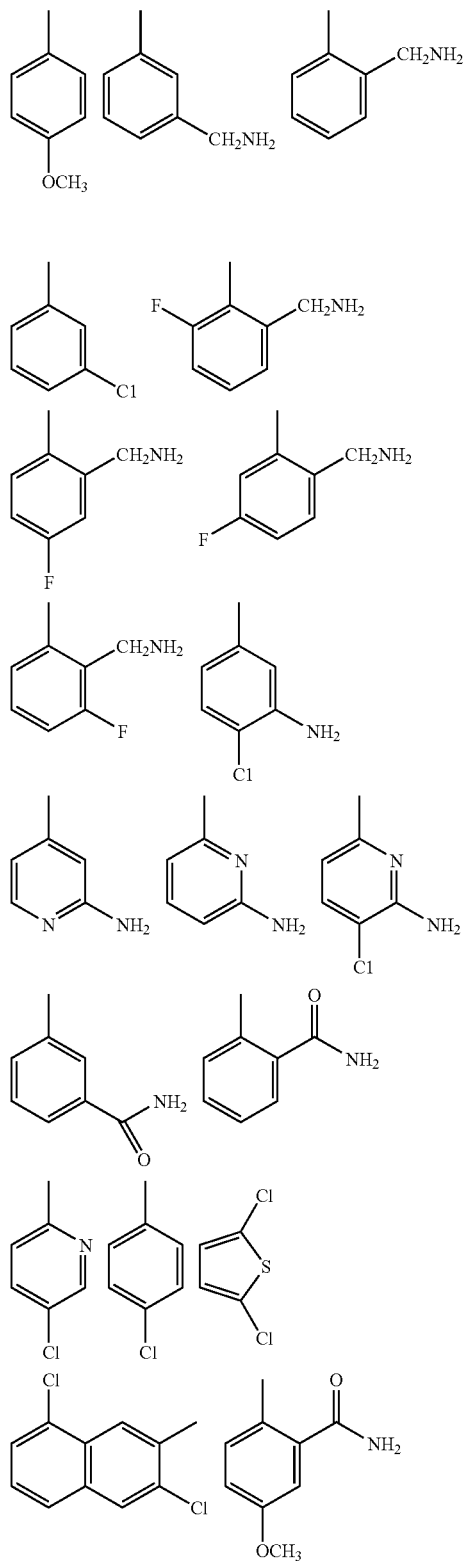
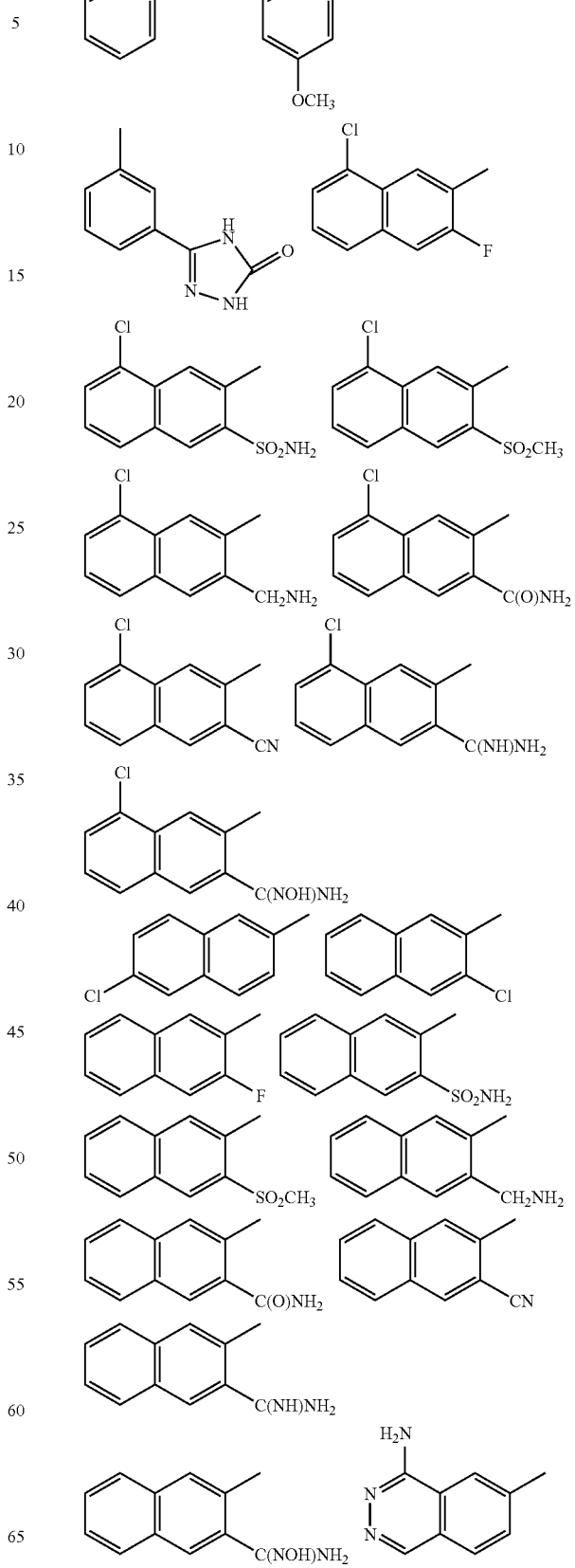

-continued

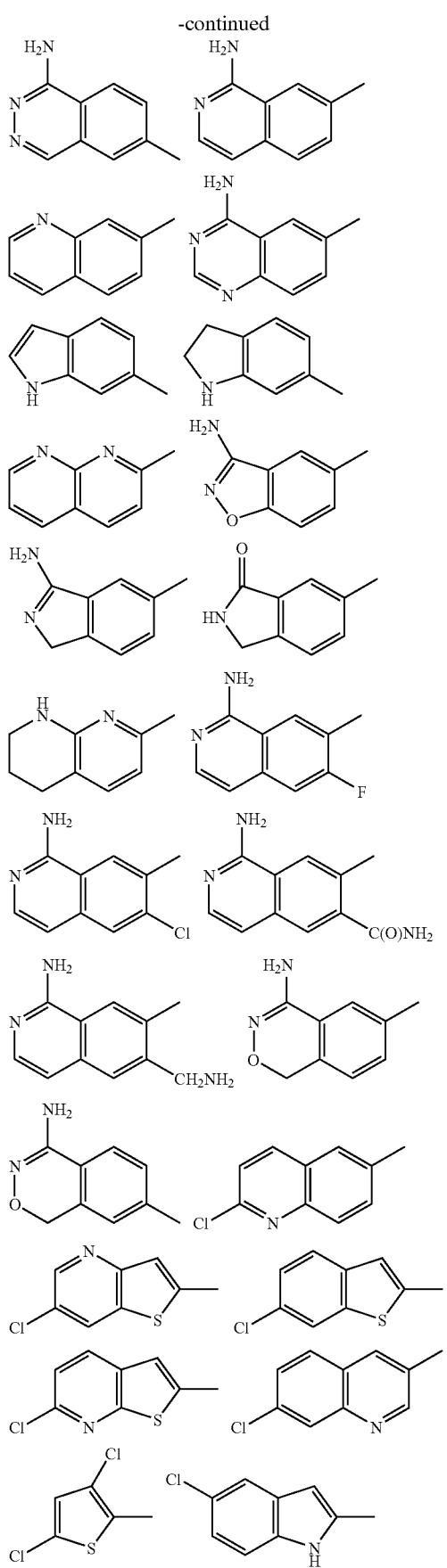

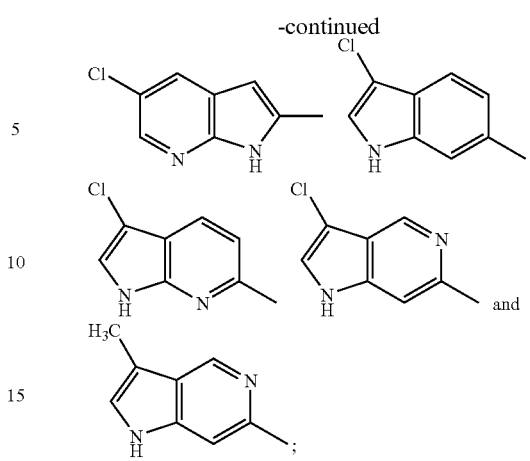

G₁ is absent or is selected from CH₂NH, NHCH₂, CH₂C(O), C(O)CH₂, C(O)NH, NHC(O), NHC(O)NH, CH₂S(O)₂, S(O)₂(CH₂), SO₂NH, and NHSO₂, provided that G₁ does not form a N—S, NCH₂N, NCH₂O, or NCH₂S bond with either group to which it is attached;

A is selected from the group: indolinyl, phenyl, 2-pyridyl, 3-pyridyl, 2-pyrimidyl, 2-Cl-phenyl, 3-Cl-phenyl, 2-F-phenyl, 3-F-phenyl, 2-methylphenyl, 2-aminophenyl, and 2-methoxyphenyl;

B is attached to a different atom on A than M and is selected from the group:

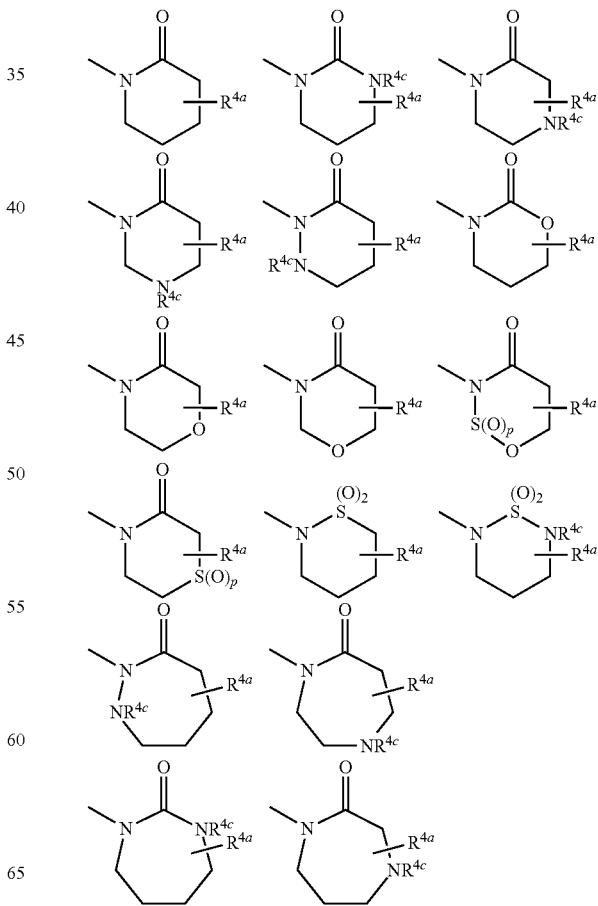

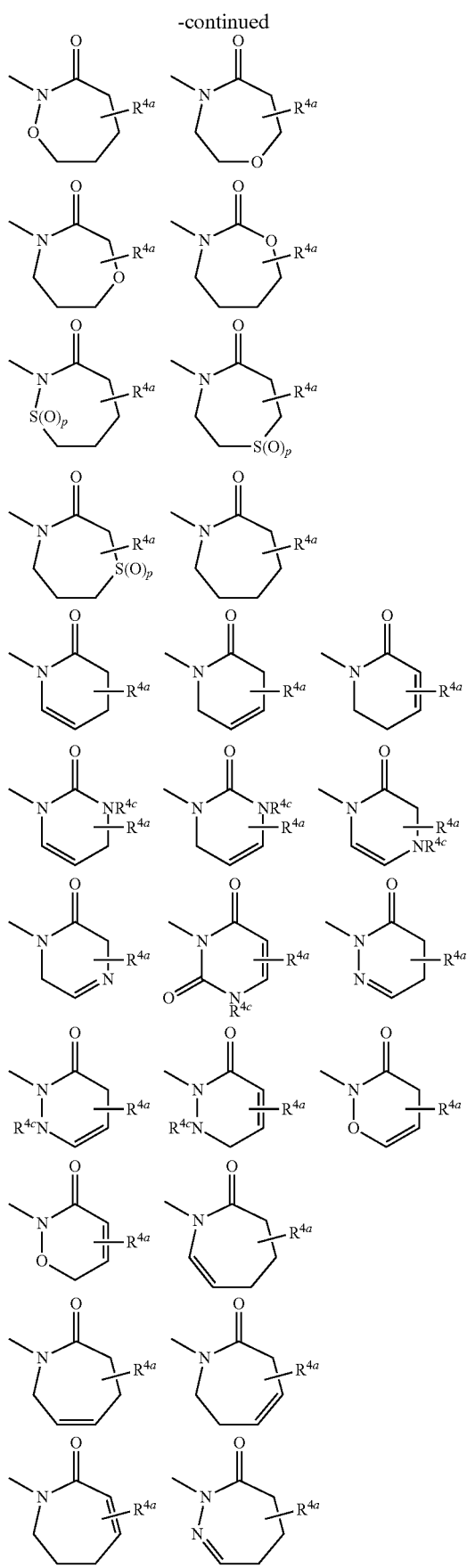
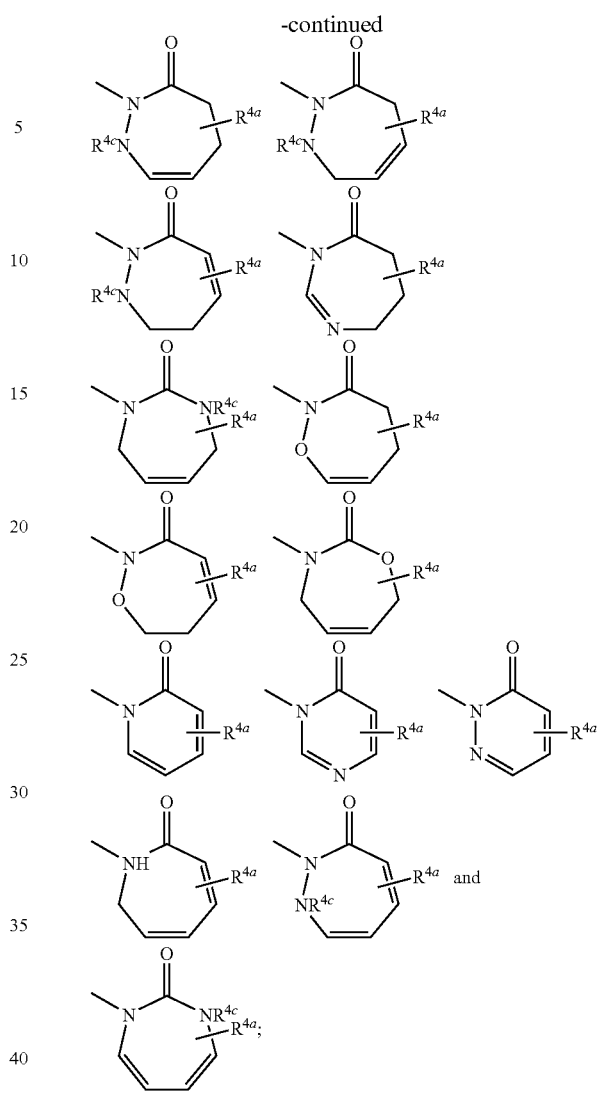

$R^{1a}$ is selected from H, $CH_3$, $CH_2CH_3$, $CH_2CH_2CH_3$, $CH_2F$, $CH_2Cl$, Br, $CH_2Br$, —CN, $CH_2CN$, $CF_3$, $CH_2CF_3$, $OCH_3$, $CH_2OH$, $C(CH_3)_2OH$, $CH_2OCH_3$, $NH_2$, $CH_2NH_2$, $NHCH_3$, $CH_2NHCH_3$, $N(CH_3)_2$, $CH_2N(CH_3)_2$, $CO_2H$, $COCH_3$, $CO_2CH_3$, $CH_2CO_2CH_3$, $SCH_3$, $CH_2SCH_3$, $S(O)CH_3$, $CH_2S(O)CH_3$, $S(O)_2CH_3$, $CH_2S(O)_2CH_3$, $C(O)NH_2$, $CH_2C(O)NH_2$, $SO_2NH_2$, $CH_2SO_2NH_2$, $NHSO_2CH_3$, $CH_2NHSO_2CH_3$, pyridin-2-yl, pyridin-3-yl, pyridin-4-yl, pyridin-2-yl-N-oxide, pyridin-3-yl-N-oxide, pyridin-4-yl-N-oxide, imidazol-1-yl, $CH_2$-imidazol-1-yl, 4-methyl-oxazol-2-yl, 4-N,N-dimethylaminomethyl-oxazol-2-yl, 1,2,3,4-tetrazol-1-yl, 1,2,3,4-tetrazol-5-yl, $CH_2$-1,2,3,4-tetrazol-1-yl, and $CH_2$-1,2,3,4-tetrazol-5-yl;

$R^2$, at each occurrence, is selected from H, $CH_3$, $CH_2CH_3$, $CH_2CH_2CH_3$, $CH(CH_3)_2$, phenyl substituted with 0-1 $R^{4b}$, benzyl substituted with 0-1 $R^{4b}$, and 5 membered aromatic heterocycle consisting of: carbon atoms and 1-4 heteroatoms selected from the group consisting of N, O, and $S(O)_p$, and substituted with 0-1 $R^{4b}$;

$R^{2a}$, at each occurrence, is selected from H, $CH_3$, and $CH_2CH_3$;

alternatively, $R^2$ and $R^{2a}$, together with the atom to which they are attached, combine to form a 5 or 6 membered saturated, partially saturated or unsaturated ring substituted with 0-1 $R^{4b}$ and consisting of: 0-1 additional heteroatoms selected from the group consisting of N, O, and $S(O)_p$;

$R^{2b}$, at each occurrence, is selected from $OCH_3$, $OCH_2CH_3$, $CH_3$, and $CH_2CH_3$;

$R^{2c}$, at each occurrence, is selected from OH, $OCH_3$, $OCH_2CH_3$, $CH_3$, and $CH_2CH_3$;

$R^{4a}$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, and $C(CH_3)_3$;

$R^{4b}$, at each occurrence, is selected from H, =O, $OR^3$, $CH_2OR^3$, F, Cl, $CH_3$, $CH_2CH_3$, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$-phenyl, $S(O)_2CH_3$, $S(O)_2$-phenyl, and $CF_3$;

$R^5$, at each occurrence, is selected from H, =O, $CH_3$, $CH_2CH_3$, $OR^3$, $CH_2OR^3$, F, Cl, $NR^3R^{3a}$, $CH_2NR^3R^{3a}$, $C(O)R^3$, $C(O)OR^{3c}$, $NR^3C(O)R^{3a}$, $C(O)NR^3R^{3a}$, $SO_2NR^3R^{3a}$, $NR^3SO_2$—$C_{1-4}$ alkyl, $NR^3SO_2$-phenyl, $S(O)_2$—$CH_3$, $S(O)_2$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $NR^2R^{2a}$, $CH_2NR^2R^{2a}$, $C(O)R^{2b}$, $CH_2C(O)R^{2b}$, $NR^2C(O)R^{2b}$, and $SO_2NR^2R^{2a}$.

[13] In another preferred embodiment, the present invention provides a novel compound, wherein the compound is selected from:

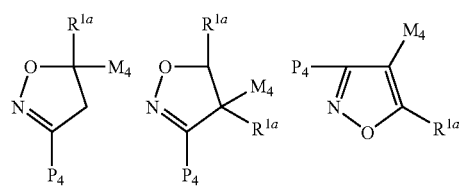

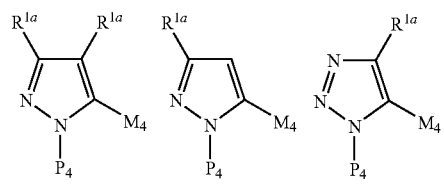

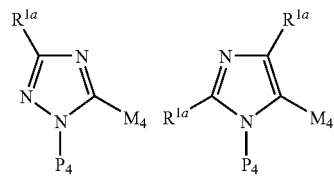

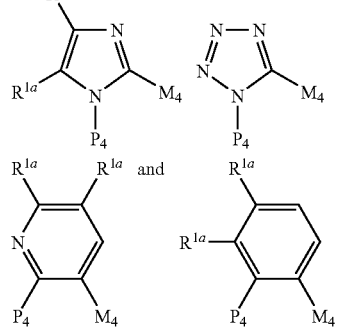

G is selected from:

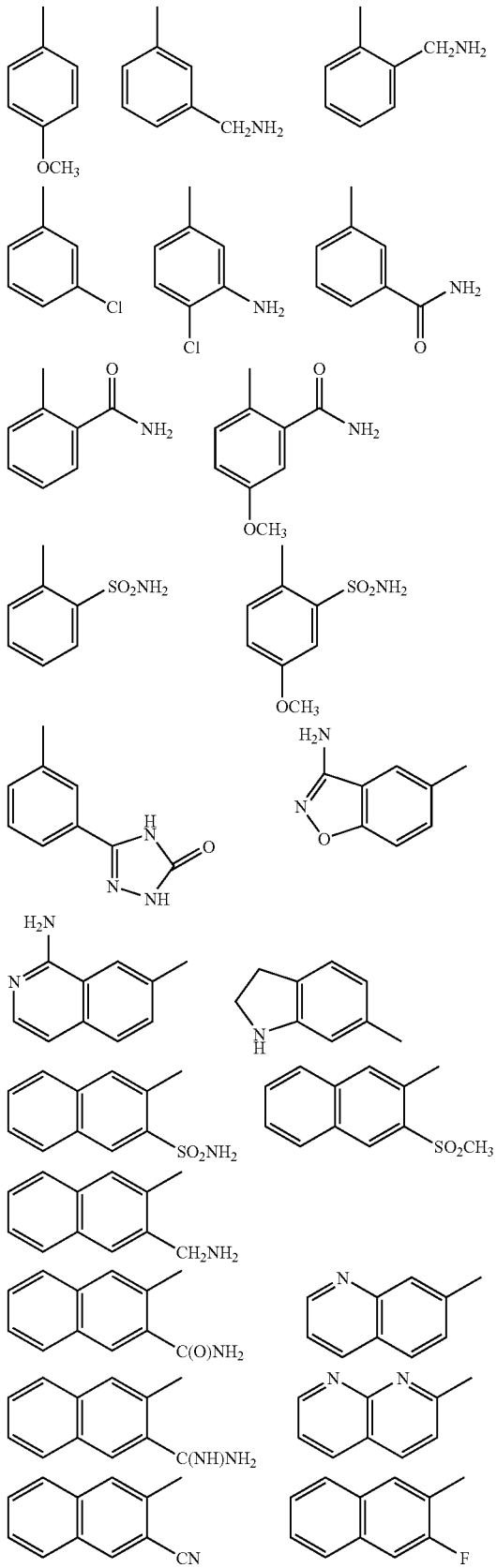

103
-continued
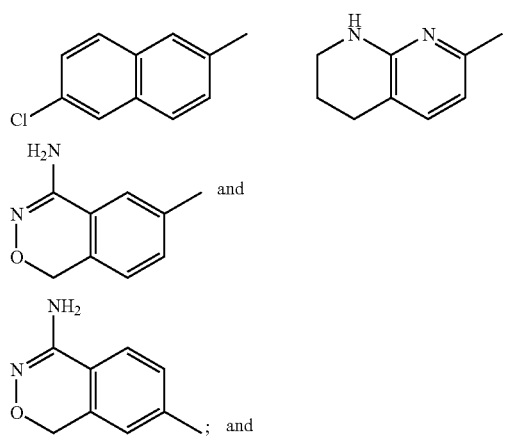
A-B is selected from:
104
-continued
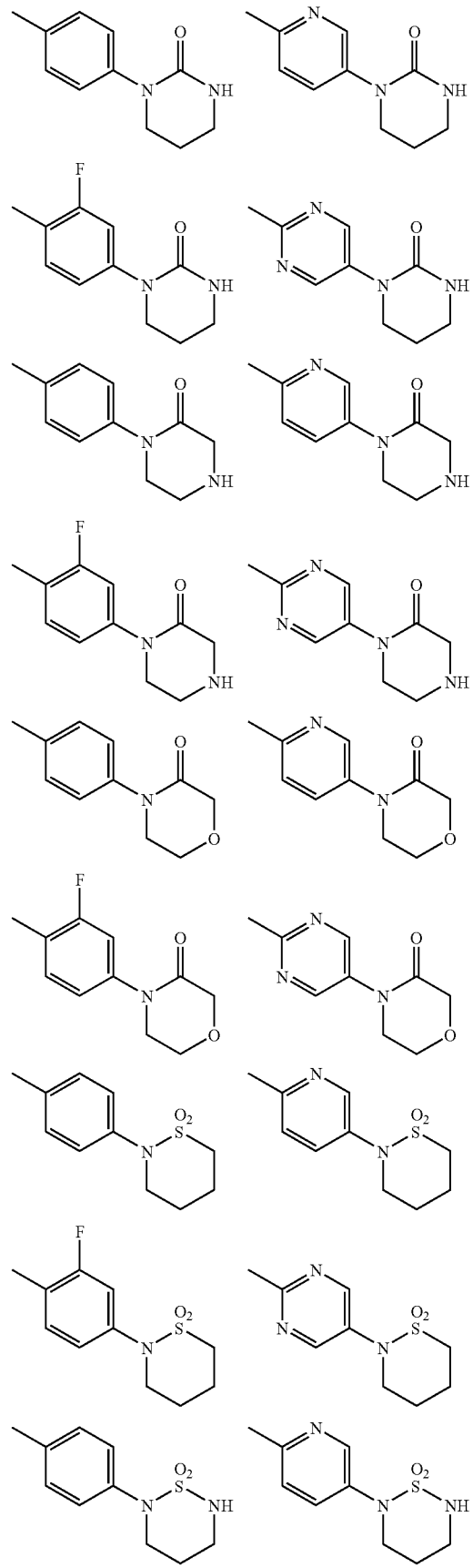

-continued

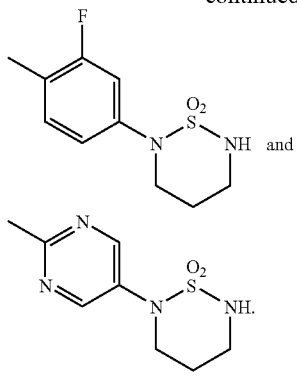

[14] In another preferred embodiment, the present invention provides a novel compound, wherein the compound is selected from:

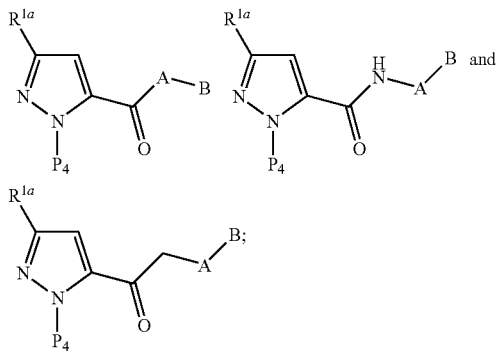

P$_4$ is -G; and
A-B is selected from:

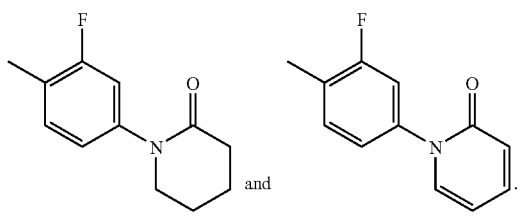

[15] In another preferred embodiment, the present invention provides a novel compound, selected from the group:
1-(3-amino-1,2-benzisoxazol-5-yl)-5-{[5-(2-oxo-1-piperidinyl)-2,3-dihydro-1H-indol-1-yl]carbonyl}-1H-pyrazole-3-carboxamide;
1-(3-amino-1,2-benzisoxazol-5-yl)-5-{[6-(2-oxo-1-piperidinyl)-2,3-dihydro-1H-indol-1-yl]carbonyl}-1H-pyrazole-3-carboxamide;
1-(3-amino-1,2-benzisoxazol-5-yl)-5-{[5-(2-oxo-hexahydro-1H-azepin-1-yl)-2,3-dihydro-1H-indol-1-yl]carbonyl}-1H-pyrazole-3-carboxamide;
1-(3-amino-1,2-benzisoxazol-5-yl)-5-{[6-(2-oxo-hexahydro-1H-azepin-1-yl)-2,3-dihydro-1H-indol-1-yl]carbonyl}-1H-pyrazole-3-carboxamide;
2-[(4-chlorobenzoyl)amino]-N-[4-(2-oxo-1-piperidinyl)phenyl]benzamide;
2-[(4-chlorobenzoyl)amino]-N-[4-(2-oxo-1(2H)-pyridinyl)phenyl]benzamide;
2-[(4-chlorobenzoyl)amino]-N-[4-(2-oxotetrahydro-1(2H)-pyrimidinyl)phenyl]benzamide;
5-chloro-N-[2-({[4-(2-oxo-1-piperidinyl)phenyl]amino}carbonyl)phenyl]-2-pyridinecarboxamide;
5-chloro-N-[2-({[4-(2-oxo-1(2H)-pyridinyl)phenyl]amino}carbonyl)phenyl]-2-pyridinecarboxamide;
5-chloro-N-[2-({[4-(2-oxotetrahydro-1(2H)-pyrimidinyl)phenyl]amino}carbonyl)phenyl]-2-pyridinecarboxamide;
4-chloro-2-[(4-chlorobenzoyl)amino]-N-[4-(2-oxo-1-piperidinyl)phenyl]benzamide;
4-chloro-2-[(4-chlorobenzoyl)amino]-N-[4-(2-oxo-1(2H)-pyridinyl)phenyl]benzamide;
4-chloro-2-[(4-chlorobenzoyl)amino]-N-[4-(2-oxotetrahydro-1(2H)-pyrimidinyl)phenyl]benzamide;
2-[(4-chlorobenzoyl)amino]-4-[(methylsulfonyl)amino]-N-[4-(2-oxo-1-piperidinyl)phenyl]benzamide;
2-[(4-chlorobenzoyl)amino]-4-[(methylsulfonyl)amino]-N-[4-(2-oxo-1(2H)-pyridinyl)phenyl]benzamide;
2-[(4-chlorobenzoyl)amino]-4-[(methylsulfonyl)amino]-N-[4-(2-oxotetrahydro-1(2H)-pyrimidinyl)phenyl]benzamide;
5-chloro-N-[5-[(methylsulfonyl)amino]-2-({[4-(2-oxo-1-piperidinyl)phenyl]amino}carbonyl)phenyl]-2-pyridinecarboxamide;
2-[(4-chlorobenzoyl)amino]-N-[4-(2-oxo-1-piperidinyl)phenyl]nicotinamide;
3-[(4-chlorobenzoyl)amino]-N-[4-(2-oxo-1-piperidinyl)phenyl]isonicotinamide;
4-[(4-chlorobenzoyl)amino]-N-[4-(2-oxo-1-piperidinyl)phenyl]nicotinamide;
5-chloro-N-[3-({[4-(2-oxo-1-piperidinyl)phenyl]amino}carbonyl)-4-pyridinyl]-2-pyridinecarboxamide;
5-chloro-N-[3-({[4-(2-oxo-1(2H)-pyridinyl)phenyl]amino}carbonyl)-4-pyridinyl]-2-pyridinecarboxamide;
5-chloro-N-[5-chloro-3-methoxy-2-({[4-(2-oxo-1(2H)-pyridinyl)phenyl]amino}carbonyl)phenyl]-2-pyridinecarboxamide;
5-chloro-N-[5-chloro-3-methoxy-2-({[4-(2-oxo-1-piperidinyl)phenyl]amino}carbonyl)phenyl]-2-pyridinecarboxamide;
methyl 2-[2-fluoro-4-(2-oxo-1(2H)-pyridinyl)phenyl]-3-[1-(4-methoxyphenyl)-3-(trifluoromethyl)-1H-pyrazol-5-yl]-3-oxopropanoate;
1-(3-fluoro-4-{2-[1-(4-methoxyphenyl)-3-(trifluoromethyl)-1H-pyrazole-5-yl]-2-oxoethyl}phenyl)-2(1H)-pyridinone;
1-(4-{2-[1-(3-amino-1,2-benzisoxazol-5-yl)-3-(trifluoromethyl)-1H-pyrazol-5-yl]-2-oxoethyl}-3-fluorophenyl)-2(1H)-pyridinone;
5-{[2-fluoro-4-(2-oxo-1(2H)-pyridinyl)phenyl]acetyl}-1-(4-methoxyphenyl)-1H-pyrazole-3-carboxamide;
1-(3-amino-1,2-benzisoxazol-5-yl)-5-{[5-(2-oxo-1(2H)-pyridinyl)-2,3-dihydro-1H-indol-1-yl]carbonyl}-1H-pyrazole-3-carboxamide;
5-chloro-N-(5-chloropyridin-2-yl)-2-({4-[(2-oxo-piperidine)-1-yl]benzoyl}amino)benzamide;
5-chloro-N-(5-chloropyridin-2-yl)-2-({4-[(2-oxo-pyridin)-1-yl]benzoyl}amino)benzamide;
N-(5-chloropyridin-2-yl)-2-({4-[(2-oxo-piperidine)-1-yl]benzoyl}amino)-5-methoxybenzamide;
N-(5-chloropyridin-2-yl)-2-({4-[(2-oxo-pyridin)-1-yl]benzoyl}amino)-5-methoxybenzamide;
N-(5-chloropyridin-2-yl)-2-({4-[(2-oxo-piperidin)-1-yl]benzoyl}amino)-5-methylbenzamide;

N-(5-chloropyridin-2-yl)-2-({4-[(2-oxo-pyridin)-1-yl]
benzoyl}amino)-5-methylbenzamide;
2-(5-chloro-pyridin-2-yl)-7-methoxy-3-[4-(2-oxo-piperidin-
1-yl)-phenyl]-2H-isoquinolin-1-one;
2-(5-chloro-pyridin-2-yl)-7-methoxy-3-[4-(2-oxo-pyridin-
1-yl)-phenyl]-2H-isoquinolin-1-one;
5-chloro-N-(5-chloropyridin-2-yl)-3-methoxy-2-[4-(2-ox-
opiperidin-1-yl)-benzoylamino]benzamide;
5-chloro-N-(5-chloropyridin-2-yl)-3-methoxy-2-[4-(2-oxo-
2H-pyridin-1-yl)-benzoylamino]benzamide;
3-chloro-N-(1,2-cis-2-{[4-(2-oxopyridin-1(2H)-yl)benzoyl]
amino}cyclohexyl)-1H-indole-6-carboxamide;
5-chloro-N-(1,2-cis-2-{[4-(2-oxopyridin-1(2H)-yl)benzoyl]
amino}cyclohexyl)-1H-indole-2-carboxamide;
5-chloro-N-(1,2-cis-2-{[4-(2-oxopyridin-1(2H)-yl)benzoyl]
amino}cyclohexyl)thiophene-2-carboxamide;
5-chloro-N-(1,2-cis-2-{[4-(2-oxopyrazin-1(2H)-yl)benzoyl]
amino}cyclohexyl)thiophene-2-carboxamide;
5-chloro-N-(1,2-cis-2-{[4-(2-oxopyrazin-1(2H)-yl)benzoyl]
amino}cyclohexyl)-1H-indole-2-carboxamide;
3-chloro-N-(1,2-cis-2-{[4-(2-oxopyrazin-1(2H)-yl)benzoyl]
amino}cyclohexyl)-1H-indole-6-carboxamide;
5-chloro-N-(1,2-cis-2-{[4-(2-oxopiperidin-1-yl)benzoyl]
amino}cyclohexyl)thiophene-2-carboxamide;
5-chloro-N-(1,2-cis-2-{[4-(2-oxopiperidin-1-yl)benzoyl]
amino}cyclohexyl)-1H-indole-2-carboxamide;
3-chloro-N-(1,2-cis-2-{[4-(2-oxopiperidin-1-yl)benzoyl]
amino}cyclohexyl)-1H-indole-6-carboxamide;
3-chloro-N-(2-{[4-(2-oxopyridin-1(2H)-yl)benzoyl]
amino}cyclohexyl)-1H-indole-6-carboxamide;
3-chloro-N-(2-{[4-(2-oxopyrazin-1(2H)-yl)benzoyl]
amino}cyclohexyl)-1H-indole-6-carboxamide;
3-chloro-N-(2-{[4-(2-oxopiperidin-1-yl)benzoyl]
amino}cyclohexyl)-1H-indole-6-carboxamide;
3-chloro-N-(2-{[4-(3-oxomorpholin-4-yl)benzoyl]
amino}cyclohexyl)-1H-indole-6-carboxamide;
3-chloro-N-(2-{[4-(2-oxopiperazin-1-yl)benzoyl]
amino}cyclohexyl)-1H-indole-6-carboxamide;
3-chloro-N-(2-{[4-(2-oxo-1,3-oxazinan-3-yl)benzoyl]
amino}cyclohexyl)-1H-indole-6-carboxamide;
3-chloro-N-(3-{[4-(2-oxopiperidin-1-yl)benzoyl]
amino}tetrahydro-2H-pyran-4-yl)-1H-indole-6-carboxa-
mide;
3-chloro-N-(4-{[4-(2-oxopiperidin-1-yl)benzoyl]
amino}tetrahydro-2H-pyran-3-yl)-1H-indole-6-carboxa-
mide;
3-chloro-N-(4-{[4-(2-oxopiperidin-1-yl)benzoyl]
amino}piperidin-3-yl)-1H-indole-6-carboxamide;
3-chloro-N-(3-{[4-(2-oxopiperidin-1-yl)benzoyl]
amino}piperidin-4-yl)-1H-indole-6-carboxamide;
3-chloro-N-(4-{[4-(2-oxopiperidin-1-yl)benzoyl]
amino}pyrrolidin-3-yl)-1H-indole-6-carboxamide;
3-chloro-N-(4-{[4-(2-oxopiperidin-1-yl)benzoyl]
amino}tetrahydrofuran-3-yl)-1H-indole-6-carboxamide;
3-chloro-N-(2-{[4-(2-oxopiperidin-1-yl)benzoyl]
amino}cyclopentyl)-1H-indole-6-carboxamide;
3-chloro-N-(1,1-dioxido-4-{[4-(2-oxopyridin-1(2H)-yl)
benzoyl]amino}tetrahydro-3-thienyl)-1H-indole-6-car-
boxamide;
3-chloro-N-(1,1-dioxido-4-{[4-(2-oxopyridin-1(2H)-yl)
benzoyl]amino}tetrahydro-2H-thiopyran-3-yl)-1H-in-
dole-6-carboxamide;
3-chloro-N-(1,1-dioxido-3-{[4-(2-oxopyridin-1(2H)-yl)
benzoyl]amino}tetrahydro-2H-thiopyran-4-yl)-1H-in-
dole-6-carboxamide;
N-(2-{[(3-chloro-1H-indol-6-yl)sulfonyl]
methyl}cyclohexyl)-4-(2-oxopiperidin-1-yl)benzamide;
N-(2-{[(6-chloro-2-naphthyl)sulfonyl]methyl}cyclohexyl)-
4-(2-oxopiperidin-1-yl)benzamide;
5-chloro-N-(2-{[4-(2-oxopiperidin-1-yl)benzoyl]
amino}cyclohexyl)thiophene-2-carboxamide;
5-chloro-N-(2-{[4-(2-oxopyridin-1(2H)-yl)benzoyl]
amino}cyclohexyl)thiophene-2-carboxamide;
5-chloro-N-(2-{[4-(2-oxopyrazin-1(2H)-yl)benzoyl]
amino}cyclohexyl)thiophene-2-carboxamide;
5-chloro-N-(2-{[4-(3-oxomorpholin-4-yl)benzoyl]
amino}cyclohexyl)thiophene-2-carboxamide;
5-chloro-N-(2-{[4-(2-oxopiperazin-1-yl)benzoyl]
amino}cyclohexyl)thiophene-2-carboxamide;
5-chloro-N-(2-{[4-(2-oxo-1,3-oxazinan-3-yl)benzoyl]
amino}cyclohexyl)thiophene-2-carboxamide;
5-chloro-N-(2-{[4-(2-oxopiperidin-1-yl)benzoyl]
amino}cyclopentyl)thiophene-2-carboxamide;
5-chloro-N-(2-{[4-(2-oxopyridin-1(2H)-yl)benzoyl]
amino}cyclopentyl)thiophene-2-carboxamide;
5-chloro-N-(2-{[4-(2-oxopiperidin-1-yl)benzoyl]
amino}cyclohexyl)-1H-indole-2-carboxamide;
5-chloro-N-(2-{[4-(2-oxopyridin-1(2H)-yl)benzoyl]
amino}cyclohexyl)-1H-indole-2-carboxamide;
5-chloro-N-(2-{[4-(2-oxopyrazin-1(2H)-yl)benzoyl]
amino}cyclohexyl)-1H-indole-2-carboxamide;
5-chloro-N-(2-{[4-(3-oxomorpholin-4-yl)benzoyl]
amino}cyclohexyl)-1H-indole-2-carboxamide;
5-chloro-N-(2-{[4-(2-oxopiperazin-1-yl)benzoyl]
amino}cyclohexyl)-1H-indole-2-carboxamide;
5-chloro-N-(2-{[4-(2-oxo-1,3-oxazinan-3-yl)benzoyl]
amino}cyclohexyl)-1H-indole-2-carboxamide;
5-chloro-N-(2-{[4-(2-oxopiperidin-1-yl)benzoyl]
amino}cyclopentyl)-1H-indole-2-carboxamide;
5-chloro-N-(2-{[4-(2-oxopyridin-1(2H)-yl)benzoyl]
amino}cyclopentyl)-1H-indole-2-carboxamide;
6-chloro-N-(2-{[4-(2-oxopyridin-1(2H)-yl)benzoyl]
amino}cyclohexyl)-2-naphthamide;
6-chloro-N-(2-{[4-(2-oxopiperazin-1-yl)benzoyl]
amino}cyclohexyl)-2-naphthamide;
6-chloro-N-(2-{[4-(2-oxopyridin-1(2H)-yl)benzoyl]
amino}cyclohexyl)-2-naphthamide;
6-chloro-N-(2-{[4-(2-oxo-1,3-oxazinan-3-yl)benzoyl]
amino}cyclohexyl)-2-naphthamide;
6-chloro-N-(2-{[4-(2-oxopiperidin-1-yl)benzoyl]
amino}cyclohexyl)-2-naphthamide;
6-chloro-N-(2-{[4-(3-oxomorpholin-4-yl)benzoyl]
amino}cyclohexyl)-2-naphthamide;
6-chloro-N-(2-{[4-(2-oxopyridin-1(2H)-yl)benzoyl]
amino}cyclopentyl)-2-naphthamide;
6-chloro-N-(2-{[4-(2-oxopiperidin-1-yl)benzoyl]
amino}cyclopentyl)-2-naphthamide;
2-chloro-N-(2-{[4-(2-oxopyridin-1(2H)-yl)benzoyl]
amino}cyclohexyl)quinoline-6-carboxamide;
2-chloro-N-(2-{[4-(2-oxopiperazin-1-yl)benzoyl]
amino}cyclohexyl)quinoline-6-carboxamide;
2-chloro-N-(2-{[4-(2-oxo-1,3-oxazinan-3-yl)benzoyl]
amino}cyclohexyl)quinoline-6-carboxamide;
2-chloro-N-(2-{[4-(2-oxopiperidin-1-yl)benzoyl]
amino}cyclohexyl)quinoline-6-carboxamide;
2-chloro-N-(2-{[4-(3-oxomorpholin-4-yl)benzoyl]
amino}cyclohexyl)quinoline-6-carboxamide;
2-chloro-N-(2-{[4-(2-oxopyridin-1(2H)-yl)benzoyl]
amino}pentyl)quinoline-6-carboxamide;
2-chloro-N-(2-{[4-(2-oxopyridin-1(2H)-yl)benzoyl]
amino}cyclopentyl)quinoline-6-carboxamide;
6-chloro-N-(2-{[4-(2-oxopyridin-1(2H)-yl)benzoyl]
amino}cyclohexyl)-1-benzothiophene-2-carboxamide;

6-chloro-N-(2-{[4-(2-oxopiperazin-1-yl)benzoyl]amino}cyclohexyl)-1-benzothiophene-2-carboxamide;
6-chloro-N-(2-{[4-(2-oxo-1,3-oxazinan-3-yl)benzoyl]amino}cyclohexyl)-1-benzothiophene-2-carboxamide;
6-chloro-N-(2-{[4-(2-oxopiperidin-1-yl)benzoyl]amino}cyclohexyl)-1-benzothiophene-2-carboxamide;
6-chloro-N-(2-{[4-(3-oxomorpholin-4-yl)benzoyl]amino}cyclohexyl)-1-benzothiophene-2-carboxamide;
6-chloro-N-(2-{[4-(2-oxopyridin-1(2H)-yl)benzoyl]amino}cyclopentyl)-1-benzothiophene-2-carboxamide;
6-chloro-N-(2-{[4-(2-oxopiperidin-1-yl)benzoyl]amino}cyclopentyl)-1-benzothiophene-2-carboxamide;
6-chloro-N-(2-{[4-(2-oxopyridin-1(2H)-yl)benzoyl]amino}cyclohexyl)thieno[2,3-b]pyridine-2-carboxamide;
6-chloro-N-(2-{[4-(2-oxopiperazin-1-yl)benzoyl]amino}cyclohexyl)thieno[2,3-b]pyridine-2-carboxamide;
6-chloro-N-(2-{[4-(2-oxo-1,3-oxazinan-3-yl)benzoyl]amino}cyclohexyl)thieno[2,3-b]pyridine-2-carboxamide;
6-chloro-N-(2-{[4-(2-oxopiperidin-1-yl)benzoyl]amino}cyclohexyl)thieno[2,3-b]pyridine-2-carboxamide;
6-chloro-N-(2-{[4-(3-oxomorpholin-4-yl)benzoyl]amino}cyclohexyl)thieno[2,3-b]pyridine-2-carboxamide;
6-chloro-N-(2-{[4-(2-oxopyridin-1(2H)-yl)benzoyl]amino}cyclopentyl)thieno[2,3-b]pyridine-2-carboxamide;
6-chloro-N-(2-{[4-(2-oxopiperidin-1-yl)benzoyl]amino}cyclopentyl)thieno[2,3-b]pyridine-2-carboxamide;
5-methoxy-N-(2-{[4-(2-oxopyridin-1(2H)-yl)benzoyl]amino}cyclohexyl)thiophene-2-carboxamide;
5-methoxy-N-(2-{[4-(2-oxopiperazin-1-yl)benzoyl]amino}cyclohexyl)thiophene-2-carboxamide;
5-methoxy-N-(2-{[4-(2-oxo-1,3-oxazinan-3-yl)benzoyl]amino}cyclohexyl)thiophene-2-carboxamide;
5-methoxy-N-(2-{[4-(2-oxopiperidin-1-yl)benzoyl]amino}cyclohexyl)thiophene-2-carboxamide;
5-methoxy-N-(2-{[4-(3-oxomorpholin-4-yl)benzoyl]amino}cyclohexyl)thiophene-2-carboxamide;
5-methoxy-N-(2-{[4-(2-oxopyridin-1(2H)-yl)benzoyl]amino}cyclopentyl)thiophene-2-carboxamide;
5-methoxy-N-(2-{[4-(2-oxopiperidin-1-yl)benzoyl]amino}cyclohexyl)thiophene-2-carboxamide;
4-methoxy-N-(2-{[4-(2-oxopyridin-1(2H)-yl)benzoyl]amino}cyclohexyl)benzamide;
4-methoxy-N-(2-{[4-(2-oxopiperazin-1-yl)benzoyl]amino}cyclohexyl)benzamide;
4-methoxy-N-(2-{[4-(2-oxo-1,3-oxazinan-3-yl)benzoyl]amino}cyclohexyl)benzamide;
4-methoxy-N-(2-{[4-(2-oxopiperidin-1-yl)benzoyl]amino}cyclohexyl)benzamide;
4-methoxy-N-(2-{[4-(3-oxomorpholin-4-yl)benzoyl]amino}cyclohexyl)benzamide;
4-methoxy-N-(2-{[4-(2-oxopyridin-1(2H)-yl)benzoyl]amino}cyclopentyl)benzamide;
4-methoxy-N-(2-{[4-(2-oxopiperidin-1-yl)benzoyl]amino}cyclopentyl)benzamide;
or a pharmaceutically acceptable salt form thereof.

In a preferred embodiment, when ring M is 1,2 substituted by $M_4$ and $P_4$, then either $G_1$ or Z is absent.

In another preferred embodiment, when ring M is 1,2 substituted by $M_4$ and $P_4$ and $G_1$ is $(CR^3R^{3a})_uNR^3(CR^3R^{3a})_w$ and u+w is 1, 2, 3, or 4, $(CR^3R^{3a})_uC(O)NR^3$ $(CR^3R^{3a})_w$, $(CR^3R^{3a})_uNR^3C(O)$ $(CR^3R^{3a})_w$, $(CR^3R^{3a})_uS(O)NR^3$ $(CR^3R^{3a})_w$, $(CR^3R^{3a})_uS(O)_2NR^3(CR^3R^{3a})_w$, or $(CR^3R^{3a})_uNR^3S(O)_2(CR^3R^{3a})_w$; then Z is other than $(CH_2)NR^3$, $NR^3(CH_2)$, $(CH_2)NR^3(CH_2)$, $(CH_2)(CH_2)NR^3$, $NR^3(CH_2)(CH_2)$, $(CH_2)_qC(O)NR^3(CH_2)_{q1}$, $(CH_2)_qNR^3C(O)(CH_2)_{q1}$, $(CH_2)_qSO_2NR^3(CH_2)_{q1}$, or $(CH_2)_qNR^3SO_2(CH_2)_{q1}$.

In another preferred embodiment, when ring M is 1,2 substituted by $M_4$ and $P_4$ and Z is $(CH_2)NR^3$, $NR^3(CH_2)$, $(CH_2)NR^3(CH_2)$, $(CH_2)(CH_2)NR^3$, $NR^3(CH_2)(CH_2)$, $(CH_2)_qC(O)NR^3(CH_2)_{q1}$, $(CH_2)_qNR^3C(O)(CH_2)_{q1}$, $(CH_2)_qSO_2NR^3(CH_2)_{q1}$, or $(CH_2)_qNR^3SO_2(CH_2)_{q1}$; then $G_1$ is other than $(CR^3R^{3a})_uNR^3(CR^3R^{3a})_w$ and u+w is 1, 2, 3, or 4, $(CR^3R^{3a})_uC(O)NR^3(CR^3R^{3a})_w$, $(CR^3R^{3a})_uNR^3C(O)(CR^3R^{3a})_w$, $(CR^3R^{3a})_uS(O)NR^3$ $(CR^3R^{3a})_w$, $(CR^3R^{3a})_uS(O)_2NR^3(CR^3R^{3a})_w$, or $(CR^3R^{3a})_uNR^3S(O)_2(CR^3R^{3a})_w$.

In another embodiment, the present invention provides a novel pharmaceutical composition, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of a thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used in combination with a second therapeutic agent to treat a thromboembolic disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides novel compounds as described above for use in therapy.

In another embodiment, the present invention provides the use of novel compounds as described above for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^6$) occurs more than one time in any constituent or formula for a compound, its definition at each occurrence is independent of its definition at every other occurrence. Thus, for example, if a group is shown to be substituted with 0-2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are amines on the compounds of this invention, these can be converted to amine N-oxides by treatment with an oxidizing agent (e.g., MCPBA and/or hydrogen peroxides) to afford other compounds of this invention. Thus, all shown and claimed amines are considered to cover both the shown amine and its N-oxide (N→O) derivative.

As used herein, "alkyl" is intended to include both branched and straight-chain saturated aliphatic hydrocarbon groups having the specified number of carbon atoms. $C_{1-6}$ alkyl, is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-6}$ alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$ Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, or unsaturated (aromatic). Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "heterocycle" or "heterocyclic group" is intended to mean a stable 5, 6, or 7-membered monocyclic or 7, 8, 9, or 10-membered bicyclic heterocyclic ring which is saturated, partially unsaturated or unsaturated (aromatic), and which consists of carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., N→O and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. It is preferred that the presently recited compounds do not contain a N-halo, $S(O)_2H$, or $S(O)H$ group.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talalay, *Adv. Enzyme Regul.* 1984, 22:27-55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

The synthesis of compounds of the present invention that involves the usage of intermediate A-B is accomplished via standard methods known to those skilled in the art. The general route that involves this type of methodology is outlined in Scheme 1.

Scheme 1

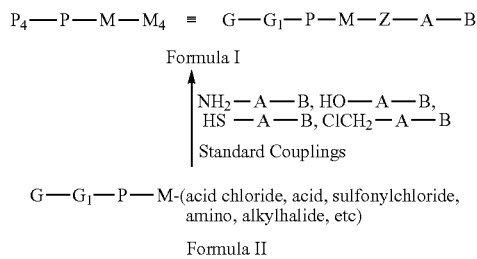

A-B intermediates can be obtained via Ullmann or Buchwald methodologies that are outlined in the schemes below.

Scheme 2

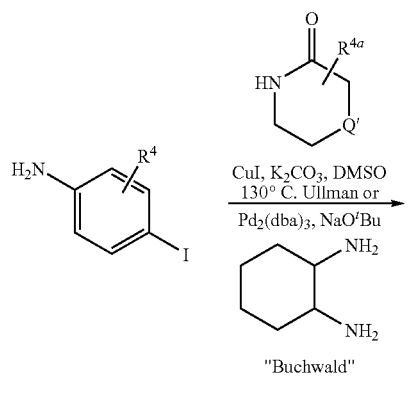

Intermediates A-B wherein the B group contains an oxidizable group can be obtained by oxidation, e.g. S to SO and SO$_2$. The pyridone analogs can also be prepared via the Ullmann methodology. The Ullmann coupling can also be applied to prepare urea analogs shown in Scheme 3.

Scheme 3

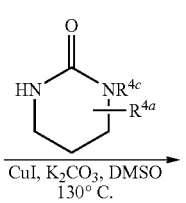

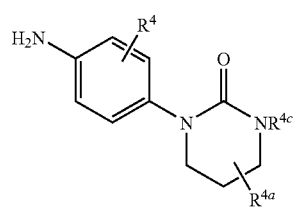

Piperidone A-B analogs can be prepared via the method outlined in Scheme 4.

Scheme 4

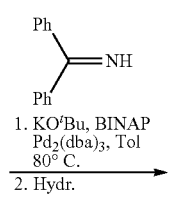

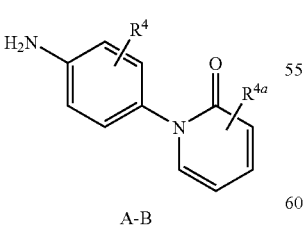

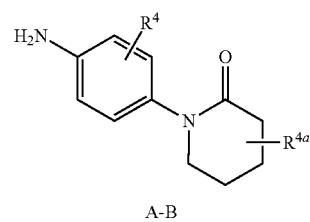

Aminopyridyl and aminopyrimidyl A-B analogs (see structures below) can also be prepared using routes similar to those of Scheme 2-4.

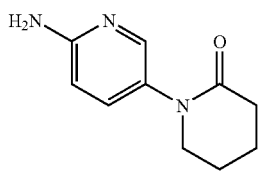

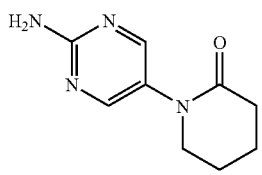

Piperidone A-B intermediates shown above can also be further elaborated to afford other compounds of the present invention by numerous methods known to those skilled in the art (e.g., see Scheme 5).

Scheme 5

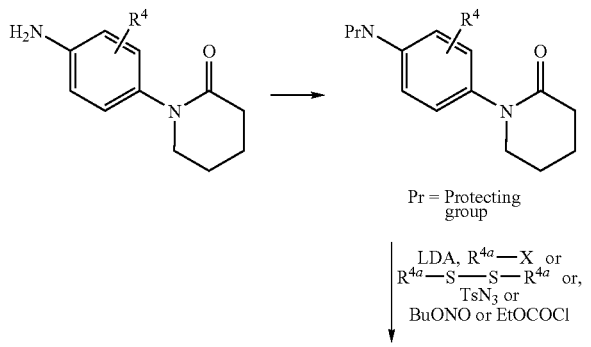

Pr = Protecting group

LDA, $R^{4a}$—X or
$R^{4a}$—S—S—$R^{4a}$ or,
$TsN_3$ or
BuONO or EtOCOCl

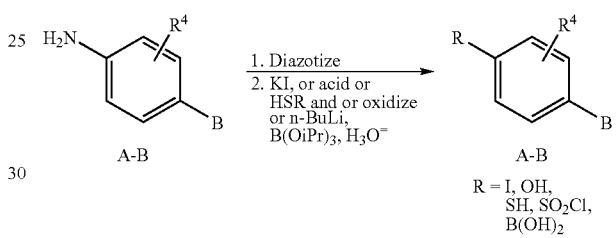

1. LDA, RSe—SeR
2. MCPBA
3. Heat

Additional A-B intermediates can be synthesized by the chemical manipulation of the amino functionality of the compounds described above (see Scheme 6).

Scheme 6

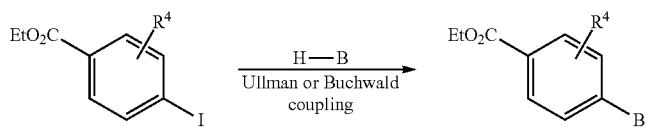

1. Diazotize
2. KI, or acid or HSR and or oxidize or n-BuLi, $B(OiPr)_3$, $H_3O^+$ R = I, OH, SH, $SO_2Cl$, $B(OH)_2$ Other possible A-B intermediates can be synthesized by the methods shown in Scheme 7. The iodo-ester intermediate can be subjected to the Ullmann and/or the Buchwald coupling methodologies to afford A-B intermediates. These intermediates in turn can be homologated via the Arndt Eistert methodology to afford other A-B intermediates. Alternatively, the ester functionality can be reduced to the alcohol that in turn can be converted to a variety of A-B intermediates by procedures known to those skilled in the art.

Scheme 7

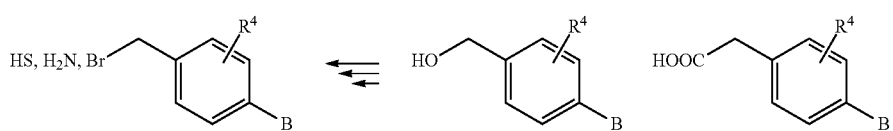

1. LiOH, THF/water
2. IBCF, $Et_3N$
3. $NaBH_4$, THF/water

1. LiOH, THF/water
2. Oxalyl chloride
3. Diazomethane, $Ag_2O$ water

Non-aromatic intermediates as shown in Scheme 8 can be synthesized via procedures known to those skilled in the art. These intermediates can than be further manipulated to incorporate $R^{4a}$ via procedures previously described.

Alternative non-aromatic intermediates can be synthesized via procedures known to those skilled in the art, e.g., see Scheme 9. These intermediates can also be further manipulated to incorporate $R^{4a}$ via procedures described previously. Further modifications of the ester functionality can be done via procedures described above.

Schemes 2-9 describe methods of preparing A-B intermediates that can then be coupled with other appropriate intermediates to form compounds of the present invention. The halogenated intermediates illustrated in the schemes shown above when subjected to the Ullmann or the Buchwald-Goldman coupling methodologies afford compounds of this invention.

In cases wherein an intermediate of the present invention has a reactive group, the Ullmann or the Buchwald-Goldman couplings are usually performed at an earlier stage of the synthesis. This intermediate may be modified later by those skilled in the art to afford compounds of the present invention (see Scheme 10).

Compounds of the present invention wherein the B subunit of the A-B substituent is a hetero substituted cyclic amide can also undergo an Ullmann or a Buchwald coupling to afford compounds of the present invention.

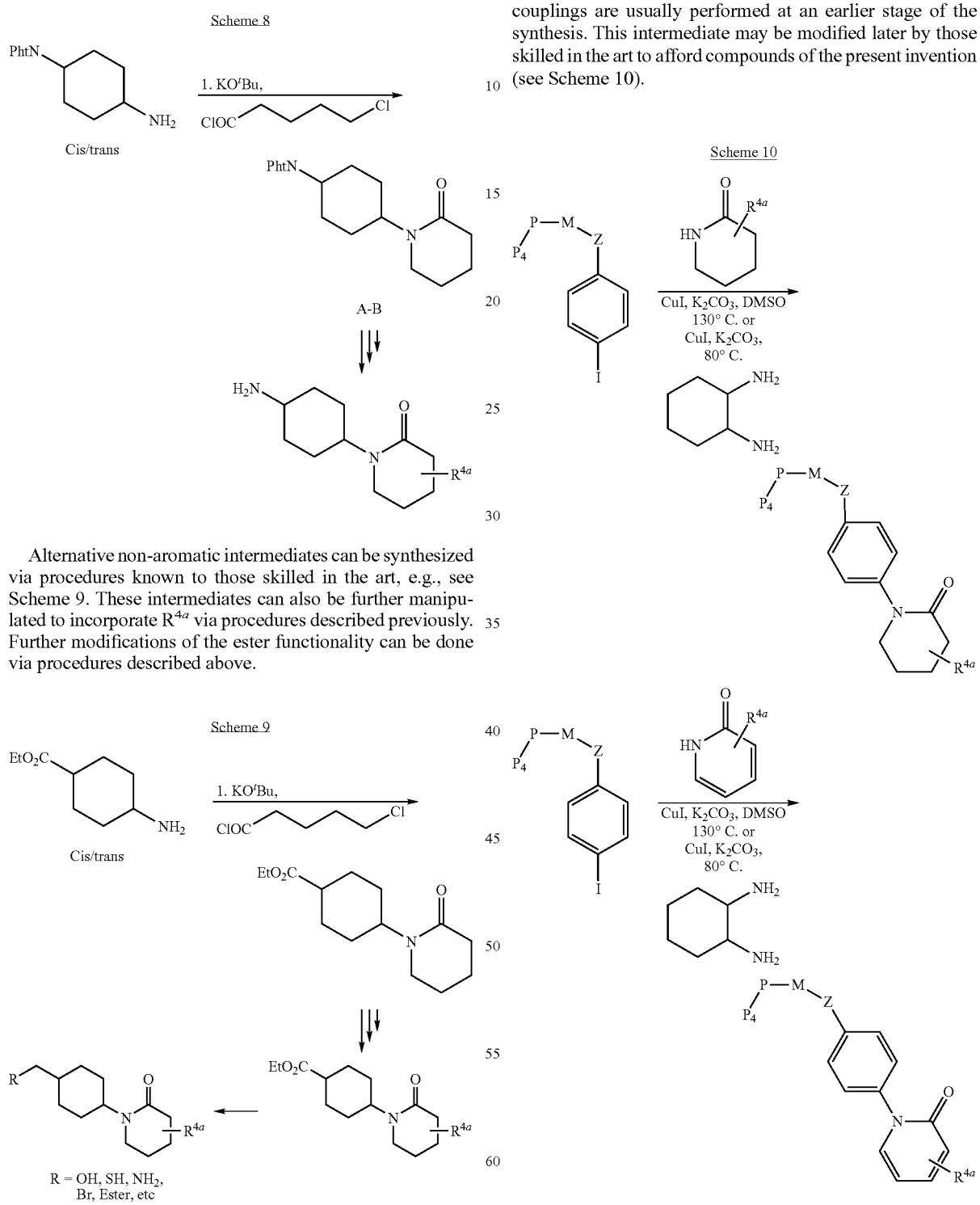

Scheme 11

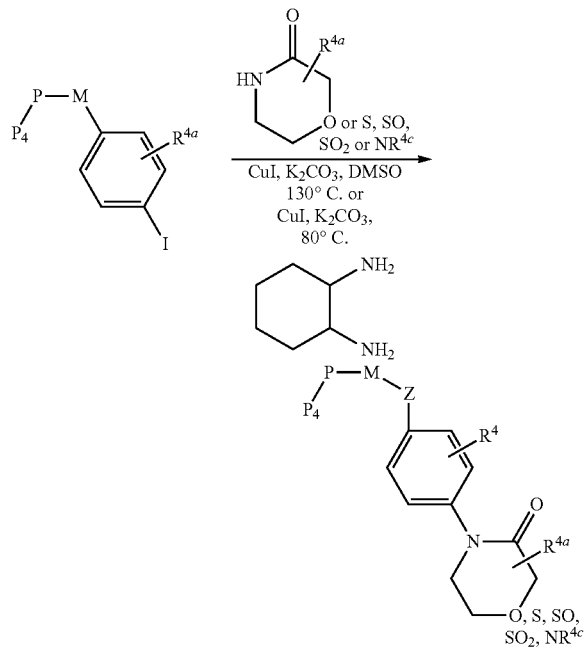

Likewise compounds of the present invention wherein B is a cyclic urea can also be prepared via the Ullmann or Buchwald methodology described in Scheme 12. Further elaboration by those skilled in the art would provide compounds of the present invention.

Scheme 12

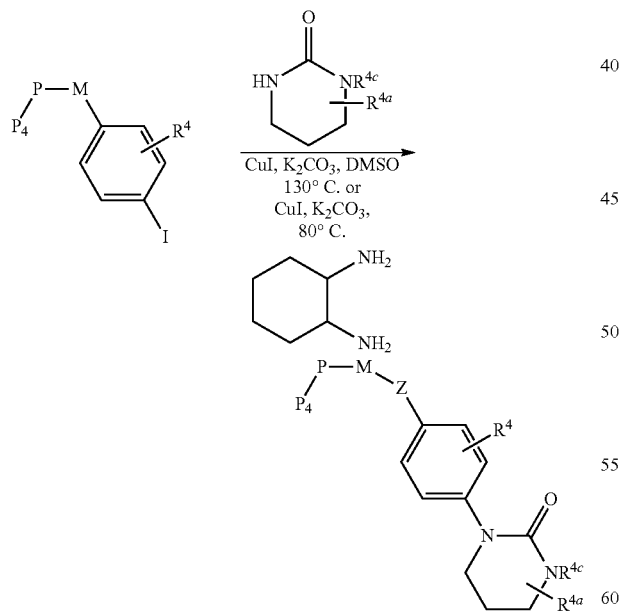

An alternate approach to compounds of the present invention wherein the B subunit of the A-B group of formula I is a bicycle is shown in Scheme 13. Further elaboration by those skilled in the art would provide compounds of the present invention.

Scheme 13

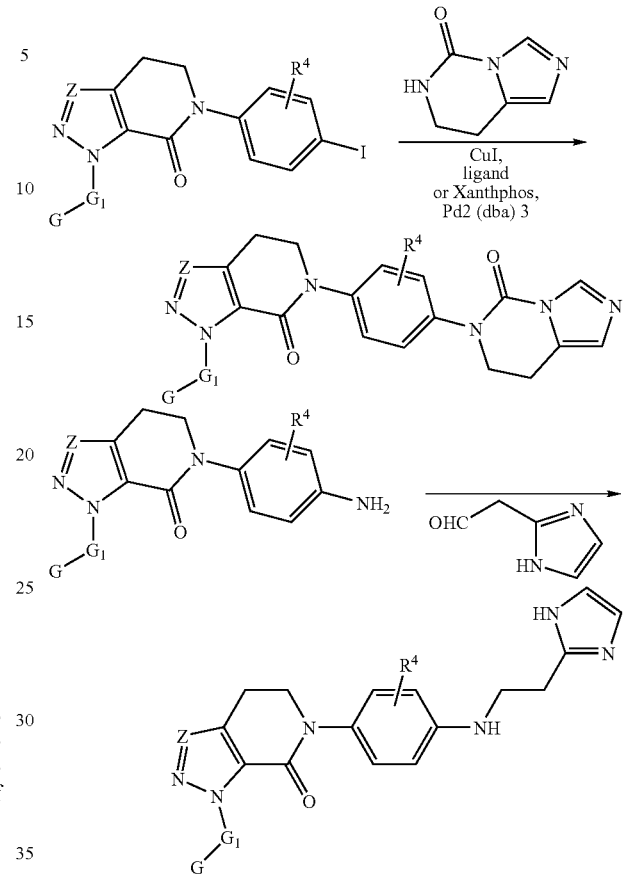

$Z = CR^{1a}$, or N

Schemes 2-13 describe how to make the A-B moieties of the present invention and how to couple them to prepare compounds of the present invention. In the above schemes, the Z group may or may not be present depending on how the A-B group is coupled. The coupling portion of the A-B group could (a) be displaced by the incoming Z or M group, (b) become the Z group, or (c) be incorporated into ring M.

The remaining portions of the compounds of the present invention, G-G$_1$-P-M-Z, G-G$_1$-M-P—Z, G-G$_1$-P-M, G-G$_1$-M-P, G-G$_1$-M-Z, and G-G$_1$-M, can be prepared using methods known to those of ordinary skill in the art. All of the following patents and publications are incorporated herein by reference. For compounds wherein ring P is absent and ring M is a 5-, 6-, or 7-membered ring, one of ordinary skill in the art can look to U.S. Pat. No. 5,939,418, U.S. Pat. No. 5,925,635, U.S. Pat. No. 6,057,342, U.S. Pat. No. 6,187,797, U.S. Pat. No. 6,020,357, U.S. Pat. No. 6,060,491, U.S. Pat. No. 5,998,424, U.S. Pat. No. 6,191,159, WO98/57951, WO99/32454, WO00/039108, WO00/059902, WO01/32628, WO01/005785, U.S. Ser. No. 09/892,319, U.S. Ser. No. 60/313,552, U.S. Ser. No. 60/246,108, and U.S. Ser. No. 09/887,936 for starting materials and intermediates to which the present B and/or A-B groups can be coupled. For compounds wherein ring P is fused to ring M (i.e., a bicyclic moiety is present), one of ordinary skill in the art can look to WO00/39131, U.S. Ser. No. 60/246,125, U.S. Ser. No. 60/292,665, U.S. Ser. No. 60/278,173, U.S. Ser. No. 60/278,165, and U.S. Ser. No. 09/887,850 for starting materials and intermediates to which the present B and/or A-B groups can be coupled.

For compounds wherein G is a ring substituted with a basic moiety, one of ordinary skill in the art can look to U.S. Pat. No. 5,939,418, U.S. Pat. No. 5,925,635, U.S. Pat. No. 6,057,342, U.S. Pat. No. 6,187,797, U.S. Pat. No. 6,020,357, U.S. Pat. No. 6,060,491, U.S. Pat. No. 6,191,159, WO98/57951, WO99/32454 WO00/059902, WO01/32628, WO00/39131, U.S. Ser. No. 09/892,319, U.S. Ser. No. 60/313,552, U.S. Ser. No. 60/246,108, U.S. Ser. No. 60/246,125, U.S. Ser. No. 60/292,665, U.S. Ser. No. 60/278,173, and U.S. Ser. No. 60/278,165 for starting materials and intermediates to form the present G-G$_1$-P-M-Z, G-G$_1$-M-P—Z, G-G$_1$-P-M-Z-A, and/or G-G$_1$-M-P—Z-A groups to which the present B and/or A-B groups can be coupled. For compounds wherein G is a ring substituted with a non-basic group, one of ordinary skill in the art can look to U.S. Pat. No. 5,998,424, WO00/39131, WO00/059902, WO01/32628, U.S. Ser. No. 09/892,319, U.S. Ser. No. 60/313,552, U.S. Ser. No. 60/246,108, U.S. Ser. No. 60/246,125, U.S. Ser. No. 60/292,665, U.S. Ser. No. 60/278,173, and U.S. Ser. No. 60/278,165 for starting materials and intermediates to form the present G-G$_1$-P-M-Z, G-G$_1$-M-P—Z, G-G$_1$-P-M-Z-A, and/or G-G$_1$-M-P—Z-A groups to which the present B and/or A-B groups can be coupled. For compounds wherein G is a bicyclic moiety, one of ordinary skill in the art can look to WO98/57951, WO00/039108, WO00/39131, U.S. Ser. No. 09/892,319, U.S. Ser. No. 60/313,552, U.S. Ser. No. 60/246,108, U.S. Ser. No. 60/246,125, U.S. Ser. No. 60/292,665, U.S. Ser. No. 60/278,173, and U.S. Ser. No. 60/278,165 for starting materials and intermediates to form the present G-G$_1$-P-M-Z, G-G$_1$-M-P—Z, G-G$_1$-P-M-Z-A, and/or G-G$_1$-M-P—Z-A groups to which the present B and/or A-B groups can be coupled. For compounds wherein A is an indoline or similar bicycle, one of ordinary skill in the art can look to WO01/005785 for starting materials and intermediates to which the present B group can be coupled or from which the present A-B groups can be formed.

Scheme 14 illustrates some of the numerous pyrrole intermediates that can be used to prepare compounds of the present invention ($R^z$ is the point of attachment for Z-A-B and can be H, a protecting group, a group modifiable to Z or Z-A, Z, Z-A, or A). These intermediates are described in the above-noted patents and publications.

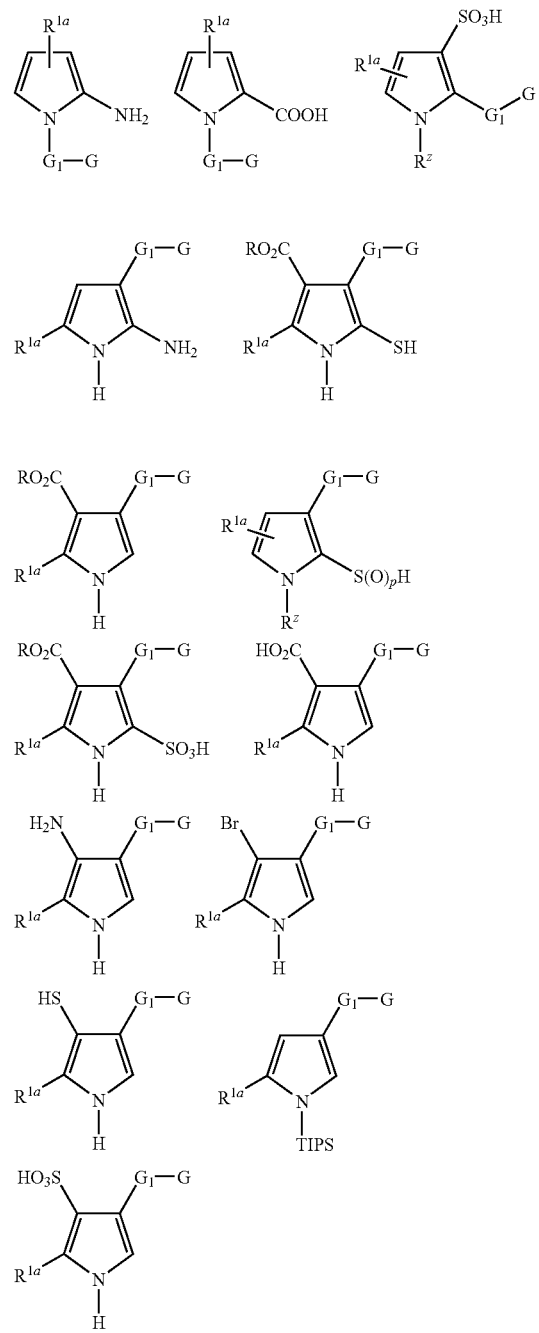

Scheme 15 illustrates some of the numerous imidazole, triazole, and tetrazole intermediates that can be used to prepare compounds of the present invention. These intermediates are described in the above-noted patents and publications. In Scheme 15, V is nitro, amino, thio, hydroxy, sulfonic acid, sulfonic ester, sulfonyl chloride, ester, acid, or halide. In Scheme 15, U is aldehyde, ester, acid, amide, amino, thio, hydroxy, sulfonic acid, sulfonic ester, sulfonyl chloride, or methylene halide.

Scheme 15

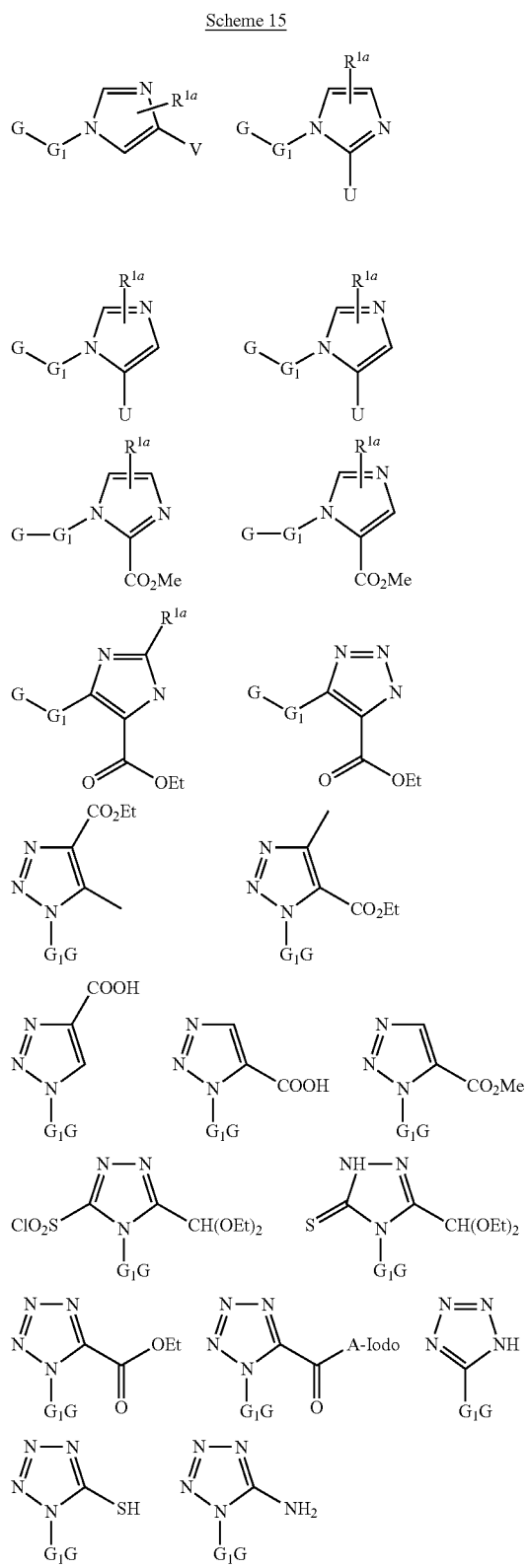

Scheme 16

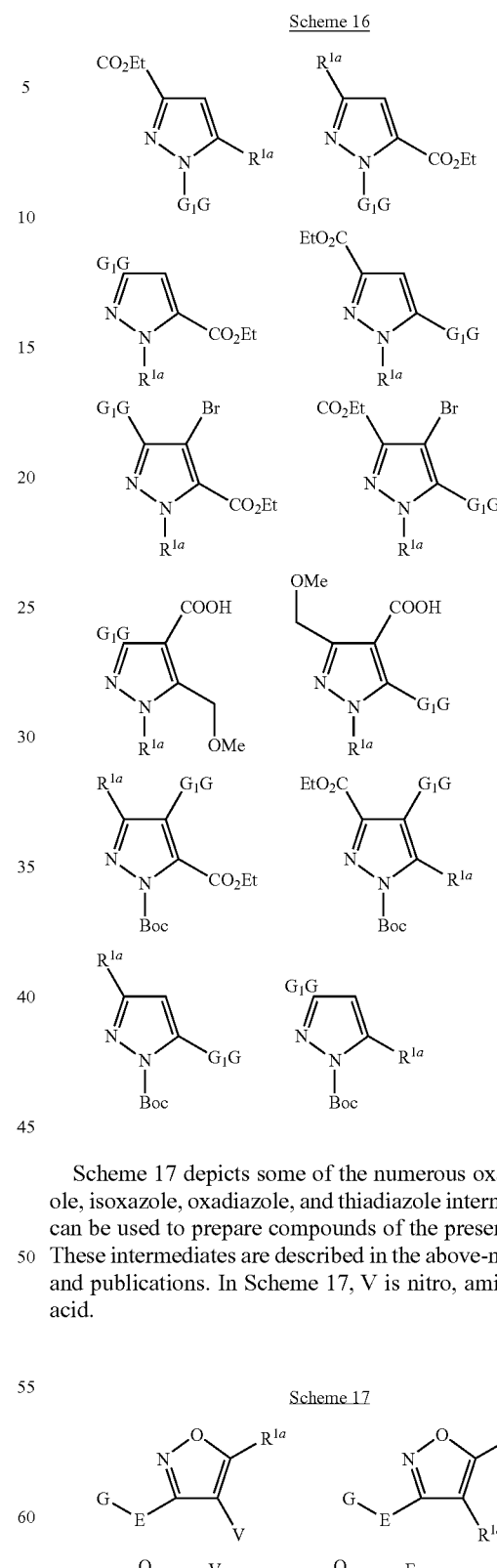

Scheme 16 shows some of the numerous pyrazole intermediates that can be used to prepare compounds of the present invention. These intermediates are described in the above-noted patents and publications.

Scheme 17 depicts some of the numerous oxazole, thiazole, isoxazole, oxadiazole, and thiadiazole intermediates that can be used to prepare compounds of the present invention. These intermediates are described in the above-noted patents and publications. In Scheme 17, V is nitro, amino, ester, or acid.

Scheme 17

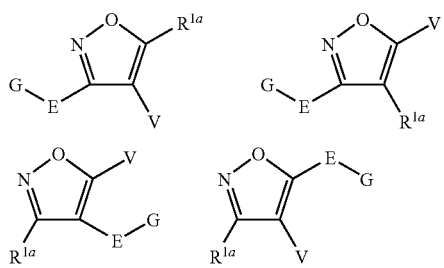

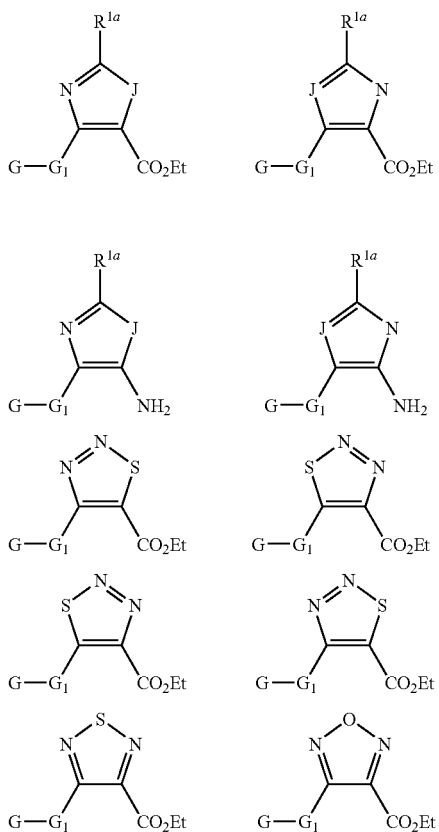

Scheme 18 illustrates two intermediates useful for making a compound of the present invention wherein ring P is fused to ring M. Scheme 18 also illustrates a number of bicyclic compounds that can be made from these intermediates or derivatives thereof. These intermediates and their modification are described in the above-noted patents and publications.

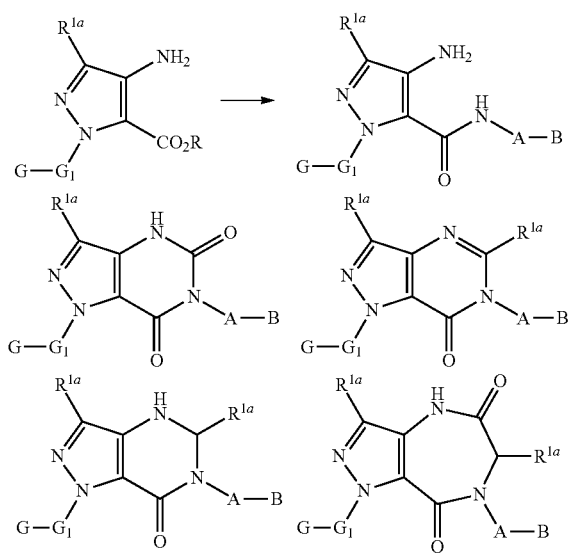

Scheme 18

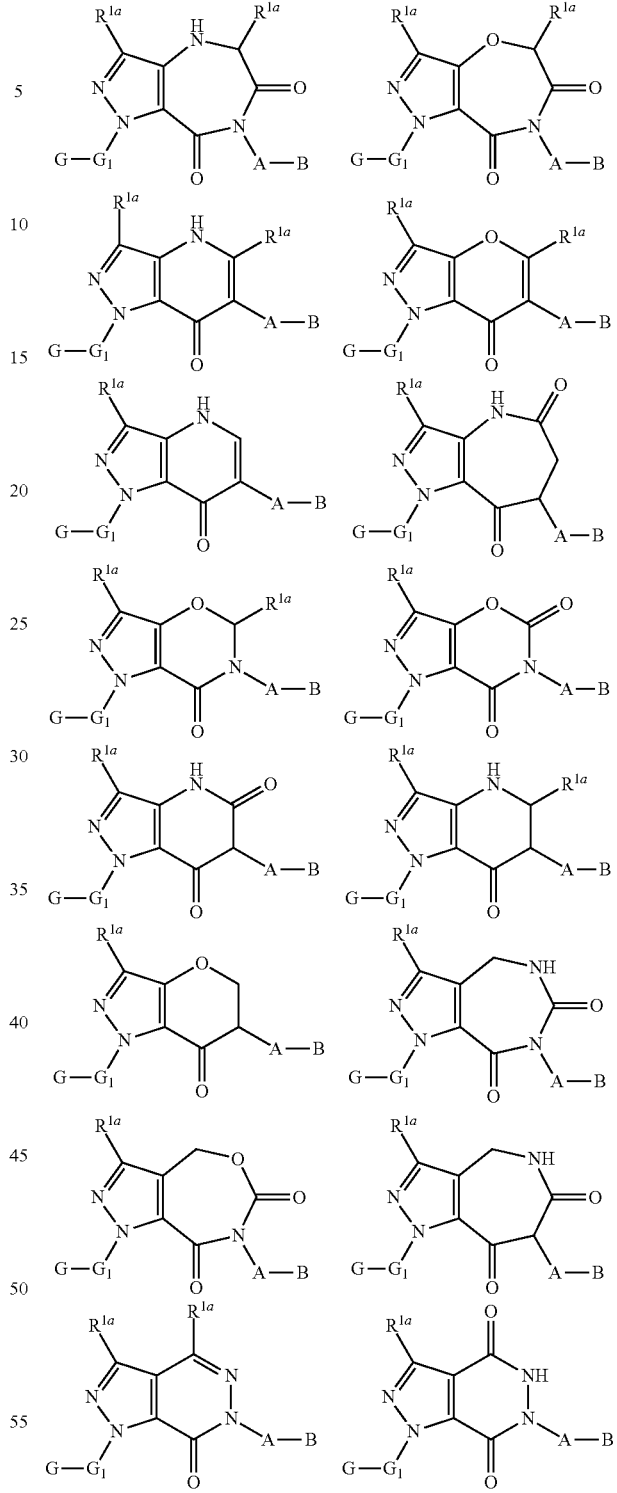

Scheme 19 depicts another intermediate useful for making a compound of the present invention wherein ring P is fused to ring M. Scheme 19 also illustrates a number of bicyclic compounds that can be made from this intermediate or derivatives thereof (e.g., the corresponding cyclohexenone). In Scheme 19, U is OH or morpholine and V is H or C(O)R$^{1a}$. This intermediate, derivatives thereof, and their modification are described in the above-noted patents and publications.

Scheme 19

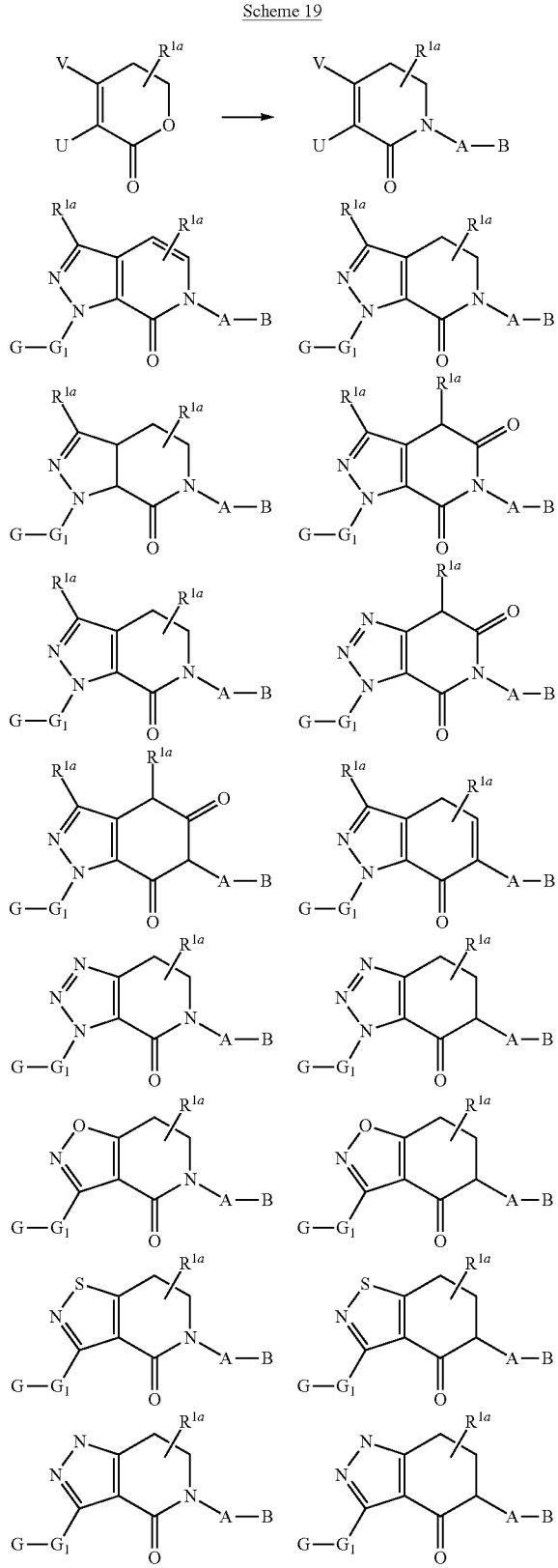

Scheme 20 shows another intermediate useful for making a compound of the present invention wherein ring P is fused to ring M. Scheme 20 also illustrates a number of bicyclic compounds that can be made from this intermediate or derivatives thereof. This intermediate, derivatives thereof, and their modification are described in the above-noted patents and publications.

Scheme 20

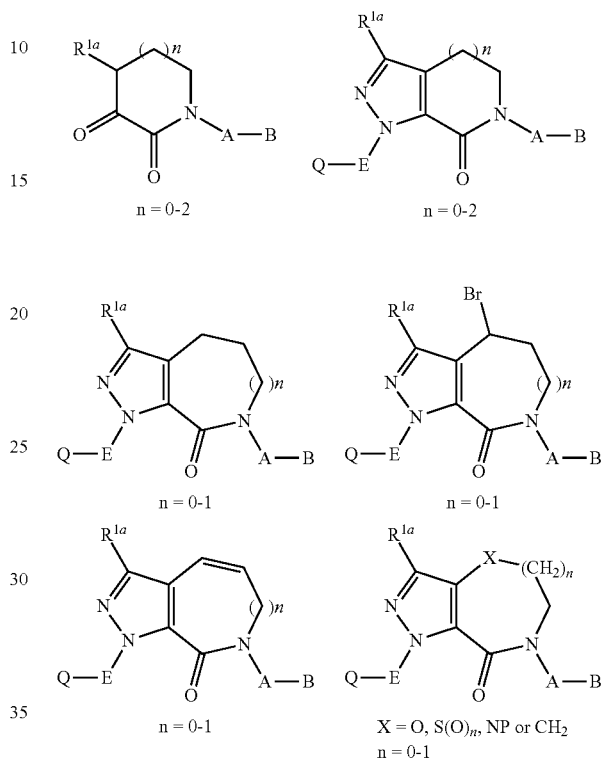

Scheme 21 illustrates a number of other bicyclic rings that are considered to be part of the present bicyclic group, rings P-M. Scheme 21 also describes a method of converting the shown rings to compounds of the present invention. As one of ordinary skill in the art would recognize, this method would be applicable to other heterobicyclics not shown.

Scheme 21

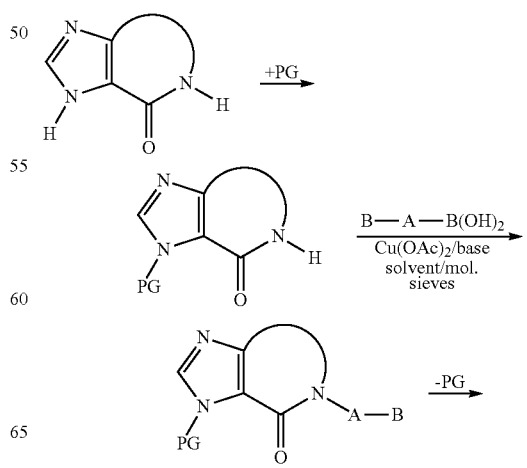

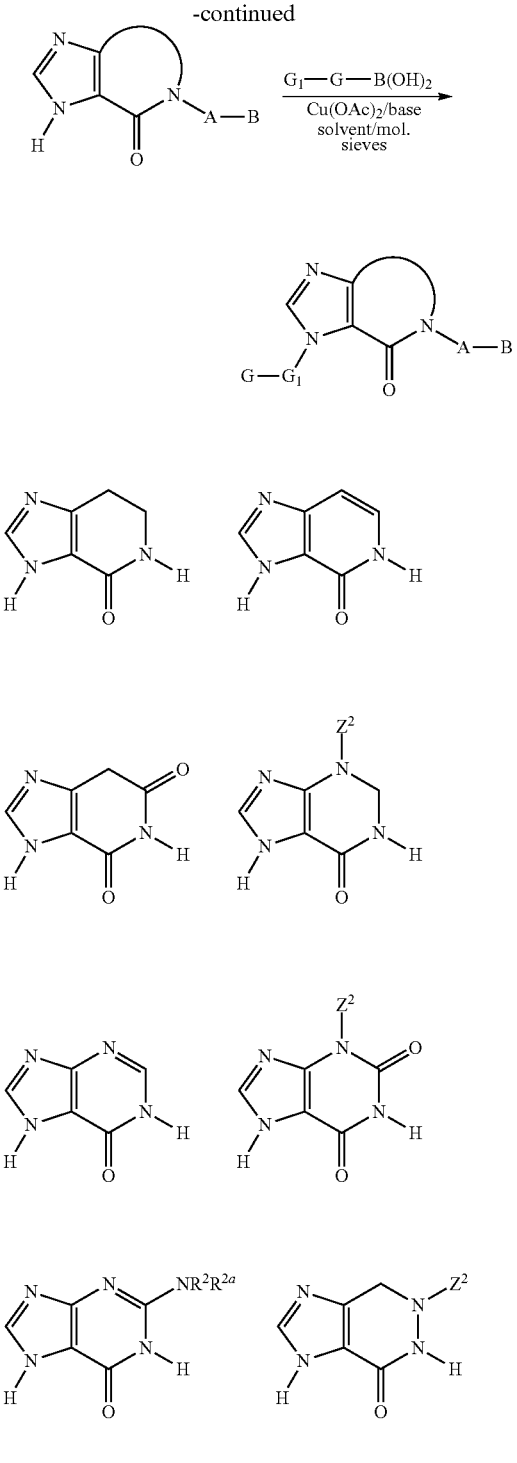

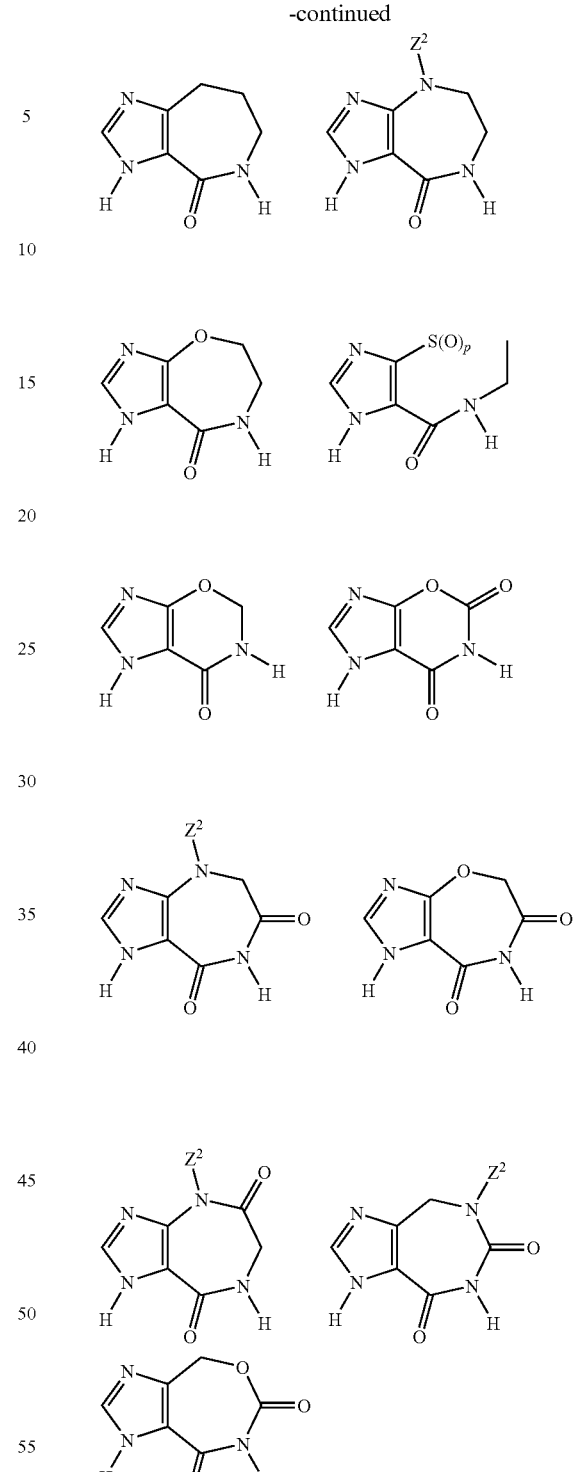

Other useful pyrazole intermediates wherein $G_1$ is an amide are exemplified in Scheme 22. Compounds of the present invention wherein the $G_1$ group is other than an amide can be easily manipulated to other linker functionalities according to the methodologies known in the art, including the methodologies outlined in WO98/28269 and WO98/28282, the contents of both are incorporated herein by reference.

Scheme 22
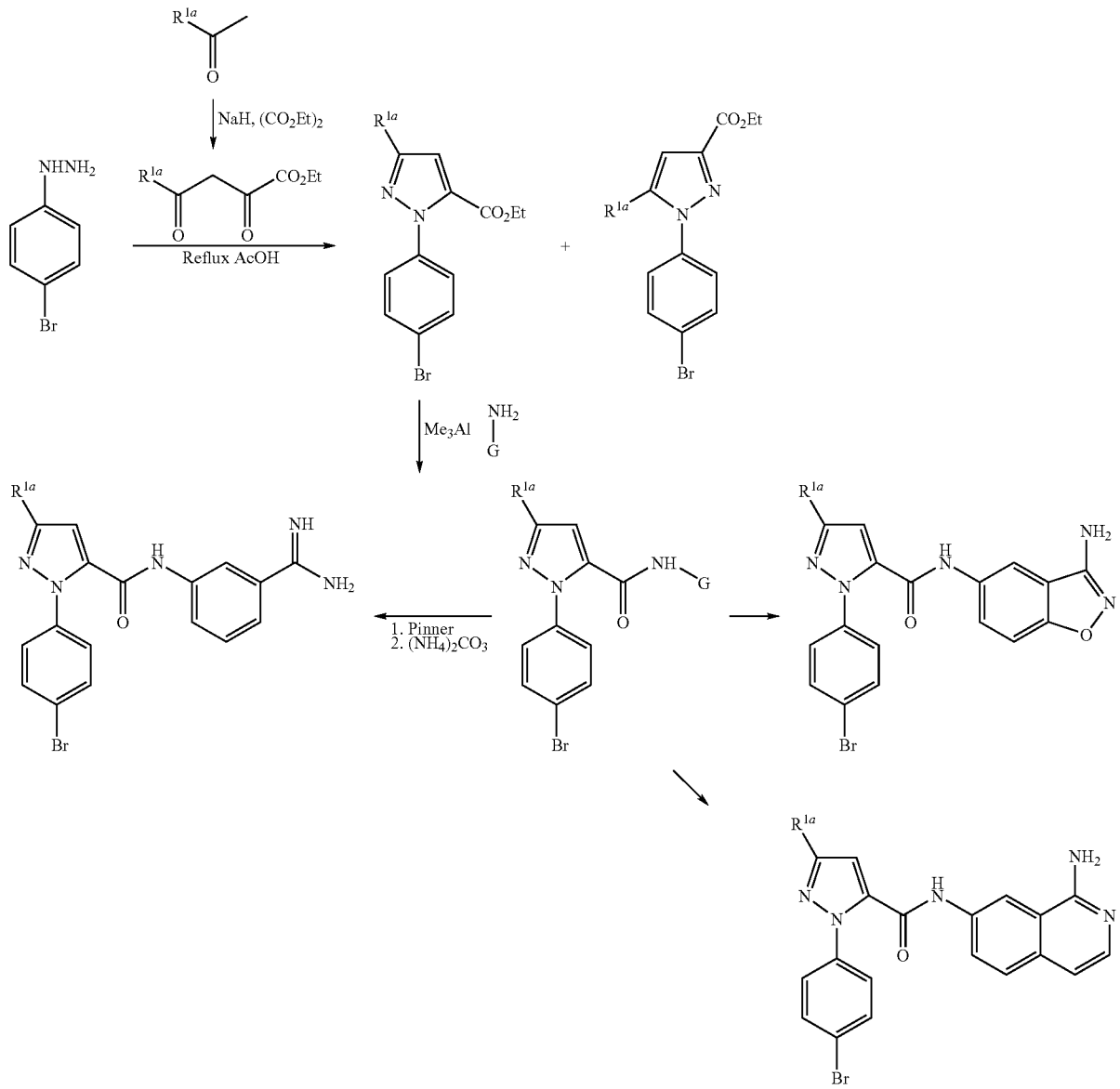
Scheme 23 depicts some of the numerous 6-membered aromatic ring intermediates that can be used to prepare compounds of the present invention. These intermediates are described in the above-noted patents and publications. In Scheme 23, V is nitro, protected sulfonamide, or ester group and is a precursor of group Z of the present invention.
Scheme 23
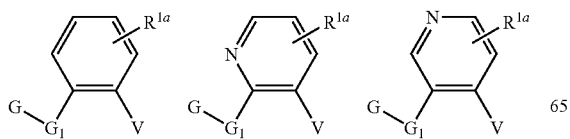
-continued
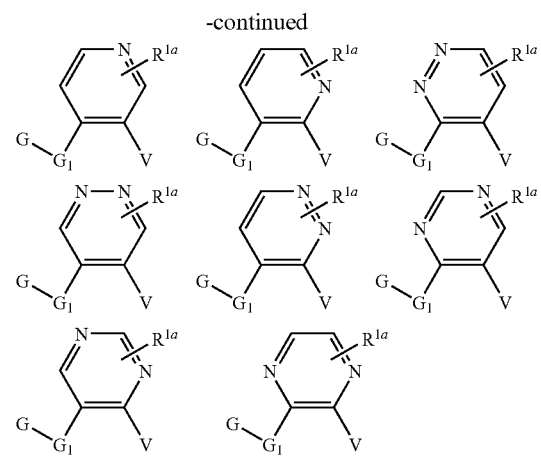

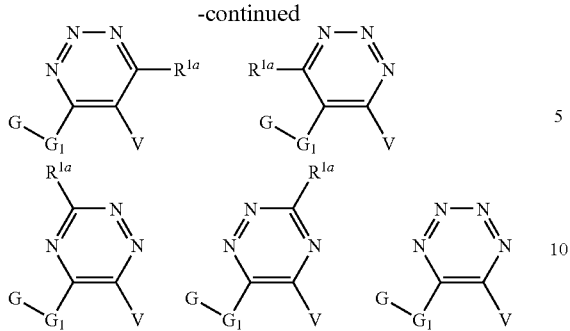
Benzo-fused dihydro-pyridone intermediates of the present invention can be prepared from readily available starting materials as shown in Scheme 24.
Scheme 24
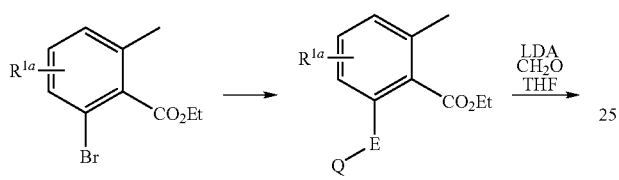
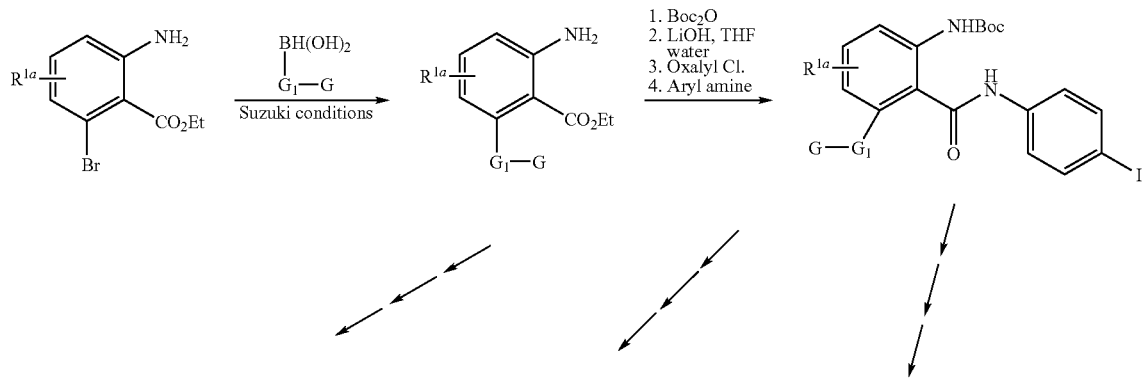
Other benzo-bicyclic compounds can be obtained as shown in Schemes 25 and 26.
Scheme 25
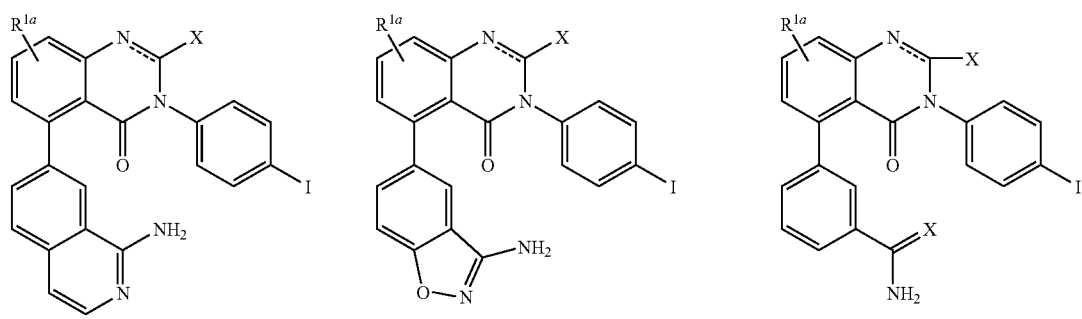

Scheme 26

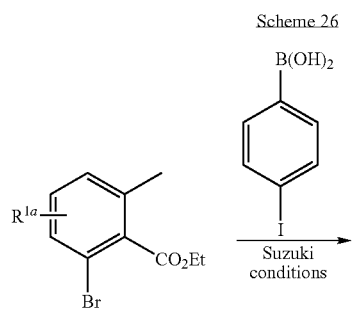

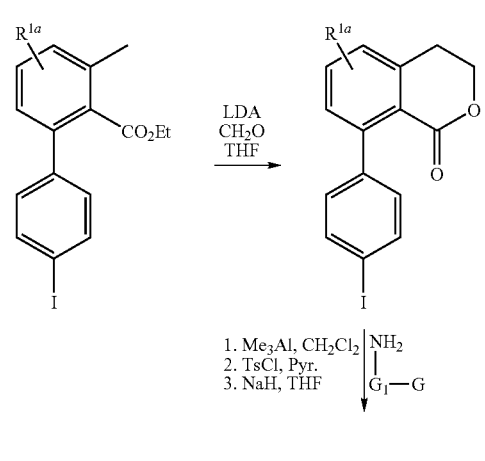

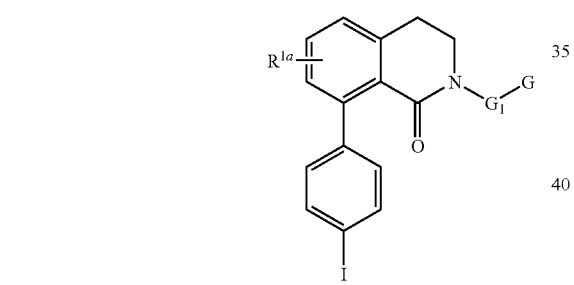

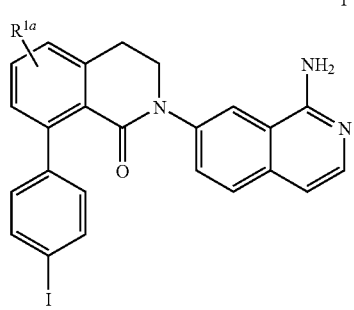

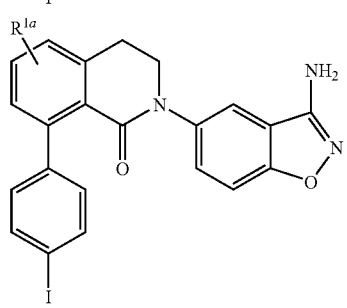

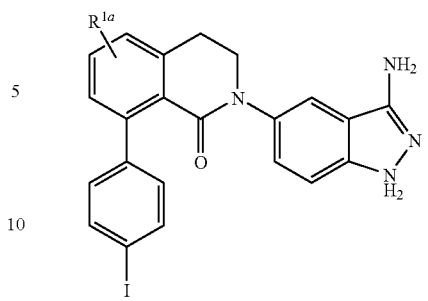

Intermediates A-B of the present invention wherein A is indoline can be prepared as shown in Scheme 27. This type of intermediate can then be attached to the remainder of the desired compound as described previously. Alternatively, the indoline can be attached to the other half of the desired compound prior to formation of the lactam ring.

Scheme 27

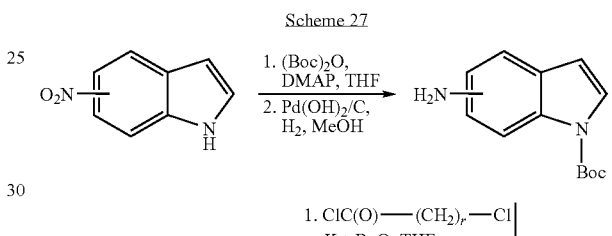

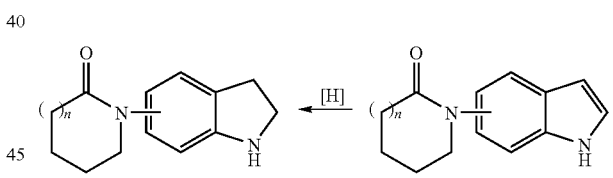

Compounds of the present invention wherein ring P is absent and ring M is a six-membered ring can be obtained as shown in scheme 28. These types of compounds can be obtained from commercially available anthranilic acids or their anthranilates. Anthranilic acids or their nitro precursors can be coupled with a suitable B-A-V (wherein V is an amino functionality) in presence of a base such as triethyl amine, pyridine, or DMAP. Subsequent coupling with an appropriate acid chloride or aniline or aminopyridyl should afford compounds of the present invention.

Scheme 28

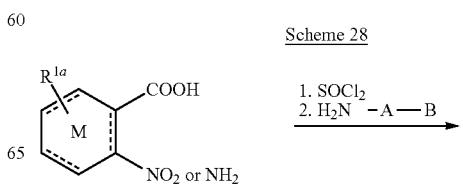

-continued

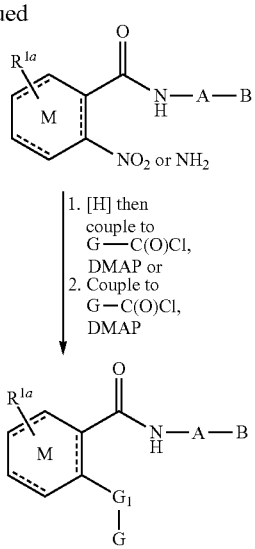

1. [H] then couple to G—C(O)Cl, DMAP or
2. Couple to G—C(O)Cl, DMAP

In an analogous fashion the anthranilates can be coupled with a suitable amine, aniline, or aminopyrimidyl to afford the corresponding benzamide. The benzamides can then be coupled with an appropriate B-A-V (wherein V is an acid chloride derivative, an alkyl halide, or a sulfonyl chloride) to afford additional compounds of the present invention (see Scheme 29).

Scheme 29

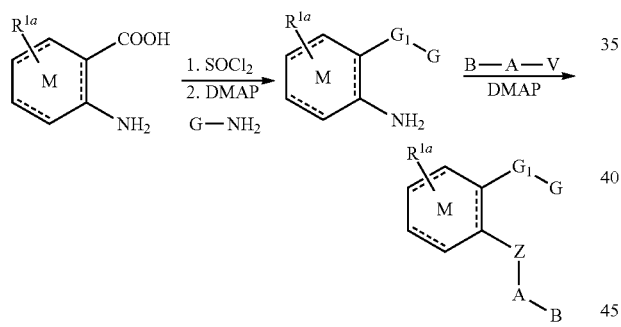

Commercially available ring M derivatives bearing a nitro and amino functionality can also be derivatized as shown above to afford bisamide analogs. In this case, coupling of the aniline with B-A-V (wherein V is an acid chloride, a sulfonyl chloride, or an alkylhalide) affords an intermediate that can be subjected to treatment with an appropriate G-U (wherein U is either an acid chloride or an alkyl halide) in presence of a suitable base such as DMAP. It should be noted that the order of addition of B-A-V and G-U can be reversed to obtain other compounds of the present invention (see Scheme 30).

Scheme 30

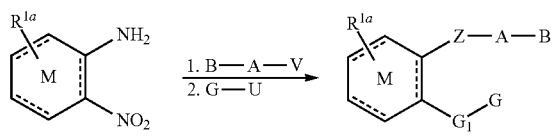

It should be noted that the syntheses shown above could be modified to use coupling intermediates such as Iodo-A-V, wherein V is an acid chloride, amino, alkylhalide, or sulfonyl chloride. These in turn could be coupled to a G-U group. The iodo intermediate could then be subjected to Ullmann or Buchwald coupling as described previously to afford compounds of the present invention. The iodo intermediate could also be converted to an amine via standard Buchwald conditions to afford the corresponding anilino intermediate. This in turn could be coupled as previously described to afford compounds of the present invention.

When M is a non-aromatic ring, the compounds of this invention with general structure of Formula I can be synthesized by using similar methods as described previously and by those skilled in the art. One diastereomer of a compound of Formula I may display better activity compared with the others. Thus, the following stereochemistries are considered to be a part of the present invention.

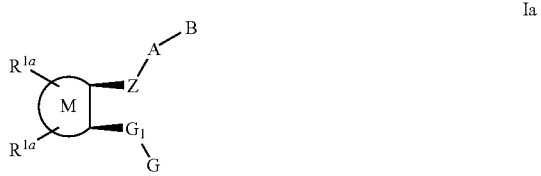

Ia

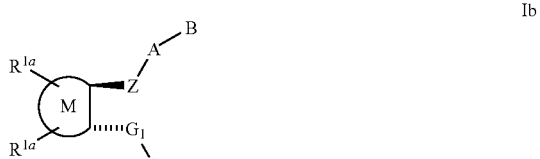

Ib

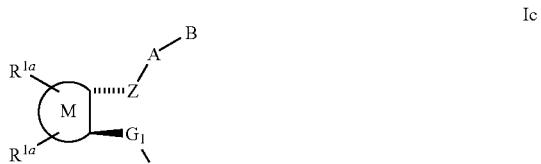

Ic

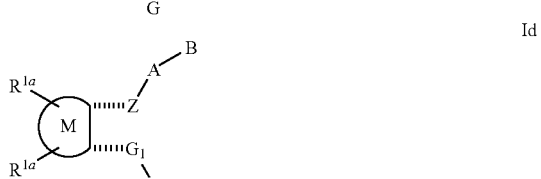

Id

When required, separation of the racemic material can be achieved by HPLC using a chiral column or by a resolution using a resolving agent such as camphonic chloride as in Wilen, S. H. *Tables of Resolving Agents and Optical Resolutions* 1972, 308 pp or using enantiomerically pure acids and bases. A chiral compound of Formula I may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Utility

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders"

as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nm. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2-0.5 nM human factor Xa (Enzyme Research Laboratories, South Bend, Ind.) to react with the substrate (0.20 mM -1 mM) in the presence of inhibitor. Reactions were allowed to go for 30 min and the velocities (rate of absorbance change vs. time) were measured in the time frame of 25-30 min. The following relationship was used to calculate $K_i$ values:

$$(v_o - v_s)/v_s = I/(K_i(1+S/K_m))$$

where:
  $v_o$ is the velocity of the control in the absence of inhibitor;
  $v_s$ is the velocity in the presence of inhibitor;
  I is the concentration of inhibitor;
  $K_i$ is the dissociation constant of the enzyme:inhibitor complex;
  S is the concentration of substrate;
  $K_m$ is the Michaelis constant.

Compounds tested in the above assay are considered to be active if they exhibit a $K_i$ of $\leq 10$ μM. Preferred compounds of the present invention have $K_i$'s of $\leq 1$ μM. More preferred compounds of the present invention have $K_i$'s of $\leq 0.1$ μM. Even more preferred compounds of the present invention have $K_i$'s of $\leq 0.01$ μM. Still more preferred compounds of the present invention have $K_i$'s of $\leq 0.001$ μM. Using the methodology described above, a number of compounds of the present invention were found to exhibit $K_i$'s of $\leq 10$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After 40 min, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein, and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289-18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 min of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μM, thereby confirming the utility of the compounds of the present invention as effective thrombin inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat a thromboembolic condition or disease.

The compounds of the present invention can be administered alone or in combination with one or more additional therapeutic agents. By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Additional therapeutic agents include other anti-coagulant or coagulation inhibitory agents, anti-platelet or platelet inhibitory agents, thrombin inhibitors, thrombolytic or fibrinolytic agents, anti-arrhythmic agents, anti-hypertensive agents, calcium channel blockers (L-type and T-type), cardiac glycosides, diuretics, mineralocorticoid receptor antagonists, phosphodiesterase inhibitors, cholesterol/lipid lowering agents and lipid profile therapies, anti-diabetic agents, anti-depressants, anti-inflammatory agents (steroidal and non-steroidal), anti-osteoporosis agents, hormone replacement therapies, oral contraceptives, anti-obesity agents, anti-anxiety agents, anti-proliferative agents, anti-tumor agents, anti-ulcer and gastroesophageal reflux disease agents, growth hormone and/or growth hormone secretagogues, thyroid mimetics (including thyroid receptor antagonist), anti-infective agents, anti-viral agents, anti-bacterial agents, and anti-fungal agents.

Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatroban as well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the puringeric receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diuretics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phosphodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents be administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

Compounds of the present invention may further be useful as diagnostic agents and adjuncts. For example, the present compounds may be useful in maintaining whole and fractionated blood in the fluid phase such as required for analytical and biological testing.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert be physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/min during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 mg to about 100 mg of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 mg of the active ingredient. The capsules should be washed and dried.

Tablets

Tablets may be prepared by conventional procedures so that the dosage unit is 100 mg of active ingredient, 0.2 mg of colloidal silicon dioxide, 5 mg of magnesium stearate, 275 mg of microcrystalline cellulose, 11 mg of starch and 98.8 mg of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P, and 0.025 mL of vanillin.

Where the compounds of this invention are combined with other anticoagulant agents, for example, a daily dosage may be about 0.1 to 100 mg of the compound of Formula I and about 1 to 7.5 mg of the second anticoagulant, per kilogram of patient body weight. For a tablet dosage form, the compounds of this invention generally may be present in an amount of about 5 to 10 mg per dosage unit, and the second anti-coagulant in an amount of about 1 to 5 mg per dosage unit.

Where the compounds of the present invention are administered in combination with an anti-platelet agent, by way of general guidance, typically a daily dosage may be about 0.01 to 25 mg of the compound of Formula I and about 50 to 150 mg of the anti-platelet agent, preferably about 0.1 to 1 mg of the compound of Formula I and about 1 to 3 mg of antiplatelet agents, per kilogram of patient body weight.

Where the compounds of Formula I are administered in combination with thrombolytic agent, typically a daily dosage may be about 0.1 to 1 mg of the compound of Formula I, per kilogram of patient body weight and, in the case of the thrombolytic agents, the usual dosage of the thrombolytic agent when administered alone may be reduced by about 70-80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Other features of the invention will become apparent in the course of the following descriptions of exemplary embodiments that are afforded for illustration of the invention and are not intended to be limiting thereof.

EXAMPLES

Example 1

3-Methoxy-1-(4-methoxyphenyl)-6-[4-(2-oxo-1-piperidinyl)phenyl]-1,4,5,6-tetrahydro-7-H-pyrazolo[3,4-c]pyridin-7-one Part A. To a solution of 1.91 g of DMAP in 10 mL of methylene chloride was added 1.45 mL of trichloroacetyl chloride at 0° C. After stirring at rt for 30 min, 1.0 g of 1-(4-iodophenyl)-3-(4-morpholinyl)-5,6-dihydro-2(1H)-pyridinone was added. The reaction mixture was refluxed overnight, then quenched with water, extracted with ether. The organic layers were dried over $Na_2SO_4$ and concentrated to dryness to provide the crude product that was used in the next step without further purification.

Part B. The crude material from above in a mixture of 20 mL of ether, 1 mL of water and 1 mL of conc. HCl was heated to reflux (oil bath 65° C.) for 3 h. The mixture was then allowed to cool to rt and filtered to collect the product as a solid (0.97 g, 81% in 2 steps). $^1$H NMR (DMSO-$d_6$, 300 MHz) δ 7.79 (2H, d, J=8.7 Hz), 7.25 (2H, d, J=8.7 Hz), 3.89 (2H, t, J=6.2 Hz), 2.92 (2H, t, J=6.2 Hz) ppm.

Part C. A mixture of the "trione" made above (0.5 g, 1.09 mmol), p-methoxyphenylhydrazine HCl salt (0.152 g, 1.09 mmol) in 20 mL of THF was treated with 0.30 mL of triethylamine at rt overnight. To the reaction mixture was added 20 mL of 1N HCl. The resulting mixture was refluxed for 2 h. After cooling to rt, the compound was collected by filtration (0.42 g, 84%). $^1$H NMR (DMSO-$d_6$, 300 MHz) δ 8.78 (1H, s), 8.26 (2H, m), 7.92 (2H, m), 7.72 (2H, m), 7.46 (2H, m), 4.59 (2H, m) 4.09 (3H, s), 3.42 (2H, m) ppm. LRMS (AP$^+$) 462 (M$^+$+1).

Part D. To a solution of the hydroxy compound (1.78 g, 3.86 mmol) in 20 mL of DMF was added sodium hydride (232 mg, 60%, 5.79 mmol) at 0° C. The mixture was stirred at rt for 30 min. To the reaction mixture was added MeI (0.36 mL, 5.79 mmol). The reaction was stirred at rt overnight, then quenched with water, extracted with ether. The organic layers were dried over $Na_2SO_4$, concentrated to dry. The residue was purified by column chromatography to yield 6-(4-iodophenyl)-3-methoxy-1-(4-methoxyphenyl)-1,4,5,6-tetrahydro-7H-pyrazolo[3,4-c]pyridin-7-one (1.67 g, 91%). $^1$H NMR (DMSO-$d_6$, 300 MHz) δ 7.67 (2H, d, J=8.8 Hz), 7.43 (2H, d, J=9.1 Hz), 7.07 (2H, d, J=8.8 Hz), 6.90 (2H, d, J=9.1 Hz), 4.02 (5H, m, with a three proton singlet), 3.80 (3H, s), 2.90 (2H, d, J=6.6 Hz) ppm.

Part E. An oven-dried flask was charged with 0.28 g of 6-(4-iodophenyl)-3-methoxy-1-(4-methoxyphenyl)-1,4,5,6-tetrahydro-7H-pyrazolo[3,4-c]pyridin-7-one, 90 mg of δ-valerolactam, and 70 mg of anhydrous (powdered) potassium carbonate. The solids were dissolved in 3 mL of degassed DMSO, after which 20 mg of copper (I) iodide was added. The flask was fitted with a reflux condenser and heated to 120° C. while stirring for 12 h. The reaction was cooled to rt, then quenched by the addition of water. Product was extracted into ethyl acetate, which was then dried over $Na_2SO_4$ and concentrated to yield a yellow solid. The residue was purified by HPLC to yield 50 mg of the title compound as a TFA salt (15% yield). $^1$H NMR (MeOH-$d_4$, 300 MHz) δ 7.38 (2H, d, J=1.5 Hz), 7.35 (2H, d, J=1.5 Hz), 7.28 (2H, d, J=10 Hz), 6.92 (2H, d, J=10 Hz), 4.06 (2H, t, J=7.0 Hz), 3.96 (3H, s), 3.79 (3H, s), 3.64 (2H, t, J=5.9 Hz), 2.89 (3H, t, J=7.0), 2.49 (3H, t, J=5.9 Hz), 1.94 (4H, m) ppm.

Example 2

1-(4-methoxyphenyl)-3-[(methylamino)methyl]-6-[4-(2-oxo-1-piperidinyl)phenyl]-1,4,5,6-tetrahydro-7H-pyrazolo[3,4-c]pyridin-7-one Part A. An oven-dried flask with stir-bar was charged with vacuum-oven dried lithium chloride (1.6 g, 38 mmol) and potassium borohydride (2.1 g, 38 mmol). The solids were dissolved in 60 mL dry THF while the system was flushed with $N_2$. The mixture was stirred at rt for 30 min before cooling to 0° C. A solution of ethyl 6-(4-iodophenyl)-1-(4-methoxyphenyl)-7-oxo-4,5,6,7-tetrahydro-1H-pyrazolo[3,4-c]pyridine-3-carboxylate (9 g, 17 mmol) dissolved in 40 mL of dry THF was slowly added to the stirring suspension, and the reaction was continued for 12 h, beginning at 0° C. and gradually warming to rt. The reaction was quenched by the addition of water and a small amount of 1N HCl aqueous solution until the pH was 7.0. The product crashed out of solution and was filtered off and vacuum dried to afford 6.9 g of the corresponding alcohol (83% yield). LRMS (ES$^+$) 476 (M+H)$^+$.

Part B. A vacuum-dried flask with stir-bar containing the alcohol (850 mg, 1.8 mmol) synthesized above was charged with 10 mL dichloromethane and purged with $N_2$ before cooling to 0° C. To the stirring solution was added phosphorus tribromide (0.170 mL, 1.8 mmol) dropwise. The reaction was stirred for 12 h beginning at 0° C. and then warmed gradually to rt. The reaction was diluted with dichloromethane, and then quenched with aqueous $NaHCO_3$ solution. The organic phase was washed with brine and dried over $Na_2SO_4$ before concentration to yield 1 g of the corresponding bromide (quantitative yield). LRMS (ES$^+$) 538, 540 (M, M+2)$^+$.

Part C. The bromide (1 g, 2 mmol) from the reaction above was added to an oven-dried flask as a solution in 10 mL dry THF. A stir-bar and a solution of methylamine (5 mL, 10 mmol in THF) was added. The reaction was stirred overnight at rt. Water was added to the reaction solution and the product was extracted with ethyl acetate. The organics were concentrated to yield 850 mg (85% yield) of the desired compound as an oil. LRMS (ES$^+$) 489 (M+H)$^+$.

Part D. A vacuum dried flask with stir-bar containing 850 mg (1.7 mmol) of the amine from the reaction above was charged with di-tert-butyl dicarbonate (860 mg, 3.5 mmol), 4-DMAP (10 mg, 0.09 mmol, triethylamine (1.2 mL, 8.7 mmol), and 10 mL of dichloromethane. The reaction was stirred at rt for 10 min and another 1.2 mL of triethylamine was added to the reaction before stirring for 12 h. The reaction was quenched by the addition of dichloromethane and 1N HCl aqueous solution. The organics were separated and washed with brine, then dried over $Na_2SO_4$. The solution was filtered and concentrated by rotovap to yield 490 mg (48% yield) of the Boc-protected amine. $^1$H NMR (CDCl$_3$, 300 MHz) δ 7.66 (2H, d, J=8.8 Hz), 7.45 (2H, d, J=8.8 Hz), 7.08 (2H, d, J=8.7 Hz), 6.91 (2H, d, J=8.7 Hz), 4.56 (2H, s), 4.05 (2H, t, J=6.6 Hz), 3.81 (3H, s), 2.88 (2H, t, J=6.6 Hz), 2.85 (3H, s), 1.49 (9H, s) ppm.

Part E. An oven-dried flask with stir-bar was charged with the previously synthesized N-Boc amino compound (100 mg, 0.17 mmol), δ-valerolactam (20 mg, 20 mmol), 4,5-bis-(diphenylphosphino)-9,9-dimethylxanthene (30 mg, 50 mmol), palladium (II) acetate (8 mg, 30 mmol), and cesium carbonate (80 mg, 30 mmol). The solids were dissolved in previously degassed 1,4-dioxane (6 mL). The flask was fitted with a reflux condenser and heated to 80° C. while stirring for 12 h. The reaction was quenched by addition of water and extracted into ethyl acetate. The organic solution was washed with brine and dried over Na$_2$SO$_4$ before concentration in vacuo to afford 45 mg of the corresponding lactam (47% yield). LRMS (ES$^+$) 560 (M+H)$^+$, Part F. A solution of the lactam (45 mg, 80 mmol) dissolved in chloroform (4 mL) was transferred into an oven-dried flask with stir-bar and purged with N$_2$ before the addition of TFA (1 mL, 13 mmol) dropwise via syringe. The reaction was stirred at rt for 12 h, then diluted with dicholoromethane and aqueous NaHCO$_3$. The organic solution was washed with brine and dried over Na$_2$SO$_4$ before concentration and purification by HPLC to afford 13 mg as a TFA salt (26% yield). LRMS (ES$^+$) 460 (M+H)$^+$. $^1$H NMR (CDCl$_3$, 300 MHz) δ 7.43 (2H, d, J=8.8 Hz), 7.38 (2H, d, J=8.8 Hz), 7.30 (2H, d, J=8.8 Hz), 6.95 (2H, d, J=8.8 Hz), 4.82 (2H, s), 4.32 (2H, s), 4.12 (2H, t, J=6.6 Hz), 3.81 (3H, s), 3.65 (2H, t, J=5.4 Hz), 3.06 (2H, t, J=6.6 Hz), 2.81 (3H, s), 2.49 (2H, t, J=6.2 Hz), 1.94 (4H, t, J=3.3 Hz) ppm.

Example 3

1-(3-chloro-4-fluorophenyl)-6-[4-(2-oxo-1-piperidinyl)phenyl]-3-(trifluoromethyl)-1,4,5,6-tetrahydro-7H-pyrazolo[3,4-c]pyridin-7-one Part A. 3-chloro-4-fluorophenyl hydrazine (5.00 g, 31.14 mmol) and 1-(4-iodophenyl)-4-(trifluoroacetyl)-2,3-piperidinedione (12.8 g, 31.14 mmol) were added together with 120 mL of ethanol and 4 mL of hydrochloric acid (12 M). The mixture was stirred at reflux under N$_2$ for overnight. The reaction was cooled down to rt. The solvents were removed, and the residue was dissolved in EtOAc (200 mL) and washed with water (100 mL×2) and brine (50 mL). It was then dried over Na$_2$SO$_4$ and concentrated. The residue was purified via flash chromatography on silica gel using 4:1 hexane:ethylacetate to give 1-(3-chloro-4-fluorophenyl)-6-[4-iodophenyl]-3-(trifluoromethyl)-1,4,5,6-tetrahydro-7H-pyrazolo[3,4-c]pyridin-7-one as a brown solid (12.5 g, 75% yield). LRMS (AP$^+$): 536.1 (M+H)$^+$. $^1$H NMR (CDCl$_3$) δ 7.72 (d, 2H), 7.67-7.64 (m, 1H), 7.49-7.44 (m, 1H), 7.19 (t, 3H), 7.06 (d, 2H), 4.12 (t, 2H), 3.17 (t, 2H).

Part B. 1-(3-chloro-4-fluorophenyl)-6-[4-iodophenyl]-3-(trifluoromethyl)-1,4,5,6-tetrahydro-7H-pyrazolo[3,4-c]pyridin-7-one (0.54 g, 1.0 mmol), δ-valerolactam (0.12 g, 1.2 mmol), 1,2-diaminocyclohexane (11.4 mg, 0.1 mmol), K$_3$PO$_4$ (0.42 g, 2 mmol) and CuI (2 mg, 0.01 mmol) were added to 5 mL of 1,4-dioxane. The mixture was degassed under argon and stirred at 110° C. under N$_2$ for 48 h. The mixture was then cooled to rt. The dioxane was removed. The residue was dissolved in EtOAc (100 mL), washed with HCl (1N, 30 mL), water (50 mL×2), and brine (50 mL), dried over Na$_2$SO$_4$, filtered, and concentrated. The residue was purified via flash chromatography on silica gel using 1:2 hexane:ethylacetate to give the desired product (0.41 g, 80% yield). LRMS (ES$^+$): 507.1 (M+H)$^+$. $^1$H NMR (CDCl$_3$) δ 7.68-7.65 (m, 1H), 7.50-7.45 (m, 1H), 7.36-7.16 (m, 5H), 4.16 (t, 2H), 3.64-3.62 (m, 2H), 3.47 (br, 3H), 3.17 (t, 2H), 2.62 (t, 2H), 1.98-1.96 (m, 3H).

Example 4

1-[3-(aminomethyl)-4-fluorophenyl)-6-[4-(2-oxo-1-piperidinyl)phenyl]-3-(trifluoromethyl)-1,4,5,6-tetrahydro-7H-pyrazolo[3,4-c]pyridin-7-one Part A. 1-(3-chloro-4-fluorophenyl)-6-[4-(2-oxo-1-piperidinyl)phenyl]-3-(trifluoromethyl)-1,4,5,6-tetrahydro-7H-pyrazolo[3,4-c]pyridin-7-one (0.35 g, 0.69 mmol), Zn(CN)$_2$ (81 mg, 0.69 mmol), Pd$_2$(dba)$_3$ (63 mg, 0.07 mmol), dppf (77 mg, 0.14 mmol), and Zn (9 mg, 0.14 mmol) were added to 15 mL of DMAC. The mixture was degassed under argon and stirred at 140° C. under N$_2$ for 12 h. The reaction was cooled to rt, ethylacetate (75 mL) was added and the mixture was filtered through Celite®. The filtrate was washed with saturated NaHCO$_3$ solution (30 mL), water (30 mL×3), and brine (20 mL). It was then dried over Na$_2$SO$_4$, filtered, and concentrated. The residue was purified via flash chromatography on silica gel with 10% methanol in dichloromethane to give 2-fluoro-5-[7-oxo-6-[4-(2-oxo-1-piperidinyl)phenyl]-3-(trifluoromethyl)-4,5,6,7-tetrahydro-1H-pyrazolo[3,4-c]pyridin-1-yl]benzonitrile (0.17 g, 50% yield). LRMS (AP$^+$): 498.2 (M+H)$^+$. $^1$H NMR (CDCl$_3$) δ 7.91-7.85 (m, 2H), 7.31 (s, 4H), 7.28-7.25 (m, 1H), 4.16 (t, 2H), 3.63-3.61 (m, 2H), 3.18 (t, 2H), 2.56 (t, 2H), 1.96-1.93 (m, 4H).

Part B. The product from part A (50 mg) was dissolved in 20 mL of MeOH in a hydrogenation bottle. To the solution was added 5% Pd/C (20 mg) and one drop of TFA. The reaction mixture was put on hydrogenation Parr shaker at rt under 50 psi for 5 h. The reaction mixture was filtered through Celite®. The filtrate was concentrated and purified via HPLC (C18 RP., 0.5% TFA, H$_2$O/MeCN gradient) to give 40 mg of the title compound as its TFA salt (65%). LRMS (ESI+): 502.4 (M+H)+. 1H NMR (CDCl$_3$) δ 7.61 (s, 1H), 7.52 (d, 1H), 7.38 (d, 2H), 7.25 (d, 2H), 7.16-7.09 (m, 1H), 4.13 (t, 2H), 3.76 (s, 2H), 3.58 (br, 2H), 3.14 (t, 2H), 2.48 (br, 2H), 1.93 (br, 4H).

Example 5

1-(3-amino-1,2-benzisoxazol-5-yl)-6-[4-(2-oxo-1-piperidinyl)phenyl]-3-(trifluoromethyl)-1,4,5,6-tetrahydro-7H-pyrazolo[3,4-c]pyridin-7-one Acetohydroxamic acid (54 mg, 0.72 mmol) and K$_2$CO$_3$ (0.2 g, 1.45 mmol) were added to 8 mL of DMF and 4 mL of H$_2$O. The mixture was stirred at rt for 15 min, followed by addition of a solution of 2-fluoro-5-[7-oxo-6-[4-(2-oxo-1-piperidinyl)phenyl]-3-(trifluoromethyl)-4,5,6,7-tetrahydro-1H-pyrazolo[3,4-c]pyridin-1-yl]benzonitrile (0.12 g, 0.24 mmol) in DMF (2 mL). The mixture was stirred at rt overnight. The mixture was then partitioned between ethylacetate (40 mL) and water (20 mL), washed with H$_2$O (20 mL×3) and brine (20 mL), dried over Na$_2$SO$_4$, filtered, and concentrated. HPLC(C18 RP., 0.5% TFA, H$_2$O/MeCN gradient) purification gave 100 mg (67% yield) of the title compound as its TFA salt. LRMS (ESI$^-$): 623.4 (M+TFA-H)$^-$. $^1$H NMR (CDCl$_3$) δ 7.80 (s, 1H), 7.72 (d, 1H), 7.44 (d, 1H), 7.34-7.24 (m, 4H), 4.16 (t, 2H), 3.98 (br, 2H), 3.61 (br, 2H), 3.20 (t, 2H), 2.60 (br, 2H), 1.98-1.89 (m, 4H).

Example 6

1-(4-methoxyphenyl)-6-[4-(2-oxo-1-piperidinyl)phenyl]-3-(trifluoromethyl)-1,4,5,6-tetrahydro-7H-pyrazolo[3,4-c]pyridin-7-one Part A. 4-iodoaniline (45.82 g, 209.2 mmol) and triethylamine (65.61 mL, 470.7 mmol) were dissolved into THF (800 mL) and cooled to 0° C. 5-Bromovaleryl chloride (50.0 g, 251.1 mmol) dissolved in THF (200 mL) was added dropwise to the reaction. The reaction was warmed to rt and stirred overnight. Reaction was cooled to 0° C. and potassium tert-butoxide (70.43 g, 627.6 mmol) was slowly added. The reaction was warmed to rt and stirred overnight. The reaction was concentrated and then redissolved in ethyl acetate (500 mL)

and 3N HCl (500 mL), extracted with ethyl acetate (2×250 mL), washed with 1N HCl (3×250 mL), washed with brine (1×250 mL), and dried (Na$_2$SO$_4$). Purification by silica gel chromatography using 0%-100% ethyl acetate/hexane gradient as eluent to afford 51.03 g (81%): $^1$H NMR (CDCl$_3$) δ 7.70 (d, j=8.4 Hz, 2H), 7.03 (d, j=8.8 Hz, 2H), 3.62 (t, j=5.9 Hz, 2H), 2.56 (t, j=5.7 Hz, 2H), 2.50-1.88 (m, 4H) ppm.

Part B. The product from part A (85.17 g, 282.8 mmol) and phosphorus pentachloride (205.91 g, 990.0 mmol) was dissolved into CHCl$_3$ (750 mL) and refluxed for 3½ h. Reaction was poured over ice and then quenched further with water, extracted with CHCl$_3$ (3×400 mL), washed with brine (1×400 mL), dried (MgSO$_4$), and concentrated. This residue was dissolved in morpholine (400 mL) and refluxed overnight. Reaction was concentrated and purified by silica gel chromatography using 0%-100% ethyl acetate/hexane gradient as eluent to afford 68 g (63%): $^1$H NMR (CDCl$_3$) δ 7.68 (d, j=8.8 Hz, 2H), 7.11 (d, j=8.8 Hz, 2H), 5.66 (t, j=4.8 Hz, 1H), 3.82 (t, j=4.8 Hz, 4H), 3.77 (t, j=6.8 Hz, 2H), 2.89 (t, j=4.8 Hz, 4H), 2.53-2.47 (m, 2H) ppm.

Part C. 4-Dimethylaminopyridine (3.92 g, 32.01 mmol) was dissolved into CH$_2$Cl$_2$ (130 mL) and cooled to 0° C. Trifluoroacetic anhydride (4.54 g, 32.01 mmol) was added and the mixture was stirred at 0° C. for 30 min. The above morpholine-enamine from part B (10.25 g, 26.68 mmol) dissolved in CH$_2$Cl$_2$ (370 mL) was added slowly and the reaction was warmed to rt and stirred overnight. Reaction was concentrated and purified by silica gel chromatography using 0%-50% ethyl acetate/hexane gradient to isolate the intermediate. The intermediate was dissolved in 20% HCl (50 mL) and diethyl ether (200 mL) and stirred at rt overnight. Reaction was quenched with water, extracted with ether (3×100 mL), washed with brine (1×100 mL), and dried (Na$_2$SO$_4$). The residue was redissolved in petroleum ether and the solids filtered. The filtrate was concentrated to afford 9.99 g (78%): $^1$H NMR (CDCl$_3$) δ 7.77 (d, j=8.8 Hz, 2H), 7.11 (d, j=8.8 Hz, 2H), 3.93 (t, j=6.8 Hz, 2H), 2.92 (t, j=6.8 Hz, 2H) ppm.

Part D. The product from part C (10.0 g, 24.3 mmol) and 4-methoxyhydrazine hydrochloride (4.28 g, 24.3 mmol) were dissolved in 1N HCl (200 mL) and methanol (400 mL) and refluxed overnight. The reaction was cooled to rt and quenched with water, extracted with ethyl acetate (3×250 mL), washed with brine (1×250 mL), and dried (Na$_2$SO$_4$). Purification by silica gel chromatography using 0%-100% ethyl acetate/hexane gradient as eluent afforded 9.28 g (74%); $^1$H NMR (CDCl$_3$) δ 7.69 (d, j=9.4 Hz, 2H), 7.45 (d, j=8.8 Hz, 2H), 7.06 (d, j=8.8 Hz, 2H), 6.92 (d, j=9.2 Hz, 2H), 4.11 (t, j=6.8 Hz, 2H), 3.81 (s, 3H), 3.15 (t, j=6.5 Hz, 2H) ppm; Mass Spec (M+H)$^+$ 514.3.

Part E. δ-Valerolactam (0.023 g, 0.214 mmol), cesium carbonate (0.095 g, 0.292 mmol), palladium (II) acetate (0.004 g, 0.019 mmol), and 9,9-dimethyl-4,5-bis(diphenylphosphino)xanthene (0.015 g, 0.029 mmol) were charged to a flask and flushed with N$_2$. The above trifluoromethyl intermediate (0.100 g, 0.195 mmol) dissolved in 1,4-dioxane (2 mL) was added via syringe and the flask was flushed with N$_2$. The reaction was heated at 100° C. overnight. The reaction was cooled to rt and diluted with ethyl acetate (25 mL) and water (25 mL), extracted with ethyl acetate (3×25 mL), washed with brine (1×25 mL), and dried (Na$_2$SO$_4$). Purification by HPLC and freeze-drying afforded 32.4 mg (34%); $^1$H NMR (CDCl$_3$) δ 7.46 (d, j=8.8 Hz, 2H), 7.35 (d, j=7.9 Hz, 2H), 7.24 (d, j=8.7 Hz, 2H), 6.93 (d, j=9.1 Hz, 2H), 4.15 (t, j=6.8 Hz, 2H), 3.82 (s, 3H), 3.63-3.60 (m, 2H), 3.17 (t, j=6.6 Hz, 2H), 2.64 (t, j=5.7 Hz, 2H), 1.98-1.94 (m, 4H) ppm; Mass Spec (M+H)$^+$ 485.5.

Example 7

1-(4-methoxyphenyl)-6-[4-(2-oxo-hexahydro-1H-azepin-1-yl)phenyl]-3-(trifluoromethyl)-1,4,5,6-tetrahydro-7H-pyrazolo[3,4-c]pyridin-7-one The title compound was synthesized following the procedure for Example 6. $^1$H NMR (CDCl$_3$) δ 7.46 (d, j=9.2 Hz, 2H), 7.32 (d, j=8.5 Hz, 2H), 7.21 (d, j=8.8 Hz, 2H), 6.92 (d, j=9.1 Hz, 2H), 4.14 (t, j=6.6 Hz, 2H), 3.81 (s, 3H), 3.76-3.72 (m, 2H), 3.16 (t, j=6.6 Hz, 2H), 2.74-2.72 (m, 2H), 1.90-1.78 (m, 6H) ppm; Mass Spec (M+H)$^+$ 499.4.

Example 8

1-(4-methoxyphenyl)-6-[4-(2-oxo-1-piperazinyl)phenyl]-3-(trifluoromethyl)-1,4,5,6-tetrahydro-7H-pyrazolo[3,4-c]pyridin-7-one Part A. 4-iodoaniline (45.82 g, 209.2 mmol) and triethylamine (65.61 mL, 470.7 mmol) were dissolved into THF (800 mL) and cooled to 0° C. 5-Bromovaleryl chloride (50.0 g, 251.1 mmol) dissolved in THF (200 mL) was added dropwise to the reaction. The reaction was warmed to rt and stirred overnight. Reaction was cooled to 0° C. and potassium tert-butoxide (70.43 g, 627.6 mmol) was slowly added. The reaction was warmed to rt and stirred overnight. The reaction was concentrated and then redissolved in ethyl acetate (500 mL) and 3N HCl (500 mL), extracted with ethyl acetate (2×250 mL), washed with 1N HCl (3×250 mL), washed with brine (1×250 mL), and dried (Na$_2$SO$_4$). Purification by silica gel chromatography using 0%-100% ethyl acetate/hexane gradient as eluent to afford 51.03 g (81%): $^1$H NMR (CDCl$_3$) δ 7.70 (d, j=8.4 Hz, 2H), 7.03 (d, j=8.8 Hz, 2H), 3.62 (t, j=5.9 Hz, 2H), 2.56 (t, j=5.7 Hz, 2H), 2.50-1.88 (m, 4H) ppm.

Part B. The product from part A (85.17 g, 282.8 mmol) and phosphorus pentachloride (205.91 g, 990.0 mmol) was dissolved into CHCl$_3$ (750 mL) and refluxed for 3½ h. Reaction was poured over ice and then quenched further with water, extracted with CHCl$_3$ (3×400 mL), washed with brine (1×400 mL), dried (MgSO$_4$), and concentrated. This residue was dissolved in morpholine (400 mL) and refluxed overnight. Reaction was concentrated and purified by silica gel chromatography using 0%-100% ethyl acetate/hexane gradient as eluent to afford 68 g (63%): $^1$H NMR (CDCl$_3$) δ 7.68 (d, j=8.8 Hz, 2H), 7.11 (d, j=8.8 Hz, 2H), 5.66 (t, j=4.8 Hz, 1H), 3.82 (t, j=4.8 Hz, 4H), 3.77 (t, j=6.8 Hz, 2H), 2.89 (t, j=4.8 Hz, 4H), 2.53-2.47 (m, 2H) ppm.

Part C. 4-Dimethylaminopyridine (3.92 g, 32.01 mmol) was dissolved into CH$_2$Cl$_2$ (130 mL) and cooled to 0° C. Trifluoroacetic anhydride (4.54 g, 32.01 mmol) was added and the mixture was stirred at 0° C. for 30 min. The above morpholine-enamine product from part B (10.25 g, 26.68 mmol) dissolved in CH$_2$Cl$_2$ (370 mL) was added slowly and the reaction was warmed to rt and stirred overnight. Reaction was concentrated and purified by silica gel chromatography using 0%-50% ethyl acetate/hexane gradient to isolate the intermediate. The intermediate was dissolved in 20% HCl (50 mL) and diethyl ether (200 mL) and stirred at rt overnight. Reaction was quenched with water, extracted with ether (3×100 mL), washed with brine (1×100 mL), and dried (Na$_2$SO$_4$). The residue was redissolved in petroleum ether and the solids filtered. The filtrate was concentrated to afford 9.99 g (78%): $^1$H NMR (CDCl$_3$) δ 7.77 (d, j=8.8 Hz, 2H), 7.11 (d, j=8.8 Hz, 2H), 3.93 (t, j=6.8 Hz, 2H), 2.92 (t, j=6.8 Hz, 2H) ppm.

Part D. The product from part C (10.0 g, 24.3 mmol) and 4-methoxyhydrazine hydrochloride (4.28 g, 24.3 mmol) were dissolved in 1N HCl (200 mL) and methanol (400 mL) and refluxed overnight. The reaction was cooled to rt and quenched with water, extracted with ethyl acetate (3×250 mL), washed with brine (1×250 mL), and dried (Na$_2$SO$_4$). Purification by silica gel chromatography using 0%-100% ethyl acetate/hexane gradient as eluent afforded 9.28 g (74%); $^1$H NMR (CDCl$_3$) δ 7.69 (d, j=9.4 Hz, 2H), 7.45 (d, j=8.8 Hz, 2H), 7.06 (d, j=8.8 Hz, 2H), 6.92 (d, j=9.2 Hz, 2H), 4.11 (t, j=6.8 Hz, 2H), 3.81 (s, 3H), 3.15 (t, j=6.5 Hz, 2H) ppm; Mass Spec (M+H)$^+$ 514.3.

Part E. 4-Benzyloxycarbonylpiperazin-2-one (0.050.214 mmol), cesium carbonate (0.095 g, 0.292 mmol), palladium (II) acetate (0.004 g, 0.019 mmol), and 9,9-dimethyl-4,5-bis (diphenylphosphino)xanthene (0.015 g, 0.029 mmol) were charged to a flask and flushed with N$_2$. The above trifluoromethyl intermediate (0.100 g, 0.195 mmol) dissolved in 1,4-dioxane (2 mL) was added via syringe and the flask was flushed with N$_2$. The reaction was heated at 100° C. overnight. The reaction was cooled to rt and diluted with ethyl acetate (25 mL) and water (25 mL), extracted with ethyl acetate (3×25 mL), washed with brine (1×25 mL), and dried (Na$_2$SO$_4$). The lactam (0.091 g, 0.146 mmol) was dissolved in 6N HCl (20 mL) and MeOH (5 mL) and refluxed for 2 h. Reaction was quenched with water (20 mL) and washed with ether (3×20 mL), basified to pH 12 with 1N NaOH, extracted again with ether (3×20 mL), washed with brine (1×20 mL), and dried (Na$_2$SO$_4$). Purification by HPLC and freeze-drying to afford 1 mg (1% overall); $^1$H NMR (CDCl$_3$) δ 7.37 (d, j=9.0 Hz, 2H), 7.32 (d, j=8.3 Hz, 2H), 7.24-7.18 (m, 2H), 6.84 (d, j=8.8 Hz, 2H), 4.05 (t, j=6.6 Hz, 2H), 3.79-3.60 (m, 5H), 3.73 (s, 3H), 3.32 (bs, 2H), 3.16 (t, j=6.5 Hz, 2H) ppm; Mass Spec (M+H)$^+$ 486.4.

Example 9

1-(4-methoxyphenyl)-6-[4-(2-oxo-1-imidazolidinyl) phenyl]-3-(trifluoromethyl)-1,4,5,6-tetrahydro-7H-pyrazolo[3,4-c]pyridin-7-one To the trifluoromethyl intermediate prepared previously (part D, example 6, 0.120 g, 0.234 mmol), 2-imidazolidone (0.025 g, 0.281 mmol), potassium carbonate (0.081 g, 0.257 mmol), 1,10-phenanthraline (0.006 g, 0.012 mmol) and DMSO (6 mL) were charged to a flask and degassed for 15 min. Copper (I) iodide (0.007 g, 0.012 mmol) was added and the reaction was heated to 130° C. overnight. The reaction was cooled to rt and quenched with H$_2$O (20 mL) and ethyl acetate (20 mL), washed with H$_2$O (3×20 mL), washed with brine (1×30 mL), and dried (Na$_2$SO$_4$). Purification by HPLC and freeze-drying afforded 29.1 mg (26%); $^1$H NMR (CDCl$_3$) δ 7.53-7.45 (m, 4H), 7.28 (d, j=11.0 Hz, 2H), 6.92 (d, j=9.1 Hz, 2H), 4.12 (t, j=6.8 Hz, 2H), 3.96 (t, j=8.1 Hz, 2H), 3.81 (s, 3H), 3.63 (t, j=8.2 Hz, 2H), 3.16 (t, j=6.6 Hz, 2H) ppm; Mass Spec (M+H)$^+$ 472.5.

Example 10

1-(4-methoxyphenyl)-6-[4-(2-oxotetrahydro-1(2H)-pyrimidinyl)phenyl]-3-(trifluoromethyl)-1,4,5,6-tetrahydro-7H-pyrazolo[3,4-c]pyridin-7-one The title compound was synthesized following the procedure for Example 6. $^1$H NMR (CDCl$_3$) δ 7.46 (d, j=8.8 Hz, 4H), 7.34-7.24 (m, 2H), 6.93 (d, j=9.1 Hz, 2H), 4.15 (t, j=6.8 Hz, 2H), 3.82 (s, 3H), 3.68 (t, j=5.7 Hz, 2H), 3.63 (t, j=5.7 Hz, 2H), 3.17 (t, j=6.4 Hz, 2H), 2.18-2.09 (m, 2H) ppm; Mass Spec (M+H)$^+$ 486.5.

Example 11

6-[4-(3-ethyl-2-oxo-2,3-dihydro-1H-benzimidazol-1-yl)phenyl]-1-(4-methoxyphenyl)-3-(trifluoromethyl)-1,4,5,6-tetrahydro-7H-pyrazolo[3,4-c]pyridin-7-one The title compound was synthesized following the procedure for Example 6. $^1$H NMR (CDCl$_3$) δ 7.58-7.47 (m, 5H), 7.28 (d, j=7.3 Hz, 1H), 7.16-7.08 (m, 1H), 7.04-6.98 (m, 4H), 6.52 (t, j=2.4 Hz, 1H), 4.14 (t, j=6.6 Hz, 2H), 3.91 (q, j=7.6 Hz, 2H), 3.78 (s, 3H), 3.18 (t, j=6.6 Hz, 2H), 1.23 (t, j=7.2 Hz, 3H) ppm; Mass Spec (M+H)$^+$ 548.5.

Example 12

1-(4-methoxyphenyl)-7-oxo-6-[4-(2-oxo-1-piperidinyl)phenyl]-4,5,6,7-tetrahydro-1H-pyrazolo[3,4-c] pyridine-3-carbonitrile Part A. 4-iodoaniline (45.82 g, 209.2 mmol) and triethylamine (65.61 mL, 470.7 mmol) were dissolved into THF (800 mL) and cooled to 0° C. 5-Bromovaleryl chloride (50.0 g, 251.1 mmol) dissolved in THF (200 mL) was added dropwise to the reaction. The reaction was warmed to rt and stirred overnight. Reaction was cooled to 0° C. and potassium tert-butoxide (70.43 g, 627.6 mmol) was slowly added. The reaction was warmed to rt and stirred overnight. The reaction was concentrated and then redissolved in ethyl acetate (500 mL) and 3N HCl (500 mL), extracted with ethyl acetate (2×250 mL), washed with 1N HCl (3×250 mL), washed with brine (1×250 mL), and dried (Na$_2$SO$_4$). Purification by silica gel chromatography using 0%-100% ethyl acetate/hexane gradient as eluent to afford 51.03 g (81%): $^1$H NMR (CDCl$_3$) δ 7.70 (d, j=8.4 Hz, 2H), 7.03 (d, j=8.8 Hz, 2H), 3.62 (t, j=5.9 Hz, 2H), 2.56 (t, j=5.7 Hz, 2H), 2.50-1.88 (m, 4H) ppm.

Part B. The product from part A (85.17 g, 282.8 mmol) and phosphorus pentachloride (205.91 g, 990.0 mmol) was dissolved into CHCl$_3$ (750 mL) and refluxed for 3½ h. Reaction was poured over ice and then quenched further with water, extracted with CHCl$_3$ (3×400 mL), washed with brine (1×400 mL), dried (MgSO$_4$), and concentrated. This residue was dissolved in morpholine (400 mL) and refluxed overnight. Reaction was concentrated and purified by silica gel chromatography using 0%-100% ethyl acetate/hexane gradient as eluent to afford 68 g (63%): $^1$H NMR (CDCl$_3$) δ 7.68 (d, j=8.8 Hz, 2H), 7.11 (d, j=8.8 Hz, 2H), 5.66 (t, j=4.8 Hz, 1H), 3.82 (t, j=4.8 Hz, 4H), 3.77 (t, j=6.8 Hz, 2H), 2.89 (t, j=4.8 Hz, 4H), 2.53-2.47 (m, 2H) ppm.

Part C. To p-anisidine (16 g, 0.129 mol) in conc. HCl (40 mL), 100 mL H$_2$O, cooled to −5° C. and sodium nitrite (9.4 g, 0.136 mol) in H$_2$O (60 mL) was added. The diazotization was stirred cold for 20 min and a mixture of ethylchloroacetoacetate (22 g, 0.133 mol), ethanol (100 mL), sodium acetate (32 g, 0.389 mol) and H$_2$O (400 mL) was added. The reaction was allowed to warm to rt and stirred for 2 h. The product precipitated as a black solid (30 g) that was collected and dried in vacuo. $^1$H NMR (CDCl$_3$) δ 8.28 (s, 1H), 7.18 (d, j=9.1 Hz, 2H), 6.90 (d, j=9.2 Hz, 2H), 4.41 (q, j=7 Hz, 2H), 3.80 (s, 3H), 1.42 (t, j=7.3 Hz, 3H) ppm.

Part D. Crude chloro ester hydrazone from Part C (30 g, 0.117 mol), iodo-morpholine enamine from example 6 (29.9 g, 0.078 mol), and triethylamine (74 mL, 0.53 mol) were heated to reflux in toluene (400 mL) for 24 h. The reaction was cooled, washed with water, dried (Na$_2$SO$_4$). Purification by silica gel chromatography using 1:1 hexane/ethyl acetate as eluent afforded the morpholine intermediate. Treatment of the morpholine intermediate with trifluoroacetic acid (50 mL) in CH$_2$Cl$_2$ (500 mL) for 24 h followed by washing with water and drying (Na$_2$SO$_4$) afforded 28.8 g (71%) of the ester/iodo; Mass Spec (M+H)$^+$ 517.9.

Part E. To ammonium chloride (1 g, 19 mmol) in xylenes (250 mL) was added trimethyl aluminum (2M heptanes, 19.3 mL, 38 mmol) and stirred for 20 min. The above ester from part D (9.1 g, 17.6 mmol) was added and the reaction was heated to reflux for 3 h. The reaction was cooled to 0° C., quenched with HCl and extracted with ethyl acetate; washed with brine and dried (Na$_2$SO$_4$). The amide/nitrile mixture obtained was treated with 30% H$_2$O$_2$ (70 mL), 10% NaOH (150 mL) in CH$_2$Cl$_2$ (400 mL) for 24 h. Extraction of the aqueous layer with CH$_2$Cl$_2$; washing with water and drying (Na$_2$SO$_4$) afforded 6.18 g of the amide (72%); $^1$H NMR (CDCl$_3$) δ 7.68 (d, j=8.5 Hz, 2H), 7.47 (d, j=8.8 Hz, 2H), 7.09 (d, j=8.8 Hz, 2H), 6.95 (d, j=8.8 Hz, 2H), 6.86 (s, 1H), 5.70 (s, 1H), 4.10 (t, j=6.6 Hz, 2H), 3.82 (s, 3H), 3.17 (t, j=6.6 Hz, 2H) ppm.

Part F. To DMF (4.28 mL, 55.3 mmol) dissolved in 150 mL acetonitrile at 0° C. was added oxalyl chloride (3.99 mL, 46.1 mmol) and stirred until all of gas evolution had stopped. The above amide from part E (9.0 g, 18.4 mmol) was added and stirred until a homogeneous mixture had formed. Pyridine (7.45 mL, 92.2 mmol) was added and the reaction was warmed to rt and stirred for 2 h. The reaction was quenched with 1N HCl, extracted with ether, washed with brine and dried (Na$_2$SO$_4$) to afford 6.54 g (75%) of the nitrile; $^1$H NMR (CDCl$_3$) δ 7.70 (d, j=8.8 Hz, 2H), 7.45 (d, j=9.2 Hz, 2H), 7.05 (d, j=8.8 Hz, 2H), 6.92 (d, j=8.8 Hz, 2H), 4.13 (t, j=6.6 Hz, 2H), 3.83 (s, 3H), 3.17 (t, j=6.6 Hz, 2H) ppm; Mass Spec (M+H)$^+$ 470.9.

Part G. δ-Valerolactam (0.127 g, 1.276 mmol), cesium carbonate (0.520 g, 1.595 mmol), palladium (II) acetate (0.024 g, 0.106 mmol), and 9,9-dimethyl-4,5-bis(diphenylphosphino)xanthene (0.092 g, 0.159 mmol) were charged to a flask and flushed with N$_2$. The above trifluoromethyl intermediate from part F (0.500 g, 1.063 mmol) dissolved in 1,4-dioxane (10 mL) was added via syringe and the flask was flushed with N$_2$. The reaction was heated at 100° C. overnight. The reaction was cooled to rt and diluted with ethyl acetate (25 mL) and water (25 mL), extracted with ethyl acetate (3×25 mL), washed with brine (1×25 mL), and dried (Na$_2$SO$_4$). Purification by HPLC and freeze-drying afforded 104.2 mg (22%); $^1$H NMR (CDCl$_3$) δ 7.46 (d, j=8.8 Hz, 2H), 7.34-7.25 (m, 4H), 6.93 (d, j=9.2 Hz, 2H), 4.15 (t, j=6.6 Hz, 2H), 3.82 (s, 3H), 3.64-3.56 (m, 2H), 3.17 (t, j=6.6 Hz, 2H), 2.60-2.52 (m, 2H), 1.98-1.90 (m, 4H) ppm; Mass Spec (M+H)$^+$ 442.3.

Example 13

1-(4-methoxyphenyl)-6-[4-(2-oxo-1-piperidinyl) phenyl]-3-(1H-tetrazol-5-yl)-1,4,5,6-tetrahydro-7H-pyrazolo[3,4-c]pyridin-7-one Part A. 4-iodoaniline (45.82 g, 209.2 mmol) and triethylamine (65.61 mL, 470.7 mmol) were dissolved into THF (800 mL) and cooled to 0° C. 5-Bromovaleryl chloride (50.0 g, 251.1 mmol) dissolved in THF (200 mL) was added dropwise to the reaction. The reaction was warmed to rt and stirred overnight. Reaction was cooled to 0° C. and potassium tert-butoxide (70.43 g, 627.6 mmol) was slowly added. The reaction was warmed to rt and stirred overnight. The reaction was concentrated and then redissolved in ethyl acetate (500 mL) and 3N HCl (500 mL), extracted with ethyl acetate (2×250 mL), washed with 1N HCl (3×250 mL), washed with brine (1×250 mL), and dried (Na$_2$SO$_4$). Purification by silica gel chromatography using 0%-100% ethyl acetate/hexane gradient as eluent to afford 51.03 g (81%): $^1$H NMR (CDCl$_3$) δ 7.70 (d, j=8.4 Hz, 2H), 7.03 (d, j=8.8 Hz, 2H), 3.62 (t, j=5.9 Hz, 2H), 2.56 (t, j=5.7 Hz, 2H), 2.50-1.88 (m, 4H) ppm.

Part B. The above lactam intermediate from part A (85.17 g, 282.8 mmol) and phosphorus pentachloride (205.91 g, 990.0 mmol) was dissolved into CHCl$_3$ (750 mL) and refluxed for 3½ h. Reaction was poured over ice and then quenched further with water, extracted with CHCl$_3$ (3×400 mL), washed with brine (1×400 mL), dried (MgSO$_4$), and concentrated. This residue was dissolved in morpholine (400 mL) and refluxed overnight. Reaction was concentrated and purified by silica gel chromatography using 0%-100% ethyl acetate/hexane gradient as eluent to afford 68 g (63%): $^1$H NMR (CDCl$_3$) δ 7.68 (d, j=8.8 Hz, 2H), 7.11 (d, j=8.8 Hz, 2H), 5.66 (t, j=4.8 Hz, 1H), 3.82 (t, j=4.8 Hz, 4H), 3.77 (t, j=6.8 Hz, 2H), 2.89 (t, j=4.8 Hz, 4H), 2.53-2.47 (m, 2H) ppm.

Part C. To p-anisidine (16 g, 0.129 mol) in conc. HCl (40 mL), 100 mL H$_2$O, cooled to −5° C. and sodium nitrite (9.4 g, 0.136 mol) in H$_2$O (60 mL) was added. The diazotization was stirred cold for 20 min and a mixture of ethylchloroacetoacetate (22 g, 0.133 mol), ethanol (100 mL), sodium acetate (32 g, 0.389 mol) and H$_2$O (400 mL) was added. The reaction was allowed to warm to rt and stirred for 2 h. The product precipitated as a black solid (30 g) which was collected and dried in vacuo. $^1$H NMR (CDCl$_3$) δ 8.28 (s, 1H), 7.18 (d, j=9.1 Hz, 2H), 6.90 (d, j=9.2 Hz, 2H), 4.41 (q, j=7 Hz, 2H), 3.80 (s, 3H), 1.42 (t, j=7.3 Hz, 3H) ppm.

Part D. Crude chloro ester hydrazone from Part C (30 g, 0.117 mol), iodo-morpholine from Part B (29.9 g, 0.078 mol), and triethylamine (74 mL, 0.53 mol) were heated to reflux in toluene (400 mL) for 24 h. The reaction was cooled, washed with water, dried (Na$_2$SO$_4$). Purification by silica gel chromatography using 1:1 hexane/ethyl acetate as eluent afforded the morpholine intermediate. Treatment of the morpholine intermediate with trifluoroacetic acid (50 mL) in CH$_2$Cl$_2$ (500 mL) for 24 h followed by washing with water and drying (Na$_2$SO$_4$) afforded 28.8 g (71%) of the ester/iodo; Mass Spec (M+H)$^+$ 517.9.

Part E. To ammonium chloride (1 g, 19 mmol) in xylenes (250 mL) was added trimethyl aluminum (2M heptanes, 19.3 mL, 38 mmol) and stirred for 20 min. The above ester (9.1 g, 17.6 mmol) was added and the reaction was heated to reflux for 3 h. The reaction was cooled to 0° C., quenched with HCl and extracted with ethyl acetate; washed with brine and dried (Na$_2$SO$_4$). The amide/nitrile mixture obtained was treated with 30% H$_2$O$_2$ (70 mL), 10% NaOH (150 mL) in CH$_2$Cl$_2$ (400 mL) for 24 h. Extraction of the aqueous layer with CH$_2$Cl$_2$; washing with water and drying (Na$_2$SO$_4$) afforded 6.18 g of the amide (72%); $^1$H NMR (CDCl$_3$) δ 7.68 (d, j=8.5 Hz, 2H), 7.47 (d, j=8.8 Hz, 2H), 7.09 (d, j=8.8 Hz, 2H), 6.95 (d, j=8.8 Hz, 2H), 6.86 (s, 1H), 5.70 (s, 1H), 4.10 (t, j=6.6 Hz, 2H), 3.82 (s, 3H), 3.17 (t, j=6.6 Hz, 2H) ppm.

Part F. To DMF (4.28 mL, 55.3 mmol) dissolved in 150 mL acetonitrile at 0° C. was added oxalyl chloride (3.99 mL, 46.1 mmol) and stirred until all of gas evolution had stopped. The above amide (9.0 g, 18.4 mmol) was added and stirred until a homogenous mixture had formed. Pyridine (7.45 mL, 92.2 mmol) was added and the reaction was warmed to rt and stirred for 2 h. The reaction was quenched with 1N HCl, extracted with ether, washed with brine and dried (Na$_2$SO$_4$) to afford 6.54 g (75%) of the nitrile; $^1$H NMR (CDCl$_3$) δ 7.70 (d, j=8.8 Hz, 2H), 7.45 (d, j=9.2 Hz, 2H), 7.05 (d, j=8.8 Hz, 2H), 6.92 (d, j=8.8 Hz, 2H), 4.13 (t, j=6.6 Hz, 2H), 3.83 (s, 3H), 3.17 (t, j=6.6 Hz, 2H) ppm; Mass Spec (M+H)+ 470.9.

Part G. Tributyl tin chloride (0.142 g, 1.06 mmol) was added dropwise to a solution of sodium azide (0.553 g, 8.51 mmol) in THF (2 mL) at 0° C. The above nitrile (0.500 g, 1.06 mmol) was added and the reaction was refluxed overnight. The reaction was cooled to rt and slowly quenched with 6N HCl (4 mL), diluted with H$_2$O (20 mL) and ethyl acetate (20 mL), extracted with ethyl acetate (3×20 mL), washed with brine (1×25 mL), and dried (Na$_2$SO$_4$) to afford 455 mg (83%); $^1$H NMR (CDCl$_3$) δ 7.69 (d, j=8.4 Hz, 2H), 7.44 (d, j=8.7 Hz, 2H), 7.18 (d, j=7.7 Hz, 1H), 7.08 (d, j=8.4 Hz, 2H), 6.92 (d, j=8.8 Hz, 2H), 4.14 (t, j=6.6 Hz, 2H), 3.82 (s, 3H), 3.48 (t, j=6.4 Hz, 2H) ppm; Mass Spec (M+H)+ 514.0.

Part H. Triphenylmethyl chloride (0.230 g, 0.826 mmol) and 10N NaOH (0.10 mL, 0.991 mmol) were added to the above tetrazole (0.424 g, 0.826 mmol) dissolved in toluene (10 mL) and stirred at rt overnight. The reaction was quenched with water (50 mL), extracted with ethyl acetate (3×75 mL), washed with brine (1×50 mL) and dried (Na$_2$SO$_4$) afforded the protected tetrazole intermediate. δ-Valerolactam (0.106 g, 1.07 mol), cesium carbonate (0.437 g, 1.34 mmol), palladium (II) acetate (0.020 g, 0.089 mmol), and 9,9-dimethyl-4,5-bis (diphenylphosphino)xanthene (0.123 g, 0.134 mmol) were charged to a flask and flushed with N$_2$. The protected tetrazole/iodo intermediate (0.676 g, 0.895 mmol) dissolved in 1,4-dioxane (10 mL) was added via syringe and the flask was flushed with N$_2$. The reaction was heated at 60° C. overnight. The reaction was cooled to rt and diluted with ethyl acetate (75 mL) and water (75 mL), extracted with ethyl acetate (3×100 mL), washed with brine (1×75 mL), and dried (Na$_2$SO$_4$). Purification by silica gel chromatography using 0%-100% ethyl acetate/hexane gradient as eluent afforded the protected tetrazole/lactam intermediate. The protected tetrazole/lactam intermediate (0.249 g, 0.322 mmol), trifluoroacetic acid (5 mL), water (5 mL) and THF (30 mL) were charged to a flask and stirred at rt for 2 h. Additional trifluoroacetic acid (20 mL) and water (20 mL) was added and the reaction was stirred overnight at rt. The reaction was basified to pH 10 with 10N NaOH and washed with CH$_2$Cl$_2$ (3×75 mL). The aqueous layer was acidified to pH 3 with 1N HCl, extracted with ethyl acetate (3×75 mL), washed with brine (1×50 mL), and dried (MgSO$_4$). Purification by HPLC and freeze-drying afforded 13.4 mg (4% overall); $^1$H NMR (CD$_3$OD) δ 7.54 (d, j=8.8 Hz, 3H), 7.43 (d, j=8.8 Hz, 2H), 7.32 (d, j=8.8 Hz, 2H), 7.00 (d, j=9.2 Hz, 2H), 4.20 (t, j=6.8 Hz, 2H), 3.84 (s, 3H), 3.67 (t, j=5.3 Hz, 2H), 3.42 (t, j=6.6 Hz, 2H), 2.51 (t, j=6.1 Hz, 2H), 1.98-1.94 (m, 4H) ppm; Mass Spec (M+H)+ 485.3.

Example 14

1-(3-amino-1,2-benzisoxazol-5-yl)-5-{[5-(2-oxo-1-piperidinyl)-2,3-dihydro-1H-indol-1-yl]carbonyl}-1H-pyrazole-3-carboxamide Part A. A 1-L flame-dried flask was charged with 130 mL of LiHMDS (130 mmol; 1.0 M in THF) and 410 mL of ethyl ether. The resulting solution was cooled to −78° C. and 2-acetylfuran (14 g, 12 m mmol) was added in one portion. After 5 min, di-tert-butyl oxalate was added dropwise over 1 h as a solution in 100 mL of ether. The resulting mixture was warmed to 23° C. over a period of 3 h and was maintained at rt for 20 h. The mixture was then filtered, and the resulting beige precipitate was washed with 100 mL of ether. The filter cake was then dried in a vacuum oven for 1 h to afford lithium 1-tert-butoxy-4-(2-furyl)-1,4-dioxo-2-buten-2-olate (25 g, 83%) as a cream colored solid. $^1$H NMR (DMSO-d$_6$) δ 7.75 (t, 1H), 6.96 (m, 1H), 6.56 (m, 1H), 3.34 (s, 2H), 1.46 (s, 9H).

Part B. To the product (13 g, 54 mmol) from Part A was added 2-fluoro-5-hydrazinobenzonitrile hydrochloride (10 g, 54 mmol) and 250 mL of acetic acid. The resulting orange mixture was maintained at rt for 20 h and then concentrated to dryness. The resulting residue was taken up in 30% CHCl$_3$ in hexanes and filtered to afford tert-butyl 1-(3-cyano-4-fluorophenyl)-5-(2-furyl)-1H-pyrazole-3-carboxylate (18 g, 95%) as a light brown solid. LC/MS (ESI+): 354.2 (M+H)+. $^1$H NMR (CDCl$_3$) δ 7.64-7.78 (m, 3H), 7.42 (s, 1H), 7.05 (s, 1H), 6.45 (s, 1H), 6.30 (s, 1H), 1.61 (s, 9H).

Part C. To the product from Part B (10 g, 28 mmol) was added 125 mL of CH$_2$Cl$_2$ and 125 mL of trifluoroacetic acid. The resulting black solution was maintained at rt under N$_2$ for 2 h and was then concentrated to dryness. The resulting solid was dried in a vacuum oven for 4 h to afford 1-(3-cyano-4-fluorophenyl)-5-(2-furyl)-1H-pyrazole-3-carboxylate (8.4 g, 99%) as a brown solid. LC/MS (ESI+): 298.1 (M+H)+. $^1$H NMR (CD$_3$OD) δ 7.90 (m, 1H), 7.75 (m, 1H), 7.51 (s, 1H), 7.46 (t, 1H), 6.98 (s, 1H), 6.47 (m, 1H), 6.35 (m, 1H).

Part D. To the product (4.1 g, 14 mmol) from Part C was added 23 mL of CH$_2$Cl$_2$ and 2.0 M oxalyl chloride (10 mL, 21 mmol) in CH$_2$Cl$_2$. Upon dropwise addition of DMF (10 drops) to the brown mixture, all solids dissolved over a period of 30 min. When no more gas evolved, the brown solution was concentrated. The resulting residue was redissolved in 100 mL of CH$_2$Cl$_2$ and 0.5 M ammonia in dioxane (110 mL, 55 mmol) was added via cannula. After 30 min, the resulting suspension was concentrated and poured into H$_2$O. The aqueous layer was washed with ethyl acetate (3×70 mL), and the combined organic layers were washed with brine, dried over Na$_2$SO$_4$, filtered and concentrated. The resulting residue was dissolved in 10 mL of CH$_2$Cl$_2$ and 50 mL of hexanes were added. The resulting suspension was filtered, and the filter cake was washed with 50 mL of hexanes. The filter cake was dried in a vacuum oven to afford 1-(3-cyano-4-fluorophenyl)-5-(2-furyl)-1H-pyrazole-3-carboxamide (2.5 g, 62%) as a brown solid. LC/MS (ESI+): 297.1 (M+H)+. $^1$H NMR (CDCl$_3$) δ 7.75 (m, 1H), 7.64 (m, 1H), 7.42 (s, 1H), 7.33 (t, 1H), 7.16 (s, 1H), 6.79 (br s, 1H), 6.46 (m, 1H), 6.36 (m, 1H), 5.50 (br s, 1H).

Part E. To the product (2.5 g, 8.3 mmol) from Part D was added H$_2$O (51 mL), 5% aqueous NaH$_2$PO$_4$ (35 mL), and tert-butanol (51 mL). The resulting mixture was warmed to 60° C., and KMnO$_4$ (8.0 g, 51 mmol) was added over a period of 10 min. After an additional 10 min, the resulting purple slurry was cooled to 0° C., and the reaction was quenched by the addition of 200 mL of saturated aqueous sodium bisulfite. The resulting mixture was filtered, washed with 300 mL of H$_2$O, and the filtrate was acidified with conc. HCl. The aqueous layer was extracted with EtOAc (6×100 mL) and the combined organic layers were washed with brine, dried over Na$_2$SO$_4$, and filtered. Concentration afforded 3-(aminocarbonyl)-1-(3-cyano-4-fluorophenyl)-1H-pyrazole-5-carboxylic acid (1.6 g, 71%) as a yellow solid. LC/MS (ESI+): 275.1 (M+H)+. $^1$H NMR (CD$_3$OD) δ 8.03 (m, 1H), 7.90 (m, 1H), 7.5 (t, 1H), 7.44 (s, 1H).

Part F. 5-Nitro-1H-indole (2.5 g, 15 mmol), di-tert-butyl dicarbonate (3.6 g, 17 mmol), and DMAP (190 mg, 1.5 mmol) were dissolved in 150 mL of THF. The solution was stirred for 12 h at rt under N$_2$ and was then concentrated. The residue was taken up in EtOAc and the mixture was filtered. The filtered solid was washed with 100 mL of hexanes and dried to give tert-butyl-5-nitro-1H-indole-1-carboxylate as an off-white solid (3.1 g, 78%). LRMS (AP+): 304.2 (M+H+

ACN)⁺. ¹H NMR (CDCl₃) δ 8.51 (d, 1H), 8.23-8.29 (m, 2H), 7.75 (d, 1H), 6.73 (d, 1H), 1.71 (s, 9H).

Part G. The product from Part F (1.0 g, 4.3 mmol) was dissolved in 100 mL of MeOH. Palladium hydroxide, 20 wt % Pd, Degussa type (100 mg), was added, and the resulting mixture was subjected to a hydrogen atmosphere (50 psi) and shaken vigorously. After 5 h, the black mixture was filtered and concentrated to afford tert-butyl-5-amino-1-indolinecarboxylate as a brown oil (0.98 g, 98%). LRMS (ESI⁺): 235.2 (M+H)⁺. ¹H NMR (CDCl₃) δ 6.88 (br m, 3H), 3.96 (m, 2H), 3.04 (m, 2H), 1.55 (br s, 9H).

Part H. To tert-butyl-5-amino-1-indolinecarboxylate (1.90 g, 8.2 mmol) was added 5-bromovaleryl chloride (1.4 mL, 9.0 mmol) and 18 mL of THF. After stirring for 5 min at rt under N₂, potassium tert-butoxide (9 mL, 9 mmol; 1.0 M in THF) was added in one portion, and the resulting brown solution was stirred under N₂ for 30 min. A second portion of potassium tert-butoxide (9 mL) was added, and the resulting brown suspension was stirred for 15 min. An additional 0.10 mL-portion of 5-bromovaleryl chloride and a 4.5 mL-portion of potassium tert-butoxide were added, and the mixture was stirred for 30 min. The reaction was then poured into H₂O (80 mL). The aqueous layer was washed with EtOAc (3×50 mL), and the combined organic layers were washed with brine, dried over Na₂SO₄, and filtered. The filtrate was concentrated and the resulting residue was purified by radial chromatography (50% EtOAc in hexanes) to afford tert-butyl 5-(2-oxo-1-piperidinyl)-1-indolinecarboxylate as a pink solid (1.30 g, 50%). LRMS (AP⁺): 317.2 (M+H)⁺. ¹H NMR (CDCl₃) δ 7.40-7.80 (br m, 1H), 7.01 (s, 1H), 6.97 (d, 1H), 3.94 (t, 2H), 3.55 (br m, 2H), 3.09 (t, 2H), 2.49 (br m, 2H), 1.91 (br m, 4H), 1.52 (s, 9H).

Part I. The product from Part H (1.30 g, 4.2 mmol) was dissolved in 30 mL of CH₂Cl₂ and stirred at rt under N₂. Trifluoroacetic acid (30 mL) was added, and the reaction was stirred for 2 h. The yellow solution was concentrated, and the resulting residue was dissolved in EtOAc (50 mL) and washed with saturated aqueous NaHCO₃. The aqueous layer was washed with EtOAc (2×50 mL) and the combined organic layers were dried over Na₂SO₄ and concentrated to afford 1-(2,3-dihydro-1H-indol-5-yl)-2-piperidinone (740 mg, 81%) as a beige solid (LC/MS (ESI⁺): 217.2 (M+H)⁺). To this solid was added 3-(aminocarbonyl)-1-(3-cyano-4-fluorophenyl)-1H-pyrazole-5-carboxylic acid (1.00 g, 3.8 mmol) (see Part E above), followed by 28 mL of pyridine and 6.8 mL of DMF. 1,3-Diisopropyl-carbodiimide (0.59 mL, 3.8 mmol) was added, and the resulting solution was stirred for 14 h. The reaction was then poured into 1N aqueous HCl (70 mL) and washed with EtOAc (3×50 mL). The combined organic layers were washed with brine, dried over Na₂SO₄, and filtered. Concentration of the filtrate afforded crude 1-(3-cyano-4-fluorophenyl)-5-{[5-(2-oxo-1-piperidinyl)-2,3-dihydro-1H-indol-1-yl]carbonyl}-1H-pyrazole-3-carboxamide (1.20 g; LC/MS (ESI⁺): 473.2 (M+H)⁺) as a brown residue. This residue was dissolved in 18 mL of DMF and 3 mL of H₂O. Potassium carbonate (1.70 g, 13 mmol) and acetohydroxamic acid (470 mg, 6.2 mmol) were added, and the resulting mixture was warmed to 50° C. under an N₂ atmosphere. After 2 h, the reaction was cooled to rt and poured into EtOAc (60 mL). The organic layer was washed with H₂O (2×50 mL), brine, and dried over Na₂SO₄. Filtration and concentration afforded a brown oily residue that was purified by preparative LC/MS (C18 reverse phase, eluted with 0.05% TFA in CH₃CN/H₂O) to give the TFA salt of the final product. This salt was dissolved in saturated aqueous NaHCO₃ (15 mL), and the aqueous layer was washed with EtOAc (3×50 mL). The combined organic layers were washed with brine, dried over Na₂SO₄, filtered, and concentrated to give 1-(3-amino-1,2-benzisoxazol-5-yl)-5-{[5-(2-oxo-1-piperidinyl)-2,3-dihydro-1H-indol-1-yl]carbonyl}-1H-pyrazole-3-carboxamide as a white solid (150 mg, 7.3% for 2 steps). LC/MS (ESI⁺): 486.2 (M+H)⁺. ¹H NMR (DMSO-d₆) δ 8.08 (s, 1H), 7.91 (d, 1H), 7.85 (s, 1H), 7.67 (m, 1H), 7.51-7.57 (br m, 2H), 7.37 (s, 1H), 7.2 (s, 1H), 7.04 (s, 1H), 6.58 (s, 2H), 4.28 (br m, 2H), 3.55 (br s, 2H), 3.15 (br m, 2H), 2.36 (br s, 2H), 1.82 (br s, 4H).

Example 15

1-(3-amino-1,2-benzisoxazol-5-yl)-5-{[6-(2-oxo-1-piperidinyl)-2,3-dihydro-1H-indol-1-yl]carbonyl}-1H-pyrazole-3-carboxamide trifluoroacetate The title compound was prepared in the same manner as Example 14 using 6-nitro-1H-indole and following the general procedures described previously. LC/MS (ESI⁺): 486.2 (M+H-TFA)⁺.

Example 16

1-(3-amino-1,2-benzisoxazol-5-yl)-5-{[5-(2-oxo-hexahydro-1H-azepin-1-yl)-2,3-dihydro-1H-indol-1-yl]carbonyl}-1H-pyrazole-3-carboxamide Part A. To tert-butyl 5-(2-oxo-hexahydro-1H-azepin-1-yl)-1-indolinecarboxylate (140 mg, 0.42 mmol) that had been prepared as in Part C of Example 15 using 6-bromohexanoyl chloride instead of 5-bromovaleryl chloride was added 10 mL of 4.0 M HCl in dioxane. The resulting solution was maintained at rt under N₂ for 2 h and was then concentrated. The resulting residue was dissolved in 25 mL of EtOAc, and the organic layer was washed with saturated aqueous NaHCO₃. The aqueous layer was washed with EtOAc (2×50 mL) and the combined organic layers were washed with brine, dried over Na₂SO₄, filtered, and concentrated to afford 1-(2,3-dihydro-1H-indol-5-yl)hexahydro-2H-azepin-2-one (96 mg, 100%) as a brown oil. LC/MS (ESI⁺): 231.2 (M+H)⁺. ¹H NMR (CDCl₃) δ 6.9 (s, 1H), 6.79 (d, 1H), 6.76 (d, 1H), 3.98 (br s, 1H), 3.66 (br m, 2H), 3.52 (t, 2H), 3.01 (t, 2H), 2.65 (br s, 2H), 1.78 (br s, 6H).

Part B. To the product from Part A (95 mg, 0.41 mmol), was added 3-(aminocarbonyl)-1-(3-cyano-4-fluorophenyl)-1H-pyrazole-5-carboxylic acid (94 mg, 0.34 mmol), 3.3 mL of pyridine, and 0.70 mL of DMF. 1,3-Diisopropylcarbodiimide (0.059 mL, 0.38 mmol) was added, and the resulting solution was stirred for 1 h. The red mixture was then poured into 1N aqueous HCl (70 mL) and washed with EtOAc (3×50 mL). The combined organic layers were washed with brine, dried over Na₂SO₄, and filtered. Concentration of the filtrate and purification of the resulting residue by radial chromatography (1-5% MeOH in CH₂Cl₂) gave 1-(3-cyano-4-fluorophenyl)-5-{[5-(2-oxo-hexahydro-1H-azepin-1-yl)-2,3-dihydro-1H-indol-1-yl]carbonyl}-1H-pyrazole-3-carboxamide (98 mg, 49%) as a brown residue. LC/MS (ESI⁺): 487.1 (M+H)⁺. ¹H NMR (CD₃OD) δ 8.08 (br m, 1H), 7.97 (br d, 1H), 7.87 (br s, 1H), 7.43 (br t, 1H), 7.28 (s, 1H), 7.12 (br s, 1H), 7.00 (br d, 1H), 4.24 (br m, 2H), 3.73 (br s, 2H), 3.16 (br m, 2H), 2.66 (br s, 2H), 1.79 (br s, 6H).

Part C. To the product from Part B (92 mg, 0.19 mmol) was added 8.8 mL of DMF and 3.4 mL of H₂O. Potassium carbonate (130 g, 0.95 mmol) and acetohydroxamic acid (36 mg, 0.47 mmol) were added, and the resulting mixture was warmed to 50° C. under an N₂ atmosphere. After 2 h, the reaction was cooled to rt and poured into EtOAc (50 mL). The organic layer was washed with H₂O (2×15 mL), brine, and dried over Na$_2$SO$_4$. Filtration and concentration afforded a brown oily residue that was purified by radial chromatography (10% MeOH in CH$_2$Cl$_2$ containing 2% NH$_4$OH) to yield 1-(3-amino-1,2-benzisoxazol-5-yl)-5-{[5-(2-oxo-hexahydro-1H-azepin-1-yl)-2,3-dihydro-1H-indol-1-yl]carbonyl}-1H-pyrazole-3-carboxamide (11 mg, 12%) as a white solid. LC/MS (ESI$^+$): 500.1 (M+H)$^+$.

Example 17

1-(3-amino-1,2-benzisoxazol-5-yl)-5-{[6-(2-oxo-hexahydro-1H-azepin-1-yl)-2,3-dihydro-1H-indol-1-yl]carbonyl}-1H-pyrazole-3-carboxamide Part A. To tert-butyl-6-nitro-1H-indole-1-carboxylate (3.80 g, 14 mmol), prepared according to Part F of Example 14 using 6-nitro-1H-indole as starting material, was added 150 mL of MeOH and 150 mL of EtOAc. The solution was covered with a stream of N$_2$, and 10 wt % Pd/C (100 mg) was added in one portion. The mixture was subjected to a hydrogen atmosphere (50 psi) for 14 h and was then filtered and concentrated. Analysis (LC/MS) of the resulting brown residue (3.34 g, 100%) showed it to be a 20:80 mixture of tert-butyl-6-amino-1-indolinecarboxylate: tert-butyl-6-amino-1H-indole-1-carboxylate. LC/MS (ESI$^+$): 233.1 (indole M+H)$^+$, 235.1 (indoline M+H)$^+$.

Part B. To the mixture from Part A (400 mg, 1.7 mmol) was added 6-bromohexanoyl chloride (0.26 mL, 1.7 mmol) and 15 mL of THF. Potassium tert-butoxide (1.90 mL, 1.9 mmol; 1.0 M in THF) was added and the cloudy mixture was stirred for 10 min. A second 1.90-mL portion of potassium tert-butoxide was added and the reaction was maintained at rt for 1 h. The reaction was then poured into 1N HCl (70 mL), and the aqueous layer was washed with EtOAc (3×50 mL). The combined organic layers were washed with brine, dried over Na$_2$SO$_4$, filtered, and concentrated. The resulting residue was purified by radial chromatography to give a mixture of tert-butyl 6-(2-oxo-hexahydro-1H-azepin-1-yl)-1-indolinecarboxylate and tert-butyl 6-(2-oxo-hexahydro-1H-azepin-1-yl)-1H-indole-1-carboxylate (340 mg, 60%) as a red oil. LC/MS (ESI$^+$): 329.3 (indole M+H)$^+$, 331.2 (indoline M+H)$^+$.

Part C. To the product from Part B was added 5 mL of trifluoroacetic acid and NaBH$_3$CN (260 mg, 4.1 mmol). After 2 h, an additional 100 mg-portion of borohydride was added. The mixture was stirred for 14 h, and another 100 mg-portion was added. After maintaining the reaction at rt under N$_2$ for 24 h, the mixture was concentrated and poured into 1N NaOH (25 mL). The aqueous layer was washed with EtOAc (3×25 mL), and the combined organic layers were washed with brine, dried over Na$_2$SO$_4$, filtered, and concentrated. The resulting residue was purified by radial chromatography (5% MeOH in CH$_2$Cl$_2$) to afford solely 1-(2,3-dihydro-1H-indol-5-yl)hexahydro-2H-azepin-2-one as a yellow foam (90 mg, 38%). $^1$H NMR (CDCl$_3$) δ 7.24 (d, 1H), 7.17 (s, 1H), 7.06 (m, 1H), 3.60-3.85 (m, 2H), 3.45 (m, 1H), 3.18 (m, 2H), 2.97 (m, 1H), 2.69 (br s, 2H), 1.82 (br s, 6H).

Part D. To the product from Part C (90 mg, 0.39 mmol), was added 3-(aminocarbonyl)-1-(3-cyano-4-fluorophenyl)-1H-pyrazole-5-carboxylic acid (89 mg, 0.33 mmol), 3.0 mL of pyridine and 1.0 mL of DMF. 1,3-Diisopropylcarbodiimide (0.056 mL, 0.36 mmol) was added, and the resulting solution was stirred for 14 h. The red mixture was poured into 1N aqueous HCl (70 mL) and washed with EtOAc (3×50 mL). The combined organic layers were washed with brine, dried over Na$_2$SO$_4$, and filtered. Concentration of the filtrate and purification of the resulting residue by preparative LC/MS (C18 reverse phase, eluted with 0.05% TFA in CH$_3$CN/H$_2$O) gave 1-(3-cyano-4-fluorophenyl)-5-{[6-(2-oxo-hexahydro-1H-azepin-1-yl)-2,3-dihydro-1H-indol-1-yl]carbonyl}-1H-pyrazole-3-carboxamide (67, 29% mg) as a white foam. LC/MS (ESI$^+$): 487.2 (M+H)$^+$.

Part E. To the product from Part D (67 mg, 0.11 mmol) was added 6.3 mL of DMF and 2.5 mL of H$_2$O. Potassium carbonate (95 g, 0.69 mmol) and acetohydroxamic acid (26 mg, 0.34 mmol) were added, and the resulting mixture was warmed to 50° C. under an N$_2$ atmosphere. After 2 h, the reaction was cooled to rt and poured into EtOAc (50 mL). The organic layer was washed with H$_2$O (2×15 mL), brine, and dried over Na$_2$SO$_4$. Filtration and concentration afforded a brown oily residue that was purified by preparative LC/MS (C18 reverse phase, eluted with 0.05% TFA in CH$_3$CN/H$_2$O) to afford 1-(3-amino-1,2-benzisoxazol-5-yl)-5-{[6-(2-oxo-hexahydro-1H-azepin-1-yl)-2,3-dihydro-1H-indol-1-yl]carbonyl}-1H-pyrazole-3-carboxamide trifluoroacetate (33 mg, 40%) as a white solid. LC/MS (ESI$^+$): 500.2 (M+H-TFA)$^+$.

Example 18

1-(4-methoxyphenyl)-7-oxo-6-[4-(2-oxo-1-piperidinyl)phenyl]-4,5,6,7-tetrahydro-1H-pyrazolo[3,4-c]pyridine-3-carboxamide Part A. 4-iodoaniline (45.82 g, 209.2 mmol) and triethylamine (65.61 mL, 470.7 mmol) were dissolved into THF (800 mL) and cooled to 0° C. 5-Bromovaleryl chloride (50.0 g, 251.1 mmol) dissolved in THF (200 mL) was added dropwise to the reaction. The reaction was warmed to rt and stirred overnight. Reaction was cooled to 0° C. and potassium tert-butoxide (70.43 g, 627.6 mmol) was slowly added. The reaction was warmed to rt and stirred overnight. The reaction was concentrated and then redissolved in ethyl acetate (500 mL) and 3N HCl (500 mL), extracted with ethyl acetate (2×250 mL), washed with 1N HCl (3×250 mL), washed with brine (1×250 mL), and dried (Na$_2$SO$_4$). Purification by silica gel chromatography using 0%-100% ethyl acetate/hexane gradient as eluent to afford 51.03 g (81%): $^1$H NMR (CDCl$_3$) δ 7.70 (d, j=8.4 Hz, 2H), 7.03 (d, j=8.8 Hz, 2H), 3.62 (t, j=5.9 Hz, 2H), 2.56 (t, j=5.7 Hz, 2H), 2.50-1.88 (m, 4H) ppm.

Part B. The above lactam intermediate from Part A (85.17 g, 282.8 mmol) and phosphorus pentachloride (205.91 g, 990.0 mmol) were dissolved into CHCl$_3$ (750 mL) and refluxed for 3½ h. Reaction was poured over ice and then quenched further with water, extracted with CHCl$_3$ (3×400 mL), washed with brine (1×400 mL), dried (MgSO$_4$), and concentrated. This residue was dissolved in morpholine (400 mL) and refluxed overnight. Reaction was concentrated and purified by silica gel chromatography using 0%-100% ethyl acetate/hexane gradient as eluent to afford 68 g (63%): $^1$H NMR (CDCl$_3$) δ 7.68 (d, j=8.8 Hz, 2H), 7.11 (d, j=8.8 Hz, 2H), 5.66 (t, j=4.8 Hz, 1H), 3.82 (t, j=4.8 Hz, 4H), 3.77 (t, j=6.8 Hz, 2H), 2.89 (t, j=4.8 Hz, 4H), 2.53-2.47 (m, 2H) ppm.

Part C. To p-anisidine (16 g, 0.129 mol) in conc. HCl (40 mL) and water (100 mL) at 0° C. was slowly added sodium nitrite (9.4 g, 0.136 mol) in water (60 mL). The reaction was stirred cold for 0.5 h. To the above reaction was poured a mixture of ethylchloroacetoacetate (22 g, 0.133 mol), ethanol (100 mL), sodium acetate (32 g, 0.389 mmol), and water (400 mL). The reaction was stirred 2 h at rt. The precipitate was filtered-off and dried to afford the hydrazone as a red gum (30.3 g, 91%): $^1$H NMR (CDCl$_3$) δ 8.28 (s, 1H), 7.18 (d, j=9.1 Hz, 2H), 6.90 (d, j=9.2 Hz, 2H), 4.41 (q, j=8 Hz, 2H), 3.80 (s, 3H), 1.42 (t, j=6.9 Hz, 3H) ppm.

Part D. To the hydrazone from Part C (0.7 g, 2.7 mmol) and the morpholine compound from Part B (0.7 g, 1.8 mol) in toluene (25 mL) was added triethylamine (2 mL, 14.2 mmol) and the reaction was heated to reflux for 6 h. The reaction was cooled to rt and water was added. The mixture was extracted with ethyl acetate, washed with water, 1N HCl, sat'd NaHCO$_3$ and dried (Na$_2$SO$_4$). Purification on silica gel using 3:2 hexanes/ethyl acetate afforded a morpholine intermediate that was dissolved in CH$_2$Cl$_2$ (50 mL) and TFA (2 mL). After 24 h the reaction was diluted with CH$_2$Cl$_2$, washed with water and sat'd NaHCO$_3$ and dried (Na$_2$SO$_4$) to afford 0.17 g (18%) foam: $^1$H NMR (CDCl$_3$) δ 7.70 (d, j=8.5 Hz, 2H), 7.47 (d, j=9.1 Hz, 2H), 7.09 (d, j=8.8 Hz, 2H), 6.93 (d, j=9.2 Hz, 2H), 4.49 (q, j=6.9 Hz, 2H), 4.12 (t, j=6.5 Hz, 2H), 3.81 (s, 3H), 3.34 (t, j=6.6 Hz, 2H), 1.45 (t, j=6.9 Hz, 3H) ppm; Mass Spec ESI(M+H)$^+$ 517.9.

Part E. To iodo compound from Part D (25 g, 0.048 mol) was added γ-valerolactam (6.7 g, 0.067 mol), K$_2$CO$_3$ (8 g, 0.058 mol), degassed DMSO (100 mL) and CuI (1.84 g, 0.009 mol). The reaction was heated to 130° C. for 24 h. The reaction was cooled, partitioned with EtOAc/H$_2$O, extracted and dried (MgSO$_4$). Purification by silica gel chromatography using 0-10% MeOH/CH$_2$Cl$_2$ as eluent afforded 5 g (21%) of ethyl 1-(4-methoxyphenyl)-7-oxo-6[4-(2-oxo-1-piperidinyl)phenyl]-4,5,6,7-tetrahydro-1H-pyrazolo[3,4-c]pyridine-3-carboxylate as a tan foam; $^1$H NMR (CDCl$_3$) δ 7.49 (d, j=9.2 Hz, 2H), 7.35 (d, j=8.8 Hz, 2H), 7.26 (d, j=8.1 Hz, 2H), 6.92 (d, j=8.8 Hz, 2H), 4.49 (q, j=7.3 Hz, 2H), 4.13 (t, j=6.6 Hz, 2H), 3.81 (s, 3H), 3.59 (m, 2H), 3.39 (t, j=6.6 Hz, 2H), 2.55 (m, 2H), 1.91 (m, 4H), 1.45 (t, j=7.3 Hz, 3H) ppm.

Part F. To ester from Part E (4.8 g, 0.009 mol) was added 5% NH$_3$ in ethylene glycol (40 mL) and the mixture was heated to 120° C. for 4 h in sealed vessel. Water was added and the resulting solid was collected. Purification by silica gel chromatography using 0-10% MeOH/CH$_2$Cl$_2$ as eluent afforded 3.5 g of a white solid. A portion of the solid was recrystallized from CH$_2$Cl$_2$/EtOAc to afford 2.5 g of the title compound. The remaining solid and filtrate material was recrystallized from isopropyl alcohol to afford an additional 0.57 g for a total of 3.07 g (68%): $^1$H NMR (CDCl$_3$) δ 7.49 (d, j=8.8 Hz, 2H), 7.37 (d, j=9.1 Hz, 2H), 7.26 (d, j=8.8 Hz, 2H), 6.98 (s, 1H) 6.95 (d, j=9.2 Hz, 2H), 6.28 (s, 1H), 4.14 (t, j=6.6 Hz, 2H), 3.81 (s, 3H), 3.61 (m, 2H), 3.39 (t, j=6.6 Hz, 2H), 2.63 (t, j=6.2 Hz, 2H), 1.96 (m, 4H) ppm.

Example 19

3-bromo-1-(4-methoxyphenyl)-6-[4-(2-oxo-1-piperidinyl)phenyl]-1,4,5,6-tetrahydro-7H-pyrazolo[3,4-c]pyridin-7-one Part A. 4-Methoxyphenyl hydrazine hydrochloride (3 g, 17 mmol) was treated with glyoxylic acid monohydrate (1.6 g, 17 mmol) in H$_2$O with conc. HCl (1 mL). After 3 h a red precipitate was filtered off and dried to afford 3.13 g (93%) hydrazone.

Part B. The hydrazone from Part A (3.13 g, 16.1 mmol) was placed in DMF (20 mL), cooled to −5° C. and NBS (5.7 g, 32 mmol) in DMF (20 mL) was added slowly. The reaction was held at rt 15 min and then 3-(4-morpholinyl)-1-(4-nitrophenyl)-5,6-dihydro-2(1H)-pyridinone (Example 1 Part A) (4.8 g, 16 mmol) was added. TEA (4.5 mL, 32 mmol) in toluene (50 mL) was added dropwise and the reaction stirred at rt for 24 h. The morpholine intermediate was extracted with EtOAc, washed with H$_2$O, dried (Na$_2$SO$_4$) then purified by silica gel chromatography using 1:1 Hexanes/EtOAc as eluent to afford a foam.

Part C. The morpholine intermediate from Part B was treated with TFA (5 mL) in CH$_2$Cl$_2$ (30 mL) for 24 h. Dilution with CH$_2$Cl$_2$, washing with H$_2$O, sat'd NaCl and drying (Na$_2$SO$_4$) afforded 2.29 g (32%) of a tan foam; $^1$H NMR (CDCl$_3$) δ 8.25 (d, j=9.1 Hz, 2H), 7.51 (d, j=8.8 Hz, 2H), 7.46 (d, j=9.1 Hz, 2H), 6.94 (d, j=9.2 Hz, 2H), 4.22 (t, j=6.6 Hz, 2H), 3.82 (s, 3H), 3.04 (t, j=6.6 Hz, 2H) ppm.

Part D. The nitro compound from Part C (0.67 g, 1.5 mmol) was heated to reflux in MeOH (25 mL) containing 5% Pt/C (0.1 g) and ammonium formate (0.25 g) for 24 h. The reaction was cooled, filtered and concentrated to afford 0.61 g (98%) aniline; Mass Spec (M+H)$^+$ (413-415).

Part E. The aniline from Part D was converted to the lactam as described for the aniline in the previous Example 1 Part D to afford the title compound. $^1$H NMR (CDCl$_3$) δ 7.46 (d, j=9.1 Hz, 2H), 7.34 (d, j=8.8 Hz, 2H), 7.26 (d, j=8.8 Hz, 2H), 6.91 (d, j=9.1 Hz, 2H), 4.14 (t, j=6.6 Hz, 2H), 3.8 (s, 3H), 3.59 (m, 2H), 2.98 (t, j=6.6 Hz, 2H), 2.55 (m, 2H), 1.95 (m, 4H) ppm. HRMS for C$_{24}$H$_{24}$Br$_1$N$_4$O$_3$ (M+H)$^+$ 495.1032.

Example 20

1-(4-methoxyphenyl)-6-[4-(2-oxo-1-piperidinyl)phenyl]-3-(4-pyridinyl)-1,4,5,6-tetrahydro-7H-pyrazolo[3,4-c]pyridin-7-one, Trifluoroacetic Acid Salt To crude 3-bromo-1-(4-methoxyphenyl)-6-[4-(2-oxo-1-piperidinyl)phenyl]-1,4,5,6-tetrahydro-7H-pyrazolo[3,4-c]pyridin-7-one (Example 19) (0.19 g, 0.4 mmol) was added toluene (25 mL), ethanol (10 mL), 2M Na$_2$CO$_3$(1 mL), and pyridine-4-boronic acid (60 mg, 0.48 mmol). The mixture was degassed with N$_2$ and tetrakistriphenylphosphine palladium (25 mg) was added and the reaction heated to reflux 24 h. The reaction was filtered, concentrated and extracted with EtOAc and dried (MgSO$_4$). Purification by HPLC and freeze-drying afforded 10 mg (4%) of the title compound; HRMS (M+H)$^+$ for C$_{29}$H$_{28}$N$_5$O$_3$ was 494.2183; $^1$H NMR (CDCl$_3$+DMSO-d$_6$) δ 8.88 (d, j=6.6 Hz, 1H), 8.22 (d, j=6.6 Hz, 1H), 7.30-7.06 (m, 6H), 6.74 (d, j=8.7 Hz, 2H), 3.98 (t, j=6.6 Hz, 2H), 3.60 (s, 3H), 3.12 (t, j=6.6 Hz, 2H), 2.36 (m, 4H), 1.73 (m, 4H) ppm.

Example 21

1-(4-methoxyphenyl)-6-[4-(2-oxo-1-piperidinyl)phenyl]-3-(4-pyridinyl-N-oxide)-1,4,5,6-tetrahydro-7H-pyrazolo[3,4-c]pyridin-7-one The pyridine compound TFA salt of Example 20 (40 mg, 0.065 mmol) was free-based with sat'd aqueous NaHCO$_3$ and extracted into ethyl acetate and dried (MgSO$_4$). The pyridine compound was dissolved in CH$_2$Cl$_2$ and excess 50% 3-chloroperbenzoic acid (50 mg) was added. The reaction was stirred 3 h, washed with sat'd aqueous NaHCO$_3$ and dried (Na$_2$SO$_4$). Purification by HPLC and freeze-drying afforded 16 mg (48%) of the title compound; HRMS (M+H)$^+$ for C$_{29}$H$_{28}$N$_5$O$_4$ was 510.2145; $^1$H NMR (CDCl$_3$) δ 8.49 (d, j=6.9 Hz, H), 7.93 (d, j=7 Hz, 2H), 7.51 (d, j=8.8 Hz, 2H), 7.37 (d, j=8.8 Hz, 2H), 7.28 (d, j=8.8 Hz, 2H), 6.97 (d, j=8.8 Hz, 2H), 4.22 (t, j=6.6 Hz, 2H), 3.83 (s, 3H), 3.61 (m, 2H), 3.30 (t, j=6.6 Hz, 2H), 2.58 (m, 2H), 1.96 (m, 4H) ppm.

Example 22

1-(4-methoxyphenyl)-6-[4-(2-oxo-1-piperidinyl)phenyl]-3-(3-pyridinyl)-1,4,5,6-tetrahydro-7H-pyrazolo[3,4-c]pyridin-7-one, Trifluoroacetic Acid Salt To 3-bromo-1-(4-methoxyphenyl)-6-[4-(2-oxo-1-piperidinyl)phenyl]-1,4,5,6-tetrahydro-7H-pyrazolo[3,4-c]pyridin-7-one (Example 19)(0.23 g, 0.46 mmol) was added 3-tributylstannylpyridine (0.222 g, 0.61 mmol) and toluene (25 mL). The mixture was degassed with $N_2$ for 10 min, then tetrakistriphenylphosphine palladium (10 mg) was added. The reaction was heated to reflux for 3 h. The cooled reaction was diluted with ethyl acetate then, washed sequentially with sat'd aqueous KF, brine and dried ($MgSO_4$). Purification by silica gel chromatography using 0-5% $MeOH/CH_2Cl_2$ (1% $NH_3$) as eluent and conversion to the TFA salt before freeze-drying afforded 0.28 g (81%) of the title compound: HRMS $(M+H)^+$ for $C_{29}H_{28}N_5O_3$ was 494.2191; $^1H$ NMR (DMSO-$d_6$) δ 9.09 (d, j=1.8 Hz, 1H), 8.76 (dd, j=5.2.1.5 Hz, 1H), 8.47 (d, j=8 Hz, 1H), 7.81 (dd, j=5.2, 7.7 Hz, 1H), 7.55 (d, j=8.8 Hz, 2H), 7.39 (d, j=8.8 Hz, 2H), 7.31 (d, j=8.8 Hz, 2H), 7.03 (d, j=9.2 Hz, 2H), 4.15 (t, j=6.6 Hz, 2H), 3.81 (s, 3H), 3.62 (t, j=5.5 Hz, 2H) 3.30 (t, j=6.6 Hz, 2H), 2.41 (t, j=6.2 Hz, 2H), 1.85 (m, 4H) ppm.

Example 23

1-(4-methoxyphenyl)-6-[4-(2-oxo-1-piperidinyl) phenyl]-3-(3-pyridinyl-N-oxide)-1,4,5,6-tetrahydro-7H-pyrazolo[3,4-c]pyridin-7-one This compound was prepared by the same procedure as Example 21: HRMS $(M+H)^+$ for $C_{29}H_{28}N_5O_4$ was 510.2121; $^1H$ NMR (DMSO-$d_6$) δ 8.57 (s, 1H), 8.25 (d, j=7 Hz, 1H), 7.91 (m, 1H), 7.71 (m, 1H), 7.54 (d, j=9.2 Hz, 2H), 7.38 (d, j=8.8 Hz, 2H), 7.31 (d, j=8.8 Hz, 2H), 7.02 (d, j=8.8 Hz, 2H), 4.11 (t, j=6.6 Hz, 2H), 3.80 (s, 3H), 3.58 (t, j=5.5 Hz, 2H), 3.25 (m, 2H), 2.40 (t, j=6 Hz, 2H), 1.86 (m, 4H) ppm.

Example 24

1-(4-methoxyphenyl)-6-[4-(2-oxo-1-piperidinyl) phenyl]-3-(2-pyridinyl)-1,4,5,6-tetrahydro-7H-pyrazolo[3,4-c]-7-one Trifluoroacetic Acid Salt To 3-bromo-1-(4-methoxyphenyl)-6-[4-(2-oxo-1-piperidinyl)phenyl]-1,4,5,6-tetrahydro-7H-pyrazolo[3,4-c]-7-one (Example 21) (0.21 g, 0.43 mmol) was added 2-tributylstannylpyridine (0.26 g, 0.55 mmol) and toluene (25 mL). The mixture was degassed with $N_2$ for 10 min, then tetrakistriphenylphosphine palladium (10 mg) was added. The reaction was heated to reflux for 24 h. The cooled reaction was diluted with ethyl acetate, washed sequentially with sat'd aqueous KF, brine and dried ($MgSO_4$). Purification by silica gel chromatography using 0-5% $MeOH/CH_2Cl_2$ (1% $NH_3$) as eluent, then by HPLC and freeze-drying afforded 0.26 g (58%) of the title compound: HRMS $(M+H)^+$ for $C_{29}H_{28}N_5O_3$ was 494.2192; $^1H$ NMR (DMSO-$d_6$) δ 8.68 (d, j=4 Hz, 1H), 8.05 (d, j=8.1 Hz, 1H), 7.95 (dt, j=1.8, 7.7 Hz, 1H), 7.55 (d, j=8.8 Hz, 2H), 7.43 (m, 1H), 7.39 (d, j=8.8 Hz, 2H), 7.30 (d, j=8.8 Hz, 2H), 7.02 (d, j=9.2 Hz, 2H), 4.13 (t, j=6.6 Hz, 2H), 3.81 (s, 3H), 3.61 (t, j=4.8 Hz, 2H) 3.43 (t, j=6.6 Hz, 2H), 2.41 (t, j=6 Hz, 2H), 1.86 (m, 4H) ppm.

Example 25

1-(4-methoxyphenyl)-6-[4-(2-oxo-1-piperidinyl) phenyl]-1,4,5,6-tetrahydro-7H-pyrazolo[3,4-c]pyridin-7-one To 3-bromo-1-(4-methoxyphenyl)-6-[4-(2-oxo-1-piperidinyl)phenyl]-1,4,5,6-tetrahydro-7H-pyrazolo[3,4-c]pyridin-7-one (Example 21) (0.15 g, 0.3 mmol), dimethylamine (2M THF, 1.5 mL, 3 mmol), sodium t-butoxide (88 mg, 0.9 mmol), 2-dicyclohexylphosphino-2'-(N,N-dimethylamino) biphenyl (7 mg), was added toluene/dioxane (1:1) (15 mL) and the mixture was degassed with $N_2$. $Pd_2(dba)_3$ was added and the reaction was heated to 85° C. for 24 h. The reaction was cooled, diluted with ethyl acetate and filtered through Celite®. Purification by HPLC and freeze-drying afforded 25 mg (18%) of the title compound; HRMS $(M+Na)^+$ for $C_{24}H_{24}NaN_4O_3$ was 439.1726; $^1H$ NMR ($CDCl_3$) δ 7.59 (s, 1H), 7.47 (d, j=8.8 Hz, 2H), 7.36 (d, j=8.8 Hz, 2H), 7.26 (d, j=9.1 Hz, 2H), 6.92 (d, j=9.2 Hz, 2H), 4.10 (t, j=6.6 Hz, 2H), 3.60 (m, 2H), 3.81 (s, 3H), 3.03 (t, j=6.6 Hz, 2H), 2.57 (m, 2H), 1.94 (m, 4H) ppm.

Example 26

1-(4-methoxyphenyl)-7-oxo-6-[5-(2-oxo-1-piperidinyl)-2-pyridinyl]-4,5,6,7-tetrahydro-1H-pyrazolo[3,4-c]pyridine-3-carboxamide, Trifluoroacetic Acid Salt Part A. To valerolactam (5.6 g, 55 mmol) in $CHCl_3$ was added $PCl_5$ (34.6 g, 166 mmol) and the reaction was heated to reflux 24 h. The reaction was cooled, quenched with $H_2O$, extracted with $CHCl_3$ and dried ($MgSO_4$) to afford crude 3,3-dichloro-2-piperidinone.

Part B. To the 3,3-dichloro-2-piperidinone (55 mmol) from Part A was added $CCl_4$ (250 mL), $AlCl_3$ (22 g, 166 mmol) and the reaction was heated to reflux 24 h. The reaction was cooled and added to 3N NaOH (200 mL) and $NH_4Cl$ (40 g). The resultant emulsion was filtered through Celite® and the aqueous layer extracted with $CH_2Cl_2$ and dried ($MgSO_4$) to afford 3.4 g (46%) of 3-chloro-5,6-dihydro-2(1H)-pyridinone; $^1H$ NMR ($CDCl_3$) δ 6.80 (t, j=4.7 Hz, 1H), 6.60 (s, 1H), 3.51 (m, 2H), 2.51 (m, 2H) ppm.

Part C. The 3-chloro-5,6-dihydro-2(1H)-pyridinone (1.5 g, 11.4 mmol) was heated to reflux in toluene (50 mL), with TEA (5 mL, 34 mmol) and ethyl (2Z)-chloro[4-methoxyphenyl)hydrazono]ethanoate (Example 19 Part B)(4 g, 15.6 mmol) for 24 h. A tan precipitate was filtered off and the filtrate purified through silica gel using 1:1 Hexane/EtOAc as eluent to afford a total of 1.4 g (38%) ethyl 1-(4-methoxyphenyl)-7-oxo-4,5,6,7-tetrahydro-1H-pyrazolo[3,4-c]pyridine-carboxylate; $^1H$ NMR ($CDCl_3$) δ 7.51 (d, j=9.2 Hz, 2H), 6.96 (d, j=9.2 Hz, 2H), 5.59 (s, 1H), 4.48 (q, j=7.3 Hz, 2H), 3.85 (s, 3H), 3.66 (dt, j=3 Hz, 2H), 3.22 (t, j=6.9 Hz, 2H), 1.44 (t, j=7 Hz, 3H) ppm.

Part D. To the ethyl 1-(4-methoxyphenyl)-7-oxo-4,5,6,7-tetrahydro-1H-pyrazolo[3,4-c]pyridine-carboxylate (0.49 g, 1.55 mmol) was added $CsCO_3$ (0.76 g, 2.3 mmol), 9,9-dimethyl-4,5-bis(diphenyphosphino)xanthene (70 mg, 0.11 mmol), and palladium(II) acetate (18 mg, 0.08 mmol) and the mixture was flushed with $N_2$. Dioxane (15 mL) and 2-bromo-5-nitropyridine (0.315 g, 1.55 mmol) were added and the reaction heated to 75° C. for 24 h. The reaction was filtered, partitioned between EtOAc and $H_2O$ and extracted. The organic layer was dried ($MgSO_4$). Purification by chromatography on silica gel using 2:1 hexane/EtOAc as eluent afforded 0.62 g (92%) of the nitro compound; Mass Spec $(M+H)^+$ 438.1.

Part E. The nitro compound from Part D (0.61 g, 1.4 mmol) was reduced with iron powder (0.9 g, 16 mmol) in acetic acid (15 mL) at 90° C. for 1.5 h. The reaction was cooled, filtered, concentrated, dissolved in $CH_2Cl_2$ and washed with sat'd $NaHCO_3$ and dried ($MgSO_4$) to afford 0.46 g (81%) of the aniline as a yellow solid; Mass Spec $(M+H)^+$ 408.1.

Part F. To the aniline from Part E (0.27 g, 0.66 mmol) was added 5-bromovaleryl chloride (0.16 g, 0.8 mmol) and TEA (0.23 mL, 1.65 mmol) in THF (20 mL) and the reaction was stirred 24 h. Potassium t-butoxide (0.24 g, 1.99 mmol) was added and the reaction was stirred 72 h. The reaction was quenched with water and extracted with EtOAc, dried (MgSO$_4$) and chromatographed on silica eluting with 1:1 Hexanes/EtOAc to afford 0.17 g (53%) of the lactam as a white solid; Mass Spec (M+H)$^+$ 490.2.

Part G. To the lactam from Part F (0.17 g, 0.34 mmol) in DMF (2.5 mL) was added formamide (0.14 mL, 3.5 mmol) and 25% NaOMe/MeOH (0.5 mL). The reaction was stirred 24 h, concentrated, and purification by HPLC and freeze-drying afforded 10 mg (5%) of the title compound; HRMS (M+H)$^+$ for $C_{24}H_{25}N_6O_4$ was 461.1918.

Example 27

1-(4-methoxyphenyl)-7-oxo-6-[4-(2-oxo-1(2H)-py-ridinyl)phenyl]-4,5,6,7-tetrahydro-1H-pyrazolo[3,4-c]pyridine-3-carboxamide Part A. Ethyl 6-(4-iodophenyl)-1-(4-methoxyphenyl)-7-oxo-4,5,6,7-tetrahydro-1H-pyrazolo[3,4-c]pyridine-3-carboxylate (0.57 g, 1.1 mmol), 2-hydroxypyridine (0.125 g, 1.3 mmol), K$_2$CO$_3$ (0.18 g, 1.3 mmol) were combined in DMSO (5 mL) and degassed with N$_2$. Copper (I) iodide (41 mg, 0.21 mmol) was added and the reaction was heated to 130° C. for 24 h. The reaction was quenched with dilute NH$_4$OH solution and filtered. The filtrate was extracted with EtOAc and dried (MgSO$_4$). Purification on silica gel using 0-5% MeOH/CH$_2$Cl$_2$ as eluent afforded 70 mg (13%) of the ester; Mass Spec (M+H)$^+$ 485.2.

Part B. To the ester from Part A (0.07 g, 0.144 mmol) in formamide (4 mL) and DMF (3 mL) was added 1 drop of 25% NaOMe/MeOH. The reaction was stirred 48 h, then partitioned between EtOAc and water. Extraction with EtOAc, drying (MgSO$_4$) and purification by HPLC afforded 25 mg (38%) of the title compound; $^1$H NMR (DMSO-d$_6$) δ 7.49 (d, j=9.2 Hz, 2H), 7.48 (m, 2H), 7.41 (d, j=8.8 Hz, 2H), 7.40 (m, 1H), 7.28 (m, 1H), 6.96 (d, j=9.2 Hz, 2H), 6.90 (s, 1H), 6.69 (d, j=8.8 Hz, 1H), 6.27 (t, j=6 Hz, 1H), 5.55 (s, 1H), 4.19 (t, j=6.6 Hz, 2H), 3.83 (s, 3H), 3.43 (t, j=6.6 Hz, 2H) ppm.

Example 28

1-(4-methoxyphenyl)-3-(methylsulfonyl)-6-[4-(2-oxo-1-piperidinyl)phenyl]-1,4,5,6-tetrahydro-7H-pyrazolo[3,4-c]pyridin-7-one Part A. To p-anisidine (4.39 g, 3.6 mmol) in conc. HCl (9.2 mL) and water (20 mL) at 0° C. was slowly added sodium nitrite (2.58 g, 3.7 mmol) in water (20 mL). The reaction was stirred cold for 0.5 h. The above mixture was poured into a mixture of 3-chloromethanesulphonyl acetone (Grossert et. al., *Can. J. Chem.* 62, 1984, 798) (6.1 g, 3.5 mmol), acetone (50 mL), sodium acetate (6.7 g, 8.2 mmol), and water (100 mL). The reaction was stirred 4 h at rt. The precipitate was filtered-off and dried to afford the hydrazone as a red solid (5.28 g, 57%); $^1$H NMR (CDCl$_3$) δ 8.05 (s, 1H), 7.12 (d, j=9.2 Hz, 2H), 6.91 (d, j=8.8 Hz, 2H), 3.80 (s, 3H), 3.23 (s, 3H) ppm.

Part B. To the hydrazone from Part A (0.78 g, 2.9 mmol) and 3-(4-morpholinyl)-1-(4-nitrophenyl)-5,6-dihydro-2 (1H)-pyridinone (0.9 g, 2.9 mmol) in toluene (30 mL) was added triethylamine (1 mL, 7.2 mmol) and the reaction was heated to reflux for 18 h. The reaction was cooled to rt and excess TFA was added. After 24 h the reaction was diluted with ethyl acetate, washed with water and sat'd NaHCO$_3$ and dried (MgSO$_4$). Purification on silica gel using 1:1 hexanes/ethyl acetate afforded 0.63 g (48%) of a tan foam: $^1$H NMR (CDCl$_3$) δ 8.26 (d, j=9.1 Hz, 2H), 7.52 (d, j=9.2 Hz, 2H), 7.46 (d, j=8.8 Hz, 2H), 6.97 (d, j=8.8 Hz, 2H), 4.24 (t, j=6.6 Hz, 2H), 3.83 (s, 3H), 3.41 (t, j=6.6 Hz, 2H), 3.32 (s, 3H) ppm; Mass Spec ESI(M+H)$^+$ 556.1.

Part C. The nitro compound of Part B (0.63 g) was hydrogenated in ethanol/ethyl acetate/HCl and 20 mg of 10% palladium on carbon at 45 psi for 3 h. The reaction was filtered and concentrated to afford the amine. To the above amine (400 mg) in THF (20 mL), 5-bromovaleryl chloride (0.14 mL, 1.0 mmol) and triethylamine (0.32 mL, 2.2 mmol) were added and stirred 24 h. Potassium t-butoxide (0.33 g, 2.6 mmol) was added and the reaction was stirred 72 h. The reaction was quenched with water, extracted with ethylacetate, washed with brine and dried (MgSO$_4$). Purification on silica gel using 1:2 hexanes/ethyl acetate to 2% MeOH/ethyl acetate and recrystallization from isopropyl alcohol afforded 0.1 g (23%): M.P.=243-245° C.; $^1$H NMR (CDCl$_3$) δ 7.49 (d, j=8.8 Hz, 2H), 7.34 (d, j=9.1 Hz, 2H), 7.27 (d, j=8.7 Hz, 2H), 6.95 (d, j=8.8 Hz, 2H), 4.16 (t, j=6.6 Hz, 2H), 3.82 (s, 3H), 3.61 (t, j=5.9 Hz, 2H), 3.57 (t, j=6.6 Hz, 2H), 3.31 (s, 3H), 2.57 (t, j=5.5 Hz, 2H), 1.95 (m, 4H) ppm.

Example 29

1-(4-methoxyphenyl)-6-(4-(2-oxo-1-(2H)-pyridinyl) phenyl]-3-(2-pyridinyl)-1,4,5,6-tetrahydro-7H-pyrazolo[3,4-c]pyridin-7-one, Trifluoroacetic Acid Salt Part A. 4-Methoxyphenyl hydrazine hydrochloride (3 g, 17 mmol) in H$_2$O (28 mL) was treated with glyoxylic acid monohydrate (1.6 g, 17 mmol) in H$_2$O (20 mL) with conc. HCl (1.8 mL). After 2 h, a red precipitate was filtered off and dried to afford 3 g (89%) hydrazone.

Part B. The hydrazone from Part A (1 g, 5.0 mmol) was placed in DMF (10 mL), cooled to -5° C. and NBS (1.8 g, 10 mmol) in DMF (10 mL) was added slowly. The reaction was held at rt for 15 min and then 3-(4-morpholinyl)-1-(4-io-dophenyl)-5,6-dihydro-2(1H)-pyridinone (1.97 g, 5.0 mmol) was added. TEA (1.4 mL, 32 mmol) in toluene (25 mL) was added dropwise and the reaction stirred at rt for 24 h. The morpholine intermediate was extracted with EtOAc, washed with H$_2$O, dried (Na$_2$SO$_4$). The morpholine intermediate was treated with TFA (5 mL) in CH$_2$Cl$_2$ (30 mL) for 24 h. Dilution with CH$_2$Cl$_2$, washing with H$_2$O, sat'd NaCl and drying (Na$_2$SO$_4$) afforded a foam. Purification on silica gel using 2:1 hexanes/ethyl acetate and recrystallization from CH$_2$Cl$_2$/Hexanes afforded 1.4 g (55%); Mass Spec (M+H)$^+$ 524-526.

Part C. The compound from Part B (0.32 g, 0.6 mmol), 2-hydroxypridine (35 mg, 0.36 mmol), K$_2$CO$_3$ (0.135 g, 0.97 mmol) were combined in DMSO (5 mL) and degassed with N$_2$. Copper (I) iodide (23 mg, 0.12 mmol) was added and the reaction was heated to 130° C. for 24 h. The reaction was quenched with dilute NH$_4$OH solution and filtered. The filtrate was extracted with EtOAc and dried (Na$_2$SO$_4$). Purification on silica gel using 0-2% MeOH/CH$_2$Cl$_2$ as eluent afforded 130 mg (43%) of the bromo compound; Mass Spec (M+H)$^+$ 513.3-515.2.

Part D. To the compound from Part C (0.13 g, 0.26 mmol) was added 2-tributylstannylpyridine (0.16 g, 0.34 mmol) and toluene (25 mL). The mixture was degassed with N$_2$ for 10 min, then tetrakistriphenylphosphine palladium (10 mg) was added. The reaction was heated to reflux for 24 h. The cooled reaction was diluted with ethyl acetate then, washed sequentially with sat'd aqueous KF, brine and dried (MgSO$_4$). Purification by silica gel chromatography using 0-5% MeOH/

CH$_2$Cl$_2$ (1% NH$_3$) as eluent, then by HPLC and freeze-drying afforded 0.20 mg (12%) of the title compound: HRMS (M+H)$^+$ for C$_{29}$H$_{24}$N$_5$O$_3$ was 490.1880; $^1$H NMR (CDCl$_3$) δ 8.85 (m, 1H), 8.11 (m, 2H), 7.57 (d, j=9.2 Hz, 2H), 7.55 (m, 2H), 7.51 (d, j=9.1 Hz, 2H), 7.42 (d, j=8.8 Hz, 2H), 7.41 (m, 1H), 6.97 (d, j=8.8 Hz, 2H), 6.84 (d, j=8.8 Hz, 2H), 6.42 (m, 1H), 4.24 (t, j=6.6 Hz, 2H), 3.83 (s, 3H), 3.47 (t, j=6.6 Hz, 2H) ppm.

Example 30

1-[3-aminomethylphenyl]-6-[4-(2-oxo-1-piperidinyl)phenyl]-3-(trifluoromethyl)-1,4,5,6-tetrahydro-7H-pyrazolo[3,4-c]pyridin-7-one, Trifluoroacetic Acid Salt The nitrile precursor was prepared following the general [3+2] procedure with the corresponding trifluoromethyl hydrazone moiety and the morpholine-enamine described in Example 3. Ullmann coupling with -valerolactam afforded the desired nitrile precursor. Reduction of the benzonitrile as in Example 4 part B followed by purification via prep HPLC afforded the desired benzylamine analog. LRMS 484 (M+H).

Example 31

3-[7-oxo-6-[4-(2-oxo-1-piperidinyl)phenyl]-3-(trifluoromethyl)-4,5,6,7-tetrahydro-1H-pyrazolo[3,4-c]pyridin-1-yl]benzamide The benzonitrile precursor from Example 30 was hydrolyzed with hydrogen peroxide in sodium hydroxide to provide the title compound which on purification via prep HPLC afforded pure compound. LRMS 498 (M+H).

Example 32

1-(3-chlorophenyl)-7-oxo-6-[4-(2-oxo-1-piperidinyl)phenyl]-4,5,6,7-tetrahydro-1H-pyrazolo[3,4-c]pyridine-3-carboxamide The title compound was prepared following the general procedure described previously. HRMS (ESI$^+$): 464.1497. (M+H)$^+$. $^1$H NMR (CDCl$_3$) δ 7.60 (s, 1H), 7.50 (d, 1H), 7.39-7.25 (m, 6H), 6.96 (s, 1H), 5.96 (s, 1H), 4.13 (t, 2H), 3.62 (t, 2H), 3.37 (t, 2H), 2.57 (t, 2H), 1.96-1.93 (m, 4H).

Example 33

1-(3-chlorophenyl)-7-oxo-6-[4-(2-oxo-1-(2H)-pyridinyl)phenyl]-4,5,6,7-tetrahydro-1H-pyrazolo[3,4-c]pyridine-3-carboxamide The title compound was prepared following the general procedure described previously. HRMS (ESI$^+$): 460.1156. (M+H)$^+$. $^1$H NMR (CD$_3$OD) δ 7.85 (s, 1H), 7.72 (s, 1H), 7.71-7.44 (m, 8H), 6.64 (d, 1H), 6.48 (t, 1H), 4.20 (t, 2H), 3.37 (t, 2H).

Example 34

1-(3-chlorophenyl)-N,N-dimethyl-7-oxo-6-[4-(2-oxo-1-piperidinyl)phenyl]-4,5,6,7-tetrahydro-1H-pyrazolo[3,4-c]pyridine-3-carboxamide The title compound was prepared following the general procedure described previously. HRMS (ESI$^+$): 492.1807. (M+H)$^+$. $^1$H NMR (CD$_3$OD) δ 7.67 (s, 1H), 7.57-7.53 (m, 1H), 7.47-7.40 (m, 4H), 7.32 (d, 2H), 4.14 (t, 2H), 3.67 (t, 2H), 3.39 (s, 3H), 3.19 (t, 2H), 3.14 (s, 3H), 2.53 (t, 2H), 1.97-1.95 (m, 4H).

Example 35

1-(3-chloro-4-fluorophenyl)-7-oxo-6-[4-(2-oxo-1-piperidinyl)phenyl]-4,5,6,7-tetrahydro-1H-pyrazolo[3,4-c]pyridine-3-carboxamide The title compound was prepared following the general procedure described previously. LRMS (ESI$^+$): 482.3. (M+H)$^+$. $^1$H NMR (CDCl$_3$) δ 7.68-7.65 (m, 1H), 7.52-7.46 (m, 1H), 7.34 (d, 2H), 7.28 (d, 2H), 7.17 (t, 1H), 6.86 (s, 1H), 5.74 (s, 1H), 4.13 (t, 2H), 3.62 (t, 2H), 3.38 (t, 2H), 2.58 (t, 2H), 1.96-1.94 (m, 4H).

Example 36

1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carbonitrile To dimethylformamide (0.2 mL, 2.6 mmol) in CH$_3$CN (20 mL) at 0° C. was added oxalyl chloride (0.23 mL, 2.6 mmol) and the reaction was stirred 0.5 h. The amide from Example 27 was added and the reaction was stirred cold 0.5 h. Pyridine (0.37 mL, 4.6 mmol) was added and the reaction was allowed to warm to rt and stirred for 24 h. The solvent was stripped, the residue was partitioned between CH$_2$Cl$_2$ and 1N HCl, and the layers separated. The aqueous layer was basified with 1N NaOH and extracted with EtOAc. The organic layers were combined and dried (MgSO$_4$). Purification by chromatography on silica gel using 3% MeOH in CH$_2$Cl$_2$ and recrystallization from CH$_2$Cl$_2$/hexanes afforded 117 mg (89%); $^1$H NMR (CDCl$_3$) δ 7.50 (d, j=8.8 Hz, 2H), 7.44 (m, 5H), 7.31 (m, 1H), 6.97 (d, j=9.2 Hz, 2H), 6.71 (d, j=9.5 Hz, 2H), 6.28 (m, 1H), 4.24 (t, j=6.6 Hz, 2H), 3.85 (s, 3H), 3.24 (t, j=6.6 Hz, 2H) ppm; LRMS (M+H)$^+$ 438.4.

Example 37

1-(3-amino-1H-indazol-5-yl)-7-oxo-6-[4-(2-oxo-1-piperidinyl)phenyl]-4,5,6,7-tetrahydro-1H-pyrazolo[3,4-c]pyridine-3-carboxamide 1-(3-Cyano-4-fluorophenyl)-6-[4-iodophenyl]-7-oxo-6-[4-(2-oxo-1-piperidinyl)phenyl]-4,5,6,7-tetrahydro-1H-pyrazolo[3,4-c]pyridine-3-carboxamide (58 mg, prepared following the general procedure described for Examples 3-5) was dissolved in 1-butanol (5 mL). To the solution was added hydrazine monohydrate (0.5 mL). The reaction mixture was brought to reflux for 4 h, cooled to rt, and the solvent removed. The residue was purified using HPLC (RP gradient) to give the title compound as its TFA salt (25 mg, 42%). HRMS (ESI$^+$): 485.2050 (M+H)$^+$. $^1$H NMR (CD$_3$OD) δ 8.06 (s, 1H), 7.78 (d, 2H), 7.74 (d, 1H), 7.44-7.40 (m, 3H), 7.30 (d, 2H), 4.18 (t, 2H), 3.65 (t, 2H), 3.38 (t, 2H), 2.52 (t, 2H), 1.98-1.96 (m, 4H).

Example 38

1-(3-amino-1,2-benzisoxazol-5-yl)-7-oxo-6-[4-(2-oxo-1-piperidinyl)phenyl]-4,5,6,7-tetrahydro-1H-pyrazolo[3,4-c]pyridine-3-carboxamide The title compound was made from its corresponding 4-fluoro-3-cyano intermediate (previously described for Examples 3-5). HRMS (ESI⁺): 486.1885 (M+H)⁺. ¹H NMR (CD₃OD) δ 7.99 (s, 1H), 7.78 (d, 1H), 7.48-7.40 (m, 4H), 7.30 (d, 2H), 4.16 (t, 2H), 3.65 (t, 2H), 3.31 (t, 2H), 2.50 (t, 2H), 1.96-1.94 (m, 4H).

Example 39

5-chloro-N-[5-chloro-3-methoxy-2-({[4-(2-oxo-1-piperidinyl)phenyl]amino}carbonyl)phenyl]-2-pyridinecarboxamide Part A. To a solution of 4-iodomethylbenzoate is added δ-valerolactam (1 eq), cesium carbonate (1.5 eq) followed by catalytic CuI. The reaction mixture is heated at 100° C. overnight, cooled, and quenched with water. The organics are extracted with ethylacetate, dried (magnesium sulfate), and evaporated to afford crude product which is purified via silica gel column chromatography (hexane:ethylacetate) to afford the coupled product.

Part B. To the product from part A in THF is added LiOH (excess of 1 eq) and water. The reaction mixture is stirred at rt overnight and quenched with dilute HCl. The desired carboxylic acid intermediate is extracted with ethyl acetate, dried, and evaporated to afford the product.

Part C. To the product from part B in dichloromethane is added 1 equivalent of thionyl chloride along with cat. DMF. The reaction mixture is stirred at rt overnight and concentrated to afford 4-(2-oxo-piperidin-1-yl)-benzoyl chloride.

Part D. To a solution of 2-nitro-5-chloro-benzoylchloride in dichloromethane is added 2-amino-5-chloropyridine (1 eq) and DMAP (excess of 2 eq). The reaction mixture is stirred at rt overnight, quenched with water, and the organics extracted with ethylacetate and dried (magnesium sulfate). Evaporation affords the coupled product.

Part E. The product from part A is dissolved in ethyl acetate. To this solution are added 3 equivalents of tin chloride, and the reaction mixture is stirred at rt for 4 h. The reaction mixture is quenched with sat'd ammonium hydroxide solution and the organics extracted with ethyl acetate, dried, and evaporated to afford the anilino derivative.

Part F. The product from part B was dissolved in dichloromethane and to this solution is added 4-(2-oxo-piperidin-1-yl)-benzoyl chloride (1 eq) and DMAP (excess of 2 eq). The reaction mixture is stirred at rt overnight, concentrated, and purified via reverse phase prep. HPLC (acetonitrile/water/TFA) to afford the title compound.

Example 40

5-chloro-N-[5-chloro-3-methoxy-2-({[4-(2-oxo-1(2H)-pyridinyl)phenyl]amino}carbonyl)phenyl]-2-pyridinecarboxamide Part A. To a solution of 4-iodomethylbenzoate is added 2-hydroxypyridine (1 eq), cesium carbonate (1.5 eq) followed by catalytic CuI. The reaction mixture is heated at 100° C. overnight, cooled, and quenched with water. The organics are extracted with ethyl acetate, dried, and evaporated to afford crude product which is purified via silica gel column chromatography (hexane:ethylacetate) to afford the coupled product.

Part B. To the product from part A in THF is added LiOH (excess of 1 eq) and water. The reaction mixture is stirred at rt overnight and quenched with dilute HCl. The desired carboxylic acid intermediate is extracted with ethyl acetate, dried, and evaporated to afford the product.

Part C. To the product from part B in dichloromethane is added 1 equivalent of thionyl chloride along with cat. DMF. The reaction mixture is stirred at rt overnight and concentrated to afford 4-(2-oxo-pyridin-1-yl)-benzoyl chloride.

Part D. To a solution of 2-nitro-5-chloro-benzoylchloride in dichloromethane is added 2-amino-5-chloropyridine (1 eq) and DMAP (excess of 2 eq). The reaction mixture is stirred at rt overnight, quenched with water, and the organics extracted with ethylacetate and dried (magnesium sulfate). Evaporation affords the coupled product.

Part E. The product from part A was dissolved in ethyl acetate. To this solution is added 3 equivalents of tin chloride, and the reaction mixture stirred at rt for 4 h. The reaction mixture is quenched with sat'd ammonium hydroxide solution and the organics extracted with ethyl acetate, dried, and evaporated to afford the anilino product.

Part F. The product from part B was dissolved in dichloromethane and to this solution is added 4-(2-oxo-pyridin-1-yl)-benzoyl chloride (1 eq) and DMAP (excess of 2 eq). The reaction mixture is stirred at rt overnight, concentrated, and purified via reverse phase prep. HPLC (acetonitrile/water/TFA) to afford the title compound.

Examples 41-53

Examples 41-53, shown below, can be prepared by following the procedures of Examples 37-38.

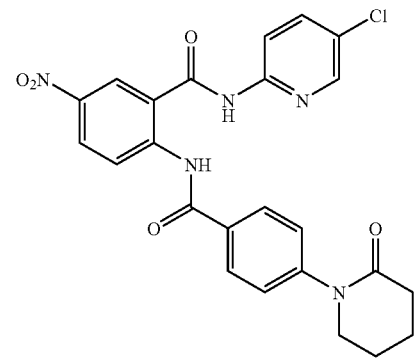

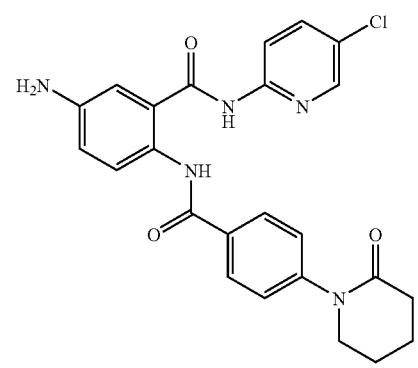

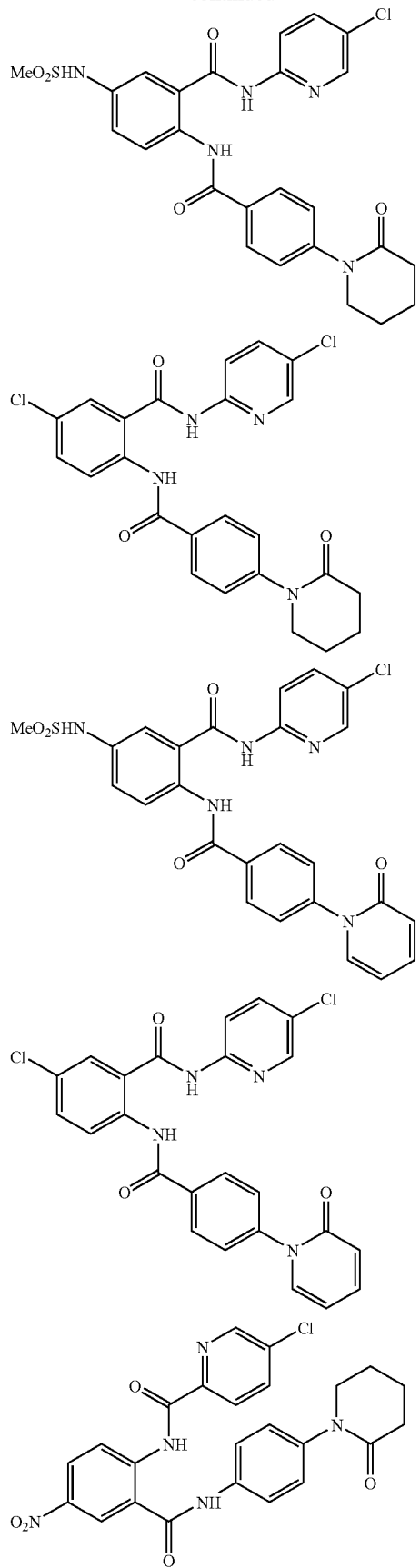
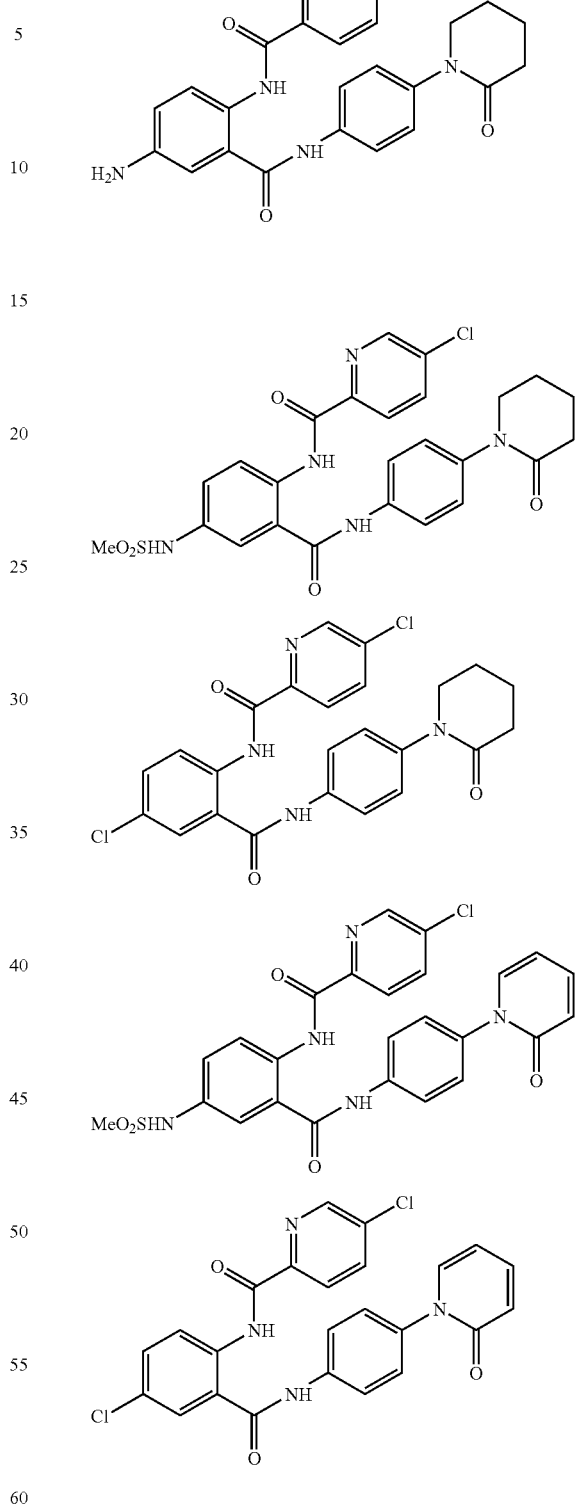
Examples 54-70
Examples 54-70, shown below, can be prepared by following the procedures of Examples 37-38 and using commercially available amino-nicotinic acids.

181
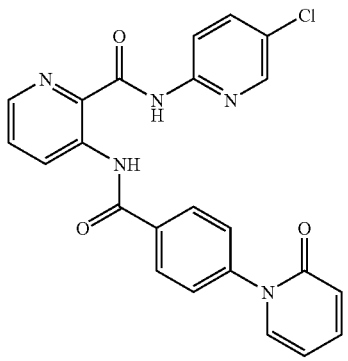
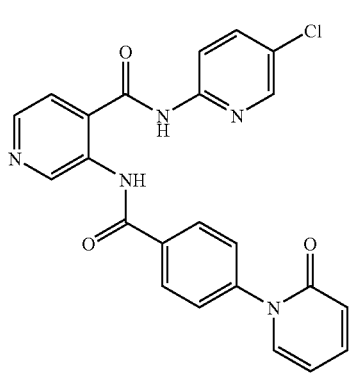
182
-continued
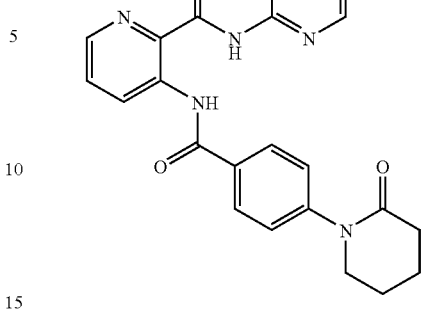
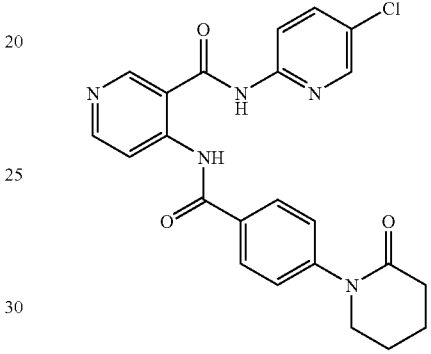
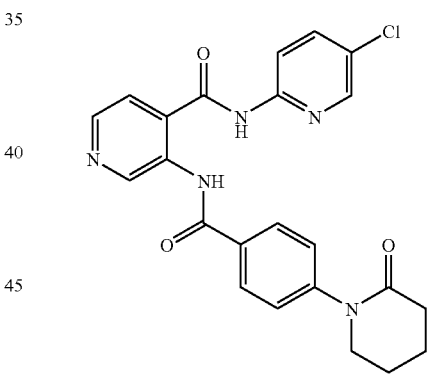
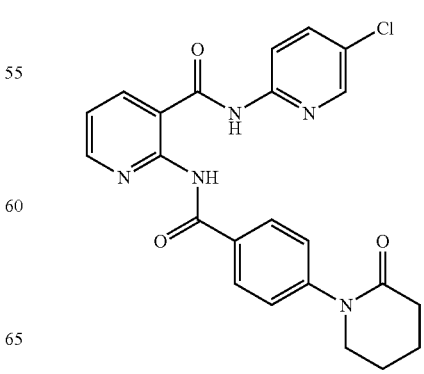

-continued

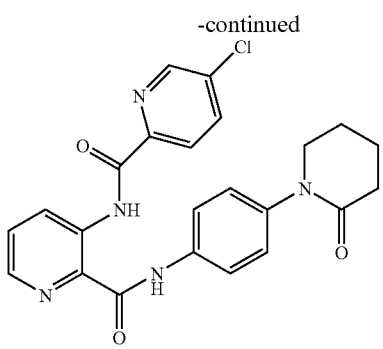

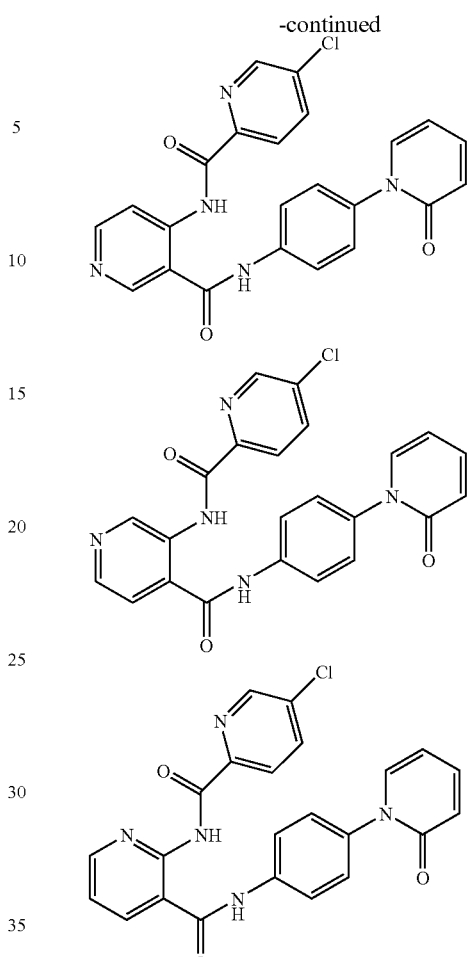

Example 71

Methyl 2-[2-fluoro-4-(2-oxo-1(2H)-pyridinyl)phenyl]-3-[1-(4-methoxyphenyl)-3-(trifluoromethyl)-1H-pyrazol-5-yl]-3-oxopropanoate Part A. In a flame-dried 1-L flask was combined anhydrous methyl alcohol (1.4 L), 4-methoxyphenylhydrazine hydrochloride (25 g, 140 mmol), 4,4,4-trifluoro-1-(2-furyl)-1,3-butanedione (30 g, 140 mmol), and trifluoroacetic acid (1.1 mL, 14 mmol). The resulting red slurry was maintained at rt for 14 h. A 50% solution of isopropyl alcohol/water (500 mL) was then added, and the mixture was stirred vigorously for 5 min. The mixture was filtered; additional material precipitated from the filtrate upon standing, and the new mixture was filtered. After another 3 h, the resulting filtrate was filtered a third time, and the combined beige solid was oven dried under vacuum to afford 5-(2-furyl)-1-(4-methoxy-phenyl)-3-(trifluoromethyl)-1H-pyrazole (42 g, 96%) as a light brown solid. $^1$H NMR (CDCl$_3$) δ 7.42 (m, 1H), 7.35 (d, 2H), 6.98 (d, 2H), 6.89 (s, 1H), 6.33 (dd, 1H), 5.90 (d, 1H), 3.88 (s, 3H).

Part B. To the product from Part A (20 g, 65 mmol) was added water (410 mL), 5% aqueous sodium dihydrogenphosphate (270 mL), and tert-butanol (410 mL). The resulting mixture was warmed to 60° C., and potassium permanganate (63, 400 mmol) was added over a period of 1.5 h. After an additional 10 min, the resulting purple slurry was cooled to 0° C., and the reaction was quenched by the addition of 400 mL of saturated aqueous sodium bisulfite. The resulting brown slurry was filtered, washed with 500 mL of water, and the filtrate was acidified to pH 1 with concentrated aqueous hydrogen chloride. The aqueous layer was extracted with ethyl acetate (6×150 mL), and the combined organic layers were washed with saturated aqueous sodium chloride, dried over sodium sulfate, and filtered. Concentration afforded 1-(4-methoxyphenyl)-3-(trifluoromethyl)-1H-pyrazole-5-carboxylic acid (16 g, 85%) as a light yellow solid. MS (APCI$^+$): 328.2 (M+H+CH$_3$CN)$^+$. $^1$H NMR (CDCl$_3$) δ 7.37 (d, 2H), 7.32 (s, 1H), 6.97 (d, 2H), 3.88 (s, 3H).

Part C. To a solution of 2-fluoro-4-iodo-1-methylbenzene (50 g, 210 mmol) in anhydrous acetone (490 mL) was added N-bromosuccinimide (42 g, 230 mmol) and 2,2'-azobisisobutyronitrile (100 mg, 0.60 mmol). The resulting solution was heated to reflux and maintained under reflux conditions for 5 h. The reaction was then cooled, concentrated, and filtered. The filtrate was concentrated, and the resulting dark red residue was purified by flash column chromatography (10% ethyl acetate in hexanes) to afford a 4:1 mixture (58 g) of 1-(bromomethyl)-2-fluoro-4-iodobenzene (49 g, 73%) and 2-fluoro-4-iodo-1-methylbenzene (9 g, 17%) as a red solid. $^1$H NMR (product) (CDCl$_3$) δ 7.40-7.49 (m, 2H), 7.13 (t, 1H), 4.45 (s, 2H).

Part D. To the product from Part C (58 g, 140 mmol) in toluene (500 mL) and water (500 mL) was added sodium cyanide (34 g, 700 mmol) and tetrabutylammonium bromide (23 g, 70 mmol). The resulting mixture was heated to reflux and maintained under reflux condition for 14 h. The dark brown mixture was then cooled, and the layers were separated. The aqueous layer was washed with ethyl acetate (200 mL), and the combined organic layers were washed with saturated aqueous sodium chloride and dried over sodium sulfate. The organic layers were concentrated, and the resulting residue was purified by flash column chromatography (10% ethyl acetate in hexanes) to give (2-fluoro-4-iodophenyl)-acetonitrile (20 g, 54%) as a yellow solid. $^1$H NMR (CDCl$_3$) δ 7.54 (dd, 1H), 7.49 (dd, 1H), 7.18 (t, 1H), 3.72 (s, 2H).

Part E. To the product from Part D (20 g, 77 mmol) was added ethyl alcohol (470 mL), water (230 mL), and sodium hydroxide (31 g, 770 mmol). The resulting mixture was heated to reflux and maintained under reflux conditions for 2 h. The reaction was then cooled, concentrated, and acidified to pH 1 with concentrated aqueous hydrochloric acid. The resulting mixture was filtered, and the filter cake was dried in a vacuum oven to afford (2-fluoro-4-iodophenyl)acetic acid (21 g, 96%) as yellow solid. $^1$H NMR (CDCl$_3$) δ 7.43-7.48 (m, 2H), 7.00 (t, 1H), 3.67 (s, 2H).

Part F. To the product from Part E (10 g, 36 mmol) was added methyl alcohol (25 mL) and benzene (250 mL). The resulting solution was cooled to 0° C., and (trimethylsilyl)diazomethane (9 mL, 38 mmol; 2.0 M in hexanes) was added dropwise over 15 min. After 1 h, the reaction was concentrated, and the resulting residue was purified by flash column chromatography (10-20% ethyl acetate in hexanes) to afford methyl (2-fluoro-4-iodophenyl)acetate (6.9 g, 66%) as a yellow oil. $^1$H NMR (CDCl$_3$) δ 7.42-7.47 (m, 2H), 7.00 (t, 1H), 3.71 (s, 3H), 3.63 (s, 2H).

Part G. To methyl (2-fluoro-4-iodophenyl)acetate (1.0 g, 3.4 mmol) in dimethylsulfoxide (68 mL) was added potassium carbonate (1.9 g, 14 mmol) and 2-hydroxypyridine (650 mg, 6.8 mmol). The resulting mixture was degassed (alternate vacuum/nitrogen three times), and copper(I) iodide (650 mg, 3.4 mmol) was added in one portion. The light green mixture was again degassed (vac/N$_2$) and warmed to 125° C. After 14 h, the brown-black mixture was cooled and poured into saturated aqueous ammonium hydroxide (50 mL) and ethyl acetate (100 mL). The layers were separated, and the organic layers were washed with water (2×50 mL) and saturated aqueous sodium chloride. The organic layers were concentrated, and the resulting residue was purified by radial chromatography (20-100% ethyl acetate in hexanes) to afford methyl [2-fluoro-4-(2-oxo-1(2H)-pyridinyl)-phenyl]acetate (340 mg, 39%) as a green-brown solid. LC/MS (ESI$^+$): 262.2 (M+H)$^+$. $^1$H NMR (CDCl$_3$) δ 7.22-7.36 (m, 3H), 7.08 (t, 2H), 6.54 (d, 1H), 6.18 (t, 1H), 3.63 (s, 5H).

Part H. To a stirring solution of trimethylacetyl chloride (0.026 mL, 0.21 mmol), triethylamine (0.058 mL, 0.42 mmol), and diethyl ether (2.6 mL) in a flame-dried flask was added 1-(4-methoxyphenyl)-3-(trifluoromethyl)-1H-pyrazole-5-carboxylic acid (60 mg, 0.21 mmol). The resulting white slurry was warmed to 23° C. and stirred for 1.5 h. The mixture was filtered, and the filtrate was concentrated. The resulting residue was partially redissolved in diethyl ether (2 mL) and filtered again. The filtrate was concentrated to give 2,2-dimethylpropanoic 1-(4-methoxyphenyl)-3-(trifluoromethyl)-1H-pyrazole-5-carboxylic anhydride as a viscous oil.

In a separate flame-dried flask was combined tetrahydrofuran (0.80 mL), hexamethylphosphoramide (0.80 mL), and diisopropylamine (0.050 mL, 0.36 mmol). The solution was cooled to −78° C., and n-butyllithium (0.176 mL, 0.44 m mmol) was added in one portion. After 20 min, methyl (2-fluoro-4-iodophenyl)acetate (110 mg, 0.42 mmol; Part F) in tetrahydrofuran (1.0 mL) was added via cannula, and the resulting red mixture was maintained at −78° C. for 20 min. The previously prepared 2,2-dimethylpropanoic 1-(4-methoxyphenyl)-3-(trifluoromethyl)-1H-pyrazole-5-carboxylic anhydride was then added via cannula as a solution in tetrahydrofuran (1.5 mL), and the resulting light yellow mixture was warmed to 23° C. After 2 h, the reaction was poured into 1N aqueous hydrochloric acid (50 mL), washed with ethyl acetate (3×50 mL), and the organic layers were washed with saturated aqueous sodium chloride, dried over sodium sulfate, and concentrated. The resulting residue was purified by radial chromatography (1-5% methyl alcohol in dichloromethane) to afford methyl 2-[2-fluoro-4-(2-oxo-1(2H)-pyridinyl)phenyl]-3-[1-(4-methoxyphenyl)-3-(trifluoromethyl)-1H-pyrazol-5-yl]-3-oxopropanoate (54 mg, 49%) as a white solid. LC/MS (ESI$^+$): 530.1 (M+H)$^+$.

Example 72

1-(3-fluoro-4-{2-[1-(4-methoxyphenyl)-3-(trifluoromethyl)-1H-pyrazole-5-yl]-2-oxoethyl}phenyl)-2(1H)-pyridinone Part A. To methyl 2-[2-fluoro-4-(2-oxo-1(2H)-pyridinyl) phenyl]-3-[1-(4-methoxyphenyl)-3-(trifluoro-methyl)-1H-pyrazol-5-yl]-3-oxopropanoate (Part H, Example 71) (24 mg, 0.045 mmol) was added methyl alcohol (2.3 mL) and concentrated aqueous dihydrogen sulfate (0.048 mL). The reaction was then warmed to reflux. After 48 h, monitoring by LC/MS (C18 reverse phase, eluted with 0.05% TFA in acetonitrile/water) showed 90% of starting material remaining. An additional 0.80 mL-portion of 4M aqueous dihydrogen sulfate was added, and the reaction was maintained under reflux conditions for 6 h. The reaction was cooled to 0° C., and the resulting white precipitate was filtered to afford 1-(3-fluoro-4-{2-[1-(4-methoxyphenyl)-3-(trifluoromethyl)-1H-pyrazole-5-yl]-2-oxoethyl}phenyl)-2(1H)-pyridinone (11 mg, 52%) as a white solid. LC/MS (ESI$^+$): 472.1 (M+H)$^+$. $^1$H NMR (enol form) (CD$_3$OD) δ 7.70 (s, 1H), 7.60 (m, 2H), 7.43

(t, 1H), 7.28 (m, 3H), 7.20 (m, 1H), 6.98 (m, 2H), 6.62 (d, 1H), 6.44 (t, 1H), 4.42 (s 0.5H), 4.39 (br s, 0.5H), 3.81 (s, 3H).

Example 73

1-(4-{2-[1-(3-amino-1,2-benzisoxazol-5-yl)-3-(trifluoromethyl)-1H-pyrazol-5-yl]-2-oxoethyl}-3-fluorophenyl)-2(1H)-pyridinone trifluoroacetate Part A. To a stirring solution of trimethylacetyl chloride (0.021 mL, 0.17 mmol), triethylamine (0.071 mL, 0.51 mmol), and diethyl ether (3.4 mL) in a flame-dried flask was added 1-(3-cyano-4-fluorophenyl)-3-(trifluoromethyl)-1H-pyrazole-5-carboxylic acid (51 mg, 0.17 mmol). The resulting white slurry was warmed to 23° C. and stirred for 1.5 h. The mixture was filtered, and the filtrate was concentrated. The resulting residue was partially redissolved in diethyl ether (5 mL) and again filtered. The filtrate was concentrated to give 1-(3-cyano-4-fluorophenyl)-3-(trifluoromethyl)-1H-pyrazole-5-carboxylic 2,2-dimethylpropanoic anhydride.

In a separate flame-dried flask were combined tetrahydrofuran (2.0 mL), hexamethylphosphoramide (1.4 mL) and diisopropylamine (0.052 mL, 0.37 mmol). The solution was cooled to −78° C., and n-butyllithium (0.142 mL, 0.35 m mmol) was added in one portion. After 20 min, methyl [2-fluoro-4-(2-oxo-1(2H)-pyridinyl)-phenyl]acetate (88 mg, 0.34 mL; Part G, Example 71) was added as a solution in tetrahydrofuran (1.5 mL) via cannula, and the resulting red mixture was maintained at −78° C. for 20 min. The previously prepared 1-(3-cyano-4-fluorophenyl)-3-(trifluoromethyl)-1H-pyrazole-5-carboxylic 2,2-dimethylpropanoic anhydride was then added via cannula as a solution in tetrahydrofuran (1.5 mL), and the resulting light yellow mixture was warmed to 23° C. After 1 h, the reaction was poured into water (50 mL) and ethyl acetate, and the organic layer was washed with saturated aqueous sodium chloride, dried over sodium sulfate, and concentrated. The resulting residue was purified by radial chromatography (15-40% ethyl acetate in hexanes) to afford methyl 3-[1-(3-cyano-4-fluorophenyl)-3-(trifluoromethyl)-1H-pyrazol-5-yl]-2-[2-fluoro-4-(2-oxo-1(2H)-pyridinyl)phenyl]-3-oxopropanoate (22 mg, 23%) as a clear oil. LC/MS (ESI+): 543.0 (M+H)+.

Part B. To the product from Part A (22 mg, 0.040 mmol) was added methyl alcohol (0.72 mL) and 4M aqueous dihydrogen sulfate (0.24 mL). The reaction was then warmed to reflux. After 24 h, the reaction was cooled to 0° C., and the resulting white precipitate was filtered to afford 2-fluoro-5-[5-{[2-fluoro-4-(2-oxo-1(2H)-pyridinyl)phenyl]acetyl}-3-(trifluoromethyl-1H-pyrazol-1-yl]benzonitrile (12 mg, 61%) as a white solid. LC/MS (ESI+): 485.1 (M+H)+. $^1$H NMR (CDCl$_3$) δ 7.62-7.71 (m, 2H), 7.46 (s, 1H), 7.35 (m, 1H), 7.33 (m, 3H), 7.22 (m, 2H), 6.57 (d, 1H), 6.27 (t, 1H), 4.30 (s, 2H).

Part C. To the product from Part B (10 mg, 0.040 mmol) was added N,N-dimethylformamide (0.50 mL), water (0.50 mL), and potassium carbonate (29 mg, 0.20 mmol). Acetohydroxamic acid (3.5 mg, 0.046 mmol) was added in one portion, and the resulting yellow mixture was warmed to 50° C. After 2 h, the reaction was cooled to rt and the reaction mixture was purified by preparative LC/MS (C18 reverse phase, eluted with 0.05% TFA in CH$_3$CN/H$_2$O) to give 1-(4-{2-[1-(3-amino-1,2-benzisoxazol-5-yl)-3-(trifluoromethyl)-1H-pyrazol-5-yl]-2-oxoethyl}-3-fluorophenyl)-2(1H)-pyridinone trifluoroacetate (8.0 mg, 67%) as a beige solid. LC/MS (ESI+): 498.0 (M+H-TFA)+. $^1$H NMR (CD$_3$OD) δ 7.83 (d, 1H), 7.80 (s, 1H), 7.52-7.62 (m, 3H), 7.40-7.48 (m, 2H), 7.16-7.26 (m, 2H), 6.60 (d, 1H), 6.40 (t, 1H), 4.46 (s, 2H).

Example 74

5-{[2-fluoro-4-(2-oxo-1(2H)-pyridinyl)phenyl]acetyl}-1-(4-methoxyphenyl)-1H-pyrazole-3-carboxamide Part A. A 1-L flame-dried flask was charged with 130 mL of LiHMDS (130 mmol; 1.0 M in THF) and 410 mL of ethyl ether. The resulting solution was cooled to −78° C. and 2-acetylfuran (14 g, 12 m mmol) was added in one portion. After 5 min, di-tert-butyl oxalate was added dropwise over 1 h as a solution in 100 mL of ether. The resulting mixture was warmed to 23° C. over a period of 3 h and was maintained at rt for 20 h. The mixture was then filtered, and the resulting beige precipitate was washed with 100 mL of ether. The filter cake was dried in a vacuum oven for 1 h to afford lithium 1-tert-butoxy-4-(2-furyl)-1,4-dioxo-2-buten-2-olate (25 g, 83%) as a cream colored solid. $^1$H NMR (DMSO-d$_6$) δ 7.75 (t, 1H), 6.96 (m, 1H), 6.56 (m, 1H), 3.34 (s, 2H), 1.46 (s, 9H).

Part B. To the product (1.0 g, 4.6 mmol) from Part A was added 4-methoxyphenylhydrazine hydrochloride (480 mg, 2.8 mmol) and glacial acetic acid (15 mL). The resulting orange mixture was warmed to 40° C. and was then cooled to rt after 1.5 h. The reaction was poured into saturated aqueous sodium bicarbonate (100 mL), and the aqueous layer was washed with ethyl acetate (3×50 mL). The combined organic layers were washed with saturated aqueous sodium chloride, dried over sodium sulfate, and concentrated to dryness. The resulting red-black residue was recrystallized from hexanes to afford tert-butyl 5-(2-furyl)-1-(4-methoxyphenyl)-1H-pyrazole-3-carboxylate (870 mg, 93%) as a yellow-orange solid. $^1$H NMR (CDCl$_3$) δ 7.40 (br s, 1H), 7.35 (d, 2H), 7.07 (s, 1H), 6.96 (d, 2H), 6.30 (m, 1H), 5.86 (d, 9H), 3.86 (s, 3H), 1.62 (s, 9H).

Part C. To tert-butyl 5-(2-furyl)-1-(4-methoxyphenyl)-1H-pyrazole-3-carboxylate (1.0 g, 3.0 mmol) was added dichloromethane (7 mL) and trifluoroacetic acid (7 mL). The resulting black solution was maintained at rt under nitrogen for 2 h and was then concentrated to dryness. The resulting mixture was triturated with chloroform, and the remaining solid was washed with 50% hexanes in chloroform to afford 5-(2-furyl)-1-(4-methoxyphenyl)-1H-pyrazole-3-carboxylic acid (800 mg, 96%) as a light brown solid. $^1$H NMR (d$_6$-DMSO) δ 7.75 (b m, 1H), 7.41 (d, 2H), 7.10 (d, 2H), 7.09 (s, 1H), 6.51 (br m, 1H), 6.09 (d, 1H), 3.84 (s, 3H).

Part D. To the product (800 mg, 2.8 mmol) from Part C was added dichloromethane (50 mL) and 2.0 M oxalyl chloride (2.1 mL, 4.2 mmol) in dichloromethane. After dropwise addition of N,N-dimethylformamide (2 drops) to the brown mixture, gas evolved and the mixture became clear over a period of 30 min. The brown solution was concentrated; the resulting residue was redissolved in dichloromethane (50 mL), and 0.5 M ammonia in dioxane (23 mL, 11 mmol) was added via cannula. After 30 min, the resulting beige suspension was poured into water (80 mL). The aqueous layer was washed with dichloromethane (3×50 mL), and the combined organic layers were dried over sodium sulfate and concentrated to afford 5-(2-furyl)-1-(4-methoxyphenyl)-1H-pyrazole-3-carboxamide (650 mg, 82%) as a beige solid. LC/MS (ESI+): 284.1 (M+H)+. $^1$H NMR (CD$_3$OD) δ 7.52 (s, 1H), 7.35 (d, 2H), 7.07 (s, 1H), 7.05 (d, 2H), 6.39 (br m, 1H), 5.96 (d, 1H), 4.88 (s, 3H).

Part E. To 5-(2-furyl)-1-(4-methoxyphenyl)-1H-pyrazole-3-carboxamide (2.0 g, 6.6 mmol) was added pyridine (1.6 mL, 20 mmol) and dioxane (66 mL). Trifluoroacetic anhydride (1.9 mL, 13 mmol) was added dropwise over 2 min, and the resulting suspension was stirred for 40 min. The now clear red solution was poured into water (70 mL) and ethyl acetate (70 mL). The layers were separated, and the organic layer was washed with 1N aqueous hydrochloric acid (2×50 mL), saturated aqueous sodium chloride, and dried over sodium sulfate. The organic layers were concentrated, and the resulting residue was purified by radial chromatography (20-80% ethyl acetate in hexanes) to afford 5-(2-furyl)-1-(4-methoxyphenyl)-1H-pyrazole-3-carbonitrile (1.4 g, 74%) as an orange solid. LC/MS (ESI$^+$): 266.0 (M+H)$^+$. $^1$H NMR (CDCl$_3$) δ 7.44 (br m, 1H), 7.34 (d, 2H), 7.01 (s, 1H), 7.00 (d, 2H), 6.34 (m, 1H), 5.92 (d, 1H), 3.85 (s, 3H).

Part F. To the product (1.4 g, 4.9 mmol) from Part E was added water (30 mL), 5% aqueous sodium dihydrogenphosphate (21 mL), and tert-butanol (30 mL). The resulting mixture was warmed to 60° C., and potassium permanganate (4.7 g, 29 mmol) was added over a period of 5 min. After an additional 5 min, the resulting purple slurry was cooled to 0° C., and the reaction was quenched by the addition of 50 mL of saturated aqueous sodium bisulfite. The resulting brown mixture was filtered, washed with 100 mL of water, and the filtrate was acidified with 6N aqueous hydrogen chloride. The resulting mixture was filtered to afford 3-cyano-1-(4-methoxyphenyl)-1H-pyrazole-5-carboxylic acid (300 mg, 25%) as a yellow solid. Extraction of the aqueous layer with ethyl acetate (2×50 mL) afforded an additional 215 mg (18%) of impure 3-cyano-1-(4-methoxyphenyl)-1H-pyrazole-5-carboxylic acid as a yellow oil. LC/MS (ESI$^+$): 244.1 (M+H)$^+$. $^1$H NMR (precipitate)(CDCl$_3$) δ 7.42 (s, 1H), 7.35 (d, 2H), 6.98 (d, 2H), 3.87 (s, 3H).

Part G. To a stirring solution of trimethylacetyl chloride (0.087 mL, 0.70 mmol), triethylamine (0.290 mL, 2.1 mmol), and diethyl ether (14 mL) in a flame-dried flask was added 3-cyano-1-(4-methoxyphenyl)-1H-pyrazole-5-carboxylic acid (170 mg, 0.70 mmol). The resulting white slurry was warmed to 23° C. and stirred for 1.5 h. The mixture was filtered, and the filtrate was concentrated. The resulting residue was partially redissolved in diethyl ether (15 mL) and again filtered. The filtrate was concentrated to give 3-cyano-1-(4-methoxyphenyl)-1H-pyrazole-5-carboxylic 2,2-dimethylpropanoic anhydride as a viscous oil.

In a separate flame-dried flask were combined tetrahydrofuran (8.0 mL), hexamethylphosphoramide (6.0 mL), and diisopropylamine (0.200 mL, 1.5 mmol). The solution was cooled to −78° C., and n-butyllithium (0.560 mL, 1.4 m mmol) was added in one portion. After 20 min, [2-fluoro-4-(2-oxo-1(2H)-pyridinyl)-phenyl]acetate (360 mg, 1.4 mL; Part G, Example 71) in tetrahydrofuran (5 mL) was added via cannula, and the resulting red mixture was maintained at −78° C. for 20 min. The previously prepared 3-cyano-1-(4-methoxyphenyl)-1H-pyrazole-5-carboxylic 2,2-dimethyl-propanoic anhydride was then added via cannula as a solution in tetrahydrofuran (5 mL), and the resulting light yellow mixture was warmed to 23° C. After 12 h, the reaction was poured into water (50 mL) and ethyl acetate (75 mL), and the organic layer was washed with saturated aqueous sodium chloride, dried over sodium sulfate, and concentrated. The resulting residue was purified by radial chromatography (50-60% ethyl acetate in hexanes) to afford 3-[3-cyano-1-(4-methoxyphenyl)-1H-pyrazol-5-yl]-2-[2-fluoro-4-(2-oxo-1(2H)-pyridinyl)phenyl]-3-oxopropanoate (131 mg, 40%) as a foamy solid. LC/MS (ESI$^+$): 487.0 (M+H)$^+$.

Part H. To 3-[3-cyano-1-(4-methoxyphenyl)-1H-pyrazol-5-yl]-2-[2-fluoro-4-(2-oxo-1(2H)-pyridinyl)phenyl]-3-oxopropanoate (100 mg, 0.210 mmol) was added methyl alcohol (1.5 mL) and 4M aqueous dihydrogen sulfate (0.50 mL). The reaction was then warmed to reflux. After 4 days, the reaction was cooled to 23° C., and the resulting white suspension was poured into saturated aqueous hydrogen carbonate (50 mL) and ethyl acetate (50 mL). The layers were separated and the aqueous layer was washed with ethyl acetate (3×25 mL). The combined organic layers were washed with saturated aqueous sodium chloride, dried over sodium sulfate, and concentrated to afford 5-{[2-fluoro-4-(2-oxo-1(2H)-pyridinyl) phenyl]acetyl}-1-(4-methoxyphenyl)-1H-pyrazole-3-carbonitrile (75 mg, 85%) as a pale yellow oil. LC/MS (ESI$^+$): 429.0 (M+H)$^+$.

Part I. To 5-{[2-fluoro-4-(2-oxo-1(2H)-pyridinyl)-phenyl]acetyl}-1-(4-methoxyphenyl)-1H-pyrazole-3-carbonitrile (75 mg, 0.175 mmol) was added concentrated aqueous dihydrogen sulfate (4.5 mL). After 2 h, the reaction was poured into ethyl acetate (50 mL) and water (50 mL), and the layers were separated. The organic layer was washed with saturated aqueous sodium chloride (50 mL), dried over sodium sulfate, and concentrated to dryness. The resulting residue was purified by radial chromatography (2% methyl alcohol in dichloromethane) to afford 5-{[2-fluoro-4-(2-oxo-1(2H)-pyridinyl) phenyl]acetyl}-1-(4-methoxyphenyl)-1H-pyrazole-3-carboxamide (32 mg, 41%) as a white solid upon lyophilization from 10% acetonitrile in water. LC/MS (ESI$^+$): 448.2 (M+H)$^+$. $^1$H NMR (CD$_3$OD) δ 7.70 (s, 1H), 7.60 (m, 2H), 7.43 (t, 1H), 7.16-7.32 (m, 4H), 6.97 (d, 2H), 6.60 (d, 1H), 6.45 (t, 1H), 4.40 (s, 2H), 3.83 (s, 3H).

Example 75

1-(3-amino-1,2-benzisoxazol-5-yl)-5-{[5-(2-oxo-1(2H)-pyridinyl)-2,3-dihydro-1H-indol-1-yl]carbonyl}-1H-pyrazole-3-carboxamide Part A. To lithium 1-tert-butoxy-4-(2-furyl)-1,4-dioxo-2-buten-2-olate (13 g, 54 mmol; Example 74, Part A) was added 2-fluoro-5-hydrazinobenzonitrile hydrochloride (10 g, 54 mmol) and 250 mL of glacial acetic acid. The resulting orange mixture was maintained at rt for 20 h and then concentrated to dryness. The resulting residue was taken up in 30% chloroform in hexanes and filtered to afford tert-butyl 1-(3-cyano-4-fluorophenyl)-5-(2-furyl)-1H-pyrazole-3-carboxylate (18 g, 95%) as a light brown solid. LC/MS (ESI$^+$): 354.2 (M+H)$^+$. $^1$H NMR (CDCl$_3$) δ 7.64-7.78 (m, 3H), 7.42 (s, 1H), 7.05 (s, 1H), 6.45 (s, 1H), 6.30 (s, 1H), 1.61 (s, 9H).

Part B. To the product from Part A (10 g, 28 mmol) was added 125 mL of dichloromethane and 125 mL of trifluoroacetic acid. The resulting black solution was maintained at rt under nitrogen for 2 h and was then concentrated to dryness. The resulting solid was triturated with ethyl acetate and then dried in a vacuum oven for 4 h to afford 1-(3-cyano-4-fluorophenyl)-5-(2-furyl)-1H-pyrazole-3-carboxylic acid (5.3 g, 63%) as a light brown solid. LC/MS (ESI$^+$): 298.1 (M+H)$^+$. $^1$H NMR (CD$_3$OD) δ 7.90 (m, 1H), 7.75 (m, 1H), 7.51 (s, 1H), 7.46 (t, 1H), 6.98 (s, 1H), 6.47 (m, 1H), 6.35 (m, 1H).

Part C. To the product (4.1 g, 14 mmol) from Part B was added 23 mL of dichloromethane and 2.0 M oxalyl chloride (10 mL, 21 mmol) in dichloromethane. After dropwise addition of N,N-dimethylformamide (10 drops), the brown mixture became a clear solution over a period of 30 min. The solution was concentrated; the resulting residue was redissolved in 100 mL of dichloromethane, and 0.5 M ammonia in dioxane (110 mL, 55 mmol) was added via cannula. After 30 min, the resulting suspension was concentrated and poured into water. The aqueous layer was washed with ethyl acetate (3×70 mL), and the combined organic layers were washed with saturated aqueous sodium chloride, dried over sodium sulfate, and concentrated. The resulting residue was dissolved in 10 mL of dichloromethane and 50 mL of hexanes were added. The resulting suspension was filtered, and the filter cake was washed with 50 mL of hexanes, and dried in a vacuum oven to afford 1-(3-cyano-4-fluorophenyl)-5-(2-furyl)-1H-pyrazole-3-carboxamide (2.5 g, 62%) as a brown solid. LC/MS (ESI$^+$): 297.1 (M+H)$^+$. $^1$H NMR (CDCl$_3$) δ 7.75 (m, 1H), 7.64 (m, 1H), 7.42 (s, 1H), 7.33 (t, 1H), 7.16 (s, 1H), 6.79 (br s, 1H), 6.46 (m, 1H), 6.36 (m, 1H), 5.50 (br s, 1H).

Part D. To the product (2.5 g, 8.3 mmol) from Part C was added water (51 mL), 5% aqueous sodium dihydrogenphosphate (35 mL), and tert-butanol (51 mL). The resulting mixture was warmed to 60° C., and potassium permanganate (8.0 g, 51 mmol) was added over a period of 10 min. After an additional 10 min, the resulting purple slurry was cooled to 0° C., and the reaction was quenched by the addition of 200 mL of saturated aqueous sodium bisulfite. The resulting mixture was filtered, washed with 300 mL of water, and the filtrate was acidified with concentrated hydrogen chloride. The aqueous layer was extracted with ethyl acetate (6×100 mL) and the combined organic layers were washed with saturated aqueous sodium chloride, dried over sodium sulfate, and filtered. Concentration afforded 3-(aminocarbonyl)-1-(3-cyano-4-fluorophenyl)-1H-pyrazole-5-carboxylic acid (1.6 g, 71%) as a yellow solid. LC/MS (ESI$^+$): 275.1 (M+H)$^+$. $^1$H NMR (CD$_3$OD) δ 8.03 (m, 1H), 7.90 (m, 1H), 7.5 (t, 1H), 7.44 (s, 1H).

Part E. Sodium cyanoborohydride (1.54 g, 25 mmol) was added in one portion to a stirring orange solution of 5-iodo-1H-indole (6.0 g, 25 mmol) in glacial acetic acid (350 mL). After 24 h, the orange solution was concentrated. To the resulting red residue was added tetrahydrofuran (250 mL) and di-tert-butyl dicarbonate (16 g, 74 mmol) followed by saturated aqueous sodium bicarbonate (20 mL). The resulting mixture was stirred for 24 h and was then poured into aqueous 1N hydrogen chloride (70 mL). The layers were separated, and the aqueous layer was washed with ethyl acetate (3×50 mL). The combined organic layers were washed with saturated aqueous sodium chloride (50 mL), dried over sodium sulfate and concentrated. The resulting residue was dissolved in THF (100 mL), and benzyl amine (6 mL, 55 mol) was added. The resulting solution was stirred for 1.5 h and was then poured into 1N hydrogen chloride (70 mL). The layers were separated and the aqueous layer was washed with ethyl acetate (3×50 mL). The combined organic layers were washed with saturated aqueous sodium chloride (50 mL), dried over sodium sulfate, and concentrated. Purification of the resulting residue by flash column chromatography (5% ethyl acetate in hexanes) afforded tert-butyl 5-iodo-1-indolinecarboxylate (3.9 g, 45%) as a white solid. LC/MS (ESI$^+$): 346.1 (M+H)$^+$. $^1$H NMR (CDCl$_3$) δ 7.43 (m, 1H), 7.15 (m, 1H), 6.89 (dt, 1H), 3.96 (m, 2H), 3.08 (t, 1H), 3.05 (t, 1H) 1H), 1.55 (s, 9H).

Part F. To the product (1.65 g, 4.8 mmol) from Part E was added dimethylsulfoxide (59 mL), 2-hydroxypyridine (910 mg, 9.6 mmol), and potassium carbonate (2.6 g, 19 mmol). The resulting mixture was degassed (alternate vacuum & nitrogen; three times), and copper(I) iodide (910 mg, 4.8 mmol) was added in one portion. The now light green mixture was again degassed (vac/N$_2$) and warmed to 122° C. After 3 h, the mixture was cooled and poured into saturated aqueous ammonium hydroxide (100 mL) and ethyl acetate (200 mL). The layers were separated, and the aqueous layer was washed with one 50 mL-portion of ethyl acetate. The combined organic layers were then washed with water (2×50 mL), saturated aqueous sodium chloride, and dried over sodium sulfate. The organic layers were concentrated, and the resulting oil was purified by flash column chromatography (10-100% ethyl acetate in hexanes) to afford tert-butyl 5-(2-oxo-1(2H)-pyridinyl)-1-indolinecarboxylate (660 mg, 44%) as a yellow solid. LC/MS (ESI$^+$): 313.2 (M+H)$^+$. $^1$H NMR (CDCl$_3$) δ 7.41 (dd, 1H), 7.34 (dd, 1H), 7.25 (s, 1H), 7.18 (d, 1H), 6.73 (d, 1H), 6.23 (t, 1H), 4.08 (br s, 2H), 3.16 (t, 2H), 1.68 (s, 9H).

Part G. To the product (610 mg, 2.0 mmol) from Part F was added dichloromethane (6 mL) and trifluoroacetic acid (6 mL). After 20 min, the reaction was concentrated to dryness and treated with saturated aqueous sodium bicarbonate (15 mL). The layers were separated, and the aqueous layer was washed with dichloromethane (2×50 mL). The organic layers were dried over sodium sulfate and concentrated to afford 1-(2,3-dihydro-1H-indol-5-yl)-2(1H)-pyridinone (410 mg, 99%). LC/MS (ESI$^+$): 213.1 (M+H)$^+$. $^1$H NMR (CDCl$_3$) δ 7.55-8.09 (br m, 1H), 7.30-7.40 (m, 2H), 7.14 (s, 1H), 6.95 (d, 1H), 6.66 (d, 1H), 6.64 (d, 1H), 6.19 (dt, 1H), 3.62 (t, 2H), 3.08 (t, 2H).

Part H. To the product from Part G (274 mg, 1.30 mmol) was added 3-(aminocarbonyl)-1-(3-cyano-4-fluorophenyl)-1H-pyrazole-5-carboxylic acid (390 mg, 1.4 mmol), followed by pyridine (11 mL) and N,N-dimethylformamide (4.0 mL). Then 1,3-diisopropylcarbodiimide (0.242 mL, 1.6 mmol) was added, and the resulting solution was stirred for 14 h. The red mixture was poured into 1N aqueous hydrochloric acid (70 mL) and washed with ethyl acetate (60 mL). The organic layer was washed with 1N aqueous hydrochloric acid (3×25 mL), saturated aqueous sodium chloride, and dried over sodium sulfate. Concentration of the organic layers and purification of the resulting residue by radial chromatography (5% methyl alcohol in dichloromethane) afforded partially pure 1-(3-cyano-4-fluorophenyl)-5-{[5-(2-oxo-1(2H)-pyridinyl)-2,3-dihydro-1H-indol-1-yl]carbonyl}-1H-pyrazole-3-carboxamide (620 mg, 62%) as a red oil (LC/MS (ESI$^+$): 469.0 (M+H)$^+$). This material was dissolved in N,N-dimethylformamide (10 mL), and potassium carbonate (910 mg, 6.6 mmol) and water (3.0 mL) were added. Acetohydroxamic acid (110 mg, 1.5 mmol) was added in one portion, and the resulting yellow mixture was warmed to 50° C. After 1.5 h, the reaction was cooled to rt, concentrated, and diluted with ethyl acetate (10 mL). Filtration afforded 1-(3-amino-1,2-benzisoxazol-5-yl)-5-{[5-(2-oxo-1(2H)-pyridinyl)-2,3-dihydro-1H-indol-1-yl]carbonyl}-1H-pyrazole-3-carboxamide (100 mg, 16%) as a white solid. LC/MS (ESI$^+$): 482.1 (M+H)$^+$. $^1$H NMR (d$_6$-DMSO) δ 8.09 (s, 1H), 8.01 (d, 1H), 7.85 (s, 1H), 7.68 (m, 1H), 7.46-7.62 (m, 3H), 7.38 (d, 2H), 7.18 (br d, 1H), 6.58 (s, 1H), 6.46 (d, 1H), 6.29 (t, 1H), 4.34 (br t, 2H), 3.22 (br t, 2H).

Example 76

1-(2,3-dihydro-1H-indol-6-yl)-6-[4-(2-oxo-1(2H)-pyridinyl)phenyl]-3-(trifluoromethyl)-1,4,5,6-tetrahydro-7H-pyrazolo[3,4-c]pyridin-7-one, Trifluoroacetic Acid Salt Part A. 1-benzyl-6-indolinamine (2.40 g, 10.85 mmol) was stirred in conc. HCl (25 mL) at 0° C. under N$_2$. A pre-cooled solution of NaNO$_2$ (0.749 g, 10.85 mmol) in H$_2$O (2 mL) was added dropwise and slowly. The mixture was then stirred at 0° C. for 40 min after the addition. A solution of SnCl$_2$.2H$_2$O (6.10 g, 2.5 eq) in conc. HCl (7 mL) was added slowly to the stirred solution at 0° C. The resulting mixture was stirred vigorously at 0° C. for 30 min. A slurry of the 1-(4-iodophenyl)-4-(2,2,2-trifluoroacetyl)-piperidine-2,3-trione (4.20 g, 1.02 mmol) in MeOH (30 mL) was added portionwise to the mixture at 0° C. The resulting mixture was gradually warmed up and stirred at rt for 2 h, then 50° C. for 5 h. LC-MS showed completion of the reaction. The solvents were evaporated. The residue was basified with aqueous NaOH; extracted with EtOAc; washed with $H_2O$, brine, dried over $MgSO_4$, and concentrated. The residue was purified by flash column chromatography (silica gel, $CH_2Cl_2$) to produce light orange-yellow crystals of 1-(1-benzyl-2,3-dihydro-1H-indol-6-yl)-6-(4-iodophenyl)-3-(trifluoromethyl)-1,4,5,6-tetrahydro-7H-pyrazolo[3,4-c]pyridin-7-one (2.05 g, 31%). $^1$H NMR ($CDCl_3$) δ 7.69 (dd, J=8.5, 1.9 Hz, 2H), 7.34-7.25 (m, 6H), 7.08 (dd, J=6.9, 2.2 Hz, 2H), 6.76 (dd, J=7.7, 1.8 Hz, 1H), 6.58 (d, J=1.8 Hz, 1H), 4.26 (s, 2H), 4.10 (t, J=6.6 Hz, 2H), 3.35 (t, J=8.4 Hz, 2H), 3.13 (t, J=6.6 Hz, 2H), 2.97 (t, J=8.4 Hz, 2H). $^{13}$C NMR ($CDCl_3$) δ 156.4, 152.9, 141.4, 138.8, 137.9, 137.8, 132.9, 131.3, 128.6, 127.9, 127.3, 127.2, 124.0, 122.0, 115.0, 104.0, 91.0, 53.6, 53.1, 50.6, 28.3, 20.4, 14. $^{19}$F NMR ($CDCl_3$) δ −61.4. LC-MS (ESI) 615.2 (M+H).

Part B. The product from Part A (0.33 g, 0.54 mmol), 2-hydroxypyridine (0.13 g, 1.37 mmol), and $K_2CO_3$ (0.20 g, 1.45 mmol) were stirred in DMSO (1.5 mL) at RT under $N_2$. CuI (44 mg, 0.23 mmol) and 1,10-phenanthroline (40 mg, 0.23 mmol) were added. The resulting mixture was stirred at 140° C. for 2.5 h under $N_2$. LC-MS showed disappearance of the starting material from Part A. The mixture was cooled to RT, and EtOAc was added. It was washed with $H_2O$, brine, dried over $MgSO_4$, and concentrated. The crude compound of 1-(1-benzyl-2,3-dihydro-1H-indol-6-yl)-6-[4-(2-oxo-1(2H)-pyridinyl)phenyl]-3-(trifluoromethyl)-1,4,5,6-tetrahydro-7H-pyrazolo[3,4-c]pyridin-7-one was used directly in the next step. $^1$H NMR ($CDCl_3$) δ 7.50-1.22 (m, 9H), 7.09 (d, J=8.4 Hz, 2H), 6.85 (dd, J=7.2, 1.2 Hz, 1H), 6.78 (d, J=8.4 Hz, 1H), 6.71 (d, J=1.2 Hz, 1H), 6.37 (td, J=7.2, 1.2 Hz, 1H), 4.29 (s, 2H), 4.19 (t, J=6.3 Hz, 2H), 3.39 (t, J=8.4 Hz, 2H), 3.17 (t, J=6.3 Hz, 2H), 2.96 (t, J=8.5 Hz, 2H). LC-MS (ESI) 582.2 (M+H).

Part C. The product from Part B (0.33 g, 0.57 mmol), NaI (0.17 g, 1.14 mmol), and 1-chloroethyl chloroformate (0.10 mL, 1.8 eq) were stirred in acetone (2 mL) for 1.5 h at RT under $N_2$. The solvent was evaporated, and the residue was dissolved in MeOH (4 mL). It was refluxed for 1 h. The residue was purified by prep LC-MS (5-98% $CH_3CN$ in $H_2O$, $t_R$=4.18 min in a 10-min run). The fractions were collected and lyophilized to give 1-(2,3-dihydro-1H-indol-6-yl)-6-[4-(2-oxo-1(2H)-pyridinyl)phenyl]-3-(trifluoromethyl)-1,4,5,6-tetrahydro-7H-pyrazolo[3,4-c]pyridin-7-one. $^1$H NMR ($CD_3COCD_3$) δ 7.56-7.41 (m, 6H), 7.07 (d, J=7.8 Hz, 1H), 6.78-6.72 (m, 2H), 6.45 (d, J=8.8 Hz, 1H), 6.28 (td, J=7.0, 1.5 Hz, 1H), 4.25 (t, J=6.6 Hz, 2H), 3.55 (t, J=8.1 Hz, 2H), 3.17 (t, J=6.6 Hz, 2H), 2.98 (t, J=8.1 Hz, 2H). LC-MS (ESI) 492.4 (M+H).

Example 77

1-(2,3-dihydro-1H-indol-6-yl)-6-[4-(2-oxo-1-piperidinyl)phenyl]-3-(trifluoromethyl)-1,4,5,6-tetrahydro-7H-pyrazolo[3,4-c]pyridin-7-one, Trifluoroacetic Acid Salt Part A. The product from Part A of Example 71 (0.89 g, 1.45 mmol), δ-valerolactam (0.20 g, 2.02 mmol), and $K_2CO_3$ (0.41 g, 2.97 mmol) were stirred in DMSO (5 mL) at RT under $N_2$. CuI (86 mg, 0.45 mmol) and 1,10-phenanthroline (80 mg, 0.43 mmol) were added. The resulting mixture was stirred at 130° C. overnight under $N_2$. The mixture was cooled to rt, and EtOAc was added. It was washed with brine (2×), dried over $MgSO_4$, and concentrated. The residue was purified by flash column chromatography (silica gel, $CH_2Cl_2$, then $CH_2Cl_2$:EtOAc=10:3) to produce the desired product 1-(1-benzyl-2,3-dihydro-1H-indol-6-yl)-6-[4-(2-oxo-1-piperidinyl)phenyl]-3-(trifluoromethyl)-1,4,5,6-tetrahydro-7H-pyrazolo[3,4-c]pyridin-7-one (0.51 g, 68% based on recovered starting material). $^1$H NMR ($CDCl_3$) δ 7.36-7.22 (m, 8H), 7.06 (d, J=7.7 Hz, 1H), 6.76 (dd, J=7.7, 1.8 Hz, 1H), 6.59 (d, J=1.8 Hz, 1H), 4.26 (s, 2H), 4.12 (m, 2H), 3.59 (m, 2H), 3.34 (t, J=8.4 Hz, 2H), 3.12 (t, J=6.6 Hz, 2H), 2.96 (t, J=8.4 Hz, 2H), 2.56 (m, 2H), 1.93 (m, 4H). LC-MS (ESI) 586.4 (M+H).

Part B. The product from Part A (0.51 g, 0.87 mmol), NaI (0.26 g, 1.74 mmol), and 2-chloroethyl chloroformate (0.16 mL, 1.8 eq) were stirred in acetone (5 mL) for 4 h at RT under $N_2$. The solvent was evaporated; and the residue was purified by flash column chromatography (silica gel, $CH_2Cl_2$, then EtOAc, then EtOAc:MeOH=10:1) to give the intermediate carbamate. The fractions were concentrated, and dried under vacuum for 10 min. It was dissolved in MeOH (30 mL), and refluxed under $N_2$ for 1 h. The residue was purified by prep LC-MS (35-98% $CH_3CN$ in $H_2O$, $t_R$=2.24 min in a 10-min run). The fractions were collected and lyophilized to yield 1-(2,3-dihydro-1H-indol-6-yl)-6-[4-(2-oxo-1-piperidinyl)phenyl]-3-(trifluoromethyl)-1,4,5,6-tetrahydro-7H-pyrazolo[3,4-c]pyridin-7-one as white solids. $^1$H NMR ($CD_3COCD_3$) δ 7.33 (AA'BB', J=9 Hz, 4H), 6.82 (d, J=7.7 Hz, 1H), 6.79 (m, 2H), 4.68 (t, J=6.6 Hz, 2H), 3.67 (t, J=6.6 Hz, 2H), 3.58 (t, J=8.4 Hz, 2H), 3.16 (t, J=6.6 Hz, 2H), 3.00 (t, J=8.1 Hz), 2.40 (t, J=6.1 Hz, 2H), 1.91 (m, 4H). LC-MS (ESI) 496.4 (M+H).

Example 78

1-(2,3-Dihydro-1H-isoindol-5-yl)-6-[4-(2-oxo-2H-pyridin-1-yl)phenyl]-3-trifluoromethyl-1,4,5,6-tetrahydropyrazolo[3,4-c]pyridin-7-one, Trifluoroacetic Acid Salt Part A. A solution of 4-nitro-o-xylene (38.64 g, 255.9 mmol), NBS (91.1 g, 511.8 mmol), benzoyl peroxide (1.239 g, 5.118 mmol), and $CCl_4$ (400 mL) was heated at reflux for 1 day, then at rt for 2 days. The solid was filtered off and washed with $CCl_4$. The filtrate was evaporated to give the crude dibromo product (80 g). A portion of which (20 g) was dissolved in acetone (170 mL) and water (45 mL), then $Na_2CO_3$ (43.1 g, 407 mmol) was slowly added, followed by $BnNH_2$ (7.05 mL, 64.6 mmol) in acetone (22 mL). After 10 h, the solution was concentrated to one-fourth its volume, the salt solid was filtered off, and the filtrate was evaporated. The residue was dissolved in EtOAc, washed with water and brine, dried over sodium sulfate, filtered, and evaporated. The residue was purified by column chromatography to provide the corresponding 2-benzyl-5-nitro-2,3-dihydro-1H-isoindole (5.41 g, 33% yield, over 2 steps): $^1$H NMR (300 MHz, $CDCl_3$) δ 8.11 (d, 1H), 8.04 (s, 1H), 7.48-7.20 (m, 6H), 4.02 (s, 4H), 3.92 (s, 2H).

Part B. To a solution of the isoindoline (5.40 g, 21.3 mmol) made above in EtOH (266 mL) under $N_2$ was added 20% $Pd(OH)_2$/C (3.00 g, 4.25 mmol). The reaction mixture was hydrogenated at 45 psi for 1 h. TLC analysis indicated that the nitro functionality was reduced and the Bn group was still intact. Therefore, concentrated HCl (1.6 mL, 19.1 mmol) was added to the reaction mixture and hydrogenation (50 psi) was continued overnight. The mixture was filtered through Celite®, washed with MeOH, and the filtrate was concentrated to one fourth of the volume. The precipitate was filtered off to provide the 5-aminoisoindoline.HCl (1.32 g, 36% yield): $^1$H NMR (500 MHz, CDCl$_3$) δ 9.88 (s, br, 2H), 7.00 (d, 1H), 6.54 (m, 2H), 5.44 (s, br, 2H), 4.32 (s, 2H), 4.28 (s, 2H); ESI MS m/z 135 (M−HCl+H)$^+$.

Part C. The 5-aminoisoindoline (700 mg, 4.11 mmol) made above was dissolved in 6 M HCl (4.6 mL) at rt, then cooled to 0° C. A solution of NaNO$_2$ (340 mg, 4.93 mmol) in water (0.8 mL) was added dropwise, maintaining the reaction temperature below 5° C. After 40 min, AcOH (1.4 mL) was added to the mixture, followed by the dropwise addition of SnCl$_2$ (1.79 g, 9.44 mmol) in concentrated HCl (2.7 mL) at 0° C. The mixture was warmed to 10° C. and stirred for 2 h, then a solution of 3-hydroxy-1-(4-iodophenyl)-4-(2,2,2-trifluoroacetyl)-5,6-dihydro-1H-pyridin-2-one (1.78 g, 4.31 mmol) in MeOH (16 mL) was added and the reaction mixture was heated at 50° C. for 16 h. Methyl alcohol was removed under vacuum and the solid was collected by filtration to give 1-(2,3-dihydro-1H-isoindol-5-yl)-6-methyl-3-trifluoromethyl-1,4,5,6-tetrahydro-pyrazolo[3,4-c]pyridin-7-one; compound with iodo-benzene as an AcOH salt (2.07 g, 86% yield): $^1$H NMR (500 MHz, DMSO-d$_6$) δ 9.82 (s, br, 2H), 7.75 (d, 2H), 7.66-7.62 (m, 2H), 7.51 (d, 1H), 7.19 (d, 2H), 4.56 (m, 4H), 4.11 (t, 2H), 3.12 (t, 2H); ESI MS m/z 585 (M+H)$^+$.

Part D. The product from Part C (540 mg, 1.03 mmol) was added to a stirred solution of Et$_3$N (143 mL, 1.03 mmol) and Boc$_2$O (225 mg, 1.03 mmol) in THF (5.2 mL) at rt. After 2.5 h, the solvent was removed under vacuum and the residue was purified by column chromatography to provide the corresponding protected isoindoline 5-(6-methyl-7-oxo-3-trifluoromethyl-4,5,6,7-tetrahydro-pyrazolo[3,4-c]pyridin-1-yl)-1,3-dihydro-isoindole-2-carboxylic acid tert-butyl ester; compound with iodo-benzene (272 mg, 42% yield): $^1$H NMR (300 MHz, CDCl$_3$) δ 7.69 (d, 2H), 7.45-7.26 (m, 3H), 7.06 (d, 2H), 4.68 (m, 4H), 4.13 (t, 2H), 3.17 (t, 2H), 1.51 (s, 9H); $^{19}$F NMR (282 MHz, CDCl$_3$) δ −61.8.

Part E. A mixture of the product from Part D (102 mg, 163 μmol), 2-hydroxy-pyridine (19 mg, 196 μmol), K$_2$CO$_3$ (25 mg, 180 μmol), 1,10-phenanthroline (3 mg, 18 mmol), CuI (4 mg, 20 μmol, and DMSO (0.3 mL) under argon atmosphere was heated at 110-120° C. for 24 h. The mixture was diluted with CH$_2$Cl$_2$, washed 1 M HCl (2×) and brine, dried over sodium sulfate, filtered, and evaporated under vacuum. The residue was purified by column chromatography to provide the corresponding biaryl lactam (17 mg), which was treated with TFA (21 mL) to provide, after purification by semi-preparative HPLC, the title compound 1-(2,3-dihydro-1H-isoindol-5-yl)-6-[4-(2-oxo-2H-pyridin-1-yl)phenyl]-3-trifluoromethyl-1,4,5,6-tetrahydropyrazolo[3,4-c]pyridin-7-one, trifluoroacetic acid salt (3.8 mg, 4% yield, 3 steps): $^1$H NMR (300 MHz, CDCl$_3$) δ 9.77 (s, br, 2H), 7.63-7.34 (m, 8H), 7.10 (d, 1H), 6.69 (d, 1H), 6.45 (t, 1H), 4.21 (t, 2H), 4.07 (s, 2H), 3.20 (t, 2H), 1.31 (m, 2H); $^{19}$F NMR (282 MHz, CDCl$_3$) δ −62.0, −76.2; ESI MS m/z 492 (M−CF$_3$CO$_2$H+H)$^+$.

Example 79

1-(4-Methoxyphenyl)-6-[4-(2-oxo-piperidin-1-yl)-phenyl]-3-(2-pyrrolidin-1-ylmethyl-phenyl)-1,4,5,6-tetrahydro-pyrazolo[3,4-c]pyridin-7-one Part A. A 250 mL flask containing a stir bar was charged with 4-methoxyphenylhydrazine HCl (3 g, 17 mmol) and 25 mL water. A solution of glyoxylic acid monohydrate (1.6 g, 17 mmol) dissolved in 15 mL water was prepared and added to the stirring solution dropwise via addition funnel. As the reagent solution was added, the reaction turned reddish-brown and precipitated while stirring over the course of 3 h at rt. The solid was filtered in a Buchner funnel and washed three times each with 1N HCl and water. The hydrazone was isolated as a dark brown solid (2.7 g, 14 mmol) in 82% yield.

Part B. A 250 mL flask containing a stir bar was charged with hydrazone (1.0 g, 5.1 mmol) from part A and 10 mL DMF, then cooled to 0° C. The system was flushed with N$_2$. A solution of N-bromosuccinimide (1.8 g, 10 mmol) in 2 mL DMF was also prepared and added to the reaction flask dropwise by syringe. Gas evolution was evident as the reagent was added. The reaction stirred for 15 min at 0° C. Iodo-morpholine enamine (3 g, 7.7 mmol) and a solution of triethylamine (1.4 mL, 10 mmol) in 20 mL toluene were added to the reaction at 0° C. The reaction stirred overnight while warming to rt. The solution was diluted by the addition of water and ethyl acetate and transferred to an addition funnel. The aqueous phase was separated and extracted three times with ethyl acetate. The organics were combined and washed with brine before drying over sodium sulfate. The solvent was removed by rotary evaporation to yield the morpholine intermediate as an orange solid. The crude material was purified by flash chromatography (eluent 50% hexane, 50% ethyl acetate on silica gel) to afford pure iodo-morpholine intermediate (1.2 g, 2.0 mmol) in 38% yield.

Part C. A 100 mL flask with a stir bar was charged with iodo-morpholine intermediate (1.2 g, 2.0 mmol) and 10 mL of methylene chloride before the dropwise syringe addition of 1 mL TFA. The system was flushed with N$_2$ while the reaction stirred overnight at rt. The solution was diluted with methylene chloride and saturated sodium bicarbonate before transfer to an addition funnel. The aqueous phase was separated and extracted three times with methylene chloride. The organics were combined and washed with brine before drying over magnesium sulfate. The solution was filtered and solvent was removed by rotary evaporation to yield the 3-bromopyrazole as an orange solid. The crude reaction product was purified by flash chromatography to produce pure 3-bromopyrazole (560 mg, 1.1 mmol) in 53% yield.

Part D. An oven-dried 100 mL flask and stir bar were charged with 3-bromopyrazole (860 mg, 1.6 mmol), 7-valerolactam (230 mg, 2.5 mmol), potassium carbonate (270 mg, 2.0 mmol), and 10 mL degassed DMF. Copper iodide (62 mg, 0.33 mmol) was added and a reflux condenser was attached. The system was flushed with N$_2$ while the reaction was heated to 120° C. overnight. The reaction was cooled to rt before dilution with ethyl acetate and water. This solution was transferred to an addition funnel and the aqueous phase extracted three times with ethyl acetate. The organics were combined and washed three times with water and once with brine before drying over sodium sulfate. The product solution was filtered and concentrated to dryness by rotary evaporation. The crude product was purified by flash chromatography to afford the bromo-lactam (150 mg, 0.3 mmol) in 19% yield.

Part E. An oven-dried, 100 mL flask containing a stir bar was charged with bromo-lactam (90 mg, 0.18 mmol), 2-formylbenzeneboronic acid, and sodium carbonate (60 mg, 0.54 mmol). The solids were dissolved in 3 mL of a 2:1 mixture of degassed THF and water. Tetrakis-(triphenylphosphine)palladium (10 mg, 0.01 mmol) was added before the flask was fitted with a reflux condenser and the system flushed with N$_2$. The reaction was heated to 110° C. while stirring overnight. The reaction was cooled to rt and diluted with water and ethyl acetate. The solution was transferred to a separation funnel and the aqueous phase extracted with ethyl acetate. The organics were combined and washed with brine before drying over sodium sulfate. The solvents were removed by rotary evaporation to afford the desired 3-aryl pyrazole (70 mg, 0.13 mmol) in 74% crude yield.

Part F. An oven-dried, 100 mL flask containing a stir bar was charged with 3-aryl pyrazole (70 mg, 0.13 mmol) and 30 mL of a 1:1 methyl alcohol/THF solution. The system was flushed with $N_2$ before the syringe addition of 60 µL of pyrrolidine. The reaction stirred at rt for 15 min. To the reaction solution was added 2M zinc chloride solution in THF (130 µL, 0.06 mmol) followed by sodium cyanoborohydride (10 mg, 0.16 mmol). The reaction was stirred at rt while stirring overnight. The reaction was diluted with ethyl acetate and water. The aqueous phase was separated and washed with brine before drying over sodium sulfate. The solution was filtered and concentrated in vacuo to afford the crude product. Purification by HPLC followed by freeze-drying produced the desired amine as a TFA salt. ESI MS m/z 576 (M+H).

Example 80

5-chloro-N-(5-chloropyridin-2-yl)-2-({4-[(2-oxo-piperidine)-1-yl]benzoyl}amino)benzamide Part A: To a solution of 2-amino-4-chloropyridine (129 mg, 1.0 mmol) in anhydrous THF at −78° C. was added KHMDS (4.0 mL, 0.5 M solution in toluene). The mixture was stirred at this temperature under $N_2$ for 30 min and a solution of 5-chloro-isatoic anhydride (198.0 mg, 1.0 mmol) in THF was added to the above mixture. The resulted mixture was warmed to rt gradually and stirred for 10 h. The reaction mixture was quenched with sat. $NH_4Cl$ solution, most of the solvent was evaporated and the residue was diluted with ethyl acetate, washed with brine, and dried over $MgSO_4$. Removal of solvent and chromatography on silica gel (20% ethyl acetate in hexane) yielded the desired product 2-amino-5-chloro-N-(5-chloro-pyridin-2-yl)-benzamide as light brown solid. MS found: $(M+1)^+$=282.2.

Part B: To a suspension of 4-[(2-oxo-piperidine)-1-yl]benzoic acid (219 mg, 1.0 mmol) in $CH_2Cl_2$ and DMF (0.1 mL) was added oxylyl chloride (2.0 mmol). The mixture was stirred for 2 h under $N_2$. Solvent was removed and the residue was dried on vacuum to give the acyl chloride. To the mixture of part A (124 mg, 0.44 mmol), TEA (0.25 mL) and DAMP (11.0 mg) in $CH_2Cl_2$ was added a solution of the above acyl chloride in $CH_2Cl_2$ at 0° C. The mixture was warmed to rt and stirred over night under $N_2$. The mixture was washed with water and purified with reverse phase HPLC (20% $CH_3CN$/$H_2O$, 40 mL/min) to provide the desired product as light brown solid. ESI MS m/z: $(M+1)^+$=483.0.

Example 81

5-chloro-N-(5-chloropyridin-2-yl)-2-({4-[(2-oxo-pyridin)-1-yl]benzoyl}amino)benzamide Following a procedure analogous to that described in Example 80, 5-chloro-N-(5-chloropyridin-2-yl)-2-({4-[(2-oxo-pyridin)-1-yl]benzoyl}amino)benzamide was obtained as light yellow solid. ESI MS m/z: $(M+1)^+$=479.0.

Example 82

N-(5-chloropyridin-2-yl)-2-({4-[(2-oxo-piperidine)-1-yl]benzoyl}amino)-5-methoxybenzamide Following a procedure analogous to that described in Example 80, the title compound was obtained as light brown solid. ESI MS m/z: $(M+1)^+$=479.1.

Example 83

N-(5-chloropyridin-2-yl)-2-([4-[(2-oxo-pyridin)-1-yl]benzoyl]amino)-5-methoxybenzamide Following a procedure analogous to that described in Example 80, N-(5-chloropyridin-2-yl)-2-({4-[(2-oxo-pyridin)-1-yl]benzoyl}amino)-5-methoxybenzamide was obtained as white solid. ESI MS m/z: $(M+1)^+$=475.2.

Example 84

N-(5-chloropyridin-2-yl)-2-([4-[(2-oxo-piperidine)-1-yl]benzoyl]amino)-5-methylbenzamide Following a procedure analogous to that described in Example 80, the title compound was obtained as white solid. ESI MS m/z: $(M+1)^+$=463.2.

Example 85

N-(5-chloropyridin-2-yl)-2-([4-[(2-oxo-pyridin)-1-yl]benzoyl]amino)-5-methylbenzamide Following a procedure analogous to that described in Example 80, the title compound was obtained as white solid. ESI MS m/z: $(M+1)^+$=459.2.

Example 86

1-(3-Chloro-phenyl)-3-methanesulfonyl-6-[4-(2-oxo-piperidin-1-yl)-phenyl]-1,4,5,6-tetrahydro-pyrazolo[3,4-c]pyridin-7-one Part A. 3-Chloroaniline (5.00 g, 39.2 mmol) was added dropwise to an ice-cold 1N hydrochloric acid solution followed by the addition of 4 mL of 12M hydrochloric acid. To this solution was slowly added an ice-cold solution of sodium nitrite (3.00 g, 43.1 mmol) in 4 mL of water while maintaining the internal temperature to less than 5° C. This solution was stirred for 45 min at 0° C. during which time a precipitate formed. Glacial acetic acid (1 mL) was added and the precipitate dissolved. To this solution was added solid sodium acetate (approx. 2 g) to adjust the pH to 4 and then 10 mL ice cold acetone was added followed by an ice cold solution of 1-chloro-1-methanesulfonyl-propan-2-one in 10 mL acetone. The reaction was allowed to warm to ambient temperature and stirred for 14 h. A stream of nitrogen was passed over the solution to slightly reduce the solvent volume. The solid precipitate was collected by filtration, washed twice with water, and dried in vacuo at 40° C. to give 8.47 g (81%) of N-(3-chlorophenyl)-1-(methylsulfonyl)-methanehydrazonoyl chloride as a light orange solid.

The methanehydrazonoyl chloride (8.47 g, 31.7 mmol) and 1-(4-iodo-phenyl)-3-morpholin-4-yl-5,6-dihydro-1H-pyridin-2-one (12.17 g, 31.7 mmol) were combined in anhydrous toluene. The solution heated to 70° C. and triethylamine (13.2 mL, 95.1 mmol) was added dropwise. After the addition was complete the reaction was warmed to 90° C. and stirred at this temperature for 14 h. Analysis by LC/MS indicated formation of 1-(3-chloro-phenyl)-6-(4-iodo-phenyl)-3-methanesulfonyl-7a-morpholin-4-yl-1,3a,4,5,6,7a-hexahydro-pyrazolo[3,4-c]pyridin-7-one complete with less than 5% of 1-(4-iodo-phenyl)-3-morpholin-4-yl-5,6-dihydro-1H-pyridin-2-one remaining. The solvent was removed in vacuo. To the viscous oil was added dichloromethane (50 mL) then trifluoroacetic acid (30 mL) and heated to reflux for 4 h. The solvent was evaporated and the residue purified by flash column chromatography eluting with a gradient of hexane to 40% ethylacetate/hexane to give 10.65 g (64%) of 1-(3-chloro-phenyl)-6-(4-iodo-phenyl)-3-methanesulfonyl-1,4,5,6-tetrahydro-pyrazolo[3,4-c]pyridin-7-one.

Part B. In a round bottomed flask were combined 1-(3-chloro-phenyl)-6-(4-iodo-phenyl)-3-methanesulfonyl-1,4,5,6-tetrahydro-pyrazolo[3,4-c]pyridin-7-one (1.00 g, 1.89 mmol), δ-valerolactam (0.36 g, 3.79 mmol), anhydrous powdered potassium carbonate (1.05 g, 7.58 mmol), cuprous iodide (0.072 g, 0.38 mmol), and 1,10-phenanthroline (0.068 g, 0.38 mmol). The flask was purged with argon and degassed methylsulfoxide (10 mL) was added before heating to 120° C. Upon completion of the reaction, as judged by TLC or LC/MS, the reaction was cooled to ambient temperature and 50 mL each of 3M ammonium hydroxide and dichloromethane were added. The phases were separated and the aqueous extracted with an additional 30 mL of dichloromethane. The combined dichloromethane extracts are washed successively four times with water and once with brine. The solution was dried over sodium sulfate, filtered, and evaporated to give an oil that was purified by flash column chromatography eluting with ethylacetate to give 0.424 g (45%) of 1-(3-chloro-phenyl)-3-methanesulfonyl-6-[4-(2-oxo-piperidin-1-yl)-phenyl]-1,4,5,6-tetrahydro-pyrazolo[3,4-c]pyridin-7-one as a colorless solid. The material may be recrystallized from acetonitrile. $^1$H NMR (DMSO-d$_6$) δ 7.79 (t, 1H, J=2 Hz), 7.63-7.49 (m, 3H), 7.32 (ab q, 4H, J=21.9 Hz), 4.10 (t, 2H, J=6 Hz), 3.58 (t, 2H, J=5 Hz), 3.36 (s, 3H), 3.19 (t, 2H, J=6 Hz), 2.37 (t, 2H, J=5 Hz), 1.83 (m, 4H). LC/MS (ES+): 498.9/500.9 (Cl pattern) (>95% pure by ELSD).

Example 87

3-(5-Chloro-pyridin-2-yl)-6-methoxy-2-[4-(2-oxo-piperidin-1-yl)-phenyl]-3H-quinazolin-4-one A mixture of the product from Example 82 (20 mg, 0.04 mmol) in 4N HCl in dioxane (5 mL) was stirred at reflux for 3.5 h. The reaction mixture was cooled to rt, and purified with HPLC (15% CH$_3$CN/H$_2$O, 20 mL/min) to provide the desired product as white solid. ESI MS m/z: (M+1)$^+$=461.1.

Example 88

3-(5-Chloro-pyridin-2-yl)-6-methoxy-2-[4-(2-oxo-pyridin-1-yl)-phenyl]-3H-quinazolin-4-one Following a procedure analogous to that described in Example 87, the title compound was obtained as white solid. ESI MS m/z: (M+1)$^+$=457.1.

Example 89

Ethyl 1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carboxylate The title compound was made in Part A of Example 27. High Resolution Mass Spec (M+H)$^+$ for $C_{27}H_{25}N_4O_5$ 485.1827.

Example 90

1-(4-Methoxyphenyl)-7-oxo-6-[4-(2-oxo-1(2H)-pyridinyl)phenyl]-4,5,6,7-tetrahydro-1H-pyrazolo[3,4-c]pyridine-3-carboxylic Acid Ethyl 1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carboxylate (0.5 g, 1.03 mmol) was hydrolyzed with lithium hydroxide (0.13 g, 3 mmol) and a mixture of methyl alcohol (5 mL), THF (25 mL) and water (25 mL) for 24 h. The reaction was acidified with conc. HCl and the resulting solid filtered off. The product was suspended in 1:1 CH$_2$Cl$_2$/hexanes, filtered, and dried to afford 0.37 g (79%) white solid; Mass Spec (M+H)$^+$ 457.3.

Example 91

1-(4-methoxyphenyl)-N,N-dimethyl-7-oxo-6-[4-(2-oxo-1(2H)-pyridinyl)phenyl]-4,5,6,7-tetrahydro-1H-pyrazolo[3,4-c]pyridine-3-carboxamide To dimethylamine hydrochloride (0.35 g, 4.3 mmol) in CH$_2$Cl$_2$ (20 mL) at 0° C. was added 2M trimethylaluminum in hexanes (2.2 mL, 4.3 mmol). After 0.5 h, ethyl 1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carboxylate (0.42 g, 0.86 mmol) was added. The reaction was stirred for 24 h and then poured into dilute HCl and ice water, extracted with CH$_2$Cl$_2$, washed with brine, and dried (MgSO$_4$). Purification by chromatography on silica gel and recrystallization from CH$_2$Cl$_2$/hexanes afforded 340 mg (81%); High Resolution Mass Spec (M+H)$^+$ for $C_{27}H_{26}N_5O_4$ 484.1980.

Example 92

N-({1-(4-methoxyphenyl)-7-oxo-6-[4-(2-oxo-1(2H)-pyridinyl)phenyl]-4,5,6,7-tetrahydro-1H-pyrazolo[3,4-c]pyridin-3-yl}carbonyl)methanesulfonamide To 1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carboxylic acid (0.2 g, 0.43 mmol) in CH$_2$Cl$_2$ (10 mL) was added 1-[3-(dimethylamino)propyl]-3-ethyl carbodiimide hydrochloride (0.1 g, 0.5 mmol) and TEA (0.18 mL, 1.3 mmol) and the reaction was stirred for 15 min. 1-Hydroxybenzotriazole (71 mg, 0.5 mmol) was added and the reaction was stirred for 15 min. Methane sulfonamide (0.125 g, 1.3 mmol) and DMF (1 mL) were added and the reaction was stirred for 72 h. The solvents were removed and after purification by HPLC and freeze-drying 75 mg (33%) white solid was obtained; High Resolution Mass Spec (M+H)$^+$ for $C_{26}H_{24}N_5O_6S$ 534.1468.

Example 93

1-(4-Hydroxy-phenyl)-7-oxo-6-[4-(2-oxo-piperidin-1-yl)-phenyl]-4,5,6,7-tetrahydro-1H-pyrazolo[3,4-c]pyridine-3-carboxylic Acid Amide To ethyl 1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carboxylate (0.2 g, 0.4 mmol) in CH$_2$Cl$_2$ (30 mL) at 0° C. was added BBr$_3$ (0.05 mL, 0.5 mmol) and the mixture was stirred for 3 h. The solvents were removed and MeOH (20 mL) and conc. HCl (0.1 mL) were added and heated to reflux for 24 h to re-esterify. The solvents were removed and the crude ester was placed in 4 mL of ethylene glycol containing 10% NH$_3$ and heated in a sealed container at 85° C. for 1.5 h. The reaction was cooled and poured into water and extracted with EtOAc. Purification by HPLC and freeze-drying afforded 11 mg (6%) of a white solid; High Resolution Mass Spec (M+H)$^+$ for $C_{24}H_{24}N_5O_4$ 446.1840.

Example 94

1-(4-methoxyphenyl)-6-[4-(2-oxo-1(2H)-pyridinyl) phenyl]-3-(1H-tetrazol-5-yl)-1,4,5,6-tetrahydro-7H-pyrazolo[3,4-c]pyridin-7-one To 1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carbonitrile (0.1 g, 0.23 mmol) in DMF (2 mL) was added NaN$_3$ (19 mg, 0.29 mmol) and NH$_4$Cl (21 mg, 0.38 mmol) and the reaction was heated to 105° C. for 24 h. The reaction was cooled, water (1 mL) was added, and the resulting solid filtered off and dried. The solid was placed in DMF (1 mL) and trityl chloride (60 mg, 0.2 mmol) and pyridine (0.2 mL) were added and stirred for 24 h. The reaction was quenched with water, extracted with EtOAc, and dried (Na$_2$SO$_4$). Purification on silica gel was not successful. The trityl group was removed with TFA (0.5 mL) in CH$_2$Cl$_2$ for 2 h. The solvents were removed and the compound was purified by HPLC and freeze-dried to afford 10 mg (9%) of a white solid; High Resolution Mass Spec (M+H)$^+$ for C$_{25}$H$_{21}$N$_8$O$_3$ 481.1749.

Example 95

3-{4-[(dimethylamino)methyl]-1,3-oxazol-2-yl}-1-(4-methoxyphenyl)-6-[4-(2-oxo-1(2H)-pyridinyl) phenyl]-1,4,5,6-tetrahydro-7H-pyrazolo[3,4-c]pyridin-7-one To 1-(4-methoxyphenyl)-7-oxo-6-[4-(2-oxo-1(2H)-pyridinyl)phenyl]-4,5,6,7-tetrahydro-1H-pyrazolo[3,4-c]pyridine-3-carboxamide (0.161 g, 0.35 mmol) was added excess 1,3-dichloroacetone (0.5 g). The reaction was heated to 130° C. for 24 h. The reaction was cooled and excess 40% NMe$_2$ in water was added and the mixture stirred for 48 h. The solvents were removed and the residue chromatographed with 5% MeOH/CH$_2$Cl$_2$ with 1% NH$_3$ to afford a tan solid (36 mg) that appeared to be the chloro-intermediate. The solid was placed in ethylene glycol (1 mL) and 40% Me$_2$N/water (1.5 mL) and heated at 80° C. for 3 h. The reaction was cooled and extracted with EtOAc. Purification by HPLC and freeze-drying afforded 35 mg (19%) of a white solid; High Resolution Mass Spec (M+H)$^+$ for C$_{30}$H$_{28}$N$_6$O$_4$ 537.2268.

Example 96

3-{4-[(dimethylamino)methyl]-1,3-oxazol-2-yl}-1-(4-methoxyphenyl)-6-[4-(2-oxo-1-piperidinyl)phenyl]-1,4,5,6-tetrahydro-7H-pyrazolo[3,4-c]pyridin-7-one To 1-(4-methoxyphenyl)-7-oxo-6-[4-(2-oxo-1-piperidinyl)phenyl]-4,5,6,7-tetrahydro-1H-pyrazolo[3,4-c]pyridine-3-carboxamide (0.142 g, 0.31 mmol) was added excess 1,3-dichloroacetone (0.2 g). The reaction was heated to 130° C. for 24 h. The reaction was cooled and excess 40% NMe$_2$ in water was added and the resulting mixture stirred for 48 h. Repeated purification by HPLC and freeze-drying afforded 2 mg (1.2%) of a white solid; High Resolution Mass Spec (M+H)$^+$ for C$_{30}$H$_{33}$N$_6$O$_4$ 541.2582.

Example 97

1-(4-methoxyphenyl)-7-oxo-6-[4-(2-oxo-1-piperazinyl)phenyl]-4,5,6,7-tetrahydro-1H-pyrazolo[3,4-c] pyridine-3-carboxamide Part A. To ethyl-6-(4-iodophenyl)-1-(4-methoxyphenyl)-7-oxo-4,5,6,7-tetrahydro-1H-pyrazolo(3,4-c)pyridine-3-carboxamide (0.52 g, 1.0 mmol), 4-benzyloxycarbonylpiperazin-2-one (0.32 g, 1.4 mmol), and K$_2$CO$_3$ (0.22 g, 1.6 mmol) was added DMSO (5 mL). The mixture was degassed with N$_2$. CuI (38 mg, 0.2 mmol) was added and the reaction was heated to 130° C. for 18 h. The reaction was diluted with EtOAc and water, extracted with EtOAc, and dried (MgSO$_4$). Purification by chromatography on silica gel using 5% MeOH/CH$_2$Cl$_2$ afforded 0.2 g (33%) of a foam; Mass Spec (M+H)$^+$ 624.6.

Part B. The product of Part A (0.2 g, 0.32 mmol) was hydrogenated at 40 psi in the presence of 10% palladium on carbon for 24 h. The reaction was filtered and then heated with 5% NH$_3$ in ethylene gylcol in a sealed vial for 1.5 h at 80° C. The reaction was diluted with water and extracted with EtOAc. Purification by HPLC and freeze-drying afforded 30 mg (16%) of a white solid; High Resolution Mass Spec (M+H)$^+$ for C$_{24}$H$_{25}$N$_6$O$_4$ 461.1938.

Example 98

1-(4-methoxyphenyl)-3-(methylsulfonyl)-6-[4-(2-oxo-1-piperazinyl)phenyl]-1,4,5,6-tetrahydro-7H-pyrazolo[3,4-c]pyridin-7-one To 6-(4-iodophenyl)-1-(4-methoxyphenyl)-3-(methylsulfonyl)-1,4,5,6-tetrahydro-7H-pyrazolo(3,4-c)pyridin-7-one (0.55 g, 1.0 mmol), 4-benzyloxycarbonylpiperazin-2-one (0.35 g, 1.4 mmol), and K$_2$CO$_3$ (0.23 g, 1.6 mmol) was added DMSO (5 mL). The mixture was degassed with N$_2$. CuI (39 mg, 0.21 mmol) was added and the reaction was heated to 130° C. for 18 h. The reaction was diluted with EtOAc and water, extracted with EtOAc, and dried (MgSO$_4$). Purification of the intermediate by chromatography on silica gel using 5% MeOH/CH$_2$Cl$_2$ was followed by deprotection in refluxing TFA. Purification by HPLC and freeze-drying afforded 175 mg (27%) of a white solid; High Resolution Mass Spec (M+H)$^+$ for C$_{24}$H$_{26}$N$_6$O$_5$S 496.1650.

Example 99

1-(4-Methoxy-phenyl)-3-(4-methyl-oxazol-2-yl)-6-[4-(2-oxo-piperidin-1-yl)-phenyl]-1,4,5,6-tetrahydro-pyrazolo[3,4-c]pyridin-7-one Part A. To 1-(4-methoxyphenyl)-7-oxo-6-[4-(2-oxo-1-piperidinyl)phenyl]-4,5,6,7-tetrahydro-1H-pyrazolo[3,4-c]pyridine-3-carboxamide (1 g, 2 mmol) was added excess 1,3-dichloroacetone (2 g). The reaction was heated to 130° C. for 24 h. The reaction was cooled and purification by chromatography using 0-3% MeOH in CH$_2$Cl$_2$ afforded 0.53 g (42%) white solid; $^1$H NMR (CDCl$_3$) δ 7.75 (s, 1H), 7.53 (d, j=8.8 Hz, 2H), 7.37 (d, j=8.8 Hz, 2H), 7.27 (d, j=8.8 Hz, 2H), 6.93 (d, j=9.1 Hz, 2H), 4.60 (s, 2H), 4.19 (t, j=6.6 Hz, 2H), 3.81 (3H, s), 3.60 (m, 2H), 3.42 (t, j=6.6 Hz, 2H), 2.57 (m, 2H), 1.95 (m, 4H) ppm.

Part B. To the product of Part A (73 mg, 0.13 mmol) was added 10% Palladium on carbon (15 mg) and EtOH (35 mL). The mixture was hydrogenated at 40 psi for 1.5 h and then filtered through Celite®. The solvent was evaporated and the residue purified by HPLC and freeze-dried to afford 40 mg (59%) of a white solid; High Resolution Mass Spec (M+H)$^+$ for C$_{28}$H$_{28}$N$_5$O$_4$ 498.2126.

Example 100

1-(4-Methoxy-phenyl)-3-(4-methyl-oxazol-2-yl)-6-[4-(2-oxo-2H-pyridin-1-yl)-phenyl]-1,4,5,6-tetrahydro-pyrazolo[3,4-c]pyridin-7-one Part A. To 1-(4-methoxyphenyl)-7-oxo-6-[4-(2-oxo-1(2H)-pyridinyl)phenyl]-4,5,6,7-tetrahydro-1H-pyrazolo[3, 4-c]pyridine-3-carboxamide (0.1 g, 0.20 mmol) was added excess 1,3-dichloroacetone (0.5 g). The reaction was heated to 130° C. for 24 h. The reaction was cooled and purification by chromatography using 0-3% MeOH in $CH_2Cl_2$ afforded 0.08 g (69%) of a tan solid.

Part B. To the product of Part A (80 mg, 0.15 mmol) was added 10% Palladium on carbon (20 mg) and EtOH (35 mL). The mixture was hydrogenated at 40 psi for 0.3 h and then filtered through Celite®. The solvent was evaporated and the residue purified by HPLC and freeze-dried to afford 10 mg (13%) of a white solid; High Resolution Mass Spec $(M+H)^+$ for $C_{28}H_{24}N_5O_3$ 494.1829.

Example 101

3-Acetyl-1-(4-methoxy-phenyl)-6-[4-(2-oxo-2H-pyridin-1-yl)-phenyl]-1,4,5,6-tetrahydro-pyrazolo[3,4-c]pyridin-7-one To 3-bromo-1-(4-methoxy-phenyl)-6-[4-(2-oxo-2H-pyridin-1-yl)-phenyl]-1,4,5,6-tetrahydro-pyrazolo[3,4-c]pyridin-7-one (0.11 g, 0.22 mmol) was added THF (25 mL), 1-(ethoxyvinyl)tributyltin (0.078 mL, 0.23 mmol), and LiCl (27 mg, 0.65 mmol) and the mixture was degassed with $N_2$ for 15 min. Tetrakistriphenylphosphine Palladium(0) (12 mg, 0.01 mmol) was added and the reaction was heated to reflux 24 h. The reaction was cooled to rt and treated with 1N HCl for 24 h. After extraction with EtOAc and drying ($MgSO_4$), the product was purified by silica gel (mixed with KF) chromatography using 0-3% MeOH in $CH_2Cl_2$ and by HPLC to afford 6 mg (6%); High Resolution Mass Spec $(M+H)^+$ for $C_{26}H_{23}N_4O_4$ 455.1713.

Example 102

3-(4,5-Dihydro-1H-imidazol-2-yl)-1-(4-methoxy-phenyl)-6-[4-(2-oxo-2H-pyridin-1-yl)-phenyl]-1,4,5,6-tetrahydro-pyrazolo[3,4-c]pyridin-7-one To ethylene diamine (0.4 mL, 6 mmol) in toluene (25 mL) at 0° C. was added 2M trimethylaluminum in heptane (1 mL, 2 mmol) and, after stirring for 20 min, 1-(4-methoxy-phenyl)-7-oxo-6-[4-(2-oxo-2H-pyridin-1-yl)-phenyl]-4,5,6,7-tetrahydro-1H-pyrazolo[3,4-c]pyridine-3-carboxylic acid ethyl ester (0.1 g, 0.2 mmol) was added and the reaction was heated to 60° C. for 24 h. The reaction was quenched with water and MeOH, dried ($Na_2SO_4$), filtered, and concentrated. The residue was suspended in EtOAc and filtered. Purification by HPLC and freeze-drying afforded 15 mg (12%) of a white solid; High Resolution Mass Spec $(M+H)^+$ for $C_{27}H_{25}N_6O_3$ 481.2003.

Example 103

1-(4-Methoxy-phenyl)-3-(1-methyl-4,5-dihydro-1H-imidazol-2-yl)-6-[4-(2-oxo-piperidin-1-yl)-phenyl]-1,4,5,6-tetrahydro-pyrazolo[3,4-c]pyridin-7-one To N-methylethylene diamine (0.47 mL, 5 mmol) in toluene (25 mL) at 0° C. was added 2M trimethylaluminum in heptane (2.7 mL, 5 mmol) and, after stirring for 20 min, 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester (0.88 g, 1.8 mmol) was added and the reaction was heated to 100° C. for 24 h. The reaction was quenched with water and MeOH, dried ($Na_2SO_4$), filtered, and concentrated. The residue was suspended in EtOAc and filtered. Purification by HPLC and freeze-drying afforded 120 mg (11%) of a white solid; Mass Spec $(M+H)^+$ 499.3.

Example 104

1-(4-Methoxy-phenyl)-3-(1-methyl-1H-imidazol-2-yl)-6-[4-(2-oxo-piperidin-1-yl)-phenyl]-1,4,5,6-tetrahydro-pyrazolo[3,4-c]pyridin-7-one To Example 103 (0.085 g, 0.14 mmol) in dioxane (15 mL) was added $KMnO_4$ (48 mg, 0.3 mmol) and the reaction was heated to 100° C. After 2 h excess $KMnO_4$ was added to accelerate the reaction and it was heated 24 h. Filtration and purification by HPLC and freeze-drying afforded 10 mg (11.7%) of a white solid; Mass Spec $(M+H)^+$ 497.3.

Example 105

1-(4-Methoxy-phenyl)-3-methyl-6-[4-(2-oxo-piperidin-1-yl)-phenyl]-1,4,5,6-tetrahydro-pyrazolo[3,4-c]pyridin-7-one To 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester (0.59 g, 1.2 mmol) in THF (25 mL) was added 2M $LiBH_4$ in THF (0.96 mL, 1.9 mmol) and the reaction was heated to reflux for 2.5 h. To the crude alcohol were added $CH_2Cl_2$ (25 mL) and $PBr_3$ (0.14 mL) and the reaction was stirred 24 h. Extraction with $CHCl_3$, washing with water, and drying ($Na_2SO_4$) afforded a crude bromo-compound. The bromo-compound was heated in AcOH (15 mL) and activated Zn (0.39 g, 6 mmol) at 120° C. for 24 h. Purification by HPLC and freeze-drying afforded 30 mg (58%) of a white solid; High Resolution Mass Spec $(M+H)^+$ for $C_{25}H_{27}N_4O_3$ 431.2092.

Example 106

3-Hydroxymethyl-1-(4-methoxy-phenyl)-6-[4-(2-oxo-2H-pyridin-1-yl)-phenyl]-1,4,5,6-tetrahydro-pyrazolo[3,4-c]pyridin-7-one To 1-(4-methoxy-phenyl)-7-oxo-6-[4-(2-oxo-2H-pyridin-1-yl)-phenyl]-4,5,6,7-tetrahydro-1H-pyrazolo[3,4-c]pyridine-3-carboxylic acid ethyl ester (0.2 g, 0.4 mmol) in THF (25 mL) was added 2M $LiBH_4$ in THF (0.31 mL, 0.66 mmol) and the reaction was heated to reflux for 3 h. After extraction into EtOAc and washing with water and brine, the product crystallized out upon standing; High Resolution Mass Spec $(M+H)^+$ for $C_{25}H_{23}N_4O_4$ 443.1730.

Example 107

3-(1-Hydroxy-1-methyl-ethyl)-1-(4-methoxy-phenyl)-6-[4-(2-oxo-piperidin-1-yl)-phenyl]-1,4,5,6-tetrahydropyrazolo[3,4-c]pyridin-7-one To 1-(4-methoxy-phenyl)-7-oxo-6-[4-(2-oxo-piperidin-1-yl)-phenyl]-4,5,6,7-tetrahydro-1H-pyrazolo[3,4-c]pyridine-3-carboxylic acid ethyl ester (0.1 g, 0.2 mmol) in THF (15 mL) at 0° C. was added MeMgBr (0.21 mL, 0.6 mmol) and the reaction was stirred at rt for 24 h. The reaction was quenched with water and purified by HPLC to afford 47 mg (48%) of a white solid; Mass Spec (M+H)+ 475.

Example 108

3-(1-Hydroxy-1-methyl-ethyl)-1-(4-methoxy-phenyl)-6-[4-(2-oxo-2H-pyridin-1-yl)-phenyl]-1,4,5,6-tetrahydro-pyrazolo[3,4-c]pyridin-7-one The title compound was prepared following the procedure employed for Example 107 using the product of Part A of Example 27. ESI MS m/z 471 (M+H).

Example 109

2-Dimethylamino-N-{1-(4-methoxyphenyl)-7-oxo-6-[4-(2-oxopiperidin-1-yl)phenyl]-4,5,6,7-tetrahydro-1H-pyrazolo[3,4-c]pyridin-3-ylmethyl}-N-methylacetamide Hydrochloric Acid Salt Part A. A mixture of 6-(4-iodophenyl)-1-(4-methoxyphenyl)-7-oxo-4,5,6,7-tetrahydro-1H-pyrazolo[3,4-c]pyridine-3-carboxylic acid ethyl ester (5 g, 9.7 mmol), $K_2CO_3$ (1.5 g, 110 mmol), piperidine-2-one (1.2 g, 11.6 mmol), CuI (228 mg, 1.2 mmol), and DMSO (10 mL) was heated at 140° C. for 24 h. The solution was cooled to rt, diluted with EtOAc, washed with brine, dried over $Na_2SO_4$, filtered, and evaporated. Purification of the residue by column chromatography provided the corresponding aryl lactam (1.3 g, 28%): ESI MS m/z 489 (M+H)+.

Part B. To a solution of the ester from above (500 mg, 1.02 mmol) in THF (5 mL), MeOH (3 mL), and $H_2O$ (2 mL) was added LiOH (52 mg, 1.2 mmol) at rt. The reaction mixture was stirred for 1 h, acidified with Dowex-50W-hydrogen ion-exchange resin, filtered, and evaporated to provide the corresponding acid as a white solid (471 mg, 99%) which was used without further purification: ESI MS m/z 461 (M+H)+.

Part C. To a cold (0° C.) solution of the acid (500 mg, 1.09 mmol) from above in THF (10 mL) was added $Et_3N$ (0.17 mL, 1.2 mmol) followed by isobutyl chloroformate (0.16 mL, 1.2 mmol). The reaction mixture was stirred for 1 h then $NaBH_4$ (82 mg, 2.2 mmol) was added. After 30 min, a small piece of ice was added and the reaction mixture was stirred for an additional 2 h. The mixture was diluted with EtOAc, washed with 0.1 N HCl and brine, dried ($Na_2SO_4$), filtered and concentrated. Purification of the residue on silica gel provided the corresponding alcohol as a white solid (317 mg, 71%): ESI MS m/z 447 (M+H)+.

Part D. A solution of the alcohol (317 mg, 0.71 mmol) prepared above in $CH_2Cl_2$ (7 mL) was cooled to 0° C. then 1M $PBr_3$ in $CH_2Cl_2$ (0.78 mL, 0.78 mmol) was added. The cooling bath was removed; the reaction mixture was stirred for 3 h, and then diluted with EtOAc. The organic layer was washed with brine, dried over $Na_2SO_4$, filtered, and concentrated to provide the corresponding bromomethyl compound (369 mg, >99%) which was used without further purification: ESI MS m/z 509, 511 (M+H)+.

Part E. A solution of the bromomethyl compound (489 mg, 0.96 mmol) prepared above and $NaN_3$ (67 mg, 1.1 mmol) in DMF (10 mL) was heated at 60° C. overnight. The reaction mixture was cooled to rt, diluted with EtOAc, washed with 1% aqueous LiCl, dried over $Na_2SO_4$, filtered, and concentrated to provide the corresponding azide (450 mg, 99%) as a white foam: ESI MS m/z 472 (M+H)+.

Part F. The azide (213 mg, 0.45 mmol) made above was dissolved in MeOH (5 mL) then 10% Pd/C (30 mg, 10 mol %) was added and the reaction mixture was exposed to an atmosphere of $H_2$ (balloon). After 3 h, the reaction mixture was filtered through Celite® and concentrated. Purification of the residue on silica gel provided the corresponding aminomethyl compound (151 mg, 75%): ESI MS m/z 446 (M+H)+.

Part G. The aminomethyl prepared above (367 mg, 0.82 mmol) was added to a solution containing N,N-dimethylglycine (127 mg, 1.2 mmol), Hünig's base (0.36 mL, 2.1 mmol), EDCI (237 mg, 1.2 mmol), HOAt (catalytic), and $CH_2Cl_2$ (1.6 mL). The reaction mixture was stirred at rt overnight then diluted with EtOAc. The organic layer was washed with brine, dried over $Na_2SO_4$, filtered, and concentrated. Chromatography of the residue on silica gel followed by treatment with 2 N HCl and lyophilization provided the title compound: ESI MS m/z 531 (M+H)+.

Example 110

2-Dimethylamino-N-{1-(4-methoxyphenyl)-7-oxo-6-[4-(2-oxo-2H-pyridin-1-yl)-phenyl]-4,5,6,7-tetrahydro-1H-pyrazolo[3,4-c]pyridin-3-ylmethyl}acetamide Hydrochloric Acid Salt The title compound was prepared according to the procedures described for Example 109: ESI MS m/z 527 (M+H)+.

Example 111

N-{1-(4-Methoxyphenyl)-7-oxo-6-[4-(2-oxopiperidin-1-yl)phenyl]-4,5,6,7-tetrahydro-1H-pyrazolo[3,4-c]pyridin-3-ylmethyl}-2-pyridin-2-yl-acetamide Hydrochloric Acid Salt The title compound was prepared according to the procedures described for Example 109: ESI MS m/z 565 (M+H)+.

Example 112

N-{1-(4-Methoxyphenyl)-7-oxo-6-[4-(2-oxopiperidin-1-yl)phenyl]-4,5,6,7-tetrahydro-1H-pyrazolo[3,4-c]pyridin-3-ylmethyl}-2-(1-oxo-pyridin-2-yl)acetamide The title compound was prepared according to the procedures described for Example 109: APCI MS m/z 581 (M+H)+.

Example 113

5-Chloro-N-(5-chloropyridin-2-yl)-3-methoxy-2-[4-(2-oxopiperidin-1-yl)-benzoylamino]benzamide Part A. To a mixture of methyl 4-iodobenzoate (10.0 g, 0.038 mol), □-valerolactam (4.53 g, 0.046 mol), PNT (0.76 g, 4.20 mmol), and $K_2CO_3$ (5.80 g, 0.042 mol) in DMSO (20 mL) was added CuI (0.87 g, 4.58 mmol) and the reaction mixture was heated at 110° C. for 24 h. The solution was cooled to rt, diluted with $CH_2Cl_2$, washed with brine, dried over $MgSO_4$, filtered, and evaporated. Purification of the residue by column chromatography (eluting with 98:2 $CH_2Cl_2$/MeOH) provided the corresponding lactam (3.4 g, 38%): $^1$H NMR (300 MHz, $CDCl_3$) δ 8.05 (d, 2H), 7.35 (d, 2H), 3.91 (s, 3H), 3.70 (m, 2H), 2.58 (m, 2H), 1.96 (m, 4H); APCI MS m/z 234 (M+H)+.

Part B. To a solution of the ester made above (1.0 g, 4.29 mmol) in THF (16 mL) and $H_2O$ (4 mL) at 0° C. was added LiOH (198 mg, 4.72 mmol). The reaction mixture was stirred at rt for 14 h and partitioned between EtOAc and 2M HCl solution. The organics were washed with brine, dried over MgSO$_4$, filtered, and evaporated to provide the corresponding acid as a white solid (525 mg, 56%): $^1$H NMR (300 MHz, DMSO-d$_6$) δ 12.95 (s, 1H), 8.07 (d, 2H), 7.57 (d, 2H), 3.81 (m, 2H), 2.57 (m, 2H), 2.00 (m, 4H); ESI MS m/z 220 (M+H)$^+$.

Part C. To a suspension of the acid (0.21 g, 0.96 mmol) made above in CH$_2$Cl$_2$ (5 mL) was added SOCl$_2$ (0.21 mL, 2.89 mmol) and the reaction mixture was stirred at rt for 3 h. The reaction mixture was concentrated to give the crude acid chloride as a white solid. The crude acid chloride was used directly in the next step.

Part D. To a solution of 2-amino-5-chloro-N-(5-chloropyridin-2-yl)-3-methoxy-benzamide (150 mg, 0.48 mmol), DMAP (24 mg, 0.19 mmol), and pyridine (95 mg, 1.21 mmol) in CH$_2$Cl$_2$ (5 mL) was added a solution of the crude acid chloride made above in CH$_2$Cl$_2$ (5 mL) and the reaction mixture was stirred at rt for 20 h. The reaction mixture was diluted with CH$_2$Cl$_2$; washed with water, 0.25 M NaOH solution, and brine; dried over MgSO$_4$; filtered; and concentrated. Purification of the residue by column chromatography provided the title compound as a white solid (99 mg, 40%): $^1$H NMR (300 MHz, DMSO-d$_6$) δ 10.78 (s, 1H), 9.73 (s, 1H), 8.36 (d, 1H), 7.99 (d, 1H), 7.87 (m, 3H), 7.33 (m, 3H), 7.27 (d, 1H), 3.85 (s, 3H), 3.64 (m, 2H), 2.41 (m, 2H), 1.86 (m, 4H); ESI MS m/z 513 (M+H)$^+$.

Example 114

5-Chloro-N-(5-chloropyridin-2-yl)-3-methoxy-2-[4-(2-oxo-2H-pyridin-1-yl)-benzoylamino]benzamide The title compound was prepared according to the procedures described for Example 113: $^1$H NMR (300 MHz, DMSO-d$_6$) δ 10.83 (s, 1H), 9.89 (s, 1H), 8.37 (d, 1H), 8.09 (d, 1H), 8.00 (d, 2H), 7.88 (dd, 1H), 7.67 (dd, 1H), 7.52 (m, 3H), 7.39 (d, 1H), 7.29 (d, 1H), 6.50 (d, 1H), 6.35 (dt, 1H), 3.89 (s, 3H); ESI MS m/z 509 (M+H)$^+$.

Example 115

6-[4-(1,1-Dioxo-1,6-isothiazolidin-2-yl)-phenyl]-1-(4-methoxy-phenyl)-7-oxo-4,5,6,7-tetrahydro-1H-pyrazolo[3,4-c]pyridine-3-carboxylic Acid Amide Part A. To 6-(4-amino-phenyl)-1-(4-methoxy-phenyl)-7-oxo-4,5,6,7-tetrahydro-1H-pyrazolo[3,4-c]pyridine-3-carboxylic acid ethyl ester (0.35 g, 0.86 mmol) and 3-chloropropanesulfonyl chloride (0.125 mL, 1 mmol) in THF (20 mL) was added triethylamine (0.144 mL, 1 mmol) and the reaction was stirred 24 h. Potassium tert-butoxide (0.31 g, 2.5 mmol) was added and the reaction was stirred 24 h. The ester was purified by chromatography using 1-5% MeOH in CH$_2$Cl$_2$.

Part B. The ester from Part A was placed in a sealed tube containing 10% NH$_3$ in ethylene glycol and heated to 80° C. for 3 h. The reaction was cooled, quenched with water, and extracted with EtOAc. Purification by HPLC and freeze-drying afforded 19 mg (4.6%) of a white solid; High Resolution Mass Spec (M+H)$^+$ for C$_{23}$H$_{24}$N$_5$O$_5$S 482.1493.

Example 116

N-Hydroxy-3-{7-oxo-6-[4-(2-oxo-2H-pyridin-1-yl)-phenyl]-3-trifluoromethyl-4,5,6,7-tetrahydro-pyrazolo[3,4-c]pyridin-1-yl}-benzamidine Part A. To a solution of 3-[6-(4-iodo-phenyl)-7-oxo-3-trifluoromethyl-4,5,6,7-tetrahydro-pyrazolo[3,4-c]pyridin-1-yl]-benzonitrile (0.403 g, 0.793 mmol) was added 2-hydroxypyridine (0.226 g, 2.38 mmol), potassium carbonate (0.328 g, 2.38 mmol) and 3 mg CuI. The reaction mixture was refluxed for 18 h, cooled and quenched with HCl (1N). The organics were extracted with ethylacetate (2×100 mL), dried (MgSO$_4$), and concentrated to afford the desired crude product. ESI mass spectrum 476 (M+H).

Part B. The crude product from part A (0.18 g, 0.37 mmol) in anhydrous methyl alcohol (10 mL) was treated with hydroxylamine hydrochloride (0.04 g, 0.57 mmol) and excess triethylamine (0.5 mL). The reaction mixture was stirred at rt for 48 h, concentrated, and purified via reverse phase HPLC to provide 78 mg (40%) of the title compound. ESI mass spectrum 509 (M+H).

Example 117

N-Methoxy-3-{7-oxo-6-[4-(2-oxo-2H-pyridin-1-yl)-phenyl]-3-trifluoromethyl-4,5,6,7-tetrahydro-pyrazolo[3,4-c]pyridin-1-yl}-benzamidine The product from part A in Example 116 (0.2 g) was dissolved in methyl alcohol (10 mL). HCl gas was bubbled for 5 min and capped. The reaction mixture was stirred at rt for 24 h, concentrated, and evaporated to a semi-solid mass. The crude was redissolved in methyl alcohol (10 mL) and this mixture was added 0.5 g of O-methoxyhydroxylamine hydrochloride and 1 mL of triethylamine. The reaction mixture was stirred at rt for 24 h and concentrated and purified via HPLC. Colorless crystals of the title compound were obtained. ESI mass spectrum 523 (M+H).

Example 118

1-(3-cyano-4-fluorophenyl)-7-oxo-6-[4-(2-oxo-1-piperidinyl)phenyl]-4,5,6,7-tetrahydro-1H-pyrazolo[3,4-c]pyridine-3-carboxamide The condensation of 3-chloro-4-fluoro-phenylhydrazine with 1-(4-iodo-phenyl)-3-morpholin-4-yl-5,6-dihydro-1H-pyridin-2-one afforded 1-(3-chloro-4-fluoro-phenyl)-6-(4-iodo-phenyl)-3-trifluoromethyl-1,4,5,6-tetrahydro-pyrazolo[3,4-c]pyridin-7-one. This was then treated under Ullmann conditions with 2-hydroxypyridine to afford 1-(3-chloro-4-fluoro-phenyl)-6-[4-(2-oxo-2H-pyridin-1-yl)-phenyl]-3-trifluoromethyl-1,4,5,6-tetrahydro-pyrazolo[3,4-c]pyridin-7-one. ESI mass spectrum 482 (M+H). The conversion of chlorine to a cyano group was accomplished via palladium catalyzed cyanation methodology employing zinc cyanide. MS (AP$^+$): 473.2 (M+H).

Example 119

1-(3-Aminomethyl-4-fluoro-phenyl)-7-oxo-6-[4-(2-oxo-piperidin-1-yl)-phenyl]-4,5,6,7-tetrahydro-1H-pyrazolo[3,4-c]pyridine-3-carboxylic Acid Amide The cyano group of Example 118 was reduced to benzylamine through hydrogenation (Parr shaker, MeOH, Pd/C 10%, AcOH) and purified via HPLC. ESI mass spectrum 477 (M+H).

Example 120

2-{7-Oxo-6-[4-(2-oxo-piperidin-1-yl)-phenyl]-3-trifluoromethyl-4,5,6,7-tetrahydro-pyrazolo[3,4-c]pyridin-1-yl}-benzenesulfonamide The title compound was synthesized in a similar fashion as Example 6, except that 2-sulfonamidophenyl-hydrazine was used in place of 4-methoxyhydrazine hydrochloride. MS (AP$^+$): 534.1 (M+H).

Example 121

2-{7-Oxo-6-[4-(2-oxo-2H-pyridin-1-yl)-phenyl]-3-trifluoromethyl-4,5,6,7-tetrahydro-pyrazolo[3,4-c]pyridin-1-yl}-benzenesulfonamide The title compound was synthesized in a similar fashion as Example 6, except that 2-sulfonamidophenyl-hydrazine was used in place of 4-methoxyhydrazine hydrochloride. MS (AP$^+$): 530.1 (M+H).

Example 122

N-Acetyl-2-{7-oxo-6-[4-(2-oxo-2H-pyridin-1-yl)-phenyl]-3-trifluoromethyl-4,5,6,7-tetrahydro-pyrazolo[3,4-c]pyridin-1-yl}-benzenesulfonamide The sulfonamide of Example 121 was acetylated with acetic anhydride to afford the title compound. MS (ES$^+$): 572.1 (M+H).

Example 123

1-(3-Chloro-phenyl)-3-methanesulfonyl-6-[4-(2-oxo-2H-pyridin-1-yl)-phenyl]-1,4,5,6-tetrahydro-pyrazolo[3,4-c]pyridin-7-one The title compound was synthesized in the same fashion as described for Example 86, parts A and B, by substituting 2-pyridone for δ-valerolactam. $^1$H NMR (CDCl$_3$) δ 7.61 (t, 1H, J=2 Hz), 7.51-7.28 (m, 9H), 6.66 (d, 1H, J=9 Hz), 6.26 (td, 1H, J=7, 1 Hz), 4.21 (t, 2H, J=7 Hz), 3.38 (t, 2H, J=7 Hz), 3.33 (s, 3H). LC/MS (ES$^+$): 494.9/496.9 (Cl pattern) (>95% by ELSD).

Example 124

1-(4-Methoxy-phenyl)-3-methyl-6-[4-(2-oxo-2H-pyridin-1-yl)-phenyl]-1,4,5,6-tetrahydro-pyrazolo[3,4-c]pyridin-7-one To 3-hydroxymethyl-1-(4-methoxy-phenyl)-6-[4-(2-oxo-2H-pyridin-1-yl)-phenyl]-1,4,5,6-tetrahydro-pyrazolo[3,4-c]pyridin-7-one (65 mg, 0.15 mmol) in CH$_2$Cl$_2$ (10 mL) was added triethylsilane (0.1 mL) and TFA (0.05 mL). After 2 h more triethylsilane (0.2 mL) and TFA (0.1 mL) were added and the reaction was stirred for 72 h. The reaction was not proceeding so the solvents were stripped and replaced with acetic acid (10 mL), triethylsilane (0.5 mL), and TFA (0.1 mL). The reaction was heated 24 h at 80° C. Mass spectra indicated only the acetyl product formed. The solvents were removed. The acetyl group was removed by stirring with LiOH (0.1 g) in THF/H$_2$O for 3 h. The reaction was quenched with 1N HCl, extracted with EtOAc, and dried (MgSO$_4$) to recover the alcohol. To the alcohol in CHCl$_3$ was added PBr$_3$ and the reaction was stirred 24 h. The reaction was quenched with ice water, extracted with CHCl$_3$, and dried (Na$_2$SO$_4$). To the crude bromide were added activated Zn (80 mg) and acetic acid (10 mL) and heated to 120° C. for 24 h. The product was purified by silica gel chromatography using 0-3% MeOH in CH$_2$Cl$_2$ and recrystallized from CH$_3$CN/H$_2$O to afford 22 mg (35%); Mass Spec (M+H)$^+$ 427.3.

Example 125

3-(4-Methoxy-phenyl)-5-[4-(2-oxo-2H-pyridin-1-yl)-phenyl]-3,5,6,7-tetrahydro-[1,2,3]triazolo[4,5-c]pyridin-4-one Part A. Para-anisidine (7 g) was dissolved in TFA (10 mL) and the solution cooled to 0° C. To this ice cold solution was added dropwise an aqueous solution containing sodium nitrite (4.8 g). After 30 min was added an aqueous solution containing sodium azide (4.43 g). The reaction became exothermic and was stirred for an additional 2 h, quenched with water (1 L), and the organics extracted with methylene chloride (2×100 mL) and dried (magnesium sulfate). Concentration afforded the desired azide that was immediately redissolved in toluene (100 mL). To this solution was added 1-(4-iodo-phenyl)-3-morpholin-4-yl-5,6-dihydro-1H-pyridin-2-one (21.85 g) and the solution was gently refluxed for 48 h. Toluene was concentrated and the crude was poured directly onto a silica gel column and eluted with hexane:ethyl acetate 7:3 to afford approx 1.2 g 5-(4-iodo-phenyl)-3-(4-methoxy-phenyl)-3,5,6,7-tetrahydro-[1,2,3]triazolo[4,5-c]pyridin-4-one. ESI mass spectrum m/z 447 (M+H).

Part B. The compound obtained from part A (0.41 g) was treated with 2-hydroxypyridine under the Ullmann conditions as previously described to obtain the title compound (50 mg). ESI mass spectrum m/z 414 (M+H).

Example 126

3-(4-Methoxy-phenyl)-5-[4-(2-oxo-piperidin-1-yl)-phenyl]-3,5,6,7-tetrahydro-[1,2,3]triazolo[4,5-c]pyridin-4-one The Ullmann coupling methodology using the δ-valerolactam previously described to afforded the title compound after purification via silica chromatography. ESI mass spectrum m/z 418 (M+H).

Example 127

3-(3-Chloro-phenyl)-5-[4-(2-oxo-piperidin-1-yl)-phenyl]-3,5,6,7-tetrahydro-[1,2,3]triazolo[4,5-c]pyridin-4-one In an identical procedure described for the para-methoxy-triazolo analogs the m-chlorophenyl title compound was prepared. ESI mass spectrum m/z 422 (M+H).

Example 128

3-(3-Chloro-phenyl)-5-[4-(2-oxo-2H-pyridin-1-yl)-phenyl]-3,5,6,7-tetrahydro-[1,2,3]triazolo[4,5-c]pyridin-4-one In an identical procedure described for the para-methoxy-triazolo analogs the m-chlorophenyl title compound was prepared. ESI mass spectrum m/z 418 (M+H).

Example 129

1-(3-Chloro-phenyl)-3-(1-hydroxy-1-methyl-ethyl)-6-[4-(2-oxo-2H-pyridin-1-yl)-phenyl]-1,4,5,6-tetrahydropyrazolo[3,4-c]pyridin-7-one 1-(3-Chloro-phenyl)-7-oxo-6-[4-(2-oxo-2H-pyridin-1-yl)-phenyl]-4,5,6,7-tetrahydro-1H-pyrazolo[3,4-c]pyridine-3-carboxylic acid ethyl ester (0.098 g, 0.216 mmol) was dissolved into THF (10 mL). Methylmagnesium bromide (0.179 mL, 0.539 mmol) was added dropwise to the reaction. The reaction was stirred at rt overnight. The reaction was quenched with 1N HCl (100 mL) and extracted into ethyl acetate (4×50 mL), washed with brine (1×50 mL), and dried (MgSO$_4$). Purification by silica gel chromatography using 0%-100% ethyl acetate/hexane gradient followed by a 0%-100% methanol/ethyl acetate gradient as the eluents afforded 54.6 mg (53%) of the title product: $^1$H NMR (CDCl$_3$) δ 7.59 (s, 1H), 7.48-7.37 (m, 7H), 7.33-7.28 (m, 2H), 6.66 (d, j=9.2 Hz, 1H), 6.25 (dt, j=1.1 Hz, 6.6 Hz, 1H), 4.16 (t, j=6.6 Hz, 2H), 3.19 (t, j=6.6 Hz, 2H), 1.68 (s, 6H) ppm; ESI Mass Spec 475.3 (M+H)$^+$.

Example 130

1-(3-Chloro-phenyl)-3-(1-hydroxy-1-methyl-ethyl)-6-[4-(2-oxo-piperidin-1-yl)-phenyl]-1,4,5,6-tetrahydro-pyrazolo[3,4-c]pyridin-7-one The meta-chloro-lactam-ethyl ester (0.036 g, 0.078 mmol) was dissolved into THF (6 mL). Methylmagnesium bromide (0.07 mL, 0.196 mmol) was added dropwise to the reaction. The reaction was stirred at rt overnight. The reaction was quenched with 1N HCl (50 mL) and extracted into ethyl acetate (4×25 mL), washed with brine (1×25 mL), and dried (MgSO$_4$). Purification by silica gel chromatography using 0%-100% ethyl acetate/hexane gradient followed by a 0%-100% methanol/ethyl acetate gradient as the eluents afforded 15.7 mg (42%): $^1$H NMR (CDCl$_3$) δ 7.59 (s, 1H), 7.47-7.43 (m, 1H), 7.36-7.24 (m, 6H), 4.12 (t, j=6.6 Hz, 2H), 3.65-3.55 (m, 2H), 3.16 (t, j=6.6 Hz, 2H), 2.60-2.49 (m, 2H), 1.96-1.93 (m, 4H), 1.67 (s, 6H) ppm; Mass Spec (M+H)$^+$ 479.3.

Example 131

3-{7-Oxo-6-[4-(2-oxo-2H-pyridin-1-yl)-phenyl]-3-trifluoromethyl-4,5,6,7-tetrahydro-pyrazolo[3,4-c]pyridin-1-yl}-benzamide The product from Example 116, part A (0.05 g) was dissolved in dichloromethane (10 mL). To this was added sodium hydroxide (1N, 5 mL), hydrogen peroxide (3 mL), and tetrabutylammonium-hydroxide (0.01 g). The reaction mixture was stirred at rt for 24 h and concentrated, quenched with water (50 mL) and the organics extracted with ethylacetate (2×50 mL), dried (MgSO$_4$) and concentrated. The crude was purified via prep HPLC to a colorless solid. ESI mass spectrum 494 (M+H) and 492 (M−H).

Example 132

3-chloro-N-(1,2-cis-2-{[4-(2-oxopyridin-1(2H)-yl)benzoyl]amino}cyclohexyl)-1H-indole-6-carboxamide Step A. 4-(2-Oxo-2H-pyridin-1-yl)benzoyl chloride (0.44 g, 2.05 mmol) was stirred in CH$_2$Cl$_2$ (10 mL) at RT under N$_2$. Cis-1,2-diaminocyclohexane (0.5 mL, 4.17 mmol) was quickly added as one portion to the stirring solution. The mixture was stirred at rt for 10 min. It was quenched with diluted aqueous HCl, and then extracted with EtOAc (2×). The water layer was basified with 1N NaOH, and then extracted with EtOAc (2×). The organic layer was washed with H$_2$O, brine, dried over MgSO$_4$, and concentrated to dryness. FCC (silica gel, CH$_2$Cl$_2$, then EtOAc) gave pure N-cis-1,2-(2-amino-cyclohexyl)-4-(2-oxo-2H-pyridin-1-yl) benzamide (0.54 g, yield: 84%).

Step B. To a solution of the product from step A (50 mg, 0.16 mmol) in DMF (0.5 mL) was added 3-chloro-1H-indole-6-carboxylic acid (47 mg, 0.24 mmol) followed by the addition of HATU (80 mg, 0.21 mmol) and DIEA (0.08 mL, 0.46 mmol). The mixture was stirred at rt overnight. The residue was diluted with MeOH and purified by LC/MS to give the desired 3-chloro-N-(1,2-cis-2-{[4-(2-oxopyridin-1(2H)-yl)benzoyl]amino}cyclohexyl)-1H-indole-6-carboxamide (14 mg, yield: 18%). LC/MS-ESI, 489.4 (M+H).

Example 133

5-chloro-N-(1,2-cis-2-{[4-(2-oxopyridin-1(2H)-yl)benzoyl]amino}cyclohexyl)-1H-indole-2-carboxamide Following a procedure analogous to that described in Example 132, the title compound was obtained. LC/MS ESI (M+H)$^+$ 489.6.

Example 134

5-chloro-N-(1,2-cis-2-{[4-(2-oxopyridin-1(2H)-yl)benzoyl]amino}cyclohexyl)thiophene-2-carboxamide Following a procedure analogous to that described in Example 132, the title compound was obtained. LC/MS ESI (M+H)$^+$ 456.6.

Example 135

5-chloro-N-(1,2-cis-2-{[4-(2-oxopyrazin-1(2H)-yl)benzoyl]amino}cyclohexyl)thiophene-2-carboxamide Following a procedure analogous to that described in Example 132, the title compound was obtained. LC/MS ESI (M+H)$^+$ 457.4.

Example 136

5-chloro-N-(1,2-cis-2-{[4-(2-oxopyrazin-1(2H)-yl)benzoyl]amino}cyclohexyl)-1H-indole-2-carboxamide Following a procedure analogous to that described in Example 132, the title compound was obtained. LC/MS ESI (M+H)$^+$ 490.4.

Example 137

3-chloro-N-(1,2-cis-2-{[4-(2-oxopyrazin-1(2H)-yl)benzoyl]amino}cyclohexyl)-1H-indole-6-carboxamide Following a procedure analogous to that described in Example 132, the title compound was obtained. LC/MS ESI (M+H)+ 490.4.

Example 138

5-chloro-N-(1,2-cis-2-{[4-(2-oxopiperidin-1-yl)benzoyl]amino}cyclohexyl)thiophene-2-carboxamide Following a procedure analogous to that described in Example 132, the title compound was obtained. LC/MS ESI (M+H)+ 457.4.

Example 139

5-chloro-N-(1,2-cis-2-{[4-(2-oxopiperidin-1-yl)benzoyl]amino}cyclohexyl)-1H-indole-2-carboxamide Following a procedure analogous to that described in Example 132, the title compound was obtained. LC/MS ESI (M+H)+ 493.4.

Example 140

3-chloro-N-(1,2-cis-2-{[4-(2-oxopiperidin-1-yl)benzoyl]amino}cyclohexyl)-1H-indole-6-carboxamide Following a procedure analogous to that described in Example 132, the title compound was obtained. LC/MS ESI (M+H)+ 493.4.

The following tables contain representative examples of the present invention. Each entry in each table is paired with each formula at the start of the table. For example, in Table 1, example 1-1 is paired with each of the formulae shown. The following nomenclature is intended for group A in the following tables.

phenyl 2-pyridyl 3-pyridyl 2-pyrimidyl

2-Cl-phenyl

2-F-phenyl

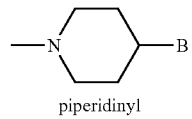

piperidinyl

TABLE 1

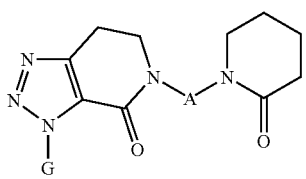

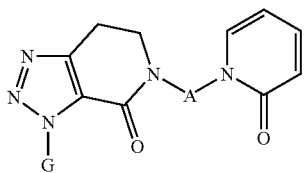

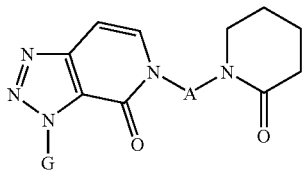

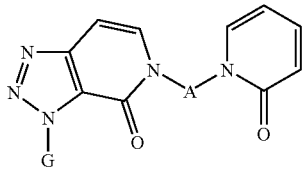

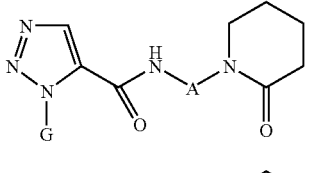

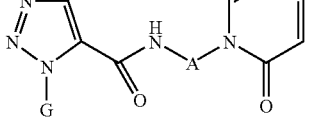

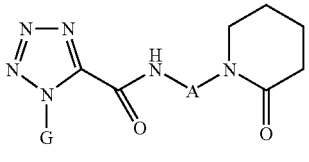

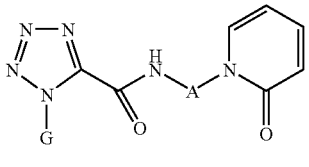

TABLE 1-continued

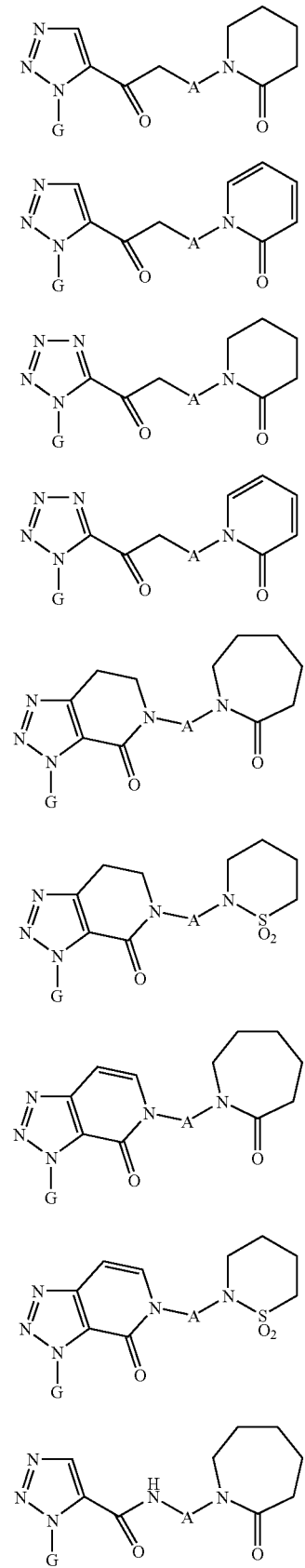

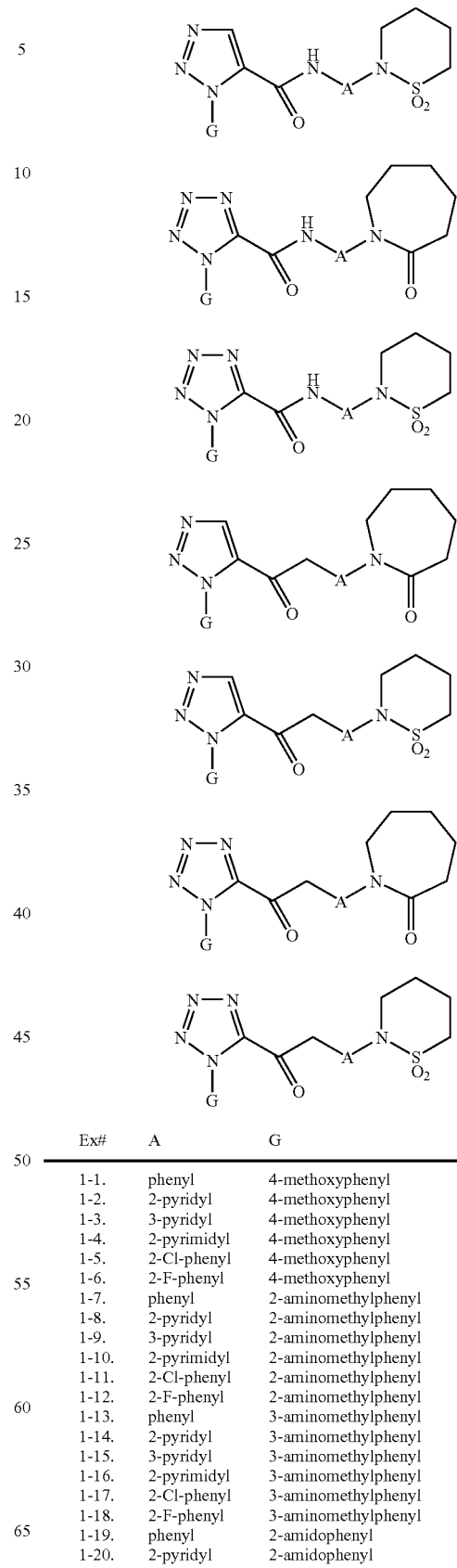

| Ex# | A | G |
|---|---|---|
| 1-1. | phenyl | 4-methoxyphenyl |
| 1-2. | 2-pyridyl | 4-methoxyphenyl |
| 1-3. | 3-pyridyl | 4-methoxyphenyl |
| 1-4. | 2-pyrimidyl | 4-methoxyphenyl |
| 1-5. | 2-Cl-phenyl | 4-methoxyphenyl |
| 1-6. | 2-F-phenyl | 4-methoxyphenyl |
| 1-7. | phenyl | 2-aminomethylphenyl |
| 1-8. | 2-pyridyl | 2-aminomethylphenyl |
| 1-9. | 3-pyridyl | 2-aminomethylphenyl |
| 1-10. | 2-pyrimidyl | 2-aminomethylphenyl |
| 1-11. | 2-Cl-phenyl | 2-aminomethylphenyl |
| 1-12. | 2-F-phenyl | 2-aminomethylphenyl |
| 1-13. | phenyl | 3-aminomethylphenyl |
| 1-14. | 2-pyridyl | 3-aminomethylphenyl |
| 1-15. | 3-pyridyl | 3-aminomethylphenyl |
| 1-16. | 2-pyrimidyl | 3-aminomethylphenyl |
| 1-17. | 2-Cl-phenyl | 3-aminomethylphenyl |
| 1-18. | 2-F-phenyl | 3-aminomethylphenyl |
| 1-19. | phenyl | 2-amidophenyl |
| 1-20. | 2-pyridyl | 2-amidophenyl |

TABLE 1-continued

| | | |
|---|---|---|
| 1-21. | 3-pyridyl | 2-amidophenyl |
| 1-22. | 2-pyrimidyl | 2-amidophenyl |
| 1-23. | 2-Cl-phenyl | 2-amidophenyl |
| 1-24. | 2-F-phenyl | 2-amidophenyl |
| 1-25. | phenyl | 2-amido-4-methoxy-phenyl |
| 1-26. | 2-pyridyl | 2-amido-4-methoxy-phenyl |
| 1-27. | 3-pyridyl | 2-amido-4-methoxy-phenyl |
| 1-28. | 2-pyrimidyl | 2-amido-4-methoxy-phenyl |
| 1-29. | 2-Cl-phenyl | 2-amido-4-methoxy-phenyl |
| 1-30. | 2-F-phenyl | 2-amido-4-methoxy-phenyl |
| 1-31. | phenyl | 3-amidophenyl |
| 1-32. | 2-pyridyl | 3-amidophenyl |
| 1-33. | 3-pyridyl | 3-amidophenyl |
| 1-34. | 2-pyrimidyl | 3-amidophenyl |
| 1-35. | 2-Cl-phenyl | 3-amidophenyl |
| 1-36. | 2-F-phenyl | 3-amidophenyl |
| 1-37. | phenyl | 3-chlorophenyl |
| 1-38. | 2-pyridyl | 3-chlorophenyl |
| 1-39. | 3-pyridyl | 3-chlorophenyl |
| 1-40. | 2-pyrimidyl | 3-chlorophenyl |
| 1-41. | 2-Cl-phenyl | 3-chlorophenyl |
| 1-42. | 2-F-phenyl | 3-chlorophenyl |
| 1-43. | phenyl | 3-amino-4-chloro-phenyl |
| 1-44. | 2-pyridyl | 3-amino-4-chloro-phenyl |
| 1-45. | 3-pyridyl | 3-amino-4-chloro-phenyl |
| 1-46. | 2-pyrimidyl | 3-amino-4-chloro-phenyl |
| 1-47. | 2-Cl-phenyl | 3-amino-4-chloro-phenyl |
| 1-48. | 2-F-phenyl | 3-amino-4-chloro-phenyl |
| 1-49. | phenyl | 2-aminosulfonyl-phenyl |
| 1-50. | 2-pyridyl | 2-aminosulfonyl-phenyl |
| 1-51. | 3-pyridyl | 2-aminosulfonyl-phenyl |
| 1-52. | 2-pyrimidyl | 2-aminosulfonyl-phenyl |
| 1-53. | 2-Cl-phenyl | 2-aminosulfonyl-phenyl |
| 1-54. | 2-F-phenyl | 2-aminosulfonyl-phenyl |
| 1-55. | phenyl | 2-aminosulfonyl-4-methoxyphenyl |
| 1-56. | 2-pyridyl | 2-aminosulfonyl-4-methoxyphenyl |
| 1-57. | 3-pyridyl | 2-aminosulfonyl-4-methoxyphenyl |
| 1-58. | 2-pyrimidyl | 2-aminosulfonyl-4-methoxyphenyl |
| 1-59. | 2-Cl-phenyl | 2-aminosulfonyl-4-methoxyphenyl |
| 1-60. | 2-F-phenyl | 2-aminosulfonyl-4-methoxyphenyl |
| 1-61. | phenyl | 3-(1',2',4'-triazolin-5'-on-3'-yl)phenyl |
| 1-62. | 2-pyridyl | 3-(1',2',4'-triazolin-5'-on-3'-yl)phenyl |
| 1-63. | 3-pyridyl | 3-(1',2',4'-triazolin-5'-on-3'-yl)phenyl |
| 1-64. | 2-pyrimidyl | 3-(1',2',4'-triazolin-5'-on-3'-yl)phenyl |
| 1-65. | 2-Cl-phenyl | 3-(1',2',4'-triazolin-5'-on-3'-yl)phenyl |
| 1-66. | 2-F-phenyl | 3-(1',2',4'-triazolin-5'-on-3'-yl)phenyl |
| 1-67. | phenyl | 1-aminoisoquinolin-6-yl |
| 1-68. | 2-pyridyl | 1-aminoisoquinolin-6-yl |
| 1-69. | 3-pyridyl | 1-aminoisoquinolin-6-yl |
| 1-70. | 2-pyrimidyl | 1-aminoisoquinolin-6-yl |
| 1-71. | 2-Cl-phenyl | 1-aminoisoquinolin-6-yl |
| 1-72. | 2-F-phenyl | 1-aminoisoquinolin-6-yl |
| 1-73. | phenyl | 1-aminoisoquinolin-7-yl |
| 1-74. | 2-pyridyl | 1-aminoisoquinolin-7-yl |
| 1-75. | 3-pyridyl | 1-aminoisoquinolin-7-yl |
| 1-76. | 2-pyrimidyl | 1-aminoisoquinolin-7-yl |
| 1-77. | 2-Cl-phenyl | 1-aminoisoquinolin-7-yl |
| 1-78. | 2-F-phenyl | 1-aminoisoquinolin-7-yl |
| 1-79. | phenyl | 4-aminoquinazol-6-yl |
| 1-80. | 2-pyridyl | 4-aminoquinazol-6-yl |
| 1-81. | 3-pyridyl | 4-aminoquinazol-6-yl |
| 1-82. | 2-pyrimidyl | 4-aminoquinazol-6-yl |
| 1-83. | 2-Cl-phenyl | 4-aminoquinazol-6-yl |
| 1-84. | 2-F-phenyl | 4-aminoquinazol-6-yl |
| 1-85. | phenyl | 4-aminoquinazol-7-yl |
| 1-86. | 2-pyridyl | 4-aminoquinazol-7-yl |
| 1-87. | 3-pyridyl | 4-aminoquinazol-7-yl |
| 1-88. | 2-pyrimidyl | 4-aminoquinazol-7-yl |
| 1-89. | 2-Cl-phenyl | 4-aminoquinazol-7-yl |
| 1-90. | 2-F-phenyl | 4-aminoquinazol-7-yl |
| 1-91. | phenyl | 3-aminobenzisoxazol-5-yl |
| 1-92. | 2-pyridyl | 3-aminobenzisoxazol-5-yl |
| 1-93. | 3-pyridyl | 3-aminobenzisoxazol-5-yl |
| 1-94. | 2-pyrimidyl | 3-aminobenzisoxazol-5-yl |
| 1-95. | 2-Cl-phenyl | 3-aminobenzisoxazol-5-yl |
| 1-96. | 2-F-phenyl | 3-aminobenzisoxazol-5-yl |
| 1-97. | phenyl | 3-aminobenzisoxazol-6-yl |
| 1-98. | 2-pyridyl | 3-aminobenzisoxazol-6-yl |
| 1-99. | 3-pyridyl | 3-aminobenzisoxazol-6-yl |
| 1-100. | 2-pyrimidyl | 3-aminobenzisoxazol-6-yl |
| 1-101. | 2-Cl-phenyl | 3-aminobenzisoxazol-6-yl |
| 1-102. | 2-F-phenyl | 3-aminobenzisoxazol-6-yl |
| 1-103. | phenyl | 3-aminoindazol-5-yl |
| 1-104. | 2-pyridyl | 3-aminoindazol-5-yl |
| 1-105. | 3-pyridyl | 3-aminoindazol-5-yl |
| 1-106. | 2-pyrimidyl | 3-aminoindazol-5-yl |
| 1-107. | 2-Cl-phenyl | 3-aminoindazol-5-yl |
| 1-108. | 2-F-phenyl | 3-aminoindazol-5-yl |
| 1-109. | phenyl | 3-aminoindazol-6-yl |
| 1-110. | 2-pyridyl | 3-aminoindazol-6-yl |
| 1-111. | 3-pyridyl | 3-aminoindazol-6-yl |
| 1-112. | 2-pyrimidyl | 3-aminoindazol-6-yl |
| 1-113. | 2-Cl-phenyl | 3-aminoindazol-6-yl |
| 1-114. | 2-F-phenyl | 3-aminoindazol-6-yl |
| 1-115. | phenyl | indolin-5-yl |
| 1-116. | 2-pyridyl | indolin-5-yl |
| 1-117. | 3-pyridyl | indolin-5-yl |
| 1-118. | 2-pyrimidyl | indolin-5-yl |
| 1-119. | 2-Cl-phenyl | indolin-5-yl |
| 1-120. | 2-F-phenyl | indolin-5-yl |
| 1-121. | phenyl | indolin-6-yl |
| 1-122. | 2-pyridyl | indolin-6-yl |
| 1-123. | 3-pyridyl | indolin-6-yl |
| 1-124. | 2-pyrimidyl | indolin-6-yl |
| 1-125. | 2-Cl-phenyl | indolin-6-yl |
| 1-126. | 2-F-phenyl | indolin-6-yl |
| 1-127. | phenyl | 2-naphthyl |
| 1-128. | 2-pyridyl | 2-naphthyl |
| 1-129. | 3-pyridyl | 2-naphthyl |
| 1-130. | 2-pyrimidyl | 2-naphthyl |
| 1-131. | 2-Cl-phenyl | 2-naphthyl |
| 1-132. | 2-F-phenyl | 2-naphthyl |
| 1-133. | phenyl | 3-amido-naphth-2-yl |
| 1-134. | 2-pyridyl | 3-amido-naphth-2-yl |
| 1-135. | 3-pyridyl | 3-amido-naphth-2-yl |
| 1-136. | 2-pyrimidyl | 3-amido-naphth-2-yl |
| 1-137. | 2-Cl-phenyl | 3-amido-naphth-2-yl |
| 1-138. | 2-F-phenyl | 3-amido-naphth-2-yl |
| 1-139. | phenyl | 3-methylsulfonyl-naphth-2-yl |
| 1-140. | 2-pyridyl | 3-methylsulfonyl-naphth-2-yl |
| 1-141. | 3-pyridyl | 3-methylsulfonyl-naphth-2-yl |
| 1-142. | 2-pyrimidyl | 3-methylsulfonyl-naphth-2-yl |
| 1-143. | 2-Cl-phenyl | 3-methylsulfonyl-naphth-2-yl |
| 1-144. | 2-F-phenyl | 3-methylsulfonyl-naphth-2-yl |
| 1-145. | phenyl | 3-aminomethyl-naphth-2-yl |
| 1-146. | 2-pyridyl | 3-aminomethyl-naphth-2-yl |
| 1-147. | 3-pyridyl | 3-aminomethyl-naphth-2-yl |
| 1-148. | 2-pyrimidyl | 3-aminomethyl-naphth-2-yl |
| 1-149. | 2-Cl-phenyl | 3-aminomethyl-naphth-2-yl |
| 1-150. | 2-F-phenyl | 3-aminomethyl-naphth-2-yl |
| 1-151. | phenyl | 3-fluoro-naphth-2-yl |
| 1-152. | 2-pyridyl | 3-fluoro-naphth-2-yl |
| 1-153. | 3-pyridyl | 3-fluoro-naphth-2-yl |
| 1-154. | 2-pyrimidyl | 3-fluoro-naphth-2-yl |
| 1-155. | 2-Cl-phenyl | 3-fluoro-naphth-2-yl |
| 1-156. | 2-F-phenyl | 3-fluoro-naphth-2-yl |
| 1-157. | phenyl | 3-cyano-naphth-2-yl |
| 1-158. | 2-pyridyl | 3-cyano-naphth-2-yl |
| 1-159. | 3-pyridyl | 3-cyano-naphth-2-yl |
| 1-160. | 2-pyrimidyl | 3-cyano-naphth-2-yl |
| 1-161. | 2-Cl-phenyl | 3-cyano-naphth-2-yl |
| 1-162. | 2-F-phenyl | 3-cyano-naphth-2-yl |
| 1-163. | phenyl | 3-aminosulfonyl-naphth-2-yl |
| 1-164. | 2-pyridyl | 3-aminosulfonyl-naphth-2-yl |
| 1-165. | 3-pyridyl | 3-aminosulfonyl-naphth-2-yl |
| 1-166. | 2-pyrimidyl | 3-aminosulfonyl-naphth-2-yl |
| 1-167. | 2-Cl-phenyl | 3-aminosulfonyl-naphth-2-yl |
| 1-168. | 2-F-phenyl | 3-aminosulfonyl-naphth-2-yl |
| 1-169. | phenyl | 6-chloro-naphth-2-yl |
| 1-170. | 2-pyridyl | 6-chloro-naphth-2-yl |
| 1-171. | 3-pyridyl | 6-chloro-naphth-2-yl |
| 1-172. | 2-pyrimidyl | 6-chloro-naphth-2-yl |
| 1-173. | 2-Cl-phenyl | 6-chloro-naphth-2-yl |
| 1-174. | 2-F-phenyl | 6-chloro-naphth-2-yl |

TABLE 2
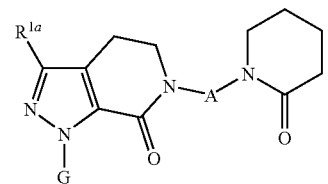
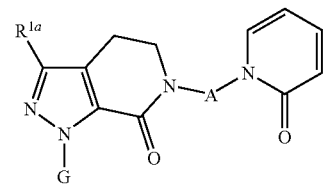
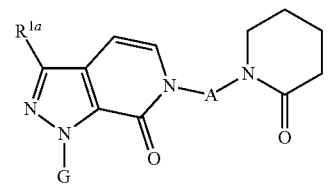
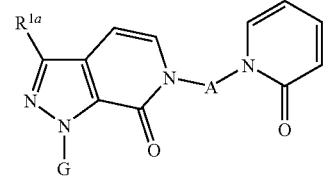
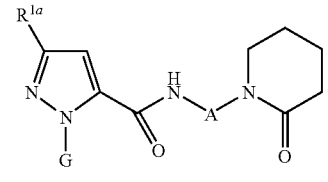
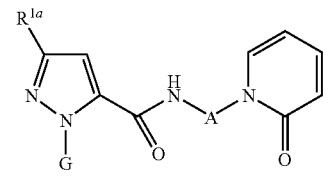
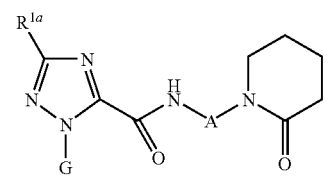
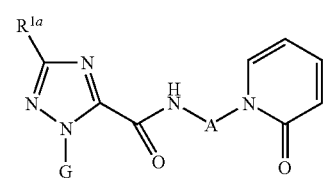
TABLE 2-continued
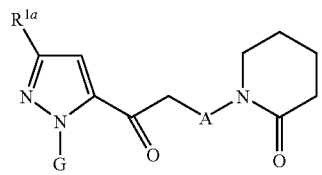
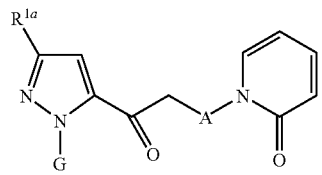
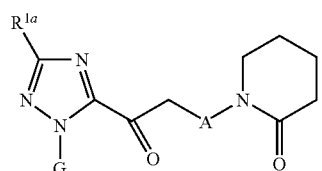
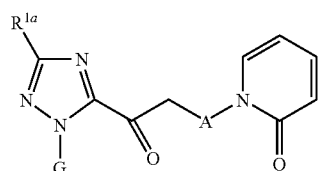
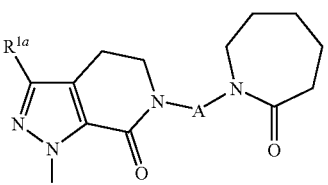
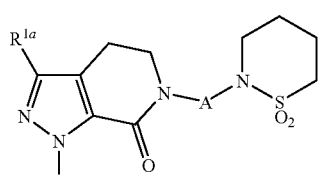
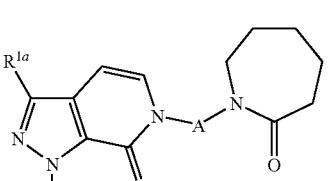
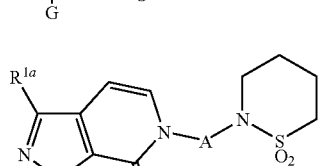

TABLE 2-continued

| Ex# | A | G |
|---|---|---|
| 2-1. | phenyl | 4-methoxyphenyl |
| 2-2. | 2-pyridyl | 4-methoxyphenyl |
| 2-3. | 3-pyridyl | 4-methoxyphenyl |
| 2-4. | 2-pyrimidyl | 4-methoxyphenyl |
| 2-5. | 2-Cl-phenyl | 4-methoxyphenyl |
| 2-6. | 2-F-phenyl | 4-methoxyphenyl |
| 2-7. | piperidinyl | 4-methoxyphenyl |
| 2-8. | phenyl | 2-aminomethylphenyl |
| 2-9. | 2-pyridyl | 2-aminomethylphenyl |
| 2-10. | 3-pyridyl | 2-aminomethylphenyl |
| 2-11. | 2-pyrimidyl | 2-aminomethylphenyl |
| 2-12. | 2-Cl-phenyl | 2-aminomethylphenyl |
| 2-13. | 2-F-phenyl | 2-aminomethylphenyl |
| 2-14. | piperidinyl | 2-aminomethylphenyl |
| 2-15. | phenyl | 3-aminomethylphenyl |
| 2-16. | 2-pyridyl | 3-aminomethylphenyl |
| 2-17. | 3-pyridyl | 3-aminomethylphenyl |
| 2-18. | 2-pyrimidyl | 3-aminomethylphenyl |
| 2-19. | 2-Cl-phenyl | 3-aminomethylphenyl |
| 2-20. | 2-F-phenyl | 3-aminomethylphenyl |
| 2-21. | piperidinyl | 3-aminomethylphenyl |
| 2-22. | phenyl | 2-amidophenyl |
| 2-23. | 2-pyridyl | 2-amidophenyl |
| 2-24. | 3-pyridyl | 2-amidophenyl |
| 2-25. | 2-pyrimidyl | 2-amidophenyl |
| 2-26. | 2-Cl-phenyl | 2-amidophenyl |
| 2-27. | 2-F-phenyl | 2-amidophenyl |
| 2-28. | piperidinyl | 2-amidophenyl |
| 2-29. | phenyl | 2-amido-4-methoxy-phenyl |
| 2-30. | 2-pyridyl | 2-amido-4-methoxy-phenyl |
| 2-31. | 3-pyridyl | 2-amido-4-methoxy-phenyl |
| 2-32. | 2-pyrimidyl | 2-amido-4-methoxy-phenyl |
| 2-33. | 2-Cl-phenyl | 2-amido-4-methoxy-phenyl |
| 2-34. | 2-F-phenyl | 2-amido-4-methoxy-phenyl |
| 2-35. | piperidinyl | 2-amido-4-methoxy-phenyl |
| 2-36. | phenyl | 3-amidophenyl |
| 2-37. | 2-pyridyl | 3-amidophenyl |
| 2-38. | 3-pyridyl | 3-amidophenyl |
| 2-39. | 2-pyrimidyl | 3-amidophenyl |
| 2-40. | 2-Cl-phenyl | 3-amidophenyl |
| 2-41. | 2-F-phenyl | 3-amidophenyl |
| 2-42. | piperidinyl | 3-amidophenyl |
| 2-43. | phenyl | 3-chlorophenyl |
| 2-44. | 2-pyridyl | 3-chlorophenyl |
| 2-45. | 3-pyridyl | 3-chlorophenyl |
| 2-46. | 2-pyrimidyl | 3-chlorophenyl |
| 2-47. | 2-Cl-phenyl | 3-chlorophenyl |
| 2-48. | 2-F-phenyl | 3-chlorophenyl |
| 2-49. | piperidinyl | 3-chlorophenyl |
| 2-50. | phenyl | 3-amino-4-chloro-phenyl |
| 2-51. | 2-pyridyl | 3-amino-4-chloro-phenyl |
| 2-52. | 3-pyridyl | 3-amino-4-chloro-phenyl |
| 2-53. | 2-pyrimidyl | 3-amino-4-chloro-phenyl |
| 2-54. | 2-Cl-phenyl | 3-amino-4-chloro-phenyl |
| 2-55. | 2-F-phenyl | 3-amino-4-chloro-phenyl |
| 2-56. | piperidinyl | 3-amino-4-chloro-phenyl |
| 2-57. | phenyl | 2-aminosulfonyl-phenyl |
| 2-58. | 2-pyridyl | 2-aminosulfonyl-phenyl |
| 2-59. | 3-pyridyl | 2-aminosulfonyl-phenyl |
| 2-60. | 2-pyrimidyl | 2-aminosulfonyl-phenyl |
| 2-61. | 2-Cl-phenyl | 2-aminosulfonyl-phenyl |
| 2-62. | 2-F-phenyl | 2-aminosulfonyl-phenyl |
| 2-63. | piperidinyl | 2-aminosulfonyl-phenyl |
| 2-64. | phenyl | 2-aminosulfonyl-4-methoxyphenyl |
| 2-65. | 2-pyridyl | 2-aminosulfonyl-4-methoxyphenyl |
| 2-66. | 3-pyridyl | 2-aminosulfonyl-4-methoxyphenyl |
| 2-67. | 2-pyrimidyl | 2-aminosulfonyl-4-methoxyphenyl |
| 2-68. | 2-Cl-phenyl | 2-aminosulfonyl-4-methoxyphenyl |
| 2-69. | 2-F-phenyl | 2-aminosulfonyl-4-methoxyphenyl |
| 2-70. | piperidinyl | 2-aminosulfonyl-4-methoxyphenyl |
| 2-71. | phenyl | 3-(1',2',4'-triazolin-5'-on-3'-yl)phenyl |
| 2-72. | 2-pyridyl | 3-(1',2',4'-triazolin-5'-on-3'-yl)phenyl |
| 2-73. | 3-pyridyl | 3-(1',2',4'-triazolin-5'-on-3'-yl)phenyl |
| 2-74. | 2-pyrimidyl | 3-(1',2',4'-triazolin-5'-on-3'-yl)phenyl |
| 2-75. | 2-Cl-phenyl | 3-(1',2',4'-triazolin-5'-on-3'-yl)phenyl |
| 2-76. | 2-F-phenyl | 3-(1',2',4'-triazolin-5'-on-3'-yl)phenyl |
| 2-77. | piperidinyl | 3-(1',2',4'-triazolin-5'-on-3'-yl)phenyl |
| 2-78. | phenyl | 1-aminoisoquinolin-6-yl |
| 2-79. | 2-pyridyl | 1-aminoisoquinolin-6-yl |
| 2-80. | 3-pyridyl | 1-aminoisoquinolin-6-yl |
| 2-81. | 2-pyrimidyl | 1-aminoisoquinolin-6-yl |
| 2-82. | 2-Cl-phenyl | 1-aminoisoquinolin-6-yl |
| 2-83. | 2-F-phenyl | 1-aminoisoquinolin-6-yl |
| 2-84. | piperidinyl | 1-aminoisoquinolin-6-yl |
| 2-85. | phenyl | 1-aminoisoquinolin-7-yl |

TABLE 2-continued

| | | |
|---|---|---|
| 2-86. | 2-pyridyl | 1-aminoisoquinolin-7-yl |
| 2-87. | 3-pyridyl | 1-aminoisoquinolin-7-yl |
| 2-88. | 2-pyrimidyl | 1-aminoisoquinolin-7-yl |
| 2-89. | 2-Cl-phenyl | 1-aminoisoquinolin-7-yl |
| 2-90. | 2-F-phenyl | 1-aminoisoquinolin-7-yl |
| 2-91. | piperidinyl | 1-aminoisoquinolin-7-yl |
| 2-92. | phenyl | 4-aminoquinazol-6-yl |
| 2-93. | 2-pyridyl | 4-aminoquinazol-6-yl |
| 2-94. | 3-pyridyl | 4-aminoquinazol-6-yl |
| 2-95. | 2-pyrimidyl | 4-aminoquinazol-6-yl |
| 2-96. | 2-Cl-phenyl | 4-aminoquinazol-6-yl |
| 2-97. | 2-F-phenyl | 4-aminoquinazol-6-yl |
| 2-98. | piperidinyl | 4-aminoquinazol-6-yl |
| 2-99. | phenyl | 4-aminoquinazol-7-yl |
| 2-100. | 2-pyridyl | 4-aminoquinazol-7-yl |
| 2-101. | 3-pyridyl | 4-aminoquinazol-7-yl |
| 2-102. | 2-pyrimidyl | 4-aminoquinazol-7-yl |
| 2-103. | 2-Cl-phenyl | 4-aminoquinazol-7-yl |
| 2-104. | 2-F-phenyl | 4-aminoquinazol-7-yl |
| 2-105. | piperidinyl | 4-aminoquinazol-7-yl |
| 2-106. | phenyl | 3-aminobenzisoxazol-5-yl |
| 2-107. | 2-pyridyl | 3-aminobenzisoxazol-5-yl |
| 2-108. | 3-pyridyl | 3-aminobenzisoxazol-5-yl |
| 2-109. | 2-pyrimidyl | 3-aminobenzisoxazol-5-yl |
| 2-110. | 2-Cl-phenyl | 3-aminobenzisoxazol-5-yl |
| 2-111. | 2-F-phenyl | 3-aminobenzisoxazol-5-yl |
| 2-112. | piperidinyl | 3-aminobenzisoxazol-5-yl |
| 2-113. | phenyl | 3-aminobenzisoxazol-6-yl |
| 2-114. | 2-pyridyl | 3-aminobenzisoxazol-6-yl |
| 2-115. | 3-pyridyl | 3-aminobenzisoxazol-6-yl |
| 2-116. | 2-pyrimidyl | 3-aminobenzisoxazol-6-yl |
| 2-117. | 2-Cl-phenyl | 3-aminobenzisoxazol-6-yl |
| 2-118. | 2-F-phenyl | 3-aminobenzisoxazol-6-yl |
| 2-119. | piperidinyl | 3-aminobenzisoxazol-6-yl |
| 2-120. | phenyl | 3-aminoindazol-5-yl |
| 2-121. | 2-pyridyl | 3-aminoindazol-5-yl |
| 2-122. | 3-pyridyl | 3-aminoindazol-5-yl |
| 2-123. | 2-pyrimidyl | 3-aminoindazol-5-yl |
| 2-124. | 2-Cl-phenyl | 3-aminoindazol-5-yl |
| 2-125. | 2-F-phenyl | 3-aminoindazol-5-yl |
| 2-126. | piperidinyl | 3-aminoindazol-5-yl |
| 2-127. | phenyl | 3-aminoindazol-6-yl |
| 2-128. | 2-pyridyl | 3-aminoindazol-6-yl |
| 2-129. | 3-pyridyl | 3-aminoindazol-6-yl |
| 2-130. | 2-pyrimidyl | 3-aminoindazol-6-yl |
| 2-131. | 2-Cl-phenyl | 3-aminoindazol-6-yl |
| 2-132. | 2-F-phenyl | 3-aminoindazol-6-yl |
| 2-133. | piperidinyl | 3-aminoindazol-6-yl |
| 2-134. | phenyl | indolin-5-yl |
| 2-135. | 2-pyridyl | indolin-5-yl |
| 2-136. | 3-pyridyl | indolin-5-yl |
| 2-137. | 2-pyrimidyl | indolin-5-yl |
| 2-138. | 2-Cl-phenyl | indolin-5-yl |
| 2-139. | 2-F-phenyl | indolin-5-yl |
| 2-140. | piperidinyl | indolin-5-yl |
| 2-141. | phenyl | indolin-6-yl |
| 2-142. | 2-pyridyl | indolin-6-yl |
| 2-143. | 3-pyridyl | indolin-6-yl |
| 2-144. | 2-pyrimidyl | indolin-6-yl |
| 2-145. | 2-Cl-phenyl | indolin-6-yl |
| 2-146. | 2-F-phenyl | indolin-6-yl |
| 2-147. | piperidinyl | indolin-6-yl |
| 2-148. | phenyl | 2-naphthyl |
| 2-149. | 2-pyridyl | 2-naphthyl |
| 2-150. | 3-pyridyl | 2-naphthyl |
| 2-151. | 2-pyrimidyl | 2-naphthyl |
| 2-152. | 2-Cl-phenyl | 2-naphthyl |
| 2-153. | 2-F-phenyl | 2-naphthyl |
| 2-154. | piperidinyl | 2-naphthyl |
| 2-155. | phenyl | 3-amido-naphth-2-yl |
| 2-156. | 2-pyridyl | 3-amido-naphth-2-yl |
| 2-157. | 3-pyridyl | 3-amido-naphth-2-yl |
| 2-158. | 2-pyrimidyl | 3-amido-naphth-2-yl |
| 2-159. | 2-Cl-phenyl | 3-amido-naphth-2-yl |
| 2-160. | 2-F-phenyl | 3-amido-naphth-2-yl |
| 2-161. | piperidinyl | 3-amido-naphth-2-yl |
| 2-162. | phenyl | 3-methylsulfonyl-naphth-2-yl |
| 2-163. | 2-pyridyl | 3-methylsulfonyl-naphth-2-yl |
| 2-164. | 3-pyridyl | 3-methylsulfonyl-naphth-2-yl |
| 2-165. | 2-pyrimidyl | 3-methylsulfonyl-naphth-2-yl |
| 2-166. | 2-Cl-phenyl | 3-methylsulfonyl-naphth-2-yl |
| 2-167. | 2-F-phenyl | 3-methylsulfonyl-naphth-2-yl |
| 2-168. | piperidinyl | 3-methylsulfonyl-naphth-2-yl |
| 2-169. | phenyl | 3-aminomethyl-naphth-2-yl |
| 2-170. | 2-pyridyl | 3-aminomethyl-naphth-2-yl |
| 2-171. | 3-pyridyl | 3-aminomethyl-naphth-2-yl |
| 2-172. | 2-pyrimidyl | 3-aminomethyl-naphth-2-yl |
| 2-173. | 2-Cl-phenyl | 3-aminomethyl-naphth-2-yl |
| 2-174. | 2-F-phenyl | 3-aminomethyl-naphth-2-yl |
| 2-175. | piperidinyl | 3-aminomethyl-naphth-2-yl |
| 2-176. | phenyl | 3-fluoro-naphth-2-yl |
| 2-177. | 2-pyridyl | 3-fluoro-naphth-2-yl |
| 2-178. | 3-pyridyl | 3-fluoro-naphth-2-yl |
| 2-179. | 2-pyrimidyl | 3-fluoro-naphth-2-yl |
| 2-180. | 2-Cl-phenyl | 3-fluoro-naphth-2-yl |
| 2-181. | 2-F-phenyl | 3-fluoro-naphth-2-yl |
| 2-182. | piperidinyl | 3-fluoro-naphth-2-yl |
| 2-183. | phenyl | 3-cyano-naphth-2-yl |
| 2-184. | 2-pyridyl | 3-cyano-naphth-2-yl |
| 2-185. | 3-pyridyl | 3-cyano-naphth-2-yl |
| 2-186. | 2-pyrimidyl | 3-cyano-naphth-2-yl |
| 2-187. | 2-Cl-phenyl | 3-cyano-naphth-2-yl |
| 2-188. | 2-F-phenyl | 3-cyano-naphth-2-yl |
| 2-189. | Piperidinyl | 3-cyano-naphth-2-yl |
| 2-190. | phenyl | 3-aminosulfonyl-naphth-2-yl |
| 2-191. | 2-pyridyl | 3-aminosulfonyl-naphth-2-yl |
| 2-192. | 3-pyridyl | 3-aminosulfonyl-naphth-2-yl |
| 2-193. | 2-pyrimidyl | 3-aminosulfonyl-naphth-2-yl |
| 2-194. | 2-Cl-phenyl | 3-aminosulfonyl-naphth-2-yl |
| 2-195. | 2-F-phenyl | 3-aminosulfonyl-naphth-2-yl |
| 2-196. | piperidinyl | 3-aminosulfonyl-naphth-2-yl |
| 2-197. | phenyl | 6-chloro-naphth-2-yl |
| 2-198. | 2-pyridyl | 6-chloro-naphth-2-yl |
| 2-199. | 3-pyridyl | 6-chloro-naphth-2-yl |
| 2-200. | 2-pyrimidyl | 6-chloro-naphth-2-yl |
| 2-201. | 2-Cl-phenyl | 6-chloro-naphth-2-yl |
| 2-202. | 2-F-phenyl | 6-chloro-naphth-2-yl |
| 2-203. | Piperidinyl | 6-chloro-naphth-2-yl |

$R^{1a}$ is $CH_3$;

TABLE 3

Examples 3-1-through 3-6090 use the structures from Table 2 and the corresponding A and G groups from Examples 1-203 of Table 2:

Examples 3-1 to 3-203, $R^{1a}$ is $CH_2CH_3$;
Examples 3-204 to 3-406, $R^{1a}$ is $CF_3$;
Examples 3-407 to 3-609, $R^{1a}$ is $SCH_3$;
Examples 3-610 to 3-812, $R^{1a}$ is $SOCH_3$;
Examples 3-813 to 3-1015, $R^{1a}$ is $SO_2CH_3$;
Examples 3-1016 to 3-1218, $R^{1a}$ is Cl;
Examples 3-1219 to 3-1421, $R^{1a}$ is F;
Examples 3-1422 to 3-1624, $R^{1a}$ is $CO_2CH_3$;
Examples 3-1625 to 3-1827, $R^{1a}$ is $CH_2OCH_3$;
Examples 3-1828 to 3-2030, $R^{1a}$ is $CONH_2$;
Examples 3-2031 to 3-2233, $R^{1a}$ is —CN;
Examples 3-2234 to 3-2436, $R^{1a}$ is $CH_2NHCH_3$;
Examples 3-2437 to 3-2639, $R^{1a}$ is $CH_2NHSO_2CH_3$;
Examples 3-2640 to 3-2842, $R^{1a}$ is 1-imidazolyl-$CH_2$;
Examples 3-2843 to 3-3045, $R^{1a}$ is Br;
Examples 3-3046 to 3-3248, $R^{1a}$ is 5-tetrazolyl;
Examples 3-3249 to 3-3451, $R^{1a}$ is $N(CH_3)_2$;
Examples 3-3452 to 3-3654, $R^{1a}$ is $NHCH_3$;
Examples 3-3655 to 3-3857, $R^{1a}$ is $SO_2NH_2$;
Examples 3-3858 to 3-4060, $R^{1a}$ is 2-pyridine;
Examples 3-4061 to 3-4263, $R^{1a}$ is 3-pyridine;
Examples 3-4264 to 3-4466, $R^{1a}$ is 4-pyridine;
Examples 3-4467 to 3-4872, $R^{1a}$ is 2-pyridine-N-oxide;
Examples 3-4873 to 3-5075, $R^{1a}$ is 3-pyridine-N-oxide;
Examples 3-5076 to 3-5287, $R^{1a}$ is 4-pyridine-N-oxide;
Examples 3-5288 to 3-5481, $R^{1a}$ is $OCH_3$;
Examples 3-5482 to 3-5684, $R^{1a}$ is $CH_2OC(O)NHCH_3$;
Examples 3-5685 to 3-5887, $R^{1a}$ is $CH_2NHCO_2CH_3$;
Examples 3-5888 to 3-6090, $R^{1a}$ is $CH_2NHC(O)NHCH_3$; and,
Examples 3-6091 to 3-6293, $R^{1a}$ is H.

TABLE 4

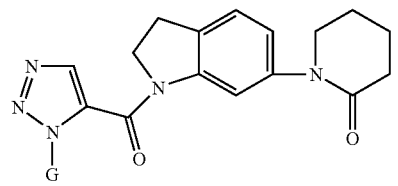
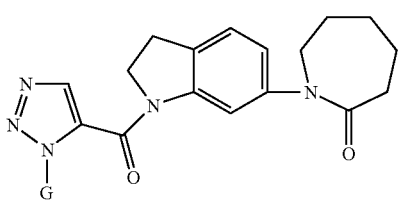
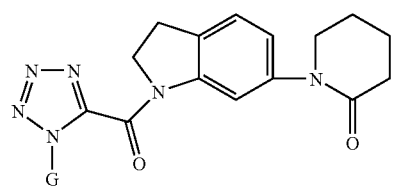
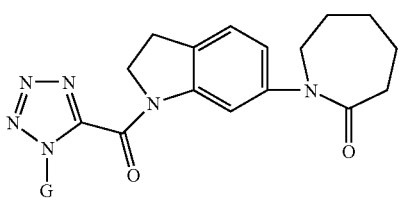
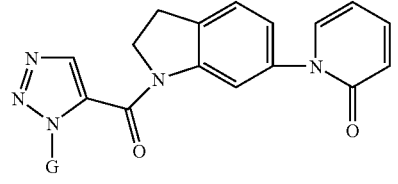
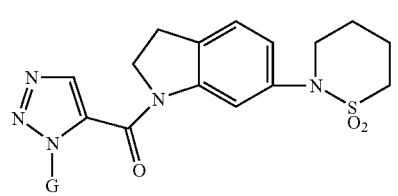
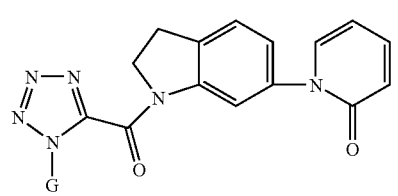

TABLE 4-continued

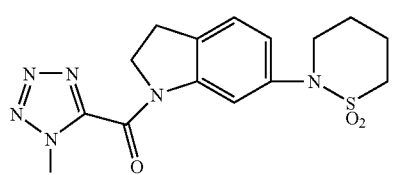

| Ex# | G |
|---|---|
| 4-1. | 4-methoxyphenyl |
| 4-2. | 2-aminomethylphenyl |
| 4-3. | 3-aminomethylphenyl |
| 4-4. | 2-amidophenyl |
| 4-5. | 2-amido-4-methoxy-phenyl |
| 4-6. | 3-amidophenyl |
| 4-7. | 3-chlorophenyl |
| 4-8. | 3-amino-4-chloro-phenyl |
| 4-9. | 2-aminosulfonyl-phenyl |
| 4-10. | 2-aminosulfonyl-4-methoxyphenyl |
| 4-11. | 3-(1',2',4'-triazolin-5'-on-3'-yl)phenyl |
| 4-12. | 1-aminoisoquinolin-6-yl |
| 4-13. | 1-aminoisoquinolin-7-yl |
| 4-14. | 4-aminoquinazol-6-yl |
| 4-15. | 4-aminoquinazol-7-yl |
| 4-16. | 3-aminobenzisoxazol-5-yl |
| 4-17. | 3-aminobenzisoxazol-6-yl |
| 4-18. | 3-aminoindazol-5-yl |
| 4-19. | 3-aminoindazol-6-yl |
| 4-20. | indolin-5-yl |
| 4-21. | indolin-6-yl |
| 4-22. | 2-naphthyl |
| 4-23. | 3-amido-naphth-2-yl |
| 4-24. | 3-methylsulfonyl-naphth-2-yl |
| 4-25. | 3-aminomethyl-naphth-2-yl |
| 4-26. | 3-fluoro-naphth-2-yl |
| 4-27. | 3-chloro-naphth-2-yl |
| 4-28. | 3-aminosulfonyl-naphth-2-yl |
| 4-29. | 6-chloro-naphth-2-yl |

TABLE 5

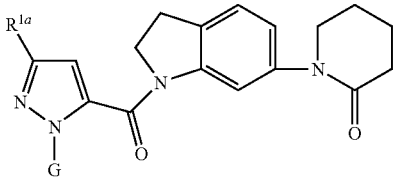

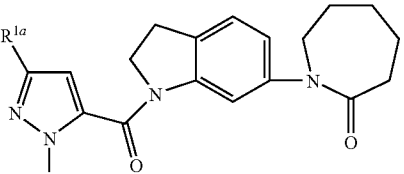

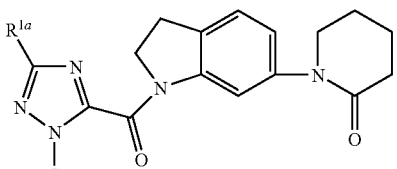

TABLE 5-continued

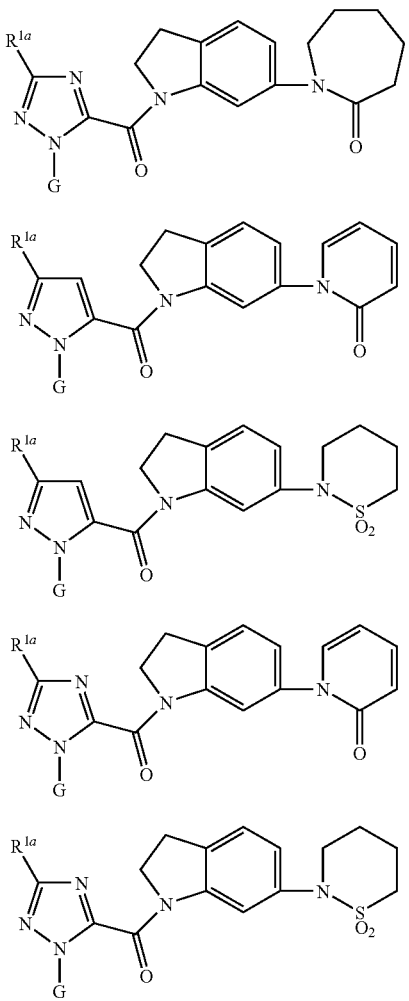

| Ex# | $R^{1a}$ | G |
| --- | --- | --- |
| 5-1. | $CH_3$ | 4-methoxyphenyl |
| 5-2. | $CH_2CH_3$ | 4-methoxyphenyl |
| 5-3. | $CF_3$ | 4-methoxyphenyl |
| 5-4. | $SCH_3$ | 4-methoxyphenyl |
| 5-5. | $SOCH_3$ | 4-methoxyphenyl |
| 5-6. | $SO_2CH_3$ | 4-methoxyphenyl |
| 5-7. | Cl | 4-methoxyphenyl |
| 5-8. | F | 4-methoxyphenyl |
| 5-9. | $CO_2CH_3$ | 4-methoxyphenyl |
| 5-10. | $CH_2OCH_3$ | 4-methoxyphenyl |
| 5-11. | $CONH_2$ | 4-methoxyphenyl |
| 5-12. | CN | 4-methoxyphenyl |
| 5-13. | $CH_2NH_2$ | 4-methoxyphenyl |
| 5-14. | $CH_2NHSO_2CH_3$ | 4-methoxyphenyl |
| 5-15. | 1-imidazolyl-$CH_2$ | 4-methoxyphenyl |
| 5-16. | 1-tetrazolyl-$CH_2$— | 4-methoxyphenyl |
| 5-17. | Br | 4-methoxyphenyl |
| 5-18. | 5-tetrazolyl | 4-methoxyphenyl |
| 5-19. | $N(CH_3)_2$ | 4-methoxyphenyl |
| 5-20. | $NHCH_3$ | 4-methoxyphenyl |
| 5-21. | $SO_2NH_2$ | 4-methoxyphenyl |
| 5-22. | 2-pyridine | 4-methoxyphenyl |
| 5-23. | 3-pyridine | 4-methoxyphenyl |
| 5-24. | 4-pyridine | 4-methoxyphenyl |
| 5-25. | 2-pyridine-N-oxide | 4-methoxyphenyl |
| 5-26. | 3-pyridine-N-oxide | 4-methoxyphenyl |
| 5-27. | 4-pyridine-N-oxide | 4-methoxyphenyl |
| 5-28. | $OCH_3$ | 4-methoxyphenyl |
| 5-29. | $CH_2OC(O)NHCH_3$ | 4-methoxyphenyl |
| 5-30. | $CH_2NHCO_2CH_3$ | 4-methoxyphenyl |
| 5-31. | $CH_2NHC(O)NHCH_3$ | 4-methoxyphenyl |
| 5-32. | H | 4-methoxyphenyl |

For Examples 5-33 through 5-64, G is 2-aminomethylphenyl and $R^{1a}$ is as shown in Examples 5-1 through 5-32.

For Examples 5-65 through 5-96, G is 3-aminomethylphenyl and $R^{1a}$ is as shown in Examples 5-1 through 5-32.

For Examples 5-97 through 5-128, G is 2-amidophenyl and $R^{1a}$ is as shown in Examples 5-1 through 5-32.

For Examples 5-129 through 5-160, G is 2-amido-4-methoxyphenyl and $R^{1a}$ is as shown in Examples 5-1 through 5-32.

For Examples 5-161 through 5-192, G is 3-amidophenyl and $R^{1a}$ is as shown in Examples 5-1 through 5-32.

For Examples 5-193 through 5-224, G is 3-chlorophenyl and $R^{1a}$ is as shown in Examples 5-1 through 5-32.

For Examples 5-225 through 5-256, G is 3-amino-4-chlorophenyl and $R^{1a}$ is as shown in Examples 5-1 through 5-32.

For Examples 5-257 through 5-288, G is 2-aminosulfonylphenyl and $R^{1a}$ is as shown in Examples 5-1 through 5-32.

For Examples 5-289 through 5-320, G is 2-aminosulfonyl-4-methoxyphenyl and $R^{1a}$ is as shown in Examples 5-1 through 5-32.

For Examples 5-321 through 5-352, G is 3-(1',2',4'-triazolin-5'-on-3'-yl)phenyl and $R^{1a}$ is as shown in Examples 5-1 through 5-32.

For Examples 5-353 through 5-384, G is 1-aminoisoquinolin-6-yl and $R^{1a}$ is as shown in Examples 5-1 through 5-32.

For Examples 5-385 through 5-416, G is 1-aminoisoquinolin-7-yl and $R^{1a}$ is as shown in Examples 5-1 through 5-32.

For Examples 5-417 through 5-448, G is 4-aminoquinazol-6-yl and $R^{1a}$ is as shown in Examples 5-1 through 5-32.

For Examples 5-449 through 5-480, G is 4-aminoquinazol-7-yl and $R^{1a}$ is as shown in Examples 5-1 through 5-32.

For Examples 5-481 through 5-512, G is 3-aminobenzisoxazol-5-yl and $R^{1a}$ is as shown in Examples 5-1 through 5-32.

For Examples 5-513 through 5-544, G is 3-aminobenzisoxazol-6-yl and $R^{1a}$ is as shown in Examples 5-1 through 5-32.

For Examples 5-545 through 5-576, G is 3-aminoindazol-5-yl and $R^{1a}$ is as shown in Examples 5-1 through 5-32.

For Examples 5-577 through 5-608, G is 3-aminoindazol-6-yl and $R^{1a}$ is as shown in Examples 5-1 through 5-32.

For Examples 5-609 through 5-640, G is indolin-5-yl and $R^{1a}$ is as shown in Examples 5-1 through 5-32.

For Examples 5-641 through 5-672, G is indolin-6-yl and $R^{1a}$ is as shown in Examples 5-1 through 5-32.

For Examples 5-673 through 5-704, G is 2-naphthyl and $R^{1a}$ is as shown in Examples 5-1 through 5-32.

For Examples 5-705 through 5-736, G is 3-amido-naphth-2-yl and $R^{1a}$ is as shown in Examples 5-1 through 5-32.

For Examples 5-737 through 5-768, G is 3-methylsulfonyl-naphth-2-yl and $R^{1a}$ is as shown in Examples 5-1 through 5-32.

For Examples 5-769 through 5-800, G is 3-aminomethyl-naphth-2-yl and $R^{1a}$ is as shown in Examples 5-1 through 5-32.

For Examples 5-801 through 5-832, G is 3-fluoro-naphth-2-yl and $R^{1a}$ is as shown in Examples 5-1 through 5-32.

For Examples 5-833 through 5-864, G is 3-chloro-naphth-2-yl and $R^{1a}$ is as shown in Examples 5-1 through 5-32.

For Examples 5-865 through 5-896, G is 3-aminosulfonyl-naphth-2-yl and $R^{1a}$ is as shown in Examples 5-1 through 5-32.

For Examples 5-897 through 5-928, G is 6-chloro-naphth-2-yl and $R^{1a}$ is as shown in Examples 5-1 through 5-32.

Numerous modifications and variations of the present invention are possible in light of the above teachings. It is therefore to be understood that within the scope of the appended claims, the invention may be practiced otherwise than as specifically described herein.

What is claimed is:

1. A compound of Formula I:

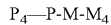

$$P_4-P-M-M_4 \qquad I$$

or a stereoisomer or pharmaceutically acceptable salt thereof, wherein:

M is phenyl or pyridyl, substituted with 0-3 $R^{1a}$ and 0-2 carbonyl groups;

P is absent, and $P_4$ and $M_4$ are attached to the 1,2, 1,3, or 1,4 positions of ring M;

$M_4$ is —Z-A-B and $P_4$ is -$G_1$-G;

G is a pyridyl group substituted with 0-2 R;

R is selected from H, $C_{1-4}$ alkyl, F, Cl, Br, I, OH, $OCH_3$, $OCH_2CH_3$, $OCH(CH_3)_2$, $OCH_2CH_2CH_3$, CN, $C(=NR^8)NR^7R^9$, $NHC(=NR^8)NR^7R^9$, $ONHC(=NR^8)NR^7R^9$, $NR^8CH(=NR^7)$, $NH_2$, $NH(C_{1-3}$ alkyl), $N(C_{1-3}$ alkyl)$_2$, $C(=NH)NH_2$, $CH_2NH_2$, $CH_2NH(C_{1-3}$ alkyl), $CH_2N(C_{1-3}$ alkyl)$_2$, $CH_2CH_2NH_2$, $CH_2CH_2NH(C_{1-3}$ alkyl), $CH_2CH_2N(C_{1-3}$ alkyl)$_2$, $(CR^8R^9)_rC(O)H$, $(CR^8R^9)_rC(O)R^{2c}$, $(CR^8R^9)_rNR^7R^8$, $(CR^8R^9)_rC(O)NR^7R^8$, $(CR^8R^9)_rNR^7C(O)R^7$, $(CR^8R^9)_rOR^3$, $(CR^8R^9)_rS(O)_pNR^7R^8$, $(CR^8R^9)_rNR^7S(O)_pR^7$, $(CR^8R^9)_rSR^3$, $(CR^8R^9)_rS(O)R^3$, $(CR^8R^9)_rS(O)_2R^3$, and $OCF_3$;

alternatively, when 2 R groups are attached to adjacent atoms, they combine to form methylenedioxy or ethylenedioxy;

A is a phenyl group substituted with 0-2 $R^4$;

B is a 2-oxo-1-piperidinyl group substituted with 0-2 $R^{4a}$;

$G_1$ is —C(O)NH— or —NHC(O)—;

Z is —C(O)NH— or —NHC(O)—;

$R^{1a}$, at each occurrence, is selected from H, $—(CR^3R^{3a})_r$ $—R^{1b}$, $—(CR^3R^{3a})_r$—$CR^3R^{1b}R^{1b}$, $—(CR^3R^{3a})_r$—O—$(CR^3R^{3a})_r$—$R^{1b}$, $—C_{2-6}$ alkenylene-$R^{1b}$, $—C_{2-6}$ alkynylene-$R^{1b}$, $—(CR^3R^{3a})_r$—$C(=NR^{1b})NR^3R^{1b}$, $NR^3CR^3R^{3a}R^{1c}$, $OCR^3R^{3a}R^{1c}$, $SCR^3R^{3a}R^{1c}$, $NR^3(CR^3R^{3a})_2(CR^3R^{3a})_rR^{1b}$, $C(O)NR^2(CR^3R^{3a})_2(CR^3R^{3a})_rR^{1b}$, $CO_2(CR^3R^{3a})_2(CR^3R^{3a})_rR^{1b}$, $O(CR^3R^{3a})_2(CR^3R^{3a})_rR^{1b}$, $S(CR^3R^{3a})_2(CR^3R^{3a})_rR^{1b}$, $S(O)_p(CR^3R^{3a})_rR^{1d}$, $O(CR^3R^{3a})_rR^{1d}$, $NR^3(CR^3R^{3a})_r R^{1d}$, $OC(O)NR^3(CR^3R^{3a})_rR^{1d}$, $NR^3C(O)NR^3(CR^3R^{3a})_r R^{1d}$, $NR^3C(O)O(CR^3R^{3a})_rR^{1d}$, and $NR^3C(O)(CR^3R^{3a})_rR^{1d}$, provided that $R^{1a}$ forms other than an N-halo, N—S, O—O, or N—CN bond;

alternatively, when two $R^{1a}$ groups are attached to adjacent atoms, together with the atoms to which they are attached they form a 5-7 membered ring consisting of: carbon atoms and 0-2 heteroatoms selected from the group consisting of N, O, and S(O)$_p$, this ring being substituted with 0-2 $R^{4b}$ and 0-3 ring double bonds;

$R^{1b}$ is selected from H, $C_{1-3}$ alkyl, F, Cl, Br, I, —CN, —$NO_2$, —CHO, $(CF_2)_rCF_3$, $(CR^3R^{3a})_rOR^2$, $NR^2R^{2a}$, $C(O)R^{2b}$, $CO_2R^{2b}$, $OC(O)R^2$, $(CF_2)_rCO_2R^{2a}$, $S(O)_pR^{2b}$, $NR^2(CH_2)_rOR^2$, $C(=NR^{2c})NR^2R^{2a}$, $NR^2C(O)R^{2b}$, $NR^2C(O)NHR^2$, $NR^2C(O)_2R^{2a}$, $OC(O)NR^2R^{2a}$, $C(O)NR^2R^{2a}$, $C(O)NR^2(CH_2)_rOR^2$, $SO_2NR^2R^{2a}$, $NR^2SO_2R^2$, $C(O)NR^2SO_2R^2$, $C_{3-6}$ carbocycle substituted with 0-2 $R^{4b}$, and 5-10 membered heterocycle consisting of carbon atoms and from 1-4 heteroatoms selected from the group consisting of N, O, and S(O)$_p$, and substituted with 0-2 $R^{4b}$, provided that $R^{1b}$ forms other than an O—O, N-halo, N—S, or N—CN bond;

$R^{1c}$ is selected from H, $CH(CH_2OR^2)_2$, $C(O)R^{2c}$, $C(O)NR^2R^{2a}$, $S(O)R^2$, $S(O)_2R^2$, and $SO_2NR^2R^{2a}$;

$R^{1d}$ is selected from $C_{3-6}$ carbocycle substituted with 0-2 $R^{4b}$ and 5-10 membered heterocycle consisting of carbon atoms and from 1-4 heteroatoms selected from the group consisting of N, O, and S(O)$_p$, and substituted with 0-2 $R^{4b}$, provided that $R^{1d}$ forms other than an N—S bond;

$R^2$, at each occurrence, is selected from H, $CF_3$, $C_{1-6}$ alkyl, benzyl, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from the group consisting of N, O, and S(O)$_p$, and substituted with 0-2 $R^{4b}$;

$R^{2a}$, at each occurrence, is selected from H, $CF_3$, $C_{1-6}$ alkyl, benzyl, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from the group consisting of N, O, and S(O)$_p$, and substituted with 0-2 $R^{4b}$;

alternatively, $R^2$ and $R^{2a}$, together with the atom to which they are attached, combine to form a 5 or 6 membered saturated, partially saturated or unsaturated ring substituted with 0-2 $R^{4b}$ and consisting of: 0-1 additional heteroatoms selected from the group consisting of N, O, and S(O)$_p$;

$R^{2b}$, at each occurrence, is selected from $CF_3$, $C_{1-4}$ alkoxy substituted with 0-2 $R^{4b}$, $C_{1-6}$ alkyl substituted with 0-2 $R^{4b}$, —$(CH_2)_r$—$C_{3-10}$ carbocycle substituted with 0-2 $R^{4b}$, and —$(CH_2)_r$-5-10 membered heterocycle consisting of: carbon atoms and 1-4 heteroatoms selected from the group consisting of N, O, and S(O)$_p$, and substituted with 0-2 $R^{4b}$;

$R^{2c}$, at each occurrence, is selected from $CF_3$, OH, $C_{1-4}$ alkoxy, $C_{1-6}$ alkyl, —$(CH_2)_r$—$C_{3-10}$ carbocycle substituted with 0-2 $R^{4b}$, and —$(CH_2)_r$-5-10 membered heterocycle containing from 1-4 heteroatoms selected from the group consisting of N, O, and S(O)$_p$, and substituted with 0-2 $R^{4b}$;

$R^3$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3a}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms, the nitrogen atom to which $R^3$ and $R^{3a}$ are attached, and 0-1 additional heteroatoms selected from the group consisting of N, O, and S(O)$_p$;

$R^{3c}$, at each occurrence, is selected from $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, and phenyl;

$R^{3d}$, at each occurrence, is selected from H, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C_{1-4}$ alkyl-phenyl, and $C(=O)R^{3c}$;

R⁴, at each occurrence, is selected from H, =O, (CR³R³ᵃ)ᵣ OR², F, Cl, Br, I, C₁₋₄ alkyl, (CR³R³ᵃ)ᵣCN, (CR³R³ᵃ)ᵣNO₂, (CR³R³ᵃ)ᵣNR²R²ᵃ, (CR³R³ᵃ)ᵣC(O)R²ᶜ, (CR³R³ᵃ)ᵣNR²C(O)R²ᵇ, (CR³R³ᵃ)ᵣC(O)NR²R²ᵃ, (CR³R³ᵃ)ᵣNR²C(O)NR²R²ᵃ, (CR³R³ᵃ)ᵣC(=NR²)NR²R²ᵃ, (CR³R³ᵃ)ᵣC(=NS(O)₂R⁵)NR²R²ᵃ, (CR³R³ᵃ)ᵣNHC(=NR²)NR²R²ᵃ, (CR³R³ᵃ)ᵣC(O)NHC(=NR²)NR²R²ᵃ, (CR³R³ᵃ)ᵣSO₂NR²R²ᵃ, (CR³R³ᵃ)ᵣNR²SO₂NR²R²ᵃ, (CR³R³ᵃ)ᵣNR²SO₂—C₁₋₄ alkyl, (CR³R³ᵃ)ᵣNR²SO₂R⁵, (CR³R³ᵃ)ᵣS(O)ₚR⁵ᵃ, (CR³R³ᵃ)ᵣ(CF₂)ᵣCF₃, NHCH₂R¹ᶜ, OCH₂R¹ᶜ, SCH₂R¹ᶜ, NH(CH₂)₂(CH₂)ᵣR¹ᵇ, O(CH₂)₂(CH₂)ᵣR¹ᵇ, S(CH₂)₂(CH₂)ᵣR¹ᵇ, (CR³R³ᵃ)ᵣ-5-6 membered carbocycle substituted with 0-1 R⁵, and a (CR³R³ᵃ)ᵣ-5-6 membered heterocycle consisting of: carbon atoms and 1-4 heteroatoms selected from the group consisting of N, O, and S(O)ₚ, and substituted with 0-1 R⁵;

R⁴ᵃ, at each occurrence, is selected from H, =O, (CR³R³ᵃ)ᵣ OR², (CR³R³ᵃ)ᵣF, (CR³R³ᵃ)ᵣBr, (CR³R³ᵃ)ᵣCl, C₁₋₄ alkyl, (CR³R³ᵃ)ᵣCN, (CR³R³ᵃ)ᵣNO₂, (CR³R³ᵃ)ᵣNR²R²ᵃ, (CR³R³ᵃ)ᵣC(O)R²ᶜ, (CR³R³ᵃ)ᵣNR²C(O)R²ᵇ, (CR³R³ᵃ)ᵣC(O)NR²R²ᵃ, (CR³R³ᵃ)ᵣN=CHOR³, (CR³R³ᵃ)ᵣC(O)NH(CH₂)₂NR²R²ᵃ, (CR³R³ᵃ)ᵣNR²C(O)NR²R²ᵃ, (CR³R³ᵃ)ᵣC(=NR²)NR²R²ᵃ, (CR³R³ᵃ)ᵣNHC(=NR²)NR²R²ᵃ, (CR³R³ᵃ)ᵣSO₂NR²R²ᵃ, (CR³R³ᵃ)ᵣNR²SO₂NR²R²ᵃ, (CR³R³ᵃ)ᵣNR²SO₂—C₁₋₄ alkyl, (CR³R³ᵃ)ᵣC(O)NHSO₂—C₁₋₄ alkyl, (CR³R³ᵃ)ᵣNR²SO₂R⁵, (CR³R³ᵃ)ᵣS(O)ₚR⁵ᵃ, (CR³R³ᵃ)ᵣ(CF₂)ᵣCF₃, (CR³R³ᵃ)ᵣ-5-6 membered carbocycle substituted with 0-1 R⁵, and a (CR³R³ᵃ)ᵣ-5-6 membered heterocycle consisting of: carbon atoms and 1-4 heteroatoms selected from the group consisting of N, O, and S(O)ₚ, and substituted with 0-1 R⁵;

R⁴ᵇ, at each occurrence, is selected from H, =O, (CH₂)ᵣOR³, (CH₂)ᵣF, (CH₂)ᵣCl, (CH₂)ᵣBr, (CH₂)₂, C₁₋₄ alkyl, (CH₂)ᵣCN, (CH₂)ᵣNO₂, (CH₂)ᵣNR³R³ᵃ, (CH₂)ᵣC(O)R³, (CH₂)ᵣC(O)OR³ᶜ, (CH₂)ᵣNR³C(O)R³ᵃ, (CH₂)ᵣC(O)NR³R³ᵃ, (CH₂)ᵣNR³C(O)NR³R³ᵃ, (CH₂)ᵣC(=NR³)NR³R³ᵃ, (CH₂)ᵣNR³C(=NR³)NR³R³ᵃ, (CH₂)ᵣSO₂NR³R³ᵃ, (CH₂)ᵣNR³SO₂NR³R³ᵃ, (CH₂)ᵣNR³SO₂—C₁₋₄ alkyl, (CH₂)ᵣNR³SO₂CF₃, (CH₂)ᵣNR³SO₂-phenyl, (CH₂)ᵣS(O)ₚCF₃, (CH₂)ᵣS(O)ₚ—C₁₋₄ alkyl, (CH₂)ᵣS(O)ₚ-phenyl, and (CH₂)ᵣ(CF₂)ᵣCF₃;

R⁵, at each occurrence, is selected from H, C₁₋₆ alkyl, =O, (CH₂)ᵣOR³, F, Cl, Br, I, —CN, NO₂, (CH₂)ᵣNR³R³ᵃ, (CH₂)ᵣC(O)R³, (CH₂)ᵣC(O)OR³ᶜ, (CH₂)ᵣNR³C(O)R³ᵃ, (CH₂)ᵣC(O)NR³R³ᵃ, (CH₂)ᵣNR³C(O)NR³R³ᵃ, (CH₂)ᵣCH(=NOR³ᵈ), (CH₂)ᵣC(=NR³)NR³R³ᵃ, (CH₂)ᵣNR³C(=NR³)NR³R³ᵃ, (CH₂)ᵣSO₂NR³R³ᵃ, (CH₂)ᵣNR³SO₂NR³R³ᵃ, (CH₂)ᵣNR³SO₂—C₁₋₄ alkyl, (CH₂)ᵣNR³SO₂CF₃, (CH₂)ᵣNR³SO₂-phenyl, (CH₂)ᵣS(O)ₚCF₃, (CH₂)ᵣS(O)ₚ—C₁₋₄ alkyl, (CH₂)ᵣS(O)ₚ-phenyl, (CF₂)ᵣCF₃, phenyl substituted with 0-2 R⁶, naphthyl substituted with 0-2 R⁶, and benzyl substituted with 0-2 R⁶;

R⁵ᵃ, at each occurrence, is selected from C₁₋₆ alkyl, (CH₂)ᵣOR³, (CH₂)ᵣNR³R³ᵃ, (CH₂)ᵣC(O)ᵣ³, (CH₂)ᵣC(O)OR³ᶜ, (CH₂)ᵣNR³C(O)R³ᵃ, (CH₂)ᵣC(O)NR³R³ᵃ, (CF₂)ᵣCF₃, phenyl substituted with 0-2 R⁶, naphthyl substituted with 0-2 R⁶, and benzyl substituted with 0-2 R⁶, provided that R⁵ᵃ does not form a S—N or S(O)ₚ—C(O) bond;

R⁶, at each occurrence, is selected from H, OH, (CH₂)ᵣOR², halo, C₁₋₄ alkyl, CN, NO₂, (CH₂)ᵣNR²R²ᵃ, (CH₂)ᵣC(O)R²ᵇ, NR²C(O)R²ᵇ, NR²C(O)NR²R²ᵃ, C(=NH)NH₂, NHC(=NH)NH₂, SO₂NR²R²ᵃ, NR²SO₂NR²R²ᵃ, and NR²SO₂C₁₋₄ alkyl;

R⁷, at each occurrence, is selected from H, OH, C₁₋₆ alkyl, C₁₋₆ alkyl-C(O)—, C₁₋₆ alkyl-O—, (CH₂)ₙ-phenyl, C₁₋₄ alkyl-OC(O)—, C₆₋₁₀ aryl-O—, C₆₋₁₀ aryl-OC(O)—, C₆₋₁₀ aryl-CH₂—C(O)—, C₁₋₄ alkyl-C(O)O—C₁₋₄ alkyl-OC(O)—, C₆₋₁₀ aryl-C(O)O—C₁₋₄ alkyl-OC(O)—, C₁₋₆ alkyl-NH₂—C(O)—, phenyl-NH₂—C(O)—, and phenyl-C₁₋₄ alkyl-C(O)—;

R⁸, at each occurrence, is selected from H, C₁₋₆ alkyl, and (CH₂)ₙ-phenyl;

alternatively, R⁷ and R⁸, when attached to the same nitrogen, combine to form a 5-10 membered heterocyclic ring consisting of carbon atoms and 0-2 additional heteroatoms selected from the group consisting of N, O, and S(O)ₚ;

R⁹, at each occurrence, is selected from H, C₁₋₆ alkyl, and (CH₂)ₙ-phenyl;

n, at each occurrence, is selected from 0, 1, 2, and 3;
p, at each occurrence, is selected from 0, 1, and 2;
r, at each occurrence, is selected from 0, 1, 2, 3, 4, 5, and 6; and
t, at each occurrence, is selected from 0, 1, 2, and 3.

2. A compound according to claim 1, wherein
R is selected from H, C₁₋₄ alkyl, F, Cl, OH, OCH₃, OCH₂CH₃, OCH(CH₃)₂, CN, C(=NH)NH₂, C(=NH)NHOH, C(=NH)NHOCH₃, NH₂, NH(C₁₋₃ alkyl), N(C₁₋₃ alkyl)₂, CH₂NH₂, CH₂NH(C₁₋₃ alkyl), CH₂N(C₁₋₃ alkyl)₂, (CR⁸R⁹)ₜNR⁷R⁸, C(O)NR⁷R⁸, CH₂C(O)NR⁷R⁸, S(O)ₚNR⁷R⁸, CH₂S(O)ₚNR⁷R⁸, SO₂R³, and OCF₃;

alternatively, when 2 R groups are attached to adjacent atoms, they combine to form methylenedioxy or ethylenedioxy;

R¹ᵃ is selected from H, —(CH₂)ᵣ—R¹ᵇ, —(CH(CH₃))ᵣ—R¹ᵇ, —(C(CH₃)₂)ᵣ—R¹ᵇ, NHCH₂R¹ᶜ, OCH₂R¹ᶜ, SCH₂R¹ᶜ, NH(CH₂)₂(CH₂)ᵣR¹ᵇ, and O(CH₂)₂(CH₂)ₜR¹ᵇ, provided that R¹ᵃ forms other than an N-halo, N—S, or N—CN bond;

alternatively, when two R¹ᵃ groups are attached to adjacent atoms, together with the atoms to which they are attached they form a 5-7 membered ring consisting of: carbon atoms and 0-2 heteroatoms selected from the group consisting of N, O, and S(O)ₚ, this ring being substituted with 0-2 R⁴ᵇ and 0-3 ring double bonds;

R¹ᵇ is selected from H, CH₃, CH₂CH₃, CH₂CH₂CH₃, CH(CH₃)₂, F, Cl, Br, I, —CN, —CHO, CF₃, OR², NR²R²ᵃ, C(O)R²ᵇ, CO₂R²ᵇ, OC(O)R², CO₂R²ᵃ, S(O)ₚR², NR²(CH₂)ᵣOR², NR²C(O)R²ᵇ, NR²C(O)NHR², NR²C(O)₂R²ᵃ, OC(O)NR²R²ᵃ, C(O)NR²R²ᵃ, C(O)NR²(CH₂)ᵣOR², SO₂NR²R²ᵃ, NR²SO₂R², C₅₋₆ carbocycle substituted with 0-2 R⁴ᵇ, and 5-6 membered heterocycle consisting of carbon atoms and from 1-4 heteroatoms selected from the group consisting of N, O, and S(O)ₚ, and substituted with 0-2 R⁴ᵇ, provided that R¹ᵇ forms other than an 0-0, N-halo, N—S, or N—CN bond;

R¹ᶜ is selected from H, CH(CH₂OR²)₂, C(O)R²ᶜ, C(O)NR²R²ᵃ, S(O)R², S(O)₂R², and SO₂NR²R²ᵃ;

R², at each occurrence, is selected from H, CF₃, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, benzyl, C₅₋₆ carbocycle substituted with 0-2 R⁴ᵇ, a C₅₋₆ carbocyclic-CH₂-group substituted with 0-2 R⁴ᵇ, and 5-6 membered heterocycle consisting of: carbon atoms and 1-4 heteroatoms selected from the group consisting of N, O, and S(O)ₚ, and substituted with 0-2 R⁴ᵇ;

R²ᵃ, at each occurrence, is selected from H, CF₃, CH₃, CH₂CH₃, CH₂CH₂CH₃, CH(CH₃)₂, CH₂CH₂CH₂CH₃, CH₂CH(CH₃)₂, CH(CH₃)CH₂CH₃, C(CH₃)₃, benzyl, $C_{5-6}$ carbocycle substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

alternatively, $R^2$ and $R^{2a}$, together with the atom to which they are attached, combine to form a 5 or 6 membered saturated, partially saturated or unsaturated ring substituted with 0-2 $R^{4b}$ and consisting of: 0-1 additional heteroatoms selected from the group consisting of N, O, and $S(O)_p$;

$R^{2b}$, at each occurrence, is selected from $CF_3$, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, and 5-6 membered heterocycle consisting of: carbon atoms and 1-4 heteroatoms selected from the group consisting of N, O, and $S(O)_p$, and substituted with 0-2 $R^{4b}$;

$R^{2c}$, at each occurrence, is selected from $CF_3$, OH, $C_{1-4}$ alkoxy, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, benzyl, $C_{5-6}$ carbocycle substituted with 0-2 $R^{4b}$, and 5-6 membered heterocycle containing from 1-4 heteroatoms selected from the group consisting of N, O, and $S(O)_p$, and substituted with 0-2 $R^{4b}$;

$R^3$, at each occurrence, is selected from H, $CH_3$, $CH_2CH_3$, $CH_2CH_2CH_3$, $CH(CH_3)_2$, benzyl, and phenyl;

$R^{3a}$, at each occurrence, is selected from H, $CH_3$, $CH_2CH_3$, $CH_2CH_2CH_3$, $CH(CH_3)_2$, benzyl, and phenyl;

alternatively, $R^3$ and $R^{3a}$, together with the nitrogen atom to which they are attached, combine to form a 5 or 6 membered saturated, partially unsaturated, or unsaturated ring consisting of: carbon atoms and the nitrogen atom to which $R^3$ and $R^{3a}$ are attached;

$R^{3c}$, at each occurrence, is selected from $CH_3$, $CH_2CH_3$, $CH_2CH_2CH_3$, $CH(CH_3)_2$, benzyl, and phenyl;

$R^{3d}$, at each occurrence, is selected from H, $CH_3$, $CH_2CH_3$, $CH_2CH_2CH_3$, $CH(CH_3)_2$, $CH_2$-phenyl, $CH_2CH_2$-phenyl, and $C(=O)R^{3c}$;

$R^4$, at each occurrence, is selected from H, =O, $OR^2$, $CH_2OR^2$, $(CH_2)_2OR^2$, F, Cl, Br, I, $C_{1-4}$ alkyl, —CN, $NO_2$, $NR^2R^{2a}$, $CH_2NR^2R^{2a}$, $(CH_2)_2NR^2R^{2a}$, $C(O)R^{2c}$, $NR^2C(O)R^{2b}$, $C(O)NR^2R^{2a}$, $SO_2NR^2R^{2a}$, $S(O)_pR^{5a}$, $CF_3$, $CF_2CF_3$, 5-6 membered carbocycle substituted with 0-1 $R^5$, and a 5-6 membered heterocycle consisting of: carbon atoms and 1-4 heteroatoms selected from the group consisting of N, O, and $S(O)_p$, and substituted with 0-1 $R^5$;

$R^{4a}$, at each occurrence, is selected from H, =O, $CH_2OR^2$, $OR^2$, $CH_2F$, F, $CH_2Br$, Br, $CH_2Cl$, Cl, $C_{1-4}$ alkyl, $CH_2$—CN, —CN, $CH_2NO_2$, $NO_2$, $CH_2NR^2R^{2a}$, $NR^2R^{2a}$, $CH_2$—$C(O)R^{2c}$, $C(O)R^{2c}$, $NR^2C(O)R^{2b}$, $(CH_2)_rC(O)NR^2R^{2a}$, $NR^2C(O)NR^2R^{2a}$, $(CH_2)_rSO_2NR^2R^{2a}$, $NR^2SO_2NR^2R^{2a}$, $NR^{2s}O_2$—$C_{1-4}$ alkyl, $NR^2SO_2R^5$, $(CH_2)_rS(O)_pR^{5a}$, $CH_2CF_3$, $CF_3$, $CH_2$-5-6 membered carbocycle substituted with 0-1 $R^5$, 5-6 membered carbocycle substituted with 0-1 $R^5$, and a $CH_2$-5-6 membered heterocycle consisting of: carbon atoms and 1-4 heteroatoms selected from the group consisting of N, O, and $S(O)_p$, and substituted with 0-1 $R^5$, and 5-6 membered heterocycle consisting of: carbon atoms and 1-4 heteroatoms selected from the group consisting of N, O, and $S(O)_p$, and substituted with 0-1 $R^5$;

$R^{4b}$, at each occurrence, is selected from H, =O, $OR^3$, $CH_2OR^3$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^3R^{3a}$, $CH_2NR^3R^{3a}$, $C(O)R^3$, $CH_2$—$C(O)R^3$, $C(O)OR^{3c}$, $CH_2C(O)OR^{3c}$, $NR^3C(O)R^{3a}$, $CH_2NR^3C(O)R^{3a}$, $C(O)NR^3R^{3a}$, $CH_2C(O)NR^3R^{3a}$, $NR^3C(O)NR^3R^{3a}$, $CH_2NR^3C(O)NR^3R^{3a}$, $C(=NR^3)NR^3R^{3a}$, $CH_2C(=NR^3)NR^3R^{3a}$, $NR^3C(=NR^3)NR^3R^{3a}$, $CH_2NR^3C(=NR^3)NR^3R^{3a}$, $SO_2NR^3R^{3a}$, $CH_2SO_2NR^3R^{3a}$, $NR^3SO_2NR^3R^{3a}$, $CH_2NR^3SO_2NR^3R^{3a}$, $NR^3SO_2$—$C_{1-4}$ alkyl, $CH_2NR^3SO_2$—$C_{1-4}$ alkyl, $NR^3SO_2CF_3$, $CH_2NR^3SO_2CF_3$, $NR^3SO_2$-phenyl, $CH_2NR^3SO_2$-phenyl, $S(O)_pCF_3$, $CH_2S(O)_pCF_3$, $S(O)_p$—$C_{1-4}$ alkyl, $CH_2S(O)_p$—$C_{1-4}$ alkyl, $S(O)_p$-phenyl, $CH_2S(O)_p$-phenyl, $CF_3$, and $CH_2CF_3$;

$R^5$, at each occurrence, is selected from H, =O, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, $OR^3$, $CH_2OR^3$, F, Cl, —CN, $NO_2$, $NR^3R^{3a}$, $CH_2NR^3R^{3a}$, $C(O)R^3$, $CH_2C(O)R^3$, $C(O)OR^{3c}$, $CH_2C(O)OR^{3c}$, $NR^3C(O)R^{3a}$, $C(O)NR^3R^{3a}$, $NR^3C(O)NR^3R^{3a}$, $CH(=NOR^{3d})$, $C(=NR^3)NR^3R^{3a}$, $NR^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, $CF_3$, phenyl substituted with 0-2 $R^6$, naphthyl substituted with 0-2 $R^6$, and benzyl substituted with 0-2 $R^6$; and $R^6$, at each occurrence, is selected from H, OH, $OR^2$, F, Cl, $CH_3$, $CH_2CH_3$, $CH_2CH_2CH_3$, $CH(CH_3)_2$, $CH_2CH_2CH_2CH_3$, $CH_2CH(CH_3)_2$, $CH(CH_3)CH_2CH_3$, $C(CH_3)_3$, —CN, $NO_2$, $NR^2R^{2a}$, $CH_2NR^2R^{2a}$, $C(O)R^{2b}$, $CH_2C(O)R^{2b}$, $NR^2C(O)R^{2b}$, $NR^2C(O)NR^2R^{2a}$, $C(=NH)NH_2$, $NHC(=NH)NH_2$, $SO_2NR^2R^{2a}$, $NR^2SO_2NR^2R^{2a}$, and $NR^2SO_2C_{1-4}$ alkyl.

3. A pharmaceutical composition, comprising: a pharmaceutically acceptable carrier and a therapeutically effective amount of a compound of claim 1 or a pharmaceutically acceptable salt form thereof.

4. A method for treating a thromboembolic disorder, comprising: administering to a patient in need thereof a therapeutically effective amount of a compound of claim 1 or a pharmaceutically acceptable salt form thereof.

5. A method according to claim 4, wherein the thromboembolic disorder is selected from the group consisting of arterial cardiovascular thromboembolic disorders, venous cardiovascular thromboembolic disorders, and thromboembolic disorders in the chambers of the heart.

6. A method according to claim 4, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

7. A compound according to claim 1, which is selected from the group consisting of formulas (II)-(XVIII):
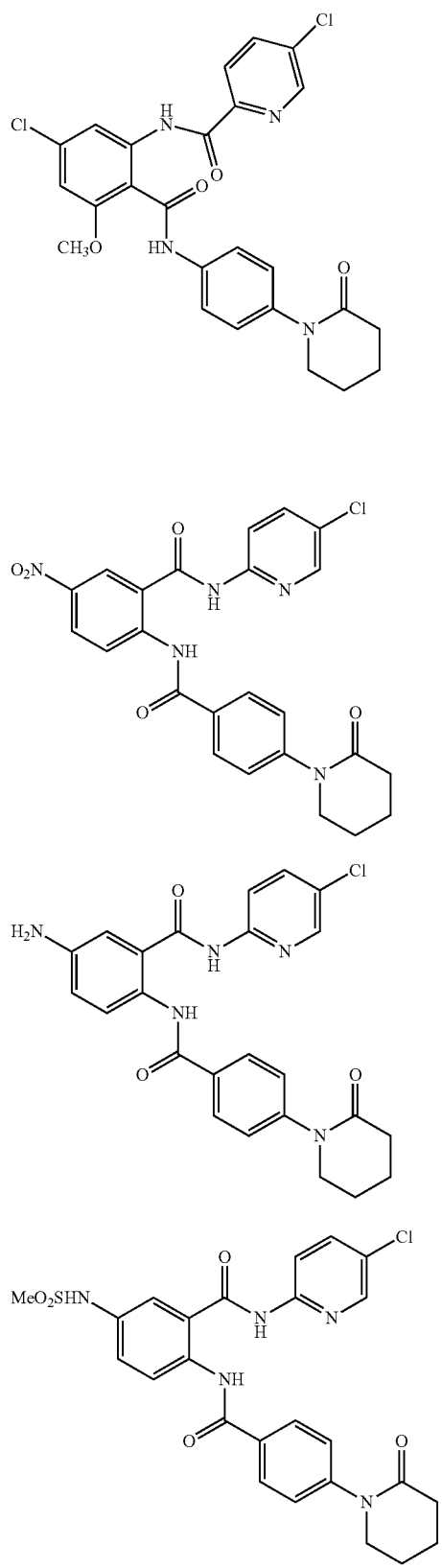
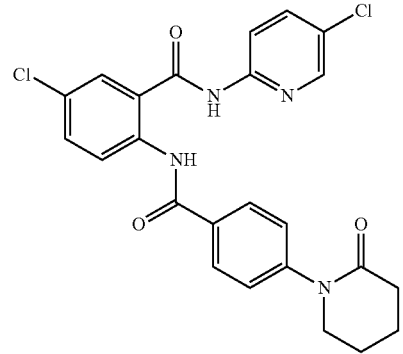
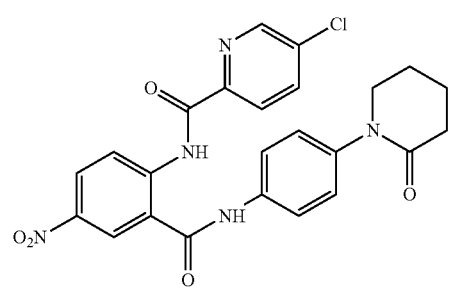
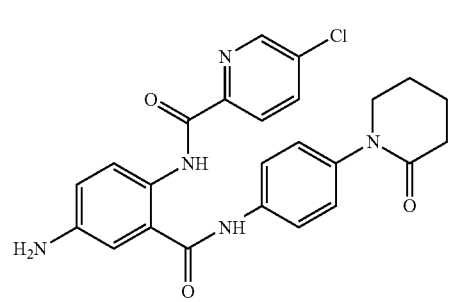
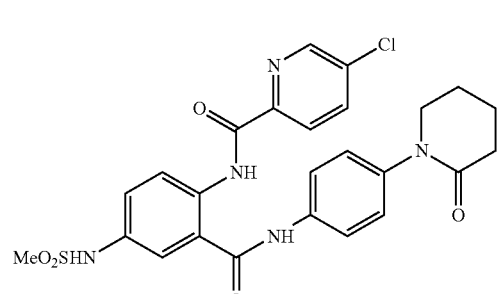
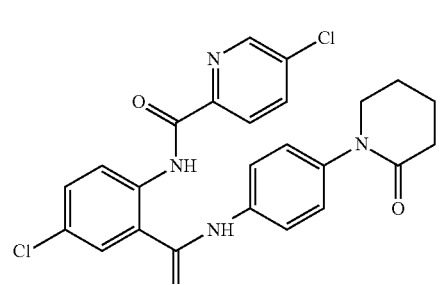

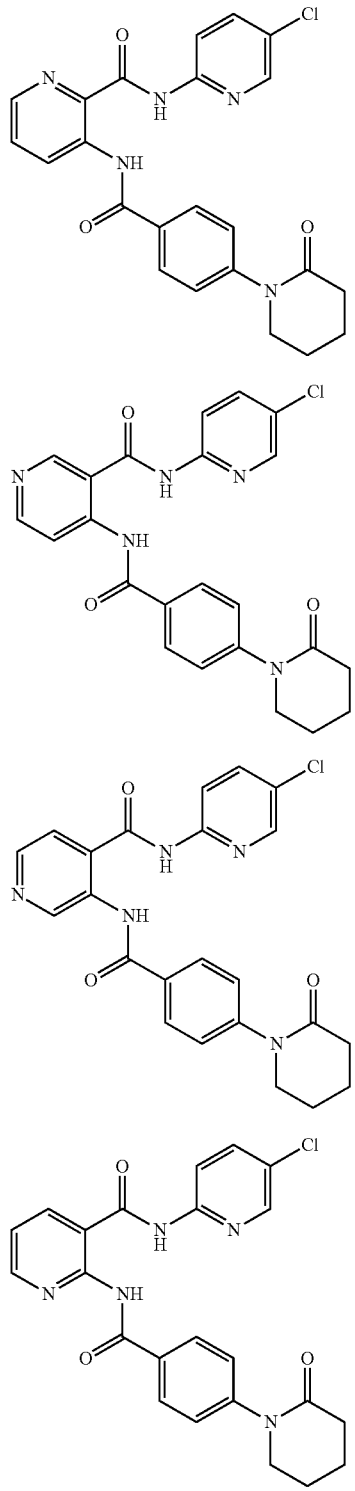
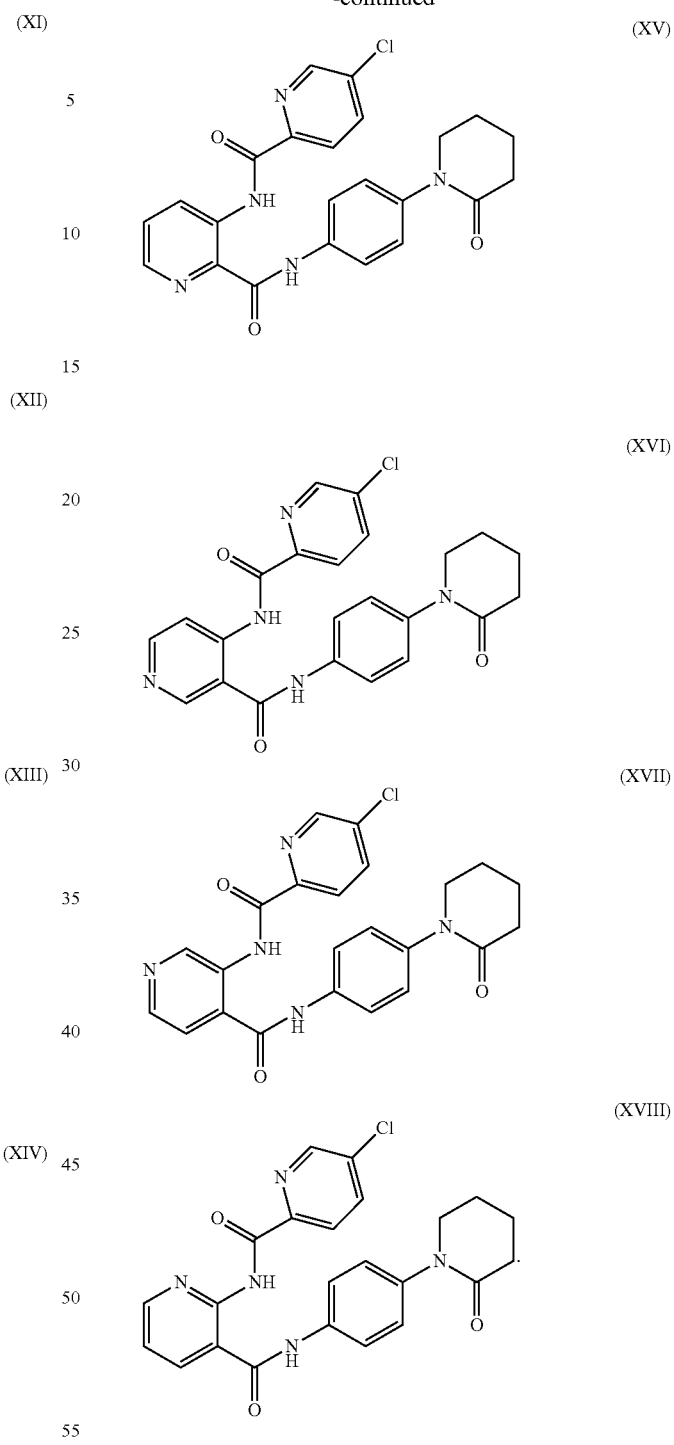
* * * * *

UNITED STATES PATENT AND TRADEMARK OFFICE
CERTIFICATE OF CORRECTION

PATENT NO. : 7,960,411 B2
APPLICATION NO. : 12/691895
DATED : June 14, 2011
INVENTOR(S) : Donald J. P. Pinto Page 1 of 1

It is certified that error appears in the above-identified patent and that said Letters Patent is hereby corrected as shown below:

Column 231
line 35, "$(CH_2)$," should read -- $(CH_2)_rI$, --; and
Line 57, "$(O)_R^3$," should read -- $(O)R^3$, --.

Column 233
Line 58, "$NR^{2S}O_2$" should read -- $NR^2SO_2$ --.

Signed and Sealed this
Twenty-second Day of November, 2011

David J. Kappos
*Director of the United States Patent and Trademark Office*